(12) United States Patent
Iwakoshi et al.

(10) Patent No.: US 8,242,133 B2
(45) Date of Patent: Aug. 14, 2012

(54) ARTHROPOD PEST CONTROL COMPOSITIONS COMPRISING SUBSTITUTED OXAZOLO [5,4-B] PYRIDINES

(75) Inventors: Mitsuhiko Iwakoshi, Toyonaka (JP); Ippei Uemura, Chiba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/937,385

(22) PCT Filed: Apr. 21, 2009

(86) PCT No.: PCT/JP2009/058236
§ 371 (c)(1),
(2), (4) Date: Oct. 12, 2010

(87) PCT Pub. No.: WO2009/131237
PCT Pub. Date: Oct. 29, 2009

(65) Prior Publication Data
US 2011/0039843 A1 Feb. 17, 2011

(30) Foreign Application Priority Data
Apr. 21, 2008 (JP) ................. 2008-109977

(51) Int. Cl.
*A61K 31/44* (2006.01)
(52) U.S. Cl. ...................... 514/302; 514/338
(58) Field of Classification Search .............. 514/302, 514/338
See application file for complete search history.

(56) References Cited

U.S. PATENT DOCUMENTS

| | | | |
|---|---|---|---|
| 3,036,084 | A | 5/1962 | Duennenberg et al. |
| 3,912,748 | A | 10/1975 | Evans et al. |
| 3,962,441 | A | 6/1976 | Evans et al. |
| 3,962,452 | A | 6/1976 | Evans et al. |
| 4,021,440 | A | 5/1977 | Evans et al. |
| 5,849,765 | A | 12/1998 | Curtis et al. |
| 6,130,217 | A | 10/2000 | Arnold et al. |
| 6,544,989 | B2 | 4/2003 | Mathews et al. |
| 7,045,539 | B2 | 5/2006 | Barlaam et al. |
| 2002/0049142 | A1 | 4/2002 | Mathews et al. |
| 2004/0102435 | A1 | 5/2004 | Barlaam et al. |
| 2006/0111408 | A1 | 5/2006 | Barlaam et al. |
| 2009/0075938 | A1 | 3/2009 | Wynne et al. |

FOREIGN PATENT DOCUMENTS

| | | |
|---|---|---|
| EP | 399409 A2 | 11/1990 |
| GB | 895431 A | 5/1962 |
| GB | 901648 A | 7/1962 |
| GB | 1094199 A | 12/1967 |
| GB | 2311010 A | 9/1997 |
| JP | 4943974 A | 4/1974 |
| WO | 9422846 A1 | 10/1994 |
| WO | 00/06566 A1 | 2/2000 |
| WO | 02051821 A1 | 7/2002 |
| WO | 2006044503 A2 | 4/2006 |
| WO | 2007010085 A2 | 1/2007 |
| WO | 2007091106 A2 | 8/2007 |
| WO | 2009027732 A1 | 3/2009 |
| WO | WO 2009/155017 | * 12/2009 |

OTHER PUBLICATIONS

Dunwell et al, "Synthesis and Antiinflammatory Activity of Some 2-Heteroaryl-a-methyl-5-benzoxazoleacetic Acids," Journal of Medicinal Chemistry, vol. 18, No. 11, pp. 1158-1159 (1975).
Haworth et al, "4-Heterocyclyl Tetrahydropyridines as Selective Ligands for the Human Dopamine D4 Receptor," Bioorganic & Medicinal Chemistry Letters, vol. 7, No. 17, pp. 2211-2216 (1997).
Hisano et al, "Synthesis of Benzoxazoles, Benzothiazoles and Benzimidazoles and Evaluation of Their Antifungal, Insecticidal and Herbicidal Activities," Chemical & Pharmaceutical Bulletin, vol. 30, No. 8, pp. 2996-3004 (1982).
Jampilek et al, "Synthesis and Hydrophobic Propertie of Benzoxazoles," 9th International Electronic Conference on Synthetic Organic Chemistry, pp. 1-8 (2005).
Jung et al, "Studies of Mescarinic Receptor Agonists: 2-(1-Methyl-1,2,3,6-Tetrahydropyridin-4-yl)Benzoxazoles/Benzothiazole," Korean Journal of Medicinal Chemistry, vol. 9, No. 2, pp. 56-62 (1999).
Maruyama et al, "Study of several fluorescent brightening agents for synthetic fibers," Kogyo Kagaku Zasshi, vol. 65, pp. 1071-1074 (1962).
Nazarova, "The Limited Electron-donor and Electron-acceptor Ability of Atoms and Groups in Organic Compounds," Zhurnal Obshchei Khimii, vol. 32, No. 5, pp. 1411-1414, translated from pp. 1423-1427 (1962).
Park et al, "Synthesis of 2-(2-, 3-, and 4-Pyridyl)benzoxazoles by the Reaction of Phenolic Schiff Bases with Thianthrene Cation Radical," Journal of Heterocyclic Chemistry, vol. 39, pp. 1279-1281 (2002).

(Continued)

*Primary Examiner* — James O Wilson
*Assistant Examiner* — Douglas M Willis
(74) *Attorney, Agent, or Firm* — Panitch Schwarze Belisario & Nadel LLP

(57) ABSTRACT

Disclosed is a harmful arthropod control composition comprising, as an active ingredient, a fused heterocyclic compound represented by formula (1) [wherein $A^1$ and $A^2$ independently represent a nitrogen atom or the like; $R^1$ and $R^4$ independently represent a halogen atom or the like; $R^2$ and $R^3$ independently represent a halogen atom or the like; $R^5$ and $R^6$ independently represent a linear C1-C6 hydrocarbon group which may be substituted, or the like (provided that both $R^5$ and $R^6$ cannot represent a hydrogen atom simultaneously); and n represents 0 or 1]. The harmful arthropod control composition has an excellent efficacy to control harmful arthropods.

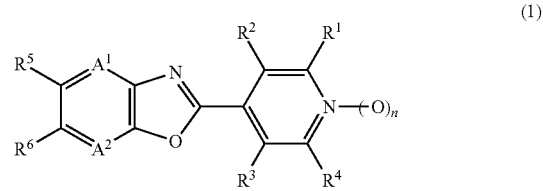

(1)

15 Claims, No Drawings

OTHER PUBLICATIONS

Szabelski et al, "Fluorogenic peptide substrates containing benzoxazol-5-yl-alanine derivatives for kinetic assay of cysteine proteases," Analytical Biochemistry, vol. 342, No. 1, pp. 20-27 (2005).

Vinsova et al, "Synthesis and antimicrobial evaluation of new 2-substituted 5,7-di-tert-butylbenzoxazoles," Bioorganic & Medicinal Chemistry, vol. 14, pp. 5850-5865 (2006).

Wright, "The Synthesis of Benzoxazole-5-acetic Acid Derivatives," Journal of Heterocyclic Chemistry, vol. 9, No. 3, pp. 681-682 (1972).

Int'l. Preliminary Report on Patentability and Written Opinion dated Dec. 29, 2010 in Int'l. Application No. PCT/JP2009/058236.

Int'l Search Report issued on Jun. 23, 2009 in Int'l Application No. PCT/JP2009/058236.

Hisano, T. et al., "Synthesis of Benzoxazoles, Benzothiazoles and Benzimidazoles and Evaluation of Their Antifungal, Insecticidal and Herbicidal Activities", Chemical & Pharmaceutical Bulletin, vol. 30, No. 8, pp. 2996-3004, (1982).

* cited by examiner

ARTHROPOD PEST CONTROL COMPOSITIONS COMPRISING SUBSTITUTED OXAZOLO [5,4-B] PYRIDINES

CROSS-REFERENCE TO RELATED APPLICATION

This application is a Section 371 of International Application No. PCT/JP2009/058236, filed Apr. 21, 2009, which was published in the Japanese language on Oct. 29, 2009, under International Publication No. WO 2009/131237 A1 and the disclosure of which is incorporated herein by reference.

TECHNICAL FIELD

The present invention relates to an arthropod pest control composition and a condensed heterocyclic compound.

BACKGROUND ART

Various compounds have been studied so far for the purpose of controlling harmful organisms, and such compounds have been practically used.

The specification of GB 895,431 A discloses that a benzoxazole compound is useful as a light-shielding agent and/or a microbicide. The specifications of GB 2,311,010 A and JP 49-43974 A disclose a benzoxazole compound as a production intermediate of a pharmaceutical compound. Chem. Pharm. Bull., 30(8), 2996 (1982) discloses a certain type of benzoxazole compound.

DISCLOSURE OF THE INVENTION

It is an object of the present invention to provide a composition having an excellent controlling effect on arthropod pests.

As a result of intensive studies directed towards achieving the aforementioned object, the present inventors have found that a condensed heterocyclic compound represented by formula (1) has an excellent controlling effect on arthropod pests, thereby completing the present invention.

Specifically, the present invention includes the following [1] to [18]:

[1] An arthropod pests control composition comprising, as an active ingredient, a condensed heterocyclic compound represented by formula (1):

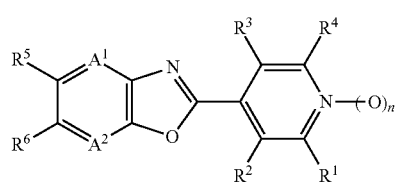

(1)

wherein each of $A^1$ and $A^2$ independently represents a nitrogen atom or $=C(R^7)-$;

each of $R^1$ and $R^4$ independently represents a halogen atom or a hydrogen atom;

each of $R^2$ and $R^3$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; $-OR^8$; $-NR^8R^9$; $-NR^8C(O)R^9$; $-NR^{10}C(O)NR^9R^{14}$; $-NR^{10}CO_2R^{15}$; $-S(O)_mR^8$; $-CO_2R^{10}$; $-CONR^8R^9$; $-C(O)R^{10}$; $-C(NOR^8)R^{10}$; $-CONR^{10}NR^{11}R^{12}$; a cyano group; a nitro group; a halogen atom; or a hydrogen atom;

each of $R^5$ and $R^6$ independently represents a C1-C6 acyclic hydrocarbon group optionally substituted with one or more members selected from Group X; a C3-C6 alicyclic hydrocarbon group optionally substituted with one or more members selected from Group X; $-OR^{13}$; $-S(O)_mR^{13}$; a halogen atom; or a hydrogen atom; except that both $R^5$ and $R^6$ represent hydrogen atoms; or $R^5$ and $R^6$, together with 6-membered ring constituent atoms to which they bind, may form a 5- or 6-membered ring optionally substituted with one or more members selected from Group Z;

$R^7$ represents a C1-C3 alkyl group optionally substituted with one or more halogen atoms; a C1-C3 alkoxy group optionally substituted with one or more halogen atoms; a cyano group; a halogen atom; or a hydrogen atom;

each of $R^8$ and $R^9$ independently represents a C1-C6 acyclic hydrocarbon group optionally substituted with one or more members selected from Group X; a C4-C7 cycloalkylmethyl group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; or a hydrogen atom; provided that $R^8$ does not represent a hydrogen atom when m in $-S(O)_mR^8$ is 1 or 2;

each of $R^{10}$ and $R^{14}$ independently represents a C1-C4 alkyl group optionally substituted with one or more halogen atoms; or a hydrogen atom;

each of $R^{11}$ and $R^{12}$ independently represents a C1-C4 alkyl group optionally substituted with one or more halogen atoms; a C2-C4 alkoxycarbonyl group; or a hydrogen atom;

$R^{13}$ represents a C1-C6 acyclic hydrocarbon group optionally substituted with one or more members selected from Group X; or a C3-C6 alicyclic hydrocarbon group optionally substituted with one or more members selected from Group X;

$R^{15}$ represents a C1-C4 alkyl group optionally substituted with one or more halogen atoms;

m represents 0, 1, or 2;

n represents 0 or 1;

Group X: the group consisting of a C1-C4 alkoxy group optionally substituted with one or more halogen atoms; a cyano group; and a halogen atom;

Group Y: the group consisting of a C1-C4 alkyl group optionally substituted with one or more halogen atoms; a C1-C4 alkoxy group optionally substituted with one or more halogen atoms; a cyano group; a nitro group; and a halogen atom; and Group Z: the group consisting of a C1-C3 alkyl group optionally substituted with one or more halogen atoms; and a halogen atom;

[2] The arthropod pest control composition according to [1] above, wherein the condensed heterocyclic compound is the compound wherein each of R² and R³ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; —OR⁸; —NR⁸R⁹; —NR⁸C(O)R⁹; —S(O)$_m$R⁸; —CO₂R¹⁰; —CONR⁸R⁹; —CONR¹⁰NR¹¹R¹²; a cyano group; a nitro group; a halogen atom; or a hydrogen atom; and each of R⁸ and R⁹ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a 5- or 6-membered heterocyclic group optionally substituted with one or more members selected from Group Y; or a hydrogen atom;

[3] The arthropod pest control composition according to [1] or [2] above, wherein the condensed heterocyclic compound is the compound wherein R¹ and R⁴ represent a hydrogen atom;

[4] The arthropod pest control composition according to [1], [2], or [3] above, wherein the condensed heterocyclic compound is the compound wherein R² represents a hydrogen atom or a halogen atom;

[5] The arthropod pest control composition according to [1], [2], [3], or [4] above, wherein the condensed heterocyclic compound is the compound wherein R³ represents a C3-C6 alicyclic hydrocarbon group optionally substituted with one or more members selected from Group X; a phenyl group optionally substituted with one or more members selected from Group Y; a benzyl group optionally substituted with one or more members selected from Group Y; or a 5- or 6-membered heterocyclic group optionally substituted with one or more members selected from Group Y;

[6] The arthropod pest control composition according [1], [3], or [4] above, wherein the condensed heterocyclic compound is the compound wherein
R³ represents a C1-C6 acyclic hydrocarbon group optionally substituted with one or more members selected from Group X; —OR⁸; —NR⁸R⁹; —NR⁸C(O)R⁹; —NR¹⁰C(O)NR⁹R¹⁴; —NR¹⁰CO₂R¹⁵; —S(O)$_m$R⁸; —CO₂R¹⁰; —CONR⁸R⁹; —C(O)R¹⁰; —C(NOR⁸)R¹⁰; —CONR¹⁰NR¹¹R¹²; a cyano group; a nitro group; a halogen atom; or a hydrogen atom; and each of R⁸ and R⁹ independently represents a C1-C6 acyclic hydrocarbon group optionally substituted with one or more members selected from Group X; or a hydrogen atom; provided that R⁸ represents a C1-C6 acyclic hydrocarbon group optionally substituted with one or more members selected from Group X when m in —S(O)$_m$R⁸ is 1 or 2;

[7] The arthropod pest control composition according to [1], [2], [3], or [4] above, wherein the condensed heterocyclic compound is the compound wherein
R³ represents a C1-C6 acyclic hydrocarbon group optionally substituted with one or more members selected from Group X; —OR⁸; —NR⁸R⁹; —S(O)$_m$R⁸; a halogen atom; or a hydrogen atom; and each of R⁸ and R⁹ independently represents a C1-C6 acyclic hydrocarbon group optionally substituted with one or more members selected from Group X; or a hydrogen atom; provided that R⁸ represents a C1-C6 acyclic hydrocarbon group optionally substituted with one or more members selected from Group X when m in —S(O)$_m$R⁸ is 1 or 2;

[8] The arthropod pest control composition according to [1], [2], [3], [4], [5], [6], or [7] above, wherein the condensed heterocyclic compound is the compound wherein
each of R⁵ and R⁶ independently represents a C1-C6 acyclic hydrocarbon group optionally substituted with one or more members selected from Group X; —OR¹³; —S(O)$_m$R¹³; a halogen atom; or a hydrogen atom; wherein at least one of R⁵ and R⁶ represents a C1-C6 acyclic hydrocarbon group optionally substituted with one or more members selected from Group X; —OR¹³; —S(O)$_m$R¹³; or a halogen atom; and R¹³ represents a C1-C6 acyclic hydrocarbon group optionally substituted with one or more members selected from Group X;

[9] An arthropod pest control method, which comprises applying, to arthropod pests or areas where arthropod pests live, an effective amount of a condensed heterocyclic compound represented by formula (1):

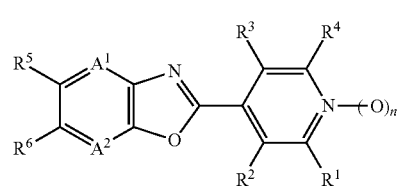

wherein
each of A¹ and A² independently represents a nitrogen atom or =C(R⁷)—;

each of R¹ and R⁴ independently represents a halogen atom or a hydrogen atom;

each of R² and R³ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; —OR⁸; —NR⁸R⁹; —NR⁸C(O)R⁹; —NR¹⁰C(O)NR⁹R¹⁴; —NR¹⁰CO₂R¹⁵; —S(O)$_m$R⁸; —CO₂R¹⁰; —CONR⁸R⁹; —C(O)R¹⁰; —C(NOR⁸)R¹⁰; —CONR¹⁰NR¹¹R¹²; a cyano group; a nitro group; a halogen atom; or a hydrogen atom;

each of R⁵ and R⁶ independently represents a C1-C6 acyclic hydrocarbon group optionally substituted with one or more members selected from Group X; a C3-C6 alicyclic hydrocarbon group optionally substituted with one or more members selected from Group X; —OR¹³; —S(O)$_m$R¹³; a halogen atom; or a hydrogen atom; except that both R⁵ and R⁶ represent hydrogen atoms; or R⁵ and R⁶, together with 6-membered ring constituent atoms to which they bind, may form a 5- or 6-membered ring optionally substituted with one or more members selected from Group Z;

R⁷ represents a C1-C3 alkyl group optionally substituted with one or more halogen atoms; a C1-C3 alkoxy group optionally substituted with one or more halogen atoms; a cyano group; a halogen atom; or a hydrogen atom;

each of R⁸ and R⁹ independently represents a C1-C6 acyclic hydrocarbon group optionally substituted with one or more members selected from Group X; a C4-C7 cycloalkylmethyl group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; or a hydrogen atom; provided that $R^8$ does not represent a hydrogen atom when m in $-S(O)_mR^8$ is 1 or 2;

each of $R^{10}$ and $R^{14}$ independently represents a C1-C4 alkyl group optionally substituted with one or more halogen atoms; or a hydrogen atom;

each of $R^{11}$ and $R^{12}$ independently represents a C1-C4 alkyl group optionally substituted with one or more halogen atoms; a C2-C4 alkoxycarbonyl group; or a hydrogen atom;

$R^{13}$ represents a C1-C6 acyclic hydrocarbon group optionally substituted with one or more members selected from Group X; or a C3-C6 alicyclic hydrocarbon group optionally substituted with one or more members selected from Group X;

$R^{15}$ represents a C1-C4 alkyl group optionally substituted with one or more halogen atoms;

m represents 0, 1, or 2;

n represents 0 or 1;

Group X: the group consisting of a C1-C4 alkoxy group optionally substituted with one or more halogen atoms; a cyano group; and a halogen atom;

Group Y: the group consisting of a C1-C4 alkyl group optionally substituted with one or more halogen atoms; a C1-C4 alkoxy group optionally substituted with one or more halogen atoms; a cyano group; a nitro group; and a halogen atom; and Group Z: the group consisting of a C1-C3 alkyl group optionally substituted with one or more halogen atoms; and a halogen atom;

[10] The arthropod pest control method according to [9] above, wherein the arthropod pests are Hemiptera insect pests;

[11] A condensed heterocyclic compound represented by formula (2):

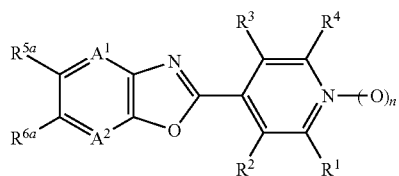

(2)

wherein each of $A^1$ and $A^2$ independently represents a nitrogen atom or $=C(R^7)-$;

each of $R^1$ and $R^4$ independently represents a halogen atom or a hydrogen atom;

each of $R^2$ and $R^3$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; $-OR^8$; $-NR^8R^9$; $-NR^8C(O)R^9$; $-NR^{10}C(O)NR^9R^{14}$; $-NR^{10}CO_2R^{15}$; $-S(O)_mR^8$; $-CO_2R^{10}$; $-CONR^8R^9$; $-C(O)R^{10}$; $-C(NOR^8)R^{10}$; $-CONR^{10}NR^{11}R^{12}$; a cyano group; a nitro group; a halogen atom; or a hydrogen atom;

each of $R^{5a}$ and $R^{6a}$ independently represents a C1-C6 acyclic hydrocarbon group which is substituted with one or more halogen atoms; a C3-C6 alicyclic hydrocarbon group which is substituted with one or more halogen atoms; $-OR^{13a}$; $-S(O)_mR^{13a}$; a halogen atom; or a hydrogen atom; except that both $R^{5a}$ and $R^{6a}$ represent members selected from the group consisting of a halogen atom and a hydrogen atom; or $R^{5a}$ and $R^{6a}$ together with 6-membered ring constituent atoms to which they bind, may form a 5- or 6-membered ring which is substituted with one or more halogen atoms;

$R^7$ represents a C1-C3 alkyl group optionally substituted with one or more halogen atoms; a C1-C3 alkoxy group optionally substituted with one or more halogen atoms; a cyano group; a halogen atom; or a hydrogen atom;

each of $R^8$ and $R^9$ independently represents a C1-C6 acyclic hydrocarbon group optionally substituted with one or more members selected from Group X; a C4-C7 cycloalkylmethyl group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; or a hydrogen atom; provided that $R^8$ does not represent a hydrogen atom when m in $-S(O)_mR^8$ is 1 or 2;

each of $R^{10}$ and $R^{14}$ independently represents a C1-C4 alkyl group optionally substituted with one or more halogen atoms; or a hydrogen atom;

each of $R^{11}$ and $R^{12}$ independently represents a C1-C4 alkyl group optionally substituted with one or more halogen atoms; a C2-C4 alkoxycarbonyl group; or a hydrogen atom;

$R^{13a}$ represents a C1-C6 acyclic hydrocarbon group which is substituted with one or more halogen atoms; or a C3-C6 alicyclic hydrocarbon group which is substituted with one or more halogen atoms;

$R^{15}$ represents a C1-C4 alkyl group optionally substituted with one or more halogen atoms;

m represents 0, 1, or 2;

n represents 0 or 1;

Group X: the group consisting of a C1-C4 alkoxy group optionally substituted with one or more halogen atoms; a cyano group; and a halogen atom; and Group Y: the group consisting of a C1-C4 alkyl group optionally substituted with one or more halogen atoms; a C1-C4 alkoxy group optionally substituted with one or more halogen atoms; a cyano group; a nitro group; and a halogen atom;

[12] The condensed heterocyclic compound according to [11] above, wherein each of $R^2$ and $R^3$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y a benzyl group optionally substituted with one or more members selected from Group Y; a 5- or 6-membered heterocyclic group optionally substituted with one or more members selected from Group Y; $-OR^8$; $-NR^8R^9$; $-NR^8C(O)R^9$;

—S(O)$_m$R$^8$; —CO$_2$R$^{10}$; —CONR$^8$R$^9$; —CONR$^{10}$NR$^{11}$R$^{12}$; a cyano group; a nitro group; a halogen atom; or a hydrogen atom; and each of R$^8$ and R$^9$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a 5- or 6-membered heterocyclic group optionally substituted with one or more members selected from Group Y; or a hydrogen atom; provided that R$^8$ does not represent a hydrogen atom when m in —S(O)$_m$R$^8$ is 1 or 2;

[13] The condensed heterocyclic compound according to [11] or [12] above, wherein R$^1$ and R$^4$ represent a hydrogen atom;

[14] The condensed heterocyclic compound according to [11], [12], or [13] above, wherein R$^2$ represents a hydrogen atom or a halogen atom;

[15] The condensed heterocyclic compound according to [11], [12], [13], or [14] above, wherein R$^3$ represents a C3-C6 alicyclic hydrocarbon group optionally substituted with one or more members selected from Group X; a phenyl group optionally substituted with one or more members selected from Group Y; a benzyl group optionally substituted with one or more members selected from Group Y; or a 5- or 6-membered heterocyclic group optionally substituted with one or more members selected from Group Y;

[16] The condensed heterocyclic compound according to [11], [13], or [14] above, wherein R$^3$ represents a C1-C6 acyclic hydrocarbon group optionally substituted with one or more members selected from Group X; —OR$^8$; —NR$^8$R$^9$; —NR$^8$C(O)R$^9$; —NR$^{10}$C(O)NR$^9$R$^{14}$; —NR$^{10}$CO$_2$R$^{15}$; —S(O)$_m$R$^8$; —CO$_2$R$^{10}$; —CONR$^8$R$^9$; —C(O)R$^{10}$; —C(NOR$^8$)R$^{10}$; —CONR$^{10}$NR$^{11}$R$^{12}$; a cyano group; a nitro group; a halogen atom; or a hydrogen atom; and each of R$^8$ and R$^9$ independently represents a C1-C6 acyclic hydrocarbon group optionally substituted with one or more members selected from Group X; or a hydrogen atom; provided that R$^8$ represents a C1-C6 acyclic hydrocarbon group optionally substituted with one or more members selected from Group X when m in —S(O)$_m$R$^8$ is 1 or 2;

[17] The condensed heterocyclic compound according to [11], [12], [13], or [14] above, wherein R$^3$ represents a C1-C6 acyclic hydrocarbon group optionally substituted with one or more members selected from Group X; —OR$^8$; —NR$^8$R$^9$; —S(O)$_m$R$^8$; a halogen atom; or a hydrogen atom; and each of R$^8$ and R$^9$ independently represents a C1-C6 acyclic hydrocarbon group optionally substituted with one or more members selected from Group X; or a hydrogen atom; provided that R$^8$ represents a C1-C6 acyclic hydrocarbon group optionally substituted with one or more members selected from Group X when m in —S(O)$_m$R$^8$ is 1 or 2; and

[18] The condensed heterocyclic compound according to [11], [12], [13], [14], [15], [16], or [17] above, wherein at least one of R$^{5a}$ and R$^{61}$ represents a C1-C6 acyclic hydrocarbon group which is substituted with one or more halogen atoms; or —OR$^{13a}$; and R$^{13a}$ represents a C1-C6 acyclic hydrocarbon group which is substituted with one or more halogen atoms.

Hereinafter, the condensed heterocyclic compound represented by the formula (1) may be referred to as "the present active compound", and the arthropod pest control composition of the present invention may be referred to as "the composition of the present invention," at times.

Advantages of the Invention

The composition of the present invention has an excellent effect of controlling arthropod pests, and it has an excellent controlling effect on such arthropod pests.

BEST MODE FOR CARRYING OUT THE INVENTION

Substituents used in the present active compound will be described below, while giving the examples.

In the present specification, for example, the term "C4-C7" used in the expression "C4-C7 cycloalkylmethyl group" means that the total number of carbon atoms constituting the cycloalkylmethyl group is within the range from 4 to 7.

The "halogen atom" means a fluorine atom, a chlorine atom, a bromine atom, and an iodine atom.

Examples of the "C1-C6 acyclic hydrocarbon group optionally substituted with one or more members selected from Group X" represented by R$^2$ or R$^3$ include:

C1-C6 alkyl groups such as a methyl group, an ethyl group, a propyl group, an isopropyl group, a butyl group, an isobutyl group, a sec-butyl group, a tert-butyl group, a pentyl group, and a hexyl group;

C1-C6 alkyl groups substituted with one or more members selected from Group X, such as a methoxymethyl group, an ethoxymethyl group, and a trifluoromethyl group;

C2-C6 alkenyl groups such as an ethenyl group, a 1-propenyl group, a 2-propenyl group, a 1-methylethenyl group, a 2-methyl-1-propenyl group, a 1-butenyl group, a 2-butenyl group, a 3-butenyl group, a 1-pentenyl group, and a 1-hexenyl group;

C2-C6 alkenyl groups substituted with one or more members selected from Group X;

C2-C6 alkynyl groups such as ethynyl group, a propargyl group, a 2-butynyl group, a 3-butynyl group, a 1-pentynyl group, and a 1-hexynyl group; and C2-C6 alkynyl groups substituted with one or more members selected from Group X.

Examples of the "C3-C6 alicyclic hydrocarbon group optionally substituted with one or more members selected from Group X" represented by R$^2$ or R$^3$ include a cyclopropyl group, a cyclobutyl group, a cyclopentyl group, and a cyclohexyl group.

Examples of the "phenyl group optionally substituted with one or more members selected from Group Y" represented by R$^2$ or R$^3$ include a phenyl group, a 2-chlorophenyl group, a 3-chlorophenyl group, a 4-chlorophenyl group, a 2-methylphenyl group, a 3-methylphenyl group, a 4-methylphenyl group, a 2-methoxyphenyl group, a 3-methoxyphenyl group, a 4-methoxyphenyl group, a 2-(trifluoromethyl)phenyl group, a 3-(trifluoromethyl)phenyl group, a 4-(trifluoromethyl)phenyl group, a 2-nitrophenyl group, a 3-nitrophenyl group, a 4-nitrophenyl group, a 2-cyanophenyl group, a 3-cyanophenyl group, and a 4-cyanophenyl group.

Examples of the "benzyl group optionally substituted with one or more members selected from Group Y" represented by R$^2$ or R$^3$ include a benzyl group, a 2-chlorobenzyl group, a 3-chlorobenzyl group, a 4-chlorobenzyl group, a 2-methylbenzyl group, a 3-methylbenzyl group, a 4-methylbenzyl group, a 2-methoxybenzyl group, a 3-methoxybenzyl group, and a 4-methoxybenzyl group.

Examples of the "5-membered heterocyclic group optionally substituted with one or more members selected from Group Y" represented by R$^2$ or R$^3$ include:

5-membered saturated heterocyclic groups such as a pyrrolidin-1-yl group and a tetrahydrofuran-2-yl group; and 5-membered aromatic heterocyclic groups such as a pyrazol-1-yl group, a 3-chloro-pyrazol-1-yl group, a 3-bromopyrazol-1-yl group, a 3-nitropyrazol-1-yl group, a 3-methylpyrazol-1-yl group, a 3-(trifluoromethyl)pyrazol-1-yl group, a 4-methylpyrazol-1-yl group, a 4-chloropyrazol-1-yl group, a 4-bromopyrazol-1-yl group, a 4-cyanopyrazol-1-yl group, an imidazol-1-yl group, a 4-(trifluoromethyl)imidazol-1-yl group, a pyrrol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, and a 3-thienyl group.

Examples of the "6-membered heterocyclic group optionally substituted with one or more members selected from Group Y" represented by $R^2$ or $R^3$ include:

6-membered saturated heterocyclic groups such as a piperidyl group, a morpholyl group, a thiomorpholyl group, and a 4-methylpiperazin-1-yl group; and 6-membered aromatic heterocyclic groups such as a 2-pyridyl group, a 3-pyridyl group, and a 4-pyridyl group.

Examples of the "C1-C6 acyclic hydrocarbon group optionally substituted with one or more members selected from Group X" represented by $R^5$ or $R^6$ include:

C1-C6 alkyl groups such as a methyl group, an ethyl group, a propyl group, an isopropyl group, an isobutyl group, a sec-butyl group, a tert-butyl group, a 1,1-dimethylpropyl group, a 2,2-dimethylpropyl group, and a 1-ethylpropyl group;

C1-C6 alkyl groups substituted with one or more members selected from Group X, such as a methoxymethyl group, a 1-methoxyethyl group, a 1,1-difluoroethyl group, a trifluoromethyl group, a pentafluoroethyl group, and a heptafluoroisopropyl group;

C2-C6 alkenyl groups such as an ethenyl group, a 1-propenyl group, a 2-propenyl group, a 1-methylethenyl group, a 1-methyl-1-propenyl group, a 1-methyl-2-propenyl group, a 1-butenyl group, a 2-butenyl group, and a 3-butenyl group;

C2-C6 alkenyl groups substituted with one or more members selected from Group X;

C2-C6 alkynyl groups such as an ethynyl group, a propargyl group, a 2-butynyl group, and a 3-butynyl group; and C2-C6 alkynyl groups substituted with one or more members selected from Group X. A preferred example is a C1-C4 alkyl group substituted with one or more halogen atoms, and a more preferred example is a trifluoromethyl group.

Examples of the "C3-C6 alicyclic hydrocarbon group optionally substituted with one or more members selected from Group X" represented by $R^5$ or $R^6$ include a cyclopropyl group, a 1-methylcyclopropyl group, a cyclobutyl group, a cyclopentyl group, a 1-methylcyclopentyl group, a 1-cyclopentenyl group, and a cyclohexyl group.

Examples of the 5- or 6-membered ring formed with $R^5$ and $R^6$, together with 6-membered ring constituent atoms to which they bind, include the rings represented by the formulae (a), (b), (c), (d), (e), (f), (g), (h), and (i) as shown below, wherein $A^5$ represents a 6-membered ring carbon atom to which $R^5$ binds, and $A^6$ represents a 6-membered ring carbon atom to which $R^6$ binds.

(a)

(b)

(c)

(d)

(e)

(f)

(g)

(h)

(i)

Examples of the "C1-C3 alkyl group optionally substituted with one or more halogen atoms" represented by $R^7$ include a methyl group, an ethyl group, a propyl group, an isopropyl group, and a trifluoromethyl group.

Examples of the "C1-C3 alkoxy group optionally substituted with one or more halogen atoms" represented by $R^7$ include a methoxy group, an ethoxy group, an isopropoxy group, a trifluoromethoxy group, and a difluoromethoxy group.

Examples of the "C1-C6 acyclic hydrocarbon group optionally substituted with one or more members selected from Group X" represented by $R^8$ or $R^9$ include:

C1-C6 alkyl groups such as a methyl group, an ethyl group, a propyl group, an isopropyl group, a butyl group, an isobutyl group, a sec-butyl group, a tert-butyl group, a 1-methylbutyl group, a 2-methylbutyl group, a 3-methylbutyl group, a 1-ethylpropyl group, a 1,2-dimethylpropyl group, a 2,2-dimethylpropyl group, a pentyl group, a 1,2-dimethylbutyl group, a 2,2-dimethylbutyl group, a 1-methylpentyl group, a 2-methylpentyl group, a 3-methylpentyl group, a 4-methylpentyl group, and a hexyl group;

C1-C6 alkyl groups substituted with one or more members selected from Group X, such as a cyanomethyl group, a difluoromethyl group, a trifluoromethyl group, a 2,2-difluoroethyl group, a 2,2,2-trifluoroethyl group, and a 1-methyl-2,2,2-trifluoroethyl group;

C3-C6 alkenyl groups such as a 2-propenyl group, a 1-methyl-2-propenyl group, a 2-methyl-2-propenyl group, a 2-butenyl group, a 3-butenyl group, a 1-methyl-2-butenyl group, and a 1-methyl-3-butenyl group;

C3-C6 alkenyl groups substituted with one or more members selected from Group X, such as a 3,3-dichloro-2-propenyl group and a 3,3-difluoro-2-propenyl group;

C3-C6 alkynyl groups such as a propargyl group, a 1-methyl-2-propynyl group, a 2-butynyl group, a 3-butynyl group, a 1-methyl-2-butynyl group, and a 1-methyl-3-butynyl group; and C3-C6 alkynyl groups substituted with one or more members selected from Group X.

Examples of the C4-C7 cycloalkylmethyl group represented by $R^8$ or $R^9$ include a cyclopropylmethyl group, a cyclobutylmethyl group, a cyclopentylmethyl group, and a cyclohexylmethyl group.

Examples of the C3-C6 alicyclic hydrocarbon group represented by $R^8$ or $R^9$ include a cyclopropyl group, a cyclobutyl group, a cyclopentyl group, a cyclohexyl group, and a 2-cyclohexenyl group.

Examples of the "phenyl group optionally substituted with one or more members selected from Group Y" represented by $R^8$ or BY include a 2-chlorophenyl group, a 3-chlorophenyl group, a 4-chlorophenyl group, a 2-methylphenyl group, a 3-methylphenyl group, a 4-methylphenyl group, a 2-methoxyphenyl group, a 3-methoxyphenyl group, a 4-methoxyphenyl group, a 2-(trifluoromethyl)phenyl group, a 3-(trifluoromethyl)phenyl group, a 4-(trifluoromethyl)phenyl group, a 2-cyanophenyl group, a 3-cyanophenyl group, a 4-cyanophenyl group, a 2-nitrophenyl group, a 3-nitrophenyl group, and a 4-nitrophenyl group.

Examples of the "benzyl group optionally substituted with one or more members selected from Group Y" represented by $R^8$ or $R^9$ include a benzyl group, a 2-chlorobenzyl group, a 3-chlorobenzyl group, a 4-chlorobenzyl group, a 2-methylbenzyl group, a 3-methylbenzyl group, a 4-methylbenzyl group, a 2-methoxybenzyl group, a 3-methoxybenzyl group, and a 4-methoxybenzyl group.

Examples of the "5-membered heterocyclic group" represented by $R^8$ or $R^9$ include 5-membered aromatic heterocyclic groups such as a 2-thienyl group and a 3-thienyl group.

Examples of the "6-membered heterocyclic group" represented by $R^8$ or $R^9$ include 6-membered aromatic heterocyclic groups such as a 2-pyridyl group, a 3-pyridyl group, a 4-pyridyl group, a 2-pyrimidinyl group, and a 4-pyrimidinyl group.

Examples of the "C1-C4 alkyl group" represented by $R^{10}$ or $R^{14}$ include a methyl group, an ethyl group, a propyl group, an isopropyl group, a butyl group, an isobutyl group, a sec-butyl group, and a tert-butyl group.

Examples of the "C1-C4 alkyl group optionally substituted with one or more halogen atoms" represented by $R^{11}$ or $R^{12}$ include a methyl group, an ethyl group, a 2,2,2-trifluoroethyl group, a propyl group, an isopropyl group, a butyl group, an isobutyl group, a sec-butyl group, and a tert-butyl group.

Examples of the "C2-C4 alkoxycarbonyl group" represented by $R^{11}$ or $R^{12}$ include a methoxycarbonyl group, an ethoxycarbonyl group, a propoxycarbonyl group, and an isopropoxycarbonyl group.

Examples of the "C1-C6 acyclic hydrocarbon group optionally substituted with one or more members selected from Group X" represented by $R^{13}$ include:

C1-C6 alkyl groups such as a methyl group, an ethyl group, a propyl group, an isopropyl group, a butyl group, an isobutyl group, a sec-butyl group, a 1-methylbutyl group, and a 2-methylbutyl group;

C1-C6 alkyl groups substituted with one or more members selected from Group X, such as a difluoromethyl group, a trifluoromethyl group, and a 2,2,2-trifluoroethyl group;

C3-C6 alkenyl groups such as a 2-propenyl group, a 1-methyl-2-propenyl group, a 2-methyl-2-propenyl group, a 2-butenyl group, and a 3-butenyl group;

C3-C6 alkenyl groups substituted with one or more members selected from Group X, such as a 2-chloro-2-propenyl group, a 3,3-difluoro-2-propenyl group, and a 3,3-dichloro-2-propenyl group;

C3-C6 alkynyl groups such as a propargyl group, a 1-methyl-2-propynyl group, a 2-butynyl group, and a 3-butynyl group; and C3-C6 alkynyl groups substituted with one or more members selected from Group X. A preferred example is a C1-C4 alkyl group substituted with one or more halogen atoms, and a more preferred example is a trifluoromethyl group.

Examples of the "C3-C6 alicyclic hydrocarbon group optionally substituted with one or more members selected from Group X" represented by $R^{13}$ include a cyclopropyl group, a cyclobutyl group, a cyclopentyl group, a cyclohexyl group, and a 2-cyclohexenyl group.

Examples of the "C1-C4 alkyl group" represented by $R^{15}$ include a methyl group, an ethyl group, a propyl group, an isopropyl group, a butyl group, an isobutyl group, a sec-butyl group, and a tert-butyl group.

One embodiment of the present active compound is the compound represented by formula (2), for example:

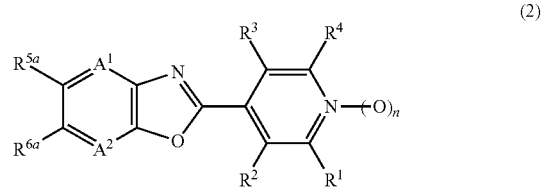

(2)

wherein $A^1$, $A^2$, $R^1$, $R^2$, $R^3$, $R^4$, and n have the same meaning as defined above, each of $R^{5a}$ and $R^{6a}$ independently represents a C1-C6 acyclic hydrocarbon group which is substituted with one or more halogen atoms; a C3-C6 alicyclic hydrocarbon group which is substituted with one or more halogen atoms; —$OR^{13a}$; —$S(O)_m R^{13a}$; a halogen atom; or a hydrogen atom; except that both $R^{5a}$ and $R^{6a}$ represent members selected from the group consisting of a halogen atom and a hydrogen atom; or $R^{5a}$ and $R^{6a}$, together with 6-membered ring constituent atoms to which they bind, may form a 5- or 6-membered ring which is substituted with one or more halogen atoms; and $R^{13a}$ represents a C1-C6 acyclic hydrocarbon group which is substituted with one or more halogen atoms; or a C3-C6 alicyclic hydrocarbon group which is substituted with one or more halogen atoms.

Examples of the "C1-C6 acyclic hydrocarbon group which is substituted with one or more halogen atoms" represented by $R^{5a}$ or $R^{6a}$ include a 1,1-difluoroethyl group, a trifluoromethyl group, a pentafluoroethyl group, and a heptafluoroisopropyl group. Of these, a trifluoromethyl group is preferable.

Examples of the C3-C6 alicyclic hydrocarbon group represented by $R^{5a}$ or $R^{6a}$ include a cyclopropyl group, a cyclobutyl group, a cyclopentyl group, and a cyclohexyl group.

Examples of the "5- or 6-membered ring substituted with one or more halogen atoms" which is formed with $R^{5a}$ and $R^6a$, together with 6-membered ring constituent atoms to which they bind, include the rings represented by the formulae (j), (k), (l), (m), (n), (o), (p), (q), (r), and (s) as shown below, wherein $A^5$ represents a 6-membered ring carbon atom to which $R^{5a}$ binds, and $A^6$ represents a 6-membered ring carbon atom to which $R^{6a}$ binds.

(j) 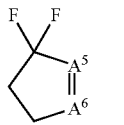

(k) 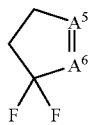

(l) 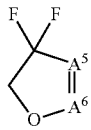

(m) 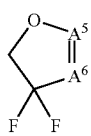

(n) 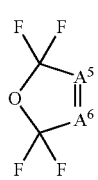

(o) 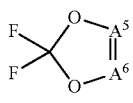

(p) 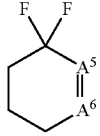

(q) 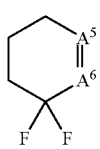

(r) 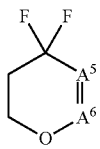

(s) 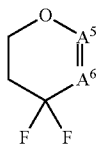

Examples of the "C1-C6 acyclic hydrocarbon group which is substituted with one or more halogen atoms" represented by $R^{13a}$ include a trifluoromethyl group, a difluoromethyl group, and a 2,2,2-trifluoroethyl group. Of these, a trifluoromethyl group is preferable.

Examples of the C3-C6 alicyclic hydrocarbon group in the "C3-C6 alicyclic hydrocarbon group which is substituted with one or more halogen atoms" represented by $R^{13a}$ include a cyclopropyl group, a cyclobutyl group, a cyclopentyl group, and a cyclohexyl group.

One embodiment of the present invention is a composition comprising at least one of the following compounds as an active ingredient, for example:

a compound, wherein, in the formula (1),
each of $R^2$ and $R^3$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; —OR$^8$; —NR$^8$R$^9$; —NR$^8$C(O)R$^9$; —S(O)$_m$R$^8$; —CO$_2$R$^{10}$; —CONR$^8$R$^9$; —CONR$^{10}$NR$^{11}$R$^{12}$; a cyano group; a nitro group; a halogen atom; or a hydrogen atom; and each of $R^8$ and $R^9$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a 5- or 6-membered heterocyclic group optionally substituted with one or more members selected from Group Y, or a hydrogen atom, provided that $R^8$ does not represent a hydrogen atom when m in —S(O)$_m$R$^8$ is 1 or 2;

a compound, wherein, in the formula (1), $R^1$ and $R^4$ represent a hydrogen atom;

a compound, wherein, in the formula (1), $R^2$ represents a hydrogen atom or a halogen atom;

a compound, wherein, in the formula (1), $R^3$ represents a C3-C6 alicyclic hydrocarbon group optionally substituted with one or more members selected from Group X, a phenyl group optionally substituted with one or more members selected from Group Y; a benzyl group optionally substituted with one or more members selected from Group Y; or a 5- or 6-membered heterocyclic group optionally substituted with one or more members selected from Group Y;

a compound, wherein, in the formula (1), $R^3$ represents a C1-C6 acyclic hydrocarbon group optionally substituted with one or more members selected from Group X; —OR$^8$; —NR$^8$R$^9$; —NR$^8$C(O)R$^9$; —NR$^{10}$C(O)NR$^9$R$^{14}$; —NR$^{10}$CO$_2$R$^{15}$; —S(O)$_m$R$^8$; —CO$_2$R$^{10}$; —CONR$^8$R$^9$; —C(O)R$^{10}$; —C(NOR$^8$)R$^{10}$; —CONR$^{10}$NR$^{11}$R$^{12}$; a cyano group; a nitro group; a halogen atom; or a hydrogen atom; and each of $R^8$ and $R^9$ independently represents a C1-C6 acyclic hydrocarbon group optionally substituted with one or more members selected from Group X; or a hydrogen atom; provided that $R^8$ represents a C1-C6 acyclic hydrocarbon group optionally substituted with one or more members selected from Group X when m in —S(O)$_m$R$^8$ is 1 or 2;

a compound, wherein, in the formula (1), $R^3$ represents a C1-C6 acyclic hydrocarbon group optionally substituted with one or more members selected from Group X; —OR$^8$; —NR$^8$R$^9$; —S(O)$_m$R$^8$; a halogen atom; or a hydrogen atom; and each of $R^8$ and $R^9$ independently represents a C1-C6 acyclic hydrocarbon group optionally substituted with one or more members selected from Group X; or a hydrogen atom; provided that $R^8$ represents a C1-C6 acyclic hydrocarbon group optionally substituted with one or more members selected from Group X when m in —$S(O)_m R^8$ is 1 or 2;

a compound, wherein, in the formula (1), each of $R^5$ and $R^6$ independently represents a C1-C6 acyclic hydrocarbon group optionally substituted with one or more members selected from Group X; —$OR^{13}$; —$S(O)_m R^{13}$; a halogen atom; or a hydrogen atom; except that both $R^5$ and $R^6$ represent hydrogen atoms; and $R^{13}$ represents a C1-C6 acyclic hydrocarbon group optionally substituted with one or more members selected from Group X;

a compound, wherein, in the formula (1), $R^5$ represents a C1-C6 acyclic hydrocarbon group optionally substituted with one or more halogen atoms, or —$OR^{13}$, and $R^{13}$ represents a C1-C6 acyclic hydrocarbon group optionally substituted with one or more halogen atoms;

a compound, wherein, in the formula (1), $R^6$ represents a C1-C6 acyclic hydrocarbon group optionally substituted with one or more halogen atoms, or —$OR^{13}$, and $R^{13}$ represents a C1-C6 acyclic hydrocarbon group optionally substituted with one or more halogen atoms;

a compound, wherein, in the formula (1), $R^5$ represents a C1-C6 acyclic hydrocarbon group substituted with one or more halogen atoms, or —$OR^{13}$, and $R^{13}$ represents a C1-C6 acyclic hydrocarbon group substituted with one or more halogen atoms;

a compound, wherein, in the formula (1), $R^6$ represents a C1-C6 acyclic hydrocarbon group substituted with one or more halogen atoms, or —$OR^{13}$, and $R^{13}$ represents a C1-C6 acyclic hydrocarbon group substituted with one or more halogen atoms;

a compound, wherein, in the formula (1), $R^5$ represents a C1-C6 acyclic hydrocarbon group substituted with one or more halogen atoms;

a compound, wherein, in the formula (1), $R^5$ represents a trifluoromethyl group;

a compound, wherein, in the formula (1), $R^5$ represents a tert-butyl group;

a compound, wherein, in the formula (1), $R^6$ represents a C1-C6 acyclic hydrocarbon group substituted with one or more halogen atoms;

a compound, wherein, in the formula (1), $R^6$ represents a trifluoromethyl group;

a compound, wherein, in the formula (1), $R^6$ represents a tert-butyl group;

a compound, wherein, in the formula (1), $R^5$ represents —$OR^{13}$, and $R^{13}$ represents a C1-C6 acyclic hydrocarbon group substituted with one or more halogen atoms;

a compound, wherein, in the formula (1), $R^5$ represents —$OR^{13}$, and $R^{13}$ represents a trifluoromethyl group or a difluoromethyl group;

a compound, wherein, in the formula (1), $R^6$ represents —$OR^{13}$, and $R^{13}$ represents a C1-C6 acyclic hydrocarbon group substituted with one or more halogen atoms;

a compound, wherein, in the formula (1), $R^6$ represents —$OR^{13}$, and $R^{13}$ represents a trifluoromethyl group or a difluoromethyl group;

a compound, wherein, in the formula (1), $R^5$ represents a C1-C6 acyclic hydrocarbon group optionally substituted with one or more halogen atoms, and $R^6$ represents a hydrogen atom or a halogen atom;

a compound, wherein, in the formula (1), $R^5$ represents —$OR^{13}$, $R^{13}$ represents a C1-C6 acyclic hydrocarbon group optionally substituted with one or more halogen atoms, and $R^6$ represents a hydrogen atom or a halogen atom;

a compound, wherein, in the formula (1), $R^5$ represents a hydrogen atom or a halogen atom, and $R^6$ represents a C1-C6 acyclic hydrocarbon group optionally substituted with one or more halogen atoms;

a compound, wherein, in the formula (1), $R^5$ represents a hydrogen atom or a halogen atom, $R^6$ represents —$OR^{13}$, and $R^{13}$ represents a C1-C6 acyclic hydrocarbon group optionally substituted with one or more halogen atoms;

a compound, wherein, in the formula (1), $R^5$ represents a C1-C6 acyclic hydrocarbon group substituted with one or more halogen atoms, $R^6$ represents a hydrogen atom or a halogen atom;

a compound, wherein, in the formula (1), $R^5$ represents —$OR^{13}$, $R^{13}$ represents a C1-C6 acyclic hydrocarbon group substituted with one or more halogen atoms, and $R^6$ represents a hydrogen atom or a halogen atom;

a compound, wherein, in the formula (1), $R^5$ represents a hydrogen atom or a halogen atom, and $R^6$ represents a C1-C6 acyclic hydrocarbon group substituted with one or more halogen atoms;

a compound, wherein, in the formula (1), $R^5$ represents a hydrogen atom or a halogen atom, $R^6$ represents —$OR^{13}$, and $R^{13}$ represents a C1-C6 acyclic hydrocarbon group substituted with one or more halogen atoms;

a compound, wherein, in the formula (1), $R^5$ represents a trifluoromethyl group, and $R^6$ represents a hydrogen atom or a halogen atom;

a compound, wherein, in the formula (1), $R^5$ represents a tert-butyl group, and $R^6$ represents a hydrogen atom or a halogen atom;

a compound, wherein, in the formula (1), $R^5$ represents —$OR^{13}$, $R^{13}$ represents a trifluoromethyl group or a difluoromethyl group, and $R^6$ represents a hydrogen atom or a halogen atom;

a compound, wherein, in the formula (1), $R^5$ represents a hydrogen atom or a halogen atom, and $R^6$ represents a trifluoromethyl group;

a compound, wherein, in the formula (1), $R^5$ represents a hydrogen atom or a halogen atom, and $R^6$ represents a tert-butyl group;

a compound, wherein, in the formula (1), $R^5$ represents a hydrogen atom or a halogen atom, $R^6$ represents —$OR^{13}$, and $R^{13}$ represents a trifluoromethyl group or a difluoromethyl group;

a compound, wherein, in the formula (1), $A^1$ represents a nitrogen atom, $A^2$ represents =$C(R^7)$—, and $R^7$ represents a hydrogen atom;

a compound, wherein, in the formula (1), $A^1$ represents =$C(R^7)$—, $A^2$ represents a nitrogen atom, and $R^7$ represents a hydrogen atom;

a compound, wherein, in the formula (1), $A^1$ and $A^2$ each represent =$C(R^7)$—, and $R^7$ represents a hydrogen atom;

a compound, wherein, in the formula (1), each of $R^2$ and $R^3$ independently represents a C1-C4 alkyl group optionally substituted with one or more halogen atoms; a C2-C4 alkoxyalkyl group; a C2-C4 alkenyl group; a pyrrolidyl group; a piperidyl group; a morpholyl group; an imidazolyl group; a pyrazolyl group; a triazolyl group; a (C1-C3 alkyl group)-substituted pyrazolyl group; a (C1-C3 halogenated alkyl group)-substituted pyrazolyl group; a phenyl group; a pyridyl group; —$OR^{8a}$, wherein $R^{8a}$ represents a C1-C4 alkyl group optionally substituted with one or more halogen atoms, a C3-C4 alkenyl group optionally substituted with one or more halogen atoms, a C3-C4 alkynyl group, a benzyl group, a C2-C4 alkoxyalkyl group, a C4-C7 cycloalkylmethyl group, or a hydrogen atom; —$NR^{8b}R^{9a}$, wherein each of $R^{8b}$ and $R^{9a}$ represents a C1-C4 alkyl group optionally substituted with one or more halogen atoms, or a hydrogen atom; —NHC(O)$R^{9b}$, wherein $R^{9b}$ represents a C1-C4 alkyl group optionally substituted with one or more halogen atoms; —NHCO$_2$R$^{15a}$, wherein $R^{15a}$ represents a C1-C4 alkyl group; —S(O)$_{m1}$R$^{8c}$, wherein $R^{8c}$ represents a C1-C4 alkyl group optionally substituted with one or more halogen atoms, and m1 represents 1 or 2; —SR$^{8d}$, wherein $R^{8d}$ represents a C1-C4 alkyl group optionally substituted with one or more halogen atoms, or a hydrogen atom; a cyano group; a halogen atom; or a hydrogen atom;

a compound, wherein, in the formula (1), each of $R^2$ and $R^3$ independently represents a C1-C4 alkyl group optionally substituted with one or more halogen atoms, —OR$^{8a}$, wherein $R^{8a}$ represents a C1-C4 alkyl group optionally substituted with one or more halogen atoms; —NR$^{8b}$R$^{9a}$, wherein each of $R^{8b}$ and $R^{9a}$ represents a C1-C4 alkyl group optionally substituted with one or more halogen atoms, or a hydrogen atom; —S(O)$_{m1}$R$^{8c}$, wherein $R^{8c}$ represents a C1-C4 alkyl group optionally substituted with one or more halogen atoms, and m1 represents 1 or 2; —SR$^{8d}$, wherein $R^{8d}$ represents a C1-C4 alkyl group optionally substituted with one or more halogen atoms, or a hydrogen atom; a halogen atom; or a hydrogen atom;

a compound, wherein, in the formula (1), at least one of $R^5$ and $R^6$ represents a C1-C3 alkyl group substituted with one or more halogen atoms, a C1-C4 alkyl group, or —OR$^{13a}$, and $R^{13a}$ represents a C1-C3 alkyl group substituted with one or more halogen atoms;

a compound, wherein, in the formula (2), each of $R^2$ and $R^3$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; —OR$^8$; —NR$^8$R$^9$; —NR$^8$C(O)R$^9$; —S(O)$_m$R$^8$; —CO$_2$R$^{10}$; —CONR$^8$R$^9$; —CONR$^{10}$NR$^{11}$R$^{12}$; a cyano group; a nitro group; a halogen atom; or a hydrogen atom; and each of $R^8$ and $R^9$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a 5- or 6-membered heterocyclic group optionally substituted with one or more members selected from Group Y; or a hydrogen atom; provided that $R^8$ does not represent a hydrogen atom when m in —S(O)$_m$R$^8$ is 1 or 2;

a compound, wherein, in the formula (2), $R^1$ and $R^4$ represent a hydrogen atom;

a compound, wherein, in the formula (2), $R^2$ represents a hydrogen atom or a halogen atom;

a compound, wherein, in the formula (2), $R^3$ represents a C3-C6 alicyclic hydrocarbon group optionally substituted with one or more members selected from Group X; a phenyl group optionally substituted with one or more members selected from Group Y; a benzyl group optionally substituted with one or more members selected from Group Y; or a 5- or 6-membered heterocyclic group optionally substituted with one or more members selected from Group Y;

a compound, wherein, in the formula (2), $R^3$ represents a C1-C6 acyclic hydrocarbon group optionally substituted with one or more members selected from Group X; —OR$^8$; —NR$^8$R$^9$; —NR$^8$C(O)R$^9$; —NR$^{10}$C(O)NR$^9$R$^{14}$; —NR$^{10}$CO$_2$R$^{15}$; —S(O)$_m$R$^8$; —CO$_2$R$^{10}$; —CONR$^8$R$^9$; —C(O)R$^{10}$; —C(NOR$^8$)R$^{10}$; —CONR$^{10}$NR$^{11}$R$^{12}$; a cyano group; a nitro group; a halogen atom; or a hydrogen atom; and each of $R^8$ and $R^9$ independently represents a C1-C6 acyclic hydrocarbon group optionally substituted with one or more members selected from Group X; or a hydrogen atom; provided that $R^8$ represents a C1-C6 acyclic hydrocarbon group optionally substituted with one or more members selected from Group X when m in —S(O)$_m$R$^8$ is 1 or 2;

a compound, wherein, in the formula (2), $R^3$ represents a C1-C6 acyclic hydrocarbon group optionally substituted with one or more members selected from Group X; —OR$^8$; —NR$^8$R$^9$; —S(O)$_m$R$^8$; a halogen atom; or a hydrogen atom; and each of $R^8$ and $R^9$ independently represents a C1-C6 acyclic hydrocarbon group optionally substituted with one or more members selected from Group X; or a hydrogen atom; provided that $R^8$ represents a C1-C6 acyclic hydrocarbon group optionally substituted with one or more members selected from Group X when m in —S(O)$_m$R$^8$ is 1 or 2;

a compound, wherein, in the formula (2), $R^{5a}$ represents a C1-C6 acyclic hydrocarbon group substituted with one or more halogen atoms, or —OR$^{13a}$, and $R^{13a}$ represents a C1-C6 acyclic hydrocarbon group substituted with one or more halogen atoms;

a compound, wherein, in the formula (2), $R^{6a}$ represents a C1-C6 acyclic hydrocarbon group substituted with one or more halogen atoms, or —OR$^{13a}$, and $R^{13a}$ represents a C1-C6 acyclic hydrocarbon group substituted with one or more halogen atoms;

a compound, wherein, in the formula (2), $R^{5a}$ represents a C1-C6 acyclic hydrocarbon group substituted with one or more halogen atoms, a compound, wherein, in the formula (2), $R^{5a}$ represents a trifluoromethyl group;

a compound, wherein, in the formula (2), $R^{6a}$ represents a C1-C6 acyclic hydrocarbon group substituted with one or more halogen atoms;

a compound, wherein, in the formula (2), $R^{6a}$ represents a trifluoromethyl group;

a compound, wherein, in the formula (2), $R^{5a}$ represents —OR$^{13a}$, and $R^{13a}$ represents a C1-C6 acyclic hydrocarbon group substituted with one or more halogen atoms;

a compound, wherein, in the formula (2), $R^{5a}$ represents —OR$^{13a}$, and $R^{13a}$ represents a trifluoromethyl group or a difluoromethyl group;

a compound, wherein, in the formula (2), $R^{6a}$ represents —OR$^{13a}$, and $R^{13a}$ represents a C1-C6 acyclic hydrocarbon group substituted with one or more halogen atoms;

a compound, wherein, in the formula (2), $R^{6a}$ represents —OR$^{13a}$, and $R^{13a}$ represents a trifluoromethyl group or a difluoromethyl group;

a compound, wherein, in the formula (2), $R^{5a}$ represents a C1-C6 acyclic hydrocarbon group substituted with one or more halogen atoms, and $R^{6a}$ represents a hydrogen atom or a halogen atom;

a compound, wherein, in the formula (2), $R^{5a}$ represents —OR$^{13a}$, $R^{13a}$ represents a C1-C6 acyclic hydrocarbon group substituted with one or more halogen atoms, and $R^{6a}$ represents a hydrogen atom or a halogen atom;

a compound, wherein, in the formula (2), $R^{5a}$ represents a hydrogen atom or a halogen atom, and $R^{6a}$ represents a C1-C6 acyclic hydrocarbon group substituted with one or more halogen atoms;

a compound, wherein, in the formula (2), $R^{5a}$ represents a hydrogen atom or a halogen atom, $R^{6a}$ represents —OR$^{13a}$, and $R^{13a}$ represents a C1-C6 acyclic hydrocarbon group substituted with one or more halogen atoms;

a compound, wherein, in the formula (2), $R^{5a}$ represents a trifluoromethyl group, and $R^{6a}$ represents a hydrogen atom or a halogen atom;

a compound, wherein, in the formula (2), $R^{5a}$ represents —$OR^{13a}$, $R^{13a}$ represents a trifluoromethyl group or a difluoromethyl group, and $R^{6a}$ represents a hydrogen atom or a halogen atom;

a compound, wherein, in the formula (2), $R^{5a}$ represents a hydrogen atom or a halogen atom, and $R^{6a}$ represents a trifluoromethyl group;

a compound, wherein, in the formula (2), $R^{5a}$ represents a hydrogen atom or a halogen atom, $R^{6a}$ represents —$OR^{13a}$, and $R^{13a}$ represents a trifluoromethyl group or a difluoromethyl group;

a compound, wherein, in the formula (2), $A^1$ represents a nitrogen atom, $A^2$ represents =$C(R^7)$—, and $R^7$ represents a hydrogen atom;

a compound, wherein, in the formula (2), $A^1$ represents =$C(R^7)$—, $A^2$ represents a nitrogen atom, and $R^7$ represents a hydrogen atom;

a compound, wherein, in the formula (2), $A^1$ and $A^2$ each represent =$C(R^7)$—, and $R^7$ represents a hydrogen atom;

a compound, wherein, in the formula (2), each of $R^2$ and $R^3$ independently represents a C1-C4 alkyl group optionally substituted with one or more halogen atoms; a C2-C4 alkoxyalkyl group; a C2-C4 alkenyl group; a pyrrolidyl group; a piperidyl group; a morpholyl group; an imidazolyl group; a pyrazolyl group; a triazolyl group; a (C1-C3 alkyl group)-substituted pyrazolyl group; a (C1-C3 halogenated alkyl group)-substituted pyrazolyl group; a phenyl group; a pyridyl group; —$OR^{8a}$, wherein $R^{8a}$ represents a C1-C4 alkyl group optionally substituted with one or more halogen atoms, a C3-C4 alkenyl group optionally substituted with one or more halogen atoms, a C3-C4 alkynyl group, a benzyl group, a C2-C4 alkoxyalkyl group, a C4-C7 cycloalkylmethyl group, or a hydrogen atom; —$NR^{8b}R^{9a}$, wherein each of $R^{8b}$ and $R^{9a}$ represents a C1-C4 alkyl group optionally substituted with one or more halogen atoms, or a hydrogen atom; —NHC(O)$R^{9b}$, wherein $R^{9b}$ represents a C1-C4 alkyl group optionally substituted with one or more halogen atoms; —$NHCO_2R^{15a}$, wherein $R^{15a}$ represents a C1-C4 alkyl group; —$S(O)_{m1}R^{8c}$, wherein $R^{8c}$ represents a C1-C4 alkyl group optionally substituted with one or more halogen atoms, and m1 represents 1 or 2; —$SR^{8d}$, wherein $R^{8d}$ represents a C1-C4 alkyl group optionally substituted with one or more halogen atoms, or a hydrogen atom; a cyano group; a halogen atom; or a hydrogen atom;

a compound, wherein, in the formula (2), each of $R^2$ and $R^3$ independently represents a C1-C4 alkyl group optionally substituted with one or more halogen atoms; —$OR^{8a}$, wherein $R^{8a}$ represents a C1-C4 alkyl group optionally substituted with one or more halogen atoms; —$NR^{8b}R^{9a}$, wherein each of $R^{8b}$ and $R^{9a}$ represents a C1-C4 alkyl group optionally substituted with one or more halogen atoms, or a hydrogen atom; —$S(O)_{m1}R^{8c}$, wherein $R^{8c}$ represents a C1-C4 alkyl group optionally substituted with one or more halogen atoms, and m1 represents 1 or 2;—$SR^{8d}$, wherein $R^{8d}$ represents a C1-C4 alkyl group optionally substituted with one or more halogen atoms, or a hydrogen atom; a halogen atom; or a hydrogen atom; and a compound, wherein, in the formula (2), at least one of $R^{5a}$ and $R^{6a}$ represents a C1-C3 alkyl group substituted with one or more halogen atoms, or —$OR^{13a}$, and $R^{13a}$ represents a C1-C3 alkyl group substituted with one or more halogen atoms.

Next, a method for producing the present active compound will be described.

The present active compound can be produced, for example, by the following (Production Method 1) to (Production Method 14).

In each production method, a compound represented by a specific formula may be indicated in the form of the compound followed by the number of the formula in parentheses. For example, a compound represented by formula (3) may be referred to as "compound (3)."

(Production Method 1)

A compound (5), i.e., a compound of the formula (1) wherein n is 0, can be produced by reacting a compound (3) with a compound (4) in the presence of an acid,

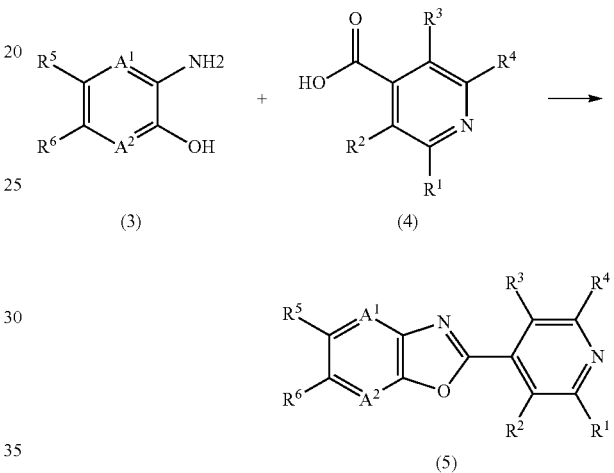

wherein $R^1$, $R^2$, $R^3$, $R^4$, $R^5$, $R^6$, $A^1$, and $A^2$ have the same meaning as defined above.

Examples of the acid include polyphosphoric acid and trimethylsilyl polyphosphate.

When polyphosphoric acid is used as an acid, the reaction is generally carried out in the absence of a solvent. However, the reaction may also be carried out in a solvent.

Examples of the solvent include: ethers such as tetrahydrofuran (hereinafter referred to as THF, at times), ethylene glycol dimethyl ether, or 1,4-dioxane; aromatic hydrocarbons such as toluene or xylene; halogenated hydrocarbons such as chlorobenzene or dichlorobenzene; and the mixtures thereof.

The compound (4) is generally used at a ratio of 1 to 3 moles relative to 1 mole of the compound (3).

The reaction temperature applied to the reaction is generally between 50° C. and 200° C., and the reaction time is generally between 0.5 and 24 hours.

After completion of the reaction, water is added to the reaction mixture, and the mixture is then extracted with an organic solvent. The organic layer is subjected to a post-treatment such as drying or concentration, so as to isolate the compound (5). The isolated compound (5) can be further purified by chromatography, recrystallization, etc.

(Production Method 2)

The above compound (5) can be produced by reacting a compound (6) in the presence of an oxidizer,

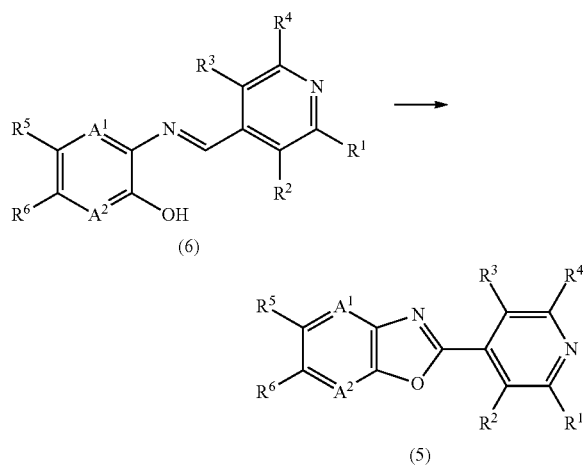

(6)

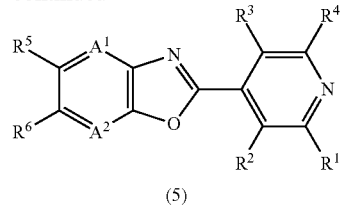

(5)

wherein $R^1$, $R^2$, $R^3$, $R^4$, $R^5$, $R^6$, $A^1$, and $A^2$ have the same meaning as defined above.

This reaction is generally carried out in the presence of a solvent.

Examples of the solvent include: ethers such as THF, ethylene glycol dimethyl ether, or 1,4-dioxane; aliphatic hydrocarbons such as hexane or heptane; aromatic hydrocarbons such as toluene or xylene; halogenated hydrocarbons such as dichloromethane, chloroform, or chlorobenzene; esters such as ethyl acetate or butyl acetate; alcohols such as methanol or ethanol; nitriles such as acetonitrile; acid amides such as N,N-dimethylformamide (hereinafter referred to as DMF, at times); sulfoxides such as dimethyl sulfoxide (hereinafter referred to as DMSO, at times); acetic acids; and the mixtures thereof.

Examples of the oxidizer include: metallic oxidizers such as lead(IV) acetate or lead(IV) oxide; and organic periodides such as iodobenzene diacetate.

Such oxidizer is generally used at a ratio of 1 to 3 moles relative to 1 mole of the compound (6).

The reaction temperature applied to the reaction is generally between 0° C. and 100° C., and the reaction time is generally between 0.1 and 24 hours.

After completion of the reaction, the reaction mixture is extracted with an organic solvent, and the organic layer is then subjected to a post-treatment such as drying or concentration, so as to isolate the compound (5). The isolated compound (5) can be further purified by chromatography, recrystallization, etc.

(Production Method 3)

The above compound (5) can be produced by reacting a compound (7) in the presence of a dehydration-condensation agent,

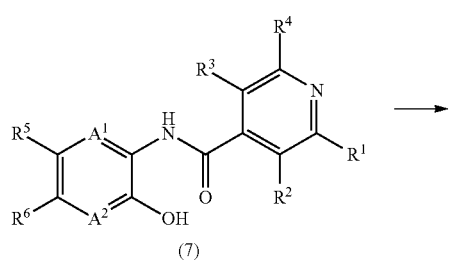

(7)

wherein $R^1$, $R^2$, $R^3$, $R^4$, $R^5$, $R^6$, $A^1$, and $A^2$ have the same meaning as defined above.

This reaction is generally carried out in the presence of a solvent.

Examples of the solvent include: ethers such as THF, ethylene glycol dimethyl ether, or 1,4-dioxane; aromatic hydrocarbons such as toluene or xylene; halogenated hydrocarbons such as dichloromethane, chloroform, carbon tetrachloride, or chlorobenzene; esters such as ethyl acetate or butyl acetate; nitriles such as acetonitrile; and the mixtures thereof. Of these, carbon tetrachloride can also be used as a dehydration-condensation agent.

Examples of the dehydration-condensation agent include: a mixture of triphenylphosphine, a base, and carbon tetrachloride or carbon tetrabromide; and a mixture of triphenylphosphine and an azodiester such as azodicarboxylic acid diethyl ester.

Examples of the base include tertiary amines such as triethylamine or diisopropylethylamine.

The dehydration-condensation agent is generally used at a ratio of 1 to 3 moles relative to 1 mole of the compound (7). The base is generally used at a ratio of 1 to 5 moles relative to 1 mole of the compound (7).

The reaction temperature applied to the reaction is generally between −30° C. and +100° C., and the reaction time is generally between 0.5 and 24 hours.

After completion of the reaction, the reaction mixture is extracted with an organic solvent, and the organic layer is then subjected to a post-treatment such as drying or concentration, so as to isolate the compound (5). The isolated compound (5) can be further purified by chromatography, recrystallization, etc.

(Production Method 4)

The above compound (5) can be produced by reacting the compound (7) in the presence of an acid,

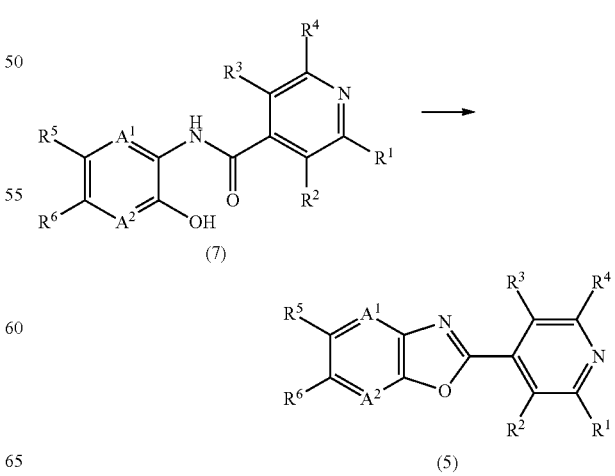

wherein $R^1$, $R^2$, $R^3$, $R^4$, $R^5$, $R^6$, $A^1$, and $A^2$ have the same meaning as defined above.

This reaction is generally carried out in the presence of a solvent.

Examples of the solvent include: ethers such as THF, ethylene glycol dimethyl ether, or 1,4-dioxane; aromatic hydrocarbons such as toluene or xylene; halogenated hydrocarbons such as dichloromethane, chloroform, or chlorobenzene; and the mixtures thereof.

Examples of the acid include: sulfonic acids such as p-toluenesulfonic acid; and polyphosphoric acid.

Such acid is generally used at a ratio of 0.1 to 3 moles relative to 1 mole of the compound (7).

The reaction temperature applied to the reaction is generally between 50° C. and 200° C., and the reaction time is generally between 1 and 24 hours.

After completion of the reaction, the reaction mixture is extracted with an organic solvent, and the organic layer is then subjected to a post-treatment such as drying or concentration, so as to isolate the compound (5). The isolated compound (5) can be further purified by chromatography, recrystallization, etc.

(Production Method 5)

A compound (5-a), i.e., a compound of the formula (1) wherein n is 0 and $R^3$ is —$OR^8$, can be produced by reacting a compound (8) with a compound (9) in the presence of a base,

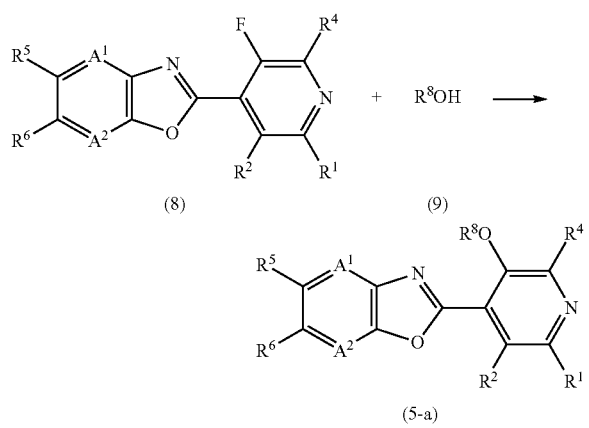

wherein $R^1$, $R^2$, $R^4$, $R^5$, $R^6$, $R^8$, $A^1$, and $A^2$ have the same meaning as defined above.

This reaction is generally carried out in the presence of a solvent. It may also be possible to use the compound (9) in a solvent amount.

Examples of the solvent include: ethers such as THF, ethylene glycol dimethyl ether, or 1,4-dioxane; aromatic hydrocarbons such as toluene or xylene; nitriles such as acetonitrile; acid amides such as DMF; sulfoxides such as DMSO; and the mixtures thereof.

Examples of the base include: alkali metal hydrides such as sodium hydride; and carbonates such as potassium carbonate.

The compound (9) is generally used at a ratio of 1 to 100 moles, and the base is generally used at a ratio of 1 to 10 moles, relative to 1 mole of the compound (8).

The reaction temperature applied to the reaction is generally between 0° C. and 120° C., and the reaction time is generally between 0.5 and 24 hours.

After completion of this reaction, known reactions such as a hydrogenation reaction, an oxidation reaction, and a reduction reaction, may be further carried out to convert $R^8$ arbitrarily.

After completion of the reaction, the reaction mixture is extracted with an organic solvent, and the organic layer is then subjected to a post-treatment such as drying or concentration, so as to isolate the compound (5-a). The isolated compound (5-a) can be further purified by chromatography, recrystallization, etc.

(Production Method 6)

A compound (5-b), i.e., a compound of the formula (1) wherein n is 0 and $R^3$ is —$SR^8$, can be produced by reacting the compound (8) with a compound (10) in the presence of a base,

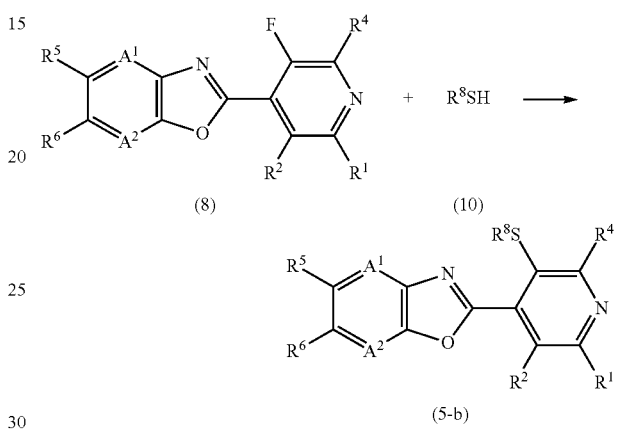

wherein $R^1$, $R^2$, $R^4$, $R^5$, $R^6$, $R^8$, $A^1$, and $A^2$ have the same meaning as defined above.

This reaction is generally carried out in the presence of a solvent.

Examples of the solvent include: ethers such as THF, ethylene glycol dimethyl ether, or 1,4-dioxane; aromatic hydrocarbons such as toluene or xylene; nitriles such as acetonitrile; acid amides such as DMF; sulfoxides such as DMSO; and the mixtures thereof.

Examples of the base include: alkali metal hydrides such as sodium hydride; and carbonates such as potassium carbonate.

The compound (10) is generally used at a ratio of 1 to 10 moles, and the base is generally used at a ratio of 1 to 10 moles, relative to 1 mole of the compound (8).

The reaction temperature applied to the reaction is generally between 0° C. and 100° C., and the reaction time is generally between 0.5 and 24 hours.

After completion of the reaction, the reaction mixture is extracted with an organic solvent, and the organic layer is then subjected to a post-treatment such as drying or concentration, so as to isolate the compound (5-b). The isolated compound (5-b) can be further purified by chromatography, recrystallization, etc.

After completion of this reaction, an oxidation reaction known to a person skilled in the art may be further carried out, so that —$SR^8$ can be converted to —$S(O)_{m1}R^8$ wherein m1 is 1 or 2.

(Production Method 7)

A compound (5-c), i.e., a compound of the formula (1) wherein n is 0 and $R^3$ is —$NR^8R^9$, can be produced by reacting the compound (8) with a compound (11) in the presence of a base,

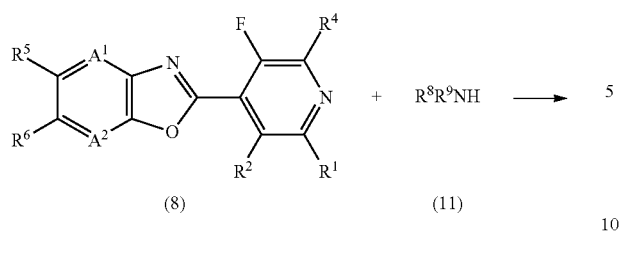

(8)                 (11)

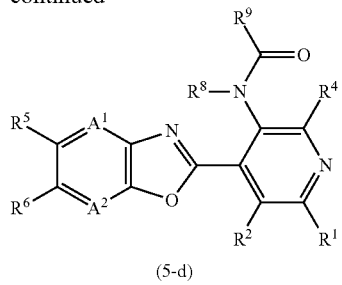

(5-d)

wherein $R^1$, $R^2$, $R^4$, $R^5$, $R^6$, $R^8$, $R^9$, $A^1$, and $A^2$ have the same meaning as defined above.

This reaction is generally carried out in the presence of a solvent.

Examples of the solvent include: ethers such as THF, ethylene glycol dimethyl ether, or 1,4-dioxane; aromatic hydrocarbons such as toluene or xylene; nitriles such as acetonitrile; acid amides such as DMF; sulfoxides such as DMSO; nitrogen-containing aromatic compounds such as pyridine or quinoline; and the mixtures thereof. When the reaction is the reaction of the compound (12) with the compound (13), the compound (13) may be used in a solvent amount, instead of the above exemplified solvents.

The reaction may also be carried out in the presence of a base, as necessary.

Examples of the base include: alkali metal hydrides such as sodium hydride; carbonates such as potassium carbonate; tertiary amines such as triethylamine or diisopropylethylamine; and nitrogen-containing aromatic compounds such as pyridine or 4-dimethylaminopyridine.

The compound (13) or the compound (14) is generally used at a ratio of 1 to 10 moles relative to 1 mole of the compound (12). When the reaction is carried out in the presence of a base, the base is generally used at a ratio of 1 to 10 moles relative to 1 mole of the compound (12).

The reaction temperature applied to the reaction is generally between 0° C. and 120° C., and the reaction time is generally between 0.1 and 24 hours.

After completion of the reaction, the reaction mixture is extracted with an organic solvent, and the organic layer is then subjected to a post-treatment such as drying or concentration, so as to isolate the compound (5-d). The isolated compound (5-d) can be further purified by chromatography, recrystallization, etc.

(Production Method 9)

A compound (5-e), i.e., a compound of the formula (1) wherein n is 0 and $R^3$ is —$R^{3x}$ shown below, can be produced by reacting a compound (15) with a boronic acid compound represented by a formula (16) or a tin compound represented by a formula (17) in the presence of a palladium compound,

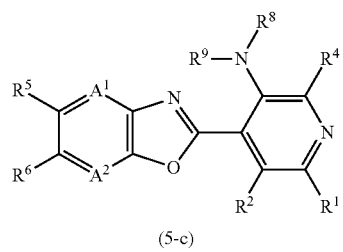

(5-c)

wherein $R^1$, $R^2$, $R^4$, $R^5$, $R^6$, $R^8$, $R^9$, $A^1$, and $A^2$ have the same meaning as defined above.

This reaction is generally carried out in the presence of a solvent.

Examples of the solvent include: ethers such as THF, ethylene glycol dimethyl ether, or 1,4-dioxane; aromatic hydrocarbons such as toluene or xylene; nitriles such as acetonitrile; acid amides such as DMF; sulfoxides such as DMSO; and the mixtures thereof.

Examples of the base include: alkali metal hydrides such as sodium hydride; and carbonates such as potassium carbonate.

The compound (11) is generally used at a ratio of 1 to 10 moles, and the base is generally used at a ratio of 1 to 10 moles, relative to 1 mole of the compound (8).

The reaction temperature applied to the reaction is generally between 0° C. and 100° C., and the reaction time is generally between 0.1 and 24 hours.

After completion of the reaction, the reaction mixture is extracted with an organic solvent, and the organic layer is then subjected to a post-treatment such as drying or concentration, so as to isolate the compound (5-c). The isolated compound (5-c) can be further purified by chromatography, recrystallization, etc.

(Production Method 8)

A compound (5-d), i.e., a compound of the formula (1) wherein n is 0 and $R^3$ is —$NR^8COR^9$, can be produced by reacting a compound (12) with an acid anhydride represented by a formula (13) or an acid chloride represented by a formula (14),

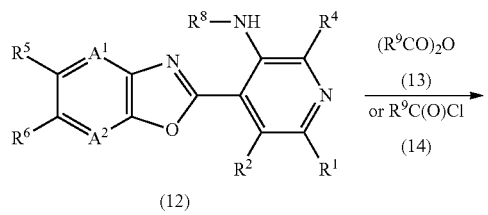

(12)

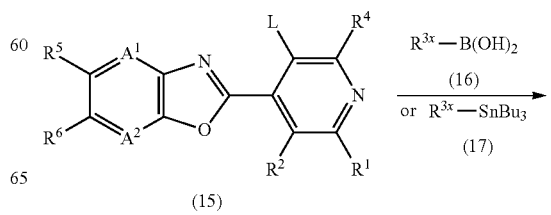

(15)

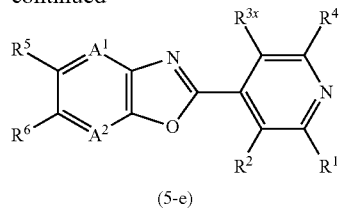

(5-e)

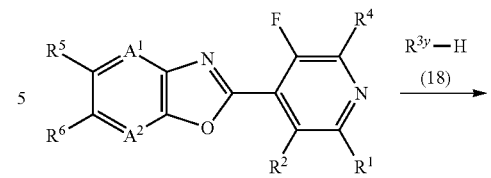

(8)

wherein $R^1$, $R^2$, $R^4$, $R^5$, $R^6$, $A^1$, A and $A^2$ have the same meaning as defined above, L represents a bromine atom or an iodine atom, and $R^{3x}$ represents a phenyl group optionally substituted with one or more members selected from Group Y, or a 5-membered aromatic heterocyclic group or 6-membered aromatic heterocyclic group optionally substituted with one or more members selected from Group Y wherein the aromatic heterocyclic group is limited to an aromatic heterocyclic group that binds to a pyridine ring on a carbon atom.

This reaction is generally carried out in the presence of a solvent.

Examples of the solvent include: ethers such as THF, ethylene glycol dimethyl ether, or 1,4-dioxane; alcohols such as methanol or ethanol; aliphatic hydrocarbons such as hexane, heptane, or octane; aromatic hydrocarbons such as toluene or xylene; acid amides such as DMF; water; and the mixtures thereof.

Examples of the palladium compound include palladium acetate, tetrakistriphenylphosphine palladium, a {1,1'-bis(diphenylphosphino)ferrocene}dichloropalladium dichloromethane complex, and dichlorobis(triphenylphosphine)palladium(II).

The compound (16) or the compound (17) is generally used at a ratio of 0.5 to 5 moles, and the palladium compound is generally used at a ratio of 0.001 to 0.1 mole, relative to 1 mole of the compound (15).

The reaction may also be carried out in the presence of a base and/or a phase transfer catalyst, as necessary.

Examples of the base include inorganic salts such as sodium acetate, potassium acetate, potassium carbonate, tripotassium phosphate, or sodium bicarbonate.

Examples of the phase transfer catalyst include quaternary ammonium salts such as tetrabutylammonium bromide or benzyltriethylammonium bromide.

The amount of the base or phase transfer catalyst may be selected, as appropriate, depending on the type of a compound used, and the like.

The reaction temperature applied to the reaction is generally between 50° C. and 120° C., and the reaction time is generally between 0.5 and 24 hours.

After completion of the reaction, the reaction mixture is extracted with an organic solvent, and the organic layer is then subjected to a post-treatment such as drying or concentration, so as to isolate the compound (5-e). The isolated compound (5-e) can be further purified by chromatography, recrystallization, etc.

(Production Method 10)

A compound (5-f), i.e., a compound of the formula (1) wherein n is 0 and $R^3$ is $R^{3y}$ as shown below, can be produced by reacting the compound (8) with a compound (18) in the presence of a base,

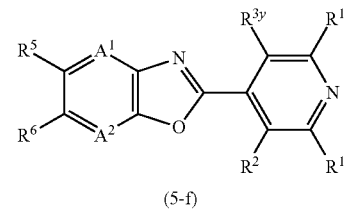

(5-f)

wherein $R^1$, $R^2$, $R^4$, $R^5$, $R^6$, $A^1$, and $A^2$ have the same meaning as defined above, and $R^{3y}$ represents a 5- or 6-membered heterocyclic group optionally substituted with one or more members selected from Group Y wherein the heterocyclic group is limited to a heterocyclic group that binds to a pyridine ring on a nitrogen atom.

This reaction is generally carried out in the presence of a solvent.

Examples of the solvent include: ethers such as THF, ethylene glycol dimethyl ether, or 1,4-dioxane; aromatic hydrocarbons such as toluene or xylene; nitriles such as acetonitrile; acid amides such as DMF; sulfoxides such as DMSO; and the mixtures thereof.

Examples of the base include: alkali metal hydrides such as sodium hydride; and carbonates such as potassium carbonate.

The compound (18) is generally used at a ratio of 1 to 10 moles, and the base is generally used at a ratio of 1 to 10 moles, relative to 1 mole of the compound (8).

The reaction temperature applied to the reaction is generally between 0° C. and 150° C., and the reaction time is generally between 0.1 and 24 hours.

After completion of this reaction, known reactions such as a hydrogenation reaction, an oxidation reaction, a reduction reaction, and a hydrolysis reaction may be further carried out to convert $R^{3y}$ arbitrarily.

After completion of the reaction, the reaction mixture is extracted with an organic solvent, and the organic layer is then subjected to a post-treatment such as drying or concentration, so as to isolate the compound (5-f). The isolated compound (5-f) can be further purified by chromatography, recrystallization, etc.

(Production Method 11)

A compound (19), i.e., a compound of the formula (1) wherein n is 1, can be produced by reacting the compound (5) in the presence of an oxidizer,

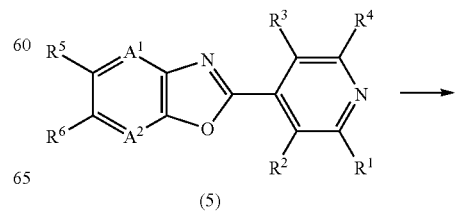

(5)

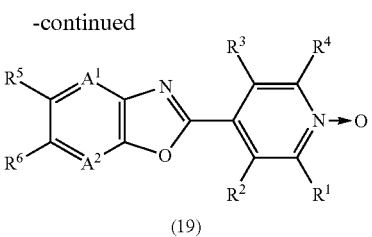

(19)

wherein $R^1$, $R^2$, $R^3$, $R^4$, $R^5$, $R^6$, $A^1$, and $A^2$ have the same meaning as defined above.

This reaction is generally carried out in the presence of a solvent.

Examples of the solvent include: aliphatic halogenated hydrocarbons such as dichloromethane or chloroform; acetic acids, water; and the mixtures thereof.

Examples of the oxidizer include: peroxycarboxylic acids, such as 3-chloroperbenzoic acid; and a hydrogen peroxide solution.

Such oxidizer is generally used at a ratio of 1 to 3 moles relative to 1 mole of the compound (5).

The reaction temperature applied to the reaction is generally between −20° C. and +100° C., and the reaction time is generally between 0.1 and 24 hours.

After completion of the reaction, the reaction mixture is extracted with an organic solvent. Thereafter, the organic layer is washed with an aqueous solution of a reducing agent and an aqueous solution of a base, as necessary, and it is then subjected to a post-treatment such as drying or concentration, so as to isolate the compound (19). The isolated compound (19) can be further purified by chromatography, recrystallization, etc.

Examples of the reducing agent include sodium sulfite and sodium thiosulfate. An example of the base is sodium bicarbonate.

(Production Method 12)

A compound (5-a), i.e., a compound of the formula (1) wherein n is 0 and $R^3$ is —$OR^8$, can be produced by reacting a compound (20) with a compound (21) in the presence of a base,

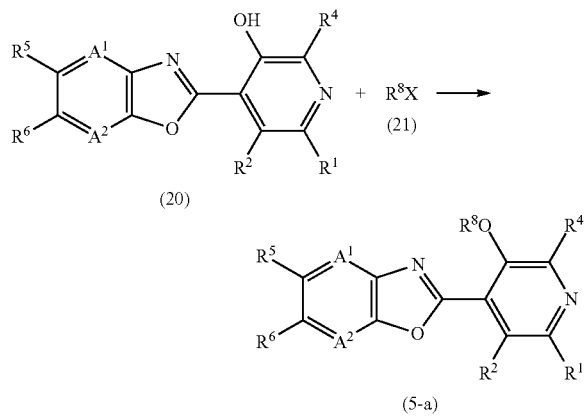

wherein $R^1$, $R^2$, $R^4$, $R^5$, $R^6$, $R^8$, $A^1$, and $A^2$ have the same meaning as defined above, and X represents a leaving group such as a chlorine atom, a bromine atom, an iodine atom, —$OS(O)_2CF_3$ and —$OS(O)_2CH_3$.

This reaction is generally carried out in the presence of a solvent.

Examples of the solvent include: ethers such as THF, ethylene glycol dimethyl ether, or 1,4-dioxane; aromatic hydrocarbons such as toluene or xylene; nitriles such as acetonitrile; acid amides such as DMF, sulfoxides such as DMSO; and the mixtures thereof.

Examples of the base include: alkali metal hydrides such as sodium hydride; and carbonates such as potassium carbonate.

The compound (21) is generally used at a ratio of 1 to 10 moles, and the base is generally used at a ratio of 1 to 10 moles, relative to 1 mole of the compound (20).

The reaction temperature applied to the reaction is generally between 0° C. and 120° C., and the reaction time is generally between 0.5 and 24 hours.

After completion of this reaction, known reactions such as a hydrogenation reaction, an oxidation reaction, and a reduction reaction, may be further carried out to convert $R^8$ arbitrarily.

After completion of the reaction, the reaction mixture is extracted with an organic solvent. Thereafter, the organic layer is subjected to a post-treatment such as drying or concentration, so as to isolate the compound (5-a). The isolated compound (5-a) can be further purified by chromatography, recrystallization, etc.

(Production Method 13)

A compound represented by the formula (5-g) can be produced by reacting the compound (15) with a compound (22) in the presence of a palladium compound, a base, and a copper salt,

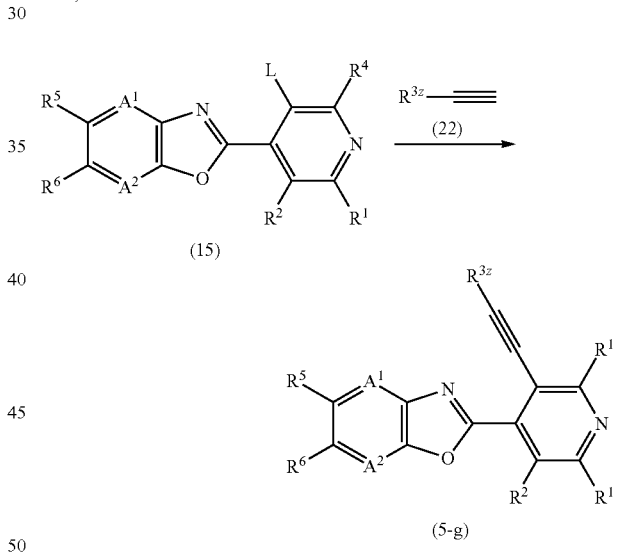

wherein $R^1$, $R^2$, $R^4$, $R^5$, $R^6$, $A^1$, $A^2$, and L have the same meaning as defined above, and $R^{3z}$ represents a C1-C4 acyclic hydrocarbon group optionally substituted with one or more members selected from Group X.

This reaction is generally carried out using a base as a solvent. An auxiliary solvent may also be used.

Examples of the base include amines such as triethylamine, diethylamine, or diisopropylethylamine.

Examples of the auxiliary solvent include: ethers such as THF, ethylene glycol dimethyl ether, or 1,4-dioxane; acid amides such as DMF; and the mixtures thereof.

Examples of the palladium compound include tetrakistriphenylphosphine palladium, a {1,1'-bis(diphenylphosphino)ferrocene}dichloropalladium dichloromethane complex, and dichlorobis(triphenylphosphine)palladium(II).

An example of the copper salt is copper(I) iodide.

The compound (22) is generally used at a ratio of 0.5 to 5 moles, the palladium compound is generally used at a ratio of 0.001 to 0.1 mole, and the copper salt is used at a ratio of 0.001 to 0.1, relative to 1 mole of the compound (15).

In addition to the palladium compound, base, and copper salt, a coordination compound capable of coordinating with the palladium compound may be further used to carry out the reaction.

Examples of the coordination compound include phosphines such as triphenylphosphine or tri(tert-butyl)phosphine.

The reaction temperature applied to the reaction is generally between 0° C. and 100° C., and the reaction time is generally between 0.5 and 24 hours.

After completion of the reaction, the reaction mixture is extracted with an organic solvent. Thereafter, the organic layer is subjected to a post-treatment such as drying or concentration, so as to isolate the compound (5-g). The isolated compound (5-g) can be further purified by chromatography, recrystallization, etc.

After completion of this reaction, known reactions such as a hydrogenation reaction, an oxidation reaction, a reduction reaction, and a hydrolysis reaction may be further carried out, so as to arbitrarily convert $R^{3z}$, and a triple bond that binds the $R^{3z}$ with a pyridine ring.

A compound (23), wherein, in a formula (22), $R^{3z}$ is a trimethylsilyl group, is reacted with the compound (15) in the presence of a palladium compound, a base, and a copper salt. A known desilylation reaction is further carried out on the compound obtained from the reaction, so as to obtain a compound (5-g1), wherein, in a formula (5-g), $R^{3z}$ is a hydrogen atom. The compound (5g-1) is subjected to a known reaction such as a hydrogenation reaction, so as to convert the triple bond arbitrarily.

(Production Method 14)

A compound (5-h), i.e., a compound of the formula (1) wherein n is 0 and $R^3$ is a cyano group, can be produced by reacting the compound (15) with a metal cyanide,

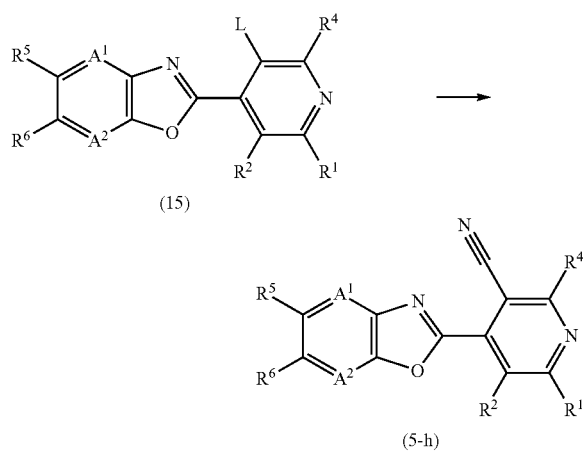

wherein $R^1$, $R^2$, $R^4$, $R^5$, $R^6$, $A^1$, $A^2$, and L have the same meaning as defined above.

This reaction is generally carried out in the presence of a solvent.

Examples of the solvent include: ethers such as THF, ethylene glycol dimethyl ether, or 1,4-dioxane; acid amides such as DMF or 1-methyl-2-pyrrolidinone; sulfoxides such as DMSO; and the mixtures thereof.

An example of the metal cyanide is copper(I) cyanide.

Such metal cyanide is generally used at a ratio of 1 to 5 moles relative to 1 mole of the compound (15).

The reaction temperature applied to the reaction is generally between 50° C. and 200° C., and the reaction time is generally between 0.5 and 24 hours.

After completion of the reaction, the reaction mixture is extracted with an organic solvent. Thereafter, the organic layer is subjected to a post-treatment such as drying or concentration, so as to isolate the compound (5-h). The isolated compound (5-h) can be further purified by chromatography, recrystallization, etc.

An intermediate used in the production of the present active compound is commercially available, or is disclosed in known publications, or can be produced according to a method known to a person skilled in the art.

The intermediate of the present invention can be produced, for example, by the following methods.

(Intermediate Production Method 1)

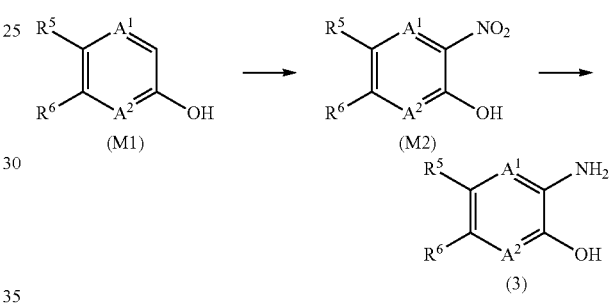

wherein $R^5$, $R^6$, $A^1$, and $A^2$ have the same meaning as defined above.

(Step 1)

The compound (M2) can be produced by reacting the compound (M1) in the presence of a nitrating agent.

This reaction is generally carried out in the presence of a solvent.

Examples of the solvent include: aliphatic halogenated hydrocarbons such as chloroform; acetic acid; concentrated sulfuric acid; concentrated nitric acid; water; and the mixtures thereof.

An example of the nitrating agent is concentrated nitric acid.

Such nitrating agent is generally used at a ratio of 1 to 3 moles relative to 1 mole of the compound (M1).

The reaction temperature applied to the reaction is generally between −10° C. and +80° C., and the reaction time is generally between 0.1 and 24 hours.

After completion of the reaction, the reaction mixture is added to water, and it is then extracted with an organic solvent. Thereafter, the organic layer is subjected to a post-treatment such as drying or concentration, so as to isolate the compound (M2). The isolated compound (M2) can be further purified by chromatography, recrystallization, etc.

(Step 2)

The compound (3) can be produced by reacting the compound (M2) with hydrogen in the presence of a catalyst for hydrogenation.

This reaction is generally carried out in a hydrogen atmosphere under 1 to 100 atmospheric pressures in the presence of a solvent.

Examples of the solvent used in the reaction include: ethers such as THF or 1,4-dioxane; esters such as ethyl acetate or butyl acetate; alcohols such as methanol or ethanol; water; and the mixtures thereof.

Examples of the catalyst for hydrogenation include transition metal compounds such as palladium on carbon, palladium hydroxide, Raney nickel, or platinum oxide.

The hydrogen is generally used at a ratio of 3 moles, and the catalyst for hydrogenation is generally used at a ratio of 0.001 to 0.5 moles, relative to 1 mole of the compound (M2).

An acid, a base, and the like may be added, as necessary, to carry out the reaction.

The reaction temperature applied to the reaction is generally between −20° C. and +100° C., and the reaction time is generally between 0.1 and 24 hours.

After completion of the reaction, the reaction mixture is filtrated, and it is then extracted with an organic solvent, as necessary. Thereafter, the organic layer is subjected to a post-treatment such as drying or concentration, so as to isolate the compound (3). The isolated compound (3) can be further purified by chromatography, recrystallization, etc.

(Intermediate Production Method 2)

The compound (6) can be produced by reacting the compound (3) with a compound (M3),

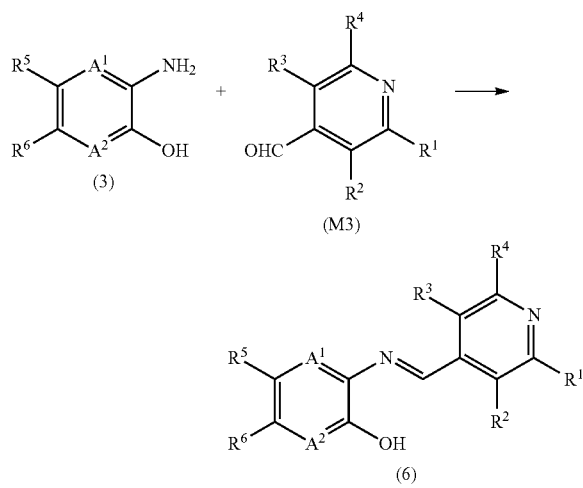

wherein $R^1$, $R^2$, $R^3$, $R^4$, $R^5$, $R^6$, $A^1$, and $A^2$ have the same meaning as defined above.

This reaction is generally carried out in the presence of a solvent.

Examples of the solvent include: alcohols such as methanol or ethanol; ethers such as THF, ethylene glycol dimethyl ether, or 1,4-dioxane; aromatic hydrocarbons such as toluene; and the mixtures thereof.

The compound (M3) is generally used at a ratio of 0.5 to 3 moles relative to 1 mole of the compound (3).

An acid, a base, and the like may be added, as necessary, to carry out the reaction.

The reaction temperature applied to the reaction is generally between 0° C. and 150° C., and the reaction time is generally between 0.1 and 24 hours.

After completion of the reaction, the reaction mixture is extracted with an organic solvent. Thereafter, the organic layer is subjected to a post-treatment such as drying or concentration, so as to isolate the compound (6). The isolated compound (6) can be further purified by chromatography, recrystallization, etc.

(Intermediate Production Method 3)

The compound (7) can be produced by reacting the compound (3) with the compound (4) in the presence of a dehydration-condensation agent,

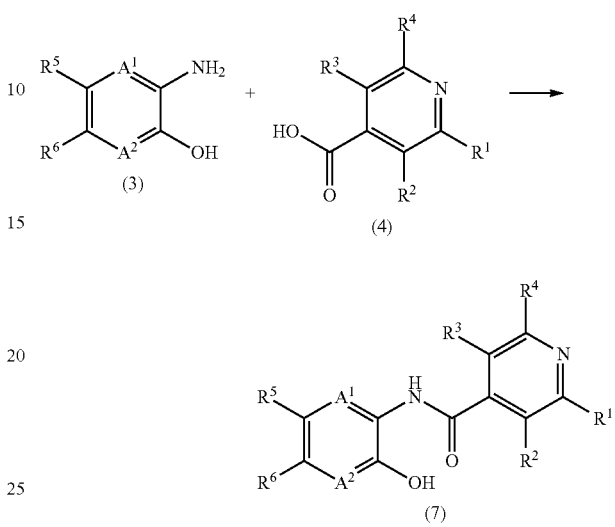

wherein $R^1$, $R^2$, $R^3$, $R^4$, $R^5$, $R^6$, $A^1$, and $A^2$ have the same meaning as defined above.

This reaction is generally carried out in the presence of a solvent.

Examples of the solvent include: ethers such as THF, ethylene glycol dimethyl ether, or 1,4-dioxane; aliphatic hydrocarbons such as hexane, heptane, or octane; aromatic hydrocarbons such as toluene or xylene; halogenated hydrocarbons such as chlorobenzene; esters such as ethyl acetate or butyl acetate; nitriles such as acetonitrile; acid amides such as DMF; sulfoxides such as DMSO; nitrogen-containing aromatic compounds such as pyridine or quinoline; and the mixtures thereof.

Examples of the dehydration-condensation agent include: carbodiimides such as 1-ethyl-3-(3-dimethylaminopropyl) carbodiimide hydrochloride (hereinafter referred to as WSC) or 1,3-dicyclohexylcarbodiimide; and (benzotriazol-1-yl-oxy)tris(dimethylamino)phosphonium hexafluorophosphate (hereinafter referred to as a BOP reagent).

The compound (4) is generally used at a ratio of 1 to 3 moles, and the dehydration-condensation agent is generally used at a ratio of 1 to 5 moles, relative to 1 mole of the compound (3).

The reaction temperature applied to the reaction is generally between 0° C. and 140° C., and the reaction time is generally between 0.1 and 24 hours.

After completion of the reaction, water is added to the reaction mixture, and it is then extracted with an organic solvent. Thereafter, the organic layer is subjected to a post-treatment such as drying or concentration, so as to isolate the compound (7). The isolated compound (7) can be further purified by chromatography, recrystallization, etc.

(Intermediate Production Method 4)

The compound (7) can be produced by reacting the compound (3) with a compound (M4) in the presence of a base,

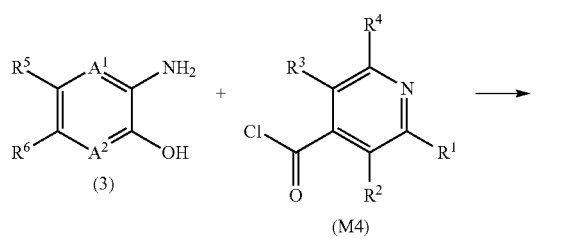

(M4)

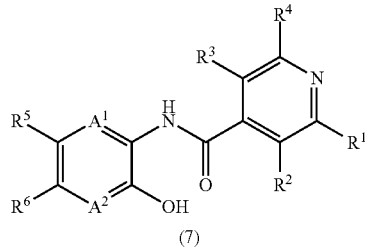

(7)

wherein $R^1$, $R^2$, $R^3$, $R^4$, $R^5$, $R^6$, $A^1$, and $A^2$ have the same meaning as defined above.

This reaction is generally carried out in the presence of a solvent.

Examples of the solvent include: ethers such as THF, ethylene glycol dimethyl ether, or 1,4-dioxane; aliphatic hydrocarbons such as hexane, heptane, or octane; aromatic hydrocarbons such as toluene or xylene; halogenated hydrocarbons such as chlorobenzene; esters such as ethyl acetate or butyl acetate; nitriles such as acetonitrile; acid amides such as DMF; sulfoxides such as DMSO; and the mixtures thereof.

Examples of the base include: alkali metal carbonates such as sodium carbonate or potassium carbonate; tertiary amines such as triethylamine or diisopropylethylamine; and nitrogen-containing aromatic compounds such as pyridine or 4-dimethylaminopyridine.

The compound (M4) is generally used at a ratio of 1 to 3 moles, and the base is generally used at a ratio of 1 to 10 moles, relative to 1 mole of the compound (3).

The reaction temperature applied to the reaction is generally between −20° C. and +100° C., and the reaction time is generally between 0.1 and 24 hours.

After completion of the reaction, water is added to the reaction mixture, and it is then extracted with an organic solvent. Thereafter, the organic layer is subjected to a post-treatment such as drying or concentration, so as to isolate the compound (7). The isolated compound (7) can be further purified by chromatography, recrystallization, etc.

(Intermediate Production Method 5)

A compound (4-a), wherein, in a formula (4), $R^1$, $R^2$, and $R^4$ represent a hydrogen atom, and $R^3$ represents the following —$R^{3p}$, can be produced by a method as shown in the following scheme,

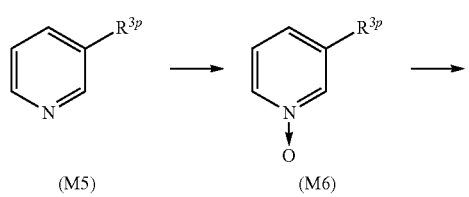

wherein $R^{3p}$ represents a C1-C6 acyclic hydrocarbon group optionally substituted with one or more members selected from Group X, and a C3-C6 alicyclic hydrocarbon group optionally substituted with one or more members selected from Group X, and Group X has the same meaning as defined above.

(Step 1)

The compound (M6) can be produced by reacting the compound (M5) in the presence of an oxidizer.

This reaction is generally carried out in the presence of a solvent.

Examples of the solvent include: aliphatic halogenated hydrocarbons such as dichloromethane or chloroform; acetic acid; water; and the mixtures thereof.

Example of the oxidizer include peroxycarboxylic acids, such as 3-chloroperbenzoic acid; and a hydrogen peroxide solution.

Such oxidizer is generally used at a ratio of 1 to 10 moles relative to 1 mole of the compound (M5).

The reaction temperature applied to the reaction is generally between −20° C. and +120° C., and the reaction time is generally between 0.1 and 24 hours.

After completion of the reaction, a base is added to the reaction mixture, as necessary, to neutralize it. Thereafter, the reaction mixture is extracted with an organic solvent, and the organic layer is then washed with an aqueous solution of a reducing agent and an aqueous solution of a base, as necessary, followed by a post-treatment such as drying or concentration, so as to isolate the compound (M6). The isolated compound (M6) can be further purified by chromatography, distillation, etc.

Examples of the base include alkali metal carbonates such as sodium carbonate, sodium bicarbonate, or potassium carbonate. Examples of the reducing agent include sodium sulfite, sodium hydrogen sulfite, and sodium thiosulfate (Step 2)

The compound (M7) can be produced by reacting the compound (M6) in the presence of an alkylating agent and a cyaniding agent.

This reaction is generally carried out in the presence of a solvent.

Examples of the solvent include: ethers such as 1,4-dioxane; water; and the mixtures thereof.

Examples of the alkylating agent include iodomethane, iodoethane, and dimethyl sulfate.

Examples of the cyaniding agent include sodium cyanide and potassium cyanide.

The alkylating agent is generally used at a ratio of 1 to 10 moles, and the cyaniding agent is generally used at a ratio of 1 to 3 moles, relative to 1 mole of the compound (M6).

The reaction temperature applied to the reaction is generally between 0° C. and 100° C., and the reaction time is generally between 0.1 and 24 hours.

After completion of the reaction, the reaction mixture is extracted with an organic solvent. Thereafter, the organic layer is subjected to a post-treatment such as drying or concentration, so as to isolate the compound (M7). The isolated compound (M7) can be further purified by chromatography, recrystallization, etc.

(Step 3)

The compound (4-a) can be produced by subjecting the compound (M7) to a hydrolysis reaction in the presence of a base.

This reaction is generally carried out in the presence of a solvent.

Examples of the solvent include: ethers such as THF, ethylene glycol dimethyl ether, tert-butyl methyl ether, or 1,4-dioxane; alcohols such as methanol or ethanol; water; and the mixtures thereof.

Examples of the base include alkali metal hydroxides such as sodium hydroxide or potassium hydroxide.

Such base is generally used at a ratio of 1 to 10 moles relative to 1 mole of the compound (M7).

The reaction temperature applied to the reaction is generally between 0° C. and 120° C., and the reaction time is generally between 0.1 and 24 hours.

After completion of the reaction, the reaction solution is converted to an acidic solution, and the reaction mixture is then extracted with an organic solvent. Thereafter, the organic layer is subjected to a post-treatment such as drying or concentration, so as to isolate the compound (4-a). The isolated compound (4-a) can be further purified by chromatography, recrystallization, etc.

(Intermediate Production Method 6)

A compound (4-b), wherein, in the formula (4), $R^3$ represents the following —$OR^8$, can be produced by a method as shown in the following scheme,

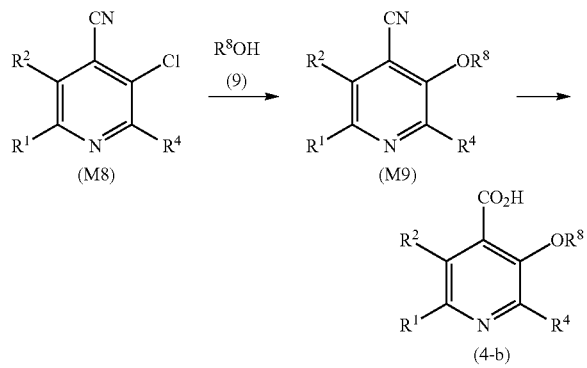

wherein $R^1$, $R^2$, $R^4$, and $R^8$ have the same meaning as defined above.

(Step 1)

The compound (M9) can be produced by reacting the compound (M8) with the compound (9) in the presence of a base.

This reaction is generally carried out in the presence of a solvent.

Examples of the solvent include: ethers such as THF, ethylene glycol dimethyl ether, or 1,4-dioxane; aromatic hydrocarbons such as toluene or xylene; nitriles such as acetonitrile; acid amides such as DMF; sulfoxides such as DMSO; and the mixtures thereof.

Example of the base include alkali metal hydrides such as sodium hydride.

The compound (9) is generally used at a ratio of 1 to 10 moles, and the base is generally used at a ratio of 1 to 10 moles, relative to 1 mole of the compound (M8).

The reaction temperature applied to the reaction is generally between −20° C. and +100° C., and the reaction time is generally between 0.5 and 24 hours.

After completion of this reaction, known reactions such as a hydrogenation reaction, an oxidation reaction, and a reduction reaction may be further carried out to convert $R^8$ arbitrarily.

After completion of the reaction, the reaction mixture is extracted with an organic solvent, and the organic layer is then subjected to a post-treatment such as drying or concentration, so as to isolate the compound (M9). The isolated compound (M9) can be further purified by chromatography, recrystallization, etc.

(Step 2)

The compound (4-b) can be produced by subjecting the compound (M9) to a hydrolysis reaction in the presence of a base.

This reaction is generally carried out in the presence of a solvent.

Examples of the solvent include: ethers such as THF, ethylene glycol dimethyl ether, tert-butyl methyl ether, or 1,4-dioxane; alcohols such as methanol or ethanol; water; and the mixtures thereof.

Examples of the base include alkali metal hydroxides such as sodium hydroxide or potassium hydroxide.

Such base is generally used at a ratio of 1 to 10 moles relative to 1 mole of the compound (M9).

The reaction temperature applied to the reaction is generally between 0° C. and 120° C., and the reaction time is generally between 0.1 and 24 hours.

After completion of the reaction, the reaction solution is converted to an acidic solution, and the reaction mixture is then extracted with an organic solvent. Thereafter, the organic layer is subjected to a post-treatment such as drying or concentration, so as to isolate the compound (4-b). The isolated compound (4-b) can be further purified by chromatography, recrystallization, etc.

(Intermediate Production Method 7)

A compound (4-c), wherein, in the formula (4), $R^3$ represents the following —$SR^8$, can be produced by a method as shown in the following scheme,

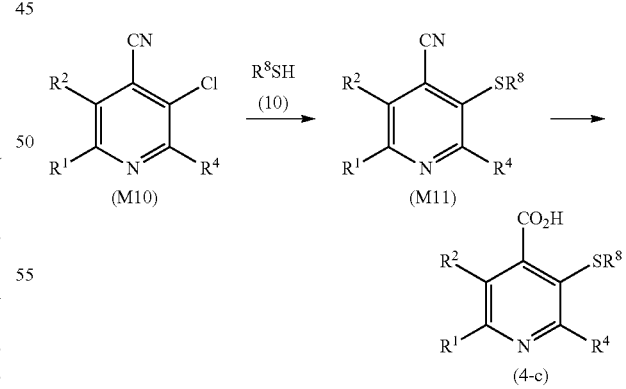

wherein $R^1$, $R^2$, $R^4$, and $R^8$ have the same meaning as defined above.

(Step 1)

The compound (M11) can be produced by reacting the compound (M10) with the compound (10) in the presence of a base.

This reaction is generally carried out in the presence of a solvent.

Examples of the solvent include: ethers such as THF, ethylene glycol dimethyl ether, or 1,4-dioxane; aromatic hydrocarbons such as toluene or xylene; nitriles such as acetonitrile; acid amides such as DMF; sulfoxides such as DMSO; and the mixtures thereof.

Example of the base include: alkali metal hydrides such as sodium hydride; and carbonates such as potassium carbonate.

The compound (10) is generally used at a ratio of 1 to 10 moles, and the base is generally used at a ratio of 1 to 10 moles, relative to 1 mole of the compound (M10).

The reaction temperature applied to the reaction is generally between −20° C. and +100° C., and the reaction time is generally between 0.5 and 24 hours.

After completion of the reaction, the reaction mixture is extracted with an organic solvent, and the organic layer is then subjected to a post-treatment such as drying or concentration, so as to isolate the compound (M11). The isolated compound (M11) can be further purified by chromatography, recrystallization, etc.

(Step 2)

The compound (4-c) can be produced by subjecting the compound (M11) to a hydrolysis reaction in the presence of a base.

This reaction is generally carried out in the presence of a solvent.

Examples of the solvent include: ethers such as THF, ethylene glycol dimethyl ether, tert-butyl methyl ether, or 1,4-dioxane; alcohols such as methanol or ethanol; water; and the mixtures thereof.

Examples of the base include alkali metal hydroxides such as sodium hydroxide or potassium hydroxide.

Such base is generally used at a ratio of 1 to 10 moles relative to 1 mole of the compound (M11). The reaction temperature applied to the reaction is generally between 0° C. and 120° C., and the reaction time is generally between 0.1 and 24 hours.

After completion of the reaction, the reaction solution is converted to an acidic solution, and the reaction mixture is then extracted with an organic solvent. Thereafter, the organic layer is subjected to a post-treatment such as drying or concentration, so as to isolate the compound (4-c). The isolated compound (4-c) can be further purified by chromatography, recrystallization, etc.

Next, specific examples of the present active compound will be given below.

In the following tables, Me represents a methyl group, Et represents an ethyl group, Pr represents a propyl group, iPr represents an isopropyl group, tBu represents a tert-butyl group, Ph represents a phenyl group, 2-Py represents a 2-pyridyl group, 3-Py represents a 3-pyridyl group, 4-Py represents a 4-pyridyl group, 1-Tz represents a 1,2,4-triazol-1-yl group, and 1-Pz represents a pyrazol-1-yl group.

The compound represented by the following formula (1-A):

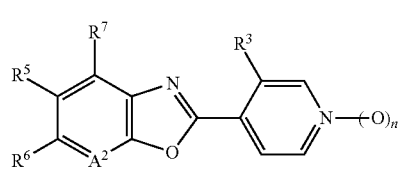

(1-A)

In the above formula (1-A), substituents used for $R^3$, $R^5$, $R^6$, $R^7$, $A^2$, and n are available in the combinations shown in the following (Table 1) to (Table 35).

TABLE 1

| $R^3$ | $R^5$ | $R^6$ | $R^7$ | $A^2$ | n |
|---|---|---|---|---|---|
| H | tBu | H | H | =C(H)— | 0 |
| F | tBu | H | H | =C(H)— | 0 |
| Cl | tBu | H | H | =C(H)— | 0 |
| Br | tBu | H | H | =C(H)— | 0 |
| I | tBu | H | H | =C(H)— | 0 |
| Me | tBu | H | H | =C(H)— | 0 |
| Et | tBu | H | H | =C(H)— | 0 |
| Pr | tBu | H | H | =C(H)— | 0 |
| MeO | tBu | H | H | =C(H)— | 0 |
| EtO | tBu | H | H | =C(H)— | 0 |
| PrO | tBu | H | H | =C(H)— | 0 |
| $CF_3CH_2O$ | tBu | H | H | =C(H)— | 0 |
| iPrO | tBu | H | H | =C(H)— | 0 |
| MeS | tBu | H | H | =C(H)— | 0 |
| EtS | tBu | H | H | =C(H)— | 0 |
| PrS | tBu | H | H | =C(H)— | 0 |
| $CF_3CH_2S$ | tBu | H | H | =C(H)— | 0 |
| iPrS | tBu | H | H | =C(H)— | 0 |
| Ph | tBu | H | H | =C(H)— | 0 |
| 2-Py | tBu | H | H | =C(H)— | 0 |
| 3-Py | tBu | H | H | =C(H)— | 0 |
| 4-Py | tBu | H | H | =C(H)— | 0 |
| 1-Tz | tBu | H | H | =C(H)— | 0 |
| 1-Pz | tBu | H | H | =C(H)— | 0 |

TABLE 2

| $R^3$ | $R^5$ | $R^6$ | $R^7$ | $A^2$ | n |
|---|---|---|---|---|---|
| H | tBu | H | H | =C(H)— | 1 |
| Cl | tBu | H | H | =C(H)— | 1 |
| Br | tBu | H | H | =C(H)— | 1 |
| I | tBu | H | H | =C(H)— | 1 |
| Me | tBu | H | H | =C(H)— | 1 |
| Et | tBu | H | H | =C(H)— | 1 |
| Pr | tBu | H | H | =C(H)— | 1 |
| MeO | tBu | H | H | =C(H)— | 1 |
| EtO | tBu | H | H | =C(H)— | 1 |
| PrO | tBu | H | H | =C(H)— | 1 |
| $CF_3CH_2O$ | tBu | H | H | =C(H)— | 1 |
| iPrO | tBu | H | H | =C(H)— | 1 |
| Ph | tBu | H | H | =C(H)— | 1 |
| H | $CF_3$ | H | H | =C(H)— | 0 |
| F | $CF_3$ | H | H | =C(H)— | 0 |
| Cl | $CF_3$ | H | H | =C(H)— | 0 |
| Br | $CF_3$ | H | H | =C(H)— | 0 |
| I | $CF_3$ | H | H | =C(H)— | 0 |
| Me | $CF_3$ | H | H | =C(H)— | 0 |
| Et | $CF_3$ | H | H | =C(H)— | 0 |
| Pr | $CF_3$ | H | H | =C(H)— | 0 |
| MeO | $CF_3$ | H | H | =C(H)— | 0 |
| EtO | $CF_3$ | H | H | =C(H)— | 0 |
| PrO | $CF_3$ | H | H | =C(H)— | 0 |

TABLE 3

| $R^3$ | $R^5$ | $R^6$ | $R^7$ | $A^2$ | n |
|---|---|---|---|---|---|
| $CF_3CH_2O$ | $CF_3$ | H | H | =C(H)— | 0 |
| iPrO | $CF_3$ | H | H | =C(H)— | 0 |
| MeS | $CF_3$ | H | H | =C(H)— | 0 |
| EtS | $CF_3$ | H | H | =C(H)— | 0 |
| PrS | $CF_3$ | H | H | =C(H)— | 0 |
| $CF_3CH_2S$ | $CF_3$ | H | H | =C(H)— | 0 |
| iPrS | $CF_3$ | H | H | =C(H)— | 0 |
| Ph | $CF_3$ | H | H | =C(H)— | 0 |
| 2-Py | $CF_3$ | H | H | =C(H)— | 0 |
| 3-Py | $CF_3$ | H | H | =C(H)— | 0 |
| 4-Py | $CF_3$ | H | H | =C(H)— | 0 |
| 1-Tz | $CF_3$ | H | H | =C(H)— | 0 |
| 1-Pz | $CF_3$ | H | H | =C(H)— | 0 |
| H | $CF_3$ | H | H | =C(H)— | 1 |
| Cl | $CF_3$ | H | H | =C(H)— | 1 |

TABLE 3-continued

| R³ | R⁵ | R⁶ | R⁷ | A² | n |
|---|---|---|---|---|---|
| Br | CF₃ | H | H | =C(H)— | 1 |
| I | CF₃ | H | H | =C(H)— | 1 |
| Me | CF₃ | H | H | =C(H)— | 1 |
| Et | CF₃ | H | H | =C(H)— | 1 |
| Pr | CF₃ | H | H | =C(H)— | 1 |
| MeO | CF₃ | H | H | =C(H)— | 1 |
| EtO | CF₃ | H | H | =C(H)— | 1 |
| PrO | CF₃ | H | H | =C(H)— | 1 |
| CF₃CH₂O | CF₃ | H | H | =C(H)— | 1 |

TABLE 4

| R³ | R⁵ | R⁶ | R⁷ | A² | n |
|---|---|---|---|---|---|
| iPrO | CF₃ | H | H | =C(H)— | 1 |
| Ph | CF₃ | H | H | =C(H)— | 1 |
| H | CF₃ | Cl | H | =C(H)— | 0 |
| F | CF₃ | Cl | H | =C(H)— | 0 |
| Cl | CF₃ | Cl | H | =C(H)— | 0 |
| Br | CF₃ | Cl | H | =C(H)— | 0 |
| I | CF₃ | Cl | H | =C(H)— | 0 |
| Me | CF₃ | Cl | H | =C(H)— | 0 |
| Et | CF₃ | Cl | H | =C(H)— | 0 |
| Pr | CF₃ | Cl | H | =C(H)— | 0 |
| MeO | CF₃ | Cl | H | =C(H)— | 0 |
| EtO | CF₃ | Cl | H | =C(H)— | 0 |
| PrO | CF₃ | Cl | H | =C(H)— | 0 |
| CF₃CH₂O | CF₃ | Cl | H | =C(H)— | 0 |
| iPrO | CF₃ | Cl | H | =C(H)— | 0 |
| MeS | CF₃ | Cl | H | =C(H)— | 0 |
| EtS | CF₃ | Cl | H | =C(H)— | 0 |
| PrS | CF₃ | Cl | H | =C(H)— | 0 |
| CF₃CH₂S | CF₃ | Cl | H | =C(H)— | 0 |
| iPrS | CF₃ | Cl | H | =C(H)— | 0 |
| Ph | CF₃ | Cl | H | =C(H)— | 0 |
| 2-Py | CF₃ | Cl | H | =C(H)— | 0 |
| 3-Py | CF₃ | Cl | H | =C(H)— | 0 |
| 4-Py | CF₃ | Cl | H | =C(H)— | 0 |

TABLE 5

| R³ | R⁵ | R⁶ | R⁷ | A² | n |
|---|---|---|---|---|---|
| 1-Tz | CF₃ | Cl | H | =C(H)— | 0 |
| 1-Pz | CF₃ | Cl | H | =C(H)— | 0 |
| H | CF₃ | Cl | H | =C(H)— | 1 |
| Cl | CF₃ | Cl | H | =C(H)— | 1 |
| Br | CF₃ | Cl | H | =C(H)— | 1 |
| I | CF₃ | Cl | H | =C(H)— | 1 |
| Me | CF₃ | Cl | H | =C(H)— | 1 |
| Et | CF₃ | Cl | H | =C(H)— | 1 |
| Pr | CF₃ | Cl | H | =C(H)— | 1 |
| MeO | CF₃ | Cl | H | =C(H)— | 1 |
| EtO | CF₃ | Cl | H | =C(H)— | 1 |
| PrO | CF₃ | Cl | H | =C(H)— | 1 |
| CF₃CH₂O | CF₃ | Cl | H | =C(H)— | 1 |
| iPrO | CF₃ | Cl | H | =C(H)— | 1 |
| Ph | CF₃ | Cl | H | =C(H)— | 1 |
| H | CF₃ | H | Cl | =C(H)— | 0 |
| F | CF₃ | H | Cl | =C(H)— | 0 |
| Cl | CF₃ | H | Cl | =C(H)— | 0 |
| Br | CF₃ | H | Cl | =C(H)— | 0 |
| I | CF₃ | H | Cl | =C(H)— | 0 |
| Me | CF₃ | H | Cl | =C(H)— | 0 |
| Et | CF₃ | H | Cl | =C(H)— | 0 |
| Pr | CF₃ | H | Cl | =C(H)— | 0 |
| MeO | CF₃ | H | Cl | =C(H)— | 0 |

TABLE 6

| R³ | R⁵ | R⁶ | R⁷ | A² | n |
|---|---|---|---|---|---|
| EtO | CF₃ | H | Cl | =C(H)— | 0 |
| PrO | CF₃ | H | Cl | =C(H)— | 0 |
| CF₃CH₂O | CF₃ | H | Cl | =C(H)— | 0 |
| iPrO | CF₃ | H | Cl | =C(H)— | 0 |
| MeS | CF₃ | H | Cl | =C(H)— | 0 |
| EtS | CF₃ | H | Cl | =C(H)— | 0 |
| PrS | CF₃ | H | Cl | =C(H)— | 0 |
| CF₃CH₂S | CF₃ | H | Cl | =C(H)— | 0 |
| iPrS | CF₃ | H | Cl | =C(H)— | 0 |
| Ph | CF₃ | H | Cl | =C(H)— | 0 |
| 2-Py | CF₃ | H | Cl | =C(H)— | 0 |
| 3-Py | CF₃ | H | Cl | =C(H)— | 0 |
| 4-Py | CF₃ | H | Cl | =C(H)— | 0 |
| 1-Tz | CF₃ | H | Cl | =C(H)— | 0 |
| 1-Pz | CF₃ | H | Cl | =C(H)— | 0 |
| H | CF₃ | H | Cl | =C(H)— | 1 |
| Cl | CF₃ | H | Cl | =C(H)— | 1 |
| Br | CF₃ | H | Cl | =C(H)— | 1 |
| I | CF₃ | H | Cl | =C(H)— | 1 |
| Me | CF₃ | H | Cl | =C(H)— | 1 |
| Et | CF₃ | H | Cl | =C(H)— | 1 |
| Pr | CF₃ | H | Cl | =C(H)— | 1 |
| MeO | CF₃ | H | Cl | =C(H)— | 1 |
| EtO | CF₃ | H | Cl | =C(H)— | 1 |

TABLE 7

| R³ | R⁵ | R⁶ | R⁷ | A² | n |
|---|---|---|---|---|---|
| PrO | CF₃ | H | Cl | =C(H)— | 1 |
| CF₃CH₂O | CF₃ | H | Cl | =C(H)— | 1 |
| iPrO | CF₃ | H | Cl | =C(H)— | 1 |
| Ph | CF₃ | H | Cl | =C(H)— | 1 |
| H | CF₃ | H | H | =N— | 0 |
| F | CF₃ | H | H | =N— | 0 |
| Cl | CF₃ | H | H | =N— | 0 |
| Br | CF₃ | H | H | =N— | 0 |
| I | CF₃ | H | H | =N— | 0 |
| Me | CF₃ | H | H | =N— | 0 |
| Et | CF₃ | H | H | =N— | 0 |
| Pr | CF₃ | H | H | =N— | 0 |
| MeO | CF₃ | H | H | =N— | 0 |
| EtO | CF₃ | H | H | =N— | 0 |
| PrO | CF₃ | H | H | =N— | 0 |
| CF₃CH₂O | CF₃ | H | H | =N— | 0 |
| iPrO | CF₃ | H | H | =N— | 0 |
| MeS | CF₃ | H | H | =N— | 0 |
| EtS | CF₃ | H | H | =N— | 0 |
| PrS | CF₃ | H | H | =N— | 0 |
| CF₃CH₂S | CF₃ | H | H | =N— | 0 |
| iPrS | CF₃ | H | H | =N— | 0 |
| Ph | CF₃ | H | H | =N— | 0 |
| 2-Py | CF₃ | H | H | =N— | 0 |

TABLE 8

| R³ | R⁵ | R⁶ | R⁷ | A² | n |
|---|---|---|---|---|---|
| 3-Py | CF₃ | H | H | =N— | 0 |
| 4-Py | CF₃ | H | H | =N— | 0 |
| 1-Tz | CF₃ | H | H | =N— | 0 |
| 1-Pz | CF₃ | H | H | =N— | 0 |
| H | CF₃O | H | H | =C(H)— | 0 |
| F | CF₃O | H | H | =C(H)— | 0 |
| Cl | CF₃O | H | H | =C(H)— | 0 |
| Br | CF₃O | H | H | =C(H)— | 0 |
| I | CF₃O | H | H | =C(H)— | 0 |
| Me | CF₃O | H | H | =C(H)— | 0 |
| Et | CF₃O | H | H | =C(H)— | 0 |
| Pr | CF₃O | H | H | =C(H)— | 0 |
| MeO | CF₃O | H | H | =C(H)— | 0 |
| EtO | CF₃O | H | H | =C(H)— | 0 |
| PrO | CF₃O | H | H | =C(H)— | 0 |

TABLE 8-continued

| R³ | R⁵ | R⁶ | R⁷ | A² | n |
|---|---|---|---|---|---|
| CF₃CH₂O | CF₃O | H | H | =C(H)— | 0 |
| iPrO | CF₃O | H | H | =C(H)— | 0 |
| MeS | CF₃O | H | H | =C(H)— | 0 |
| EtS | CF₃O | H | H | =C(H)— | 0 |
| PrS | CF₃O | H | H | =C(H)— | 0 |
| CF₃CH₂S | CF₃O | H | H | =C(H)— | 0 |
| iPrS | CF₃O | H | H | =C(H)— | 0 |
| Ph | CF₃O | H | H | =C(H)— | 0 |
| 2-Py | CF₃O | H | H | =C(H)— | 0 |

TABLE 9

| R³ | R⁵ | R⁶ | R⁷ | A² | n |
|---|---|---|---|---|---|
| 3-Py | CF₃O | H | H | =C(H)— | 0 |
| 4-Py | CF₃O | H | H | =C(H)— | 0 |
| 1-Tz | CF₃O | H | H | =C(H)— | 0 |
| 1-Pz | CF₃O | H | H | =C(H)— | 0 |
| H | CF₃O | H | H | =C(H)— | 1 |
| Cl | CF₃O | H | H | =C(H)— | 1 |
| Br | CF₃O | H | H | =C(H)— | 1 |
| I | CF₃O | H | H | =C(H)— | 1 |
| Me | CF₃O | H | H | =C(H)— | 1 |
| Et | CF₃O | H | H | =C(H)— | 1 |
| Pr | CF₃O | H | H | =C(H)— | 1 |
| MeO | CF₃O | H | H | =C(H)— | 1 |
| EtO | CF₃O | H | H | =C(H)— | 1 |
| PrO | CF₃O | H | H | =C(H)— | 1 |
| CF₃CH₂O | CF₃O | H | H | =C(H)— | 1 |
| iPrO | CF₃O | H | H | =C(H)— | 1 |
| Ph | CF₃O | H | H | =C(H)— | 1 |
| H | CF₃S | H | H | =C(H)— | 0 |
| F | CF₃S | H | H | =C(H)— | 0 |
| Cl | CF₃S | H | H | =C(H)— | 0 |
| Br | CF₃S | H | H | =C(H)— | 0 |
| I | CF₃S | H | H | =C(H)— | 0 |
| Me | CF₃S | H | H | =C(H)— | 0 |
| Et | CF₃S | H | H | =C(H)— | 0 |

TABLE 10

| R³ | R⁵ | R⁶ | R⁷ | A² | n |
|---|---|---|---|---|---|
| Pr | CF₃S | H | H | =C(H)— | 0 |
| MeO | CF₃S | H | H | =C(H)— | 0 |
| EtO | CF₃S | H | H | =C(H)— | 0 |
| PrO | CF₃S | H | H | =C(H)— | 0 |
| CF₃CH₂O | CF₃S | H | H | =C(H)— | 0 |
| iPrO | CF₃S | H | H | =C(H)— | 0 |
| MeS | CF₃S | H | H | =C(H)— | 0 |
| EtS | CF₃S | H | H | =C(H)— | 0 |
| PrS | CF₃S | H | H | =C(H)— | 0 |
| CF₃CH₂S | CF₃S | H | H | =C(H)— | 0 |
| iPrS | CF₃S | H | H | =C(H)— | 0 |
| Ph | CF₃S | H | H | =C(H)— | 0 |
| 2-Py | CF₃S | H | H | =C(H)— | 0 |
| 3-Py | CF₃S | H | H | =C(H)— | 0 |
| 4-Py | CF₃S | H | H | =C(H)— | 0 |
| 1-Tz | CF₃S | H | H | =C(H)— | 0 |
| 1-Pz | CF₃S | H | H | =C(H)— | 0 |
| H | H | tBu | H | =C(H)— | 0 |
| F | H | tBu | H | =C(H)— | 0 |
| Cl | H | tBu | H | =C(H)— | 0 |
| Br | H | tBu | H | =C(H)— | 0 |
| I | H | tBu | H | =C(H)— | 0 |
| Me | H | tBu | H | =C(H)— | 0 |
| Et | H | tBu | H | =C(H)— | 0 |

TABLE 11

| R³ | R⁵ | R⁶ | R⁷ | A² | n |
|---|---|---|---|---|---|
| Pr | H | tBu | H | =C(H)— | 0 |
| MeO | H | tBu | H | =C(H)— | 0 |
| EtO | H | tBu | H | =C(H)— | 0 |
| PrO | H | tBu | H | =C(H)— | 0 |
| CF₃CH₂O | H | tBu | H | =C(H)— | 0 |
| iPrO | H | tBu | H | =C(H)— | 0 |
| MeS | H | tBu | H | =C(H)— | 0 |
| EtS | H | tBu | H | =C(H)— | 0 |
| PrS | H | tBu | H | =C(H)— | 0 |
| CF₃CH₂S | H | tBu | H | =C(H)— | 0 |
| iPrS | H | tBu | H | =C(H)— | 0 |
| Ph | H | tBu | H | =C(H)— | 0 |
| 2-Py | H | tBu | H | =C(H)— | 0 |
| 3-Py | H | tBu | H | =C(H)— | 0 |
| 4-Py | H | tBu | H | =C(H)— | 0 |
| 1-Tz | H | tBu | H | =C(H)— | 0 |
| 1-Pz | H | tBu | H | =C(H)— | 0 |
| H | H | tBu | H | =C(H)— | 1 |
| Cl | H | tBu | H | =C(H)— | 1 |
| Br | H | tBu | H | =C(H)— | 1 |
| I | H | tBu | H | =C(H)— | 1 |
| Me | H | tBu | H | =C(H)— | 1 |
| Et | H | tBu | H | =C(H)— | 1 |
| Pr | H | tBu | H | =C(H)— | 1 |

TABLE 12

| R³ | R⁵ | R⁶ | R⁷ | A² | n |
|---|---|---|---|---|---|
| MeO | H | tBu | H | =C(H)— | 1 |
| EtO | H | tBu | H | =C(H)— | 1 |
| PrO | H | tBu | H | =C(H)— | 1 |
| CF₃CH₂O | H | tBu | H | =C(H)— | 1 |
| iPrO | H | tBu | H | =C(H)— | 1 |
| Ph | H | tBu | H | =C(H)— | 1 |
| H | H | CF₃ | H | =C(H)— | 0 |
| F | H | CF₃ | H | =C(H)— | 0 |
| Cl | H | CF₃ | H | =C(H)— | 0 |
| Br | H | CF₃ | H | =C(H)— | 0 |
| I | H | CF₃ | H | =C(H)— | 0 |
| Me | H | CF₃ | H | =C(H)— | 0 |
| Et | H | CF₃ | H | =C(H)— | 0 |
| Pr | H | CF₃ | H | =C(H)— | 0 |
| MeO | H | CF₃ | H | =C(H)— | 0 |
| EtO | H | CF₃ | H | =C(H)— | 0 |
| PrO | H | CF₃ | H | =C(H)— | 0 |
| CF₃CH₂O | H | CF₃ | H | =C(H)— | 0 |
| iPrO | H | CF₃ | H | =C(H)— | 0 |
| MeS | H | CF₃ | H | =C(H)— | 0 |
| EtS | H | CF₃ | H | =C(H)— | 0 |
| PrS | H | CF₃ | H | =C(H)— | 0 |
| CF₃CH₂S | H | CF₃ | H | =C(H)— | 0 |
| iPrS | H | CF₃ | H | =C(H)— | 0 |

TABLE 13

| R³ | R⁵ | R⁶ | R⁷ | A² | n |
|---|---|---|---|---|---|
| Ph | H | CF₃ | H | =C(H)— | 0 |
| 2-Py | H | CF₃ | H | =C(H)— | 0 |
| 3-Py | H | CF₃ | H | =C(H)— | 0 |
| 4-Py | H | CF₃ | H | =C(H)— | 0 |
| 1-Tz | H | CF₃ | H | =C(H)— | 0 |
| 1-Pz | H | CF₃ | H | =C(H)— | 0 |
| H | H | CF₃ | H | =C(H)— | 1 |
| Cl | H | CF₃ | H | =C(H)— | 1 |
| Br | H | CF₃ | H | =C(H)— | 1 |
| I | H | CF₃ | H | =C(H)— | 1 |
| Me | H | CF₃ | H | =C(H)— | 1 |
| Et | H | CF₃ | H | =C(H)— | 1 |
| Pr | H | CF₃ | H | =C(H)— | 1 |
| MeO | H | CF₃ | H | =C(H)— | 1 |
| EtO | H | CF₃ | H | =C(H)— | 1 |

TABLE 13-continued

| R³ | R⁵ | R⁶ | R⁷ | A² | n |
|---|---|---|---|---|---|
| PrO | H | CF₃ | H | =C(H)— | 1 |
| CF₃CH₂O | H | CF₃ | H | =C(H)— | 1 |
| iPrO | H | CF₃ | H | =C(H)— | 1 |
| Ph | H | CF₃ | H | =C(H)— | 1 |
| H | Cl | CF₃ | H | =C(H)— | 0 |
| F | Cl | CF₃ | H | =C(H)— | 0 |
| Cl | Cl | CF₃ | H | =C(H)— | 0 |
| Br | Cl | CF₃ | H | =C(H)— | 0 |
| I | Cl | CF₃ | H | =C(H)— | 0 |

TABLE 14

| R³ | R⁵ | R⁶ | R⁷ | A² | n |
|---|---|---|---|---|---|
| Me | Cl | CF₃ | H | =C(H)— | 0 |
| Et | Cl | CF₃ | H | =C(H)— | 0 |
| Pr | Cl | CF₃ | H | =C(H)— | 0 |
| MeO | Cl | CF₃ | H | =C(H)— | 0 |
| EtO | Cl | CF₃ | H | =C(H)— | 0 |
| PrO | Cl | CF₃ | H | =C(H)— | 0 |
| CF₃CH₂O | Cl | CF₃ | H | =C(H)— | 0 |
| iPrO | Cl | CF₃ | H | =C(H)— | 0 |
| MeS | Cl | CF₃ | H | =C(H)— | 0 |
| EtS | Cl | CF₃ | H | =C(H)— | 0 |
| PrS | Cl | CF₃ | H | =C(H)— | 0 |
| CF₃CH₂S | Cl | CF₃ | H | =C(H)— | 0 |
| iPrS | Cl | CF₃ | H | =C(H)— | 0 |
| Ph | Cl | CF₃ | H | =C(H)— | 0 |
| 2-Py | Cl | CF₃ | H | =C(H)— | 0 |
| 3-Py | Cl | CF₃ | H | =C(H)— | 0 |
| 4-Py | Cl | CF₃ | H | =C(H)— | 0 |
| 1-Tz | Cl | CF₃ | H | =C(H)— | 0 |
| 1-Pz | Cl | CF₃ | H | =C(H)— | 0 |
| H | Cl | CF₃ | H | =C(H)— | 1 |
| Cl | Cl | CF₃ | H | =C(H)— | 1 |
| Br | Cl | CF₃ | H | =C(H)— | 1 |
| I | Cl | CF₃ | H | =C(H)— | 1 |
| Me | Cl | CF₃ | H | =C(H)— | 1 |

TABLE 15

| R³ | R⁵ | R⁶ | R⁷ | A² | n |
|---|---|---|---|---|---|
| Et | Cl | CF₃ | H | =C(H)— | 1 |
| Pr | Cl | CF₃ | H | =C(H)— | 1 |
| MeO | Cl | CF₃ | H | =C(H)— | 1 |
| EtO | Cl | CF₃ | H | =C(H)— | 1 |
| PrO | Cl | CF₃ | H | =C(H)— | 1 |
| CF₃CH₂O | Cl | CF₃ | H | =C(H)— | 1 |
| iPrO | Cl | CF₃ | H | =C(H)— | 1 |
| Ph | Cl | CF₃ | H | =C(H)— | 1 |
| H | H | CF₃ | Cl | =C(H)— | 0 |
| F | H | CF₃ | Cl | =C(H)— | 0 |
| Cl | H | CF₃ | Cl | =C(H)— | 0 |
| Br | H | CF₃ | Cl | =C(H)— | 0 |
| I | H | CF₃ | Cl | =C(H)— | 0 |
| Me | H | CF₃ | Cl | =C(H)— | 0 |
| Et | H | CF₃ | Cl | =C(H)— | 0 |
| Pr | H | CF₃ | Cl | =C(H)— | 0 |
| MeO | H | CF₃ | Cl | =C(H)— | 0 |
| EtO | H | CF₃ | Cl | =C(H)— | 0 |
| PrO | H | CF₃ | Cl | =C(H)— | 0 |
| CF₃CH₂O | H | CF₃ | Cl | =C(H)— | 0 |
| iPrO | H | CF₃ | Cl | =C(H)— | 0 |
| MeS | H | CF₃ | Cl | =C(H)— | 0 |
| EtS | H | CF₃ | Cl | =C(H)— | 0 |
| PrS | H | CF₃ | Cl | =C(H)— | 0 |

TABLE 16

| R³ | R⁵ | R⁶ | R⁷ | A² | n |
|---|---|---|---|---|---|
| CF₃CH₂S | H | CF₃ | Cl | =C(H)— | 0 |
| iPrS | H | CF₃ | Cl | =C(H)— | 0 |
| Ph | H | CF₃ | Cl | =C(H)— | 0 |
| 2-Py | H | CF₃ | Cl | =C(H)— | 0 |
| 3-Py | H | CF₃ | Cl | =C(H)— | 0 |
| 4-Py | H | CF₃ | Cl | =C(H)— | 0 |
| 1-Tz | H | CF₃ | Cl | =C(H)— | 0 |
| 1-Pz | H | CF₃ | Cl | =C(H)— | 0 |
| H | H | CF₃ | Cl | =C(H)— | 1 |
| Cl | H | CF₃ | Cl | =C(H)— | 1 |
| Br | H | CF₃ | Cl | =C(H)— | 1 |
| I | H | CF₃ | Cl | =C(H)— | 1 |
| Me | H | CF₃ | Cl | =C(H)— | 1 |
| Et | H | CF₃ | Cl | =C(H)— | 1 |
| Pr | H | CF₃ | Cl | =C(H)— | 1 |
| MeO | H | CF₃ | Cl | =C(H)— | 1 |
| EtO | H | CF₃ | Cl | =C(H)— | 1 |
| PrO | H | CF₃ | Cl | =C(H)— | 1 |
| CF₃CH₂O | H | CF₃O | H | =C(H)— | 1 |
| iPrO | H | CF₃O | H | =C(H)— | 1 |
| Ph | H | CF₃O | H | =C(H)— | 1 |
| H | H | CF₃O | H | =C(H)— | 0 |
| F | H | CF₃O | H | =C(H)— | 0 |
| Cl | H | CF₃O | H | =C(H)— | 0 |

TABLE 17

| R³ | R⁵ | R⁶ | R⁷ | A² | n |
|---|---|---|---|---|---|
| Br | H | CF₃O | H | =C(H)— | 0 |
| I | H | CF₃O | H | =C(H)— | 0 |
| Me | H | CF₃O | H | =C(H)— | 0 |
| Et | H | CF₃O | H | =C(H)— | 0 |
| Pr | H | CF₃O | H | =C(H)— | 0 |
| MeO | H | CF₃O | H | =C(H)— | 0 |
| EtO | H | CF₃O | H | =C(H)— | 0 |
| PrO | H | CF₃O | H | =C(H)— | 0 |
| CF₃CH₂O | H | CF₃O | H | =C(H)— | 0 |
| iPrO | H | CF₃O | H | =C(H)— | 0 |
| MeS | H | CF₃O | H | =C(H)— | 0 |
| EtS | H | CF₃O | H | =C(H)— | 0 |
| PrS | H | CF₃O | H | =C(H)— | 0 |
| CF₃CH₂S | H | CF₃O | H | =C(H)— | 0 |
| iPrS | H | CF₃O | H | =C(H)— | 0 |
| Ph | H | CF₃O | H | =C(H)— | 0 |
| 2-Py | H | CF₃O | H | =C(H)— | 0 |
| 3-Py | H | CF₃O | H | =C(H)— | 0 |
| 4-Py | H | CF₃O | H | =C(H)— | 0 |
| 1-Tz | H | CF₃O | H | =C(H)— | 0 |
| 1-Pz | H | CF₃O | H | =C(H)— | 0 |
| H | H | CF₃O | H | =C(H)— | 1 |
| Cl | H | CF₃O | H | =C(H)— | 1 |
| Br | H | CF₃O | H | =C(H)— | 1 |

TABLE 18

| R³ | R⁵ | R⁶ | R⁷ | A² | n |
|---|---|---|---|---|---|
| I | H | CF₃O | H | =C(H)— | 1 |
| Me | H | CF₃O | H | =C(H)— | 1 |
| Et | H | CF₃O | H | =C(H)— | 1 |
| Pr | H | CF₃O | H | =C(H)— | 1 |
| MeO | H | CF₃O | H | =C(H)— | 1 |
| EtO | H | CF₃O | H | =C(H)— | 1 |
| PrO | H | CF₃O | H | =C(H)— | 1 |
| CF₃CH₂O | H | CF₃O | H | =C(H)— | 1 |
| iPrO | H | CF₃O | H | =C(H)— | 1 |
| Ph | H | CF₃O | H | =C(H)— | 1 |
| H | H | CF₃S | H | =C(H)— | 0 |
| F | H | CF₃S | H | =C(H)— | 0 |
| Cl | H | CF₃S | H | =C(H)— | 0 |
| Br | H | CF₃S | H | =C(H)— | 0 |
| I | H | CF₃S | H | =C(H)— | 0 |

TABLE 18-continued

| R³ | R⁵ | R⁶ | R⁷ | A² | n |
|---|---|---|---|---|---|
| Me | H | CF₃S | H | =C(H)— | 0 |
| Et | H | CF₃S | H | =C(H)— | 0 |
| Pr | H | CF₃S | H | =C(H)— | 0 |
| MeO | H | CF₃S | H | =C(H)— | 0 |
| EtO | H | CF₃S | H | =C(H)— | 0 |
| PrO | H | CF₃S | H | =C(H)— | 0 |
| CF₃CH₂O | H | CF₃S | H | =C(H)— | 0 |
| iPrO | H | CF₃S | H | =C(H)— | 0 |
| MeS | H | CF₃S | H | =C(H)— | 0 |

TABLE 19

| R³ | R⁵ | R⁶ | R⁷ | A² | n |
|---|---|---|---|---|---|
| EtS | H | CF₃S | H | =C(H)— | 0 |
| PrS | H | CF₃S | H | =C(H)— | 0 |
| CF₃CH₂S | H | CF₃S | H | =C(H)— | 0 |
| iPrS | H | CF₃S | H | =C(H)— | 0 |
| Ph | H | CF₃S | H | =C(H)— | 0 |
| 2-Py | H | CF₃S | H | =C(H)— | 0 |
| 3-Py | H | CF₃S | H | =C(H)— | 0 |
| 4-Py | H | CF₃S | H | =C(H)— | 0 |
| 1-Tz | H | CF₃S | H | =C(H)— | 0 |
| 1-Pz | H | CF₃S | H | =C(H)— | 0 |
| H | —CF₂OCF₂— | | H | =C(H)— | 0 |
| F | —CF₂OCF₂— | | H | =C(H)— | 0 |
| Cl | —CF₂OCF₂— | | H | =C(H)— | 0 |
| Br | —CF₂OCF₂— | | H | =C(H)— | 0 |
| I | —CF₂OCF₂— | | H | =C(H)— | 0 |
| Me | —CF₂OCF₂— | | H | =C(H)— | 0 |
| Et | —CF₂OCF₂— | | H | =C(H)— | 0 |
| Pr | —CF₂OCF₂— | | H | =C(H)— | 0 |
| MeO | —CF₂OCF₂— | | H | =C(H)— | 0 |
| EtO | —CF₂OCF₂— | | H | =C(H)— | 0 |
| PrO | —CF₂OCF₂— | | H | =C(H)— | 0 |
| CF₃CH₂O | —CF₂OCF₂— | | H | =C(H)— | 0 |
| iPrO | —CF₂OCF₂— | | H | =C(H)— | 0 |
| MeS | —CF₂OCF₂— | | H | =C(H)— | 0 |

TABLE 20

| R³ | R⁵ | R⁶ | R⁷ | A² | n |
|---|---|---|---|---|---|
| EtS | —CF₂OCF₂— | | H | =C(H)— | 0 |
| PrS | —CF₂OCF₂— | | H | =C(H)— | 0 |
| CF₃CH₂S | —CF₂OCF₂— | | H | =C(H)— | 0 |
| iPrS | —CF₂OCF₂— | | H | =C(H)— | 0 |
| Ph | —CF₂OCF₂— | | H | =C(H)— | 0 |
| 2-Py | —CF₂OCF₂— | | H | =C(H)— | 0 |
| 3-Py | —CF₂OCF₂— | | H | =C(H)— | 0 |
| 4-Py | —CF₂OCF₂— | | H | =C(H)— | 0 |
| 1-Tz | —CF₂OCF₂— | | H | =C(H)— | 0 |
| 1-Pz | —CF₂OCF₂— | | H | =C(H)— | 0 |
| H | —CF₂OCF₂— | | H | =C(H)— | 1 |
| Cl | —CF₂OCF₂— | | H | =C(H)— | 1 |
| Br | —CF₂OCF₂— | | H | =C(H)— | 1 |
| I | —CF₂OCF₂— | | H | =C(H)— | 1 |
| Me | —CF₂OCF₂— | | H | =C(H)— | 1 |
| Et | —CF₂OCF₂— | | H | =C(H)— | 1 |
| Pr | —CF₂OCF₂— | | H | =C(H)— | 1 |
| MeO | —CF₂OCF₂— | | H | =C(H)— | 1 |
| EtO | —CF₂OCF₂— | | H | =C(H)— | 1 |
| PrO | —CF₂OCF₂— | | H | =C(H)— | 1 |
| CF₃CH₂O | —CF₂OCF₂— | | H | =C(H)— | 1 |
| iPrO | —CF₂OCF₂— | | H | =C(H)— | 1 |
| Ph | —CF₂OCF₂— | | H | =C(H)— | 1 |
| H | —CF₂CH₂CH₂— | | H | =C(H)— | 0 |

TABLE 21

| R³ | R⁵ | R⁶ | R⁷ | A² | n |
|---|---|---|---|---|---|
| F | —CF₂CH₂CH₂— | | H | =C(H)— | 0 |
| Cl | —CF₂CH₂CH₂— | | H | =C(H)— | 0 |
| Br | —CF₂CH₂CH₂— | | H | =C(H)— | 0 |
| I | —CF₂CH₂CH₂— | | H | =C(H)— | 0 |
| Me | —CF₂CH₂CH₂— | | H | =C(H)— | 0 |
| Et | —CF₂CH₂CH₂— | | H | =C(H)— | 0 |
| Pr | —CF₂CH₂CH₂— | | H | =C(H)— | 0 |
| MeO | —CF₂CH₂CH₂— | | H | =C(H)— | 0 |
| EtO | —CF₂CH₂CH₂— | | H | =C(H)— | 0 |
| PrO | —CF₂CH₂CH₂— | | H | =C(H)— | 0 |
| CF₃CH₂O | —CF₂CH₂CH₂— | | H | =C(H)— | 0 |
| iPrO | —CF₂CH₂CH₂— | | H | =C(H)— | 0 |
| MeS | —CF₂CH₂CH₂— | | H | =C(H)— | 0 |
| EtS | —CF₂CH₂CH₂— | | H | =C(H)— | 0 |
| PrS | —CF₂CH₂CH₂— | | H | =C(H)— | 0 |
| CF₃CH₂S | —CF₂CH₂CH₂— | | H | =C(H)— | 0 |
| iPrS | —CF₂CH₂CH₂— | | H | =C(H)— | 0 |
| Ph | —CF₂CH₂CH₂— | | H | =C(H)— | 0 |
| 2-Py | —CF₂CH₂CH₂— | | H | =C(H)— | 0 |
| 3-Py | —CF₂CH₂CH₂— | | H | =C(H)— | 0 |
| 4-Py | —CF₂CH₂CH₂— | | H | =C(H)— | 0 |
| 1-Tz | —CF₂CH₂CH₂— | | H | =C(H)— | 0 |
| 1-Pz | —CF₂CH₂CH₂— | | H | =C(H)— | 0 |
| H | —CF₂CH₂O— | | H | =C(H)— | 0 |

TABLE 22

| R³ | R⁵ | R⁶ | R⁷ | A² | n |
|---|---|---|---|---|---|
| F | —CF₂CH₂O— | | H | =C(H)— | 0 |
| Cl | —CF₂CH₂O— | | H | =C(H)— | 0 |
| Br | —CF₂CH₂O— | | H | =C(H)— | 0 |
| I | —CF₂CH₂O— | | H | =C(H)— | 0 |
| Me | —CF₂CH₂O— | | H | =C(H)— | 0 |
| Et | —CF₂CH₂O— | | H | =C(H)— | 0 |
| Pr | —CF₂CH₂O— | | H | =C(H)— | 0 |
| MeO | —CF₂CH₂O— | | H | =C(H)— | 0 |
| EtO | —CF₂CH₂O— | | H | =C(H)— | 0 |
| PrO | —CF₂CH₂O— | | H | =C(H)— | 0 |
| CF₃CH₂O | —CF₂CH₂O— | | H | =C(H)— | 0 |
| iPrO | —CF₂CH₂O— | | H | =C(H)— | 0 |
| MeS | —CF₂CH₂O— | | H | =C(H)— | 0 |
| EtS | —CF₂CH₂O— | | H | =C(H)— | 0 |
| PrS | —CF₂CH₂O— | | H | =C(H)— | 0 |
| CF₃CH₂S | —CF₂CH₂O— | | H | =C(H)— | 0 |
| iPrS | —CF₂CH₂O— | | H | =C(H)— | 0 |
| Ph | —CF₂CH₂O— | | H | =C(H)— | 0 |
| 2-Py | —CF₂CH₂O— | | H | =C(H)— | 0 |
| 3-Py | —CF₂CH₂O— | | H | =C(H)— | 0 |
| 4-Py | —CF₂CH₂O— | | H | =C(H)— | 0 |
| 1-Tz | —CF₂CH₂O— | | H | =C(H)— | 0 |
| 1-Pz | —CF₂CH₂O— | | H | =C(H)— | 0 |
| H | —CH₂CH₂CF₂— | | H | =C(H)— | 0 |

TABLE 23

| R³ | R⁵ | R⁶ | R⁷ | A² | n |
|---|---|---|---|---|---|
| F | —CH₂CH₂CF₂— | | H | =C(H)— | 0 |
| Cl | —CH₂CH₂CF₂— | | H | =C(H)— | 0 |
| Br | —CH₂CH₂CF₂— | | H | =C(H)— | 0 |
| I | —CH₂CH₂CF₂— | | H | =C(H)— | 0 |
| Me | —CH₂CH₂CF₂— | | H | =C(H)— | 0 |
| Et | —CH₂CH₂CF₂— | | H | =C(H)— | 0 |
| Pr | —CH₂CH₂CF₂— | | H | =C(H)— | 0 |
| MeO | —CH₂CH₂CF₂— | | H | =C(H)— | 0 |
| EtO | —CH₂CH₂CF₂— | | H | =C(H)— | 0 |
| PrO | —CH₂CH₂CF₂— | | H | =C(H)— | 0 |
| CF₃CH₂O | —CH₂CH₂CF₂— | | H | =C(H)— | 0 |
| iPrO | —CH₂CH₂CF₂— | | H | =C(H)— | 0 |
| MeS | —CH₂CH₂CF₂— | | H | =C(H)— | 0 |
| EtS | —CH₂CH₂CF₂— | | H | =C(H)— | 0 |
| PrS | —CH₂CH₂CF₂— | | H | =C(H)— | 0 |

TABLE 23-continued

| R³ | R⁵ | R⁶ | R⁷ | A² | n |
|---|---|---|---|---|---|
| CF₃CH₂S | —CH₂CH₂CF₂— | | H | =C(H)— | 0 |
| iPrS | —CH₂CH₂CF₂— | | H | =C(H)— | 0 |
| Ph | —CH₂CH₂CF₂— | | H | =C(H)— | 0 |
| 2-Py | —CH₂CH₂CF₂— | | H | =C(H)— | 0 |
| 3-Py | —CH₂CH₂CF₂— | | H | =C(H)— | 0 |
| 4-Py | —CH₂CH₂CF₂— | | H | =C(H)— | 0 |
| 1-Tz | —CH₂CH₂CF₂— | | H | =C(H)— | 0 |
| 1-Pz | —CH₂CH₂CF₂— | | H | =C(H)— | 0 |
| H | —CF₂CH₂CH₂CH₂— | | H | =C(H)— | 0 |

TABLE 24

| R³ | R⁵ | R⁶ | R⁷ | A² | n |
|---|---|---|---|---|---|
| F | —CF₂CH₂CH₂CH₂— | | H | =C(H)— | 0 |
| Cl | —CF₂CH₂CH₂CH₂— | | H | =C(H)— | 0 |
| Br | —CF₂CH₂CH₂CH₂— | | H | =C(H)— | 0 |
| I | —CF₂CH₂CH₂CH₂— | | H | =C(H)— | 0 |
| Me | —CF₂CH₂CH₂CH₂— | | H | =C(H)— | 0 |
| Et | —CF₂CH₂CH₂CH₂— | | H | =C(H)— | 0 |
| Pr | —CF₂CH₂CH₂CH₂— | | H | =C(H)— | 0 |
| MeO | —CF₂CH₂CH₂CH₂— | | H | =C(H)— | 0 |
| EtO | —CF₂CH₂CH₂CH₂— | | H | =C(H)— | 0 |
| PrO | —CF₂CH₂CH₂CH₂— | | H | =C(H)— | 0 |
| CF₃CH₂O | —CF₂CH₂CH₂CH₂— | | H | =C(H)— | 0 |
| iPrO | —CF₂CH₂CH₂CH₂— | | H | =C(H)— | 0 |
| MeS | —CF₂CH₂CH₂CH₂— | | H | =C(H)— | 0 |
| EtS | —CF₂CH₂CH₂CH₂— | | H | =C(H)— | 0 |
| PrS | —CF₂CH₂CH₂CH₂— | | H | =C(H)— | 0 |
| CF₃CH₂S | —CF₂CH₂CH₂CH₂— | | H | =C(H)— | 0 |
| iPrS | —CF₂CH₂CH₂CH₂— | | H | =C(H)— | 0 |
| Ph | —CF₂CH₂CH₂CH₂— | | H | =C(H)— | 0 |
| 2-Py | —CF₂CH₂CH₂CH₂— | | H | =C(H)— | 0 |
| 3-Py | —CF₂CH₂CH₂CH₂— | | H | =C(H)— | 0 |
| 4-Py | —CF₂CH₂CH₂CH₂— | | H | =C(H)— | 0 |
| 1-Tz | —CF₂CH₂CH₂CH₂— | | H | =C(H)— | 0 |
| 1-Pz | —CF₂CH₂CH₂CH₂— | | H | =C(H)— | 0 |
| H | —CF₂CH₂CH₂O— | | H | =C(H)— | 0 |

TABLE 25

| R³ | R⁵ | R⁶ | R⁷ | A² | n |
|---|---|---|---|---|---|
| F | —CF₂CH₂CH₂O— | | H | =C(H)— | 0 |
| Cl | —CF₂CH₂CH₂O— | | H | =C(H)— | 0 |
| Br | —CF₂CH₂CH₂O— | | H | =C(H)— | 0 |
| I | —CF₂CH₂CH₂O— | | H | =C(H)— | 0 |
| Me | —CF₂CH₂CH₂O— | | H | =C(H)— | 0 |
| Et | —CF₂CH₂CH₂O— | | H | =C(H)— | 0 |
| Pr | —CF₂CH₂CH₂O— | | H | =C(H)— | 0 |
| MeO | —CF₂CH₂CH₂O— | | H | =C(H)— | 0 |
| EtO | —CF₂CH₂CH₂O— | | H | =C(H)— | 0 |
| PrO | —CF₂CH₂CH₂O— | | H | =C(H)— | 0 |
| CF₃CH₂O | —CF₂CH₂CH₂O— | | H | =C(H)— | 0 |
| iPrO | —CF₂CH₂CH₂O— | | H | =C(H)— | 0 |
| MeS | —CF₂CH₂CH₂O— | | H | =C(H)— | 0 |
| EtS | —CF₂CH₂CH₂O— | | H | =C(H)— | 0 |
| PrS | —CF₂CH₂CH₂O— | | H | =C(H)— | 0 |
| CF₃CH₂S | —CF₂CH₂CH₂O— | | H | =C(H)— | 0 |
| iPrS | —CF₂CH₂CH₂O— | | H | =C(H)— | 0 |
| Ph | —CF₂CH₂CH₂O— | | H | =C(H)— | 0 |
| 2-Py | —CF₂CH₂CH₂O— | | H | =C(H)— | 0 |
| 3-Py | —CF₂CH₂CH₂O— | | H | =C(H)— | 0 |
| 4-Py | —CF₂CH₂CH₂O— | | H | =C(H)— | 0 |
| 1-Tz | —CF₂CH₂CH₂O— | | H | =C(H)— | 0 |
| 1-Pz | —CF₂CH₂CH₂O— | | H | =C(H)— | 0 |
| H | —CH₂CH₂CH₂CF₂— | | H | =C(H)— | 0 |

TABLE 26

| R³ | R⁵ | R⁶ | R⁷ | A² | n |
|---|---|---|---|---|---|
| F | —CH₂CH₂CH₂CF₂— | | H | =C(H)— | 0 |
| Cl | —CH₂CH₂CH₂CF₂— | | H | =C(H)— | 0 |
| Br | —CH₂CH₂CH₂CF₂— | | H | =C(H)— | 0 |
| I | —CH₂CH₂CH₂CF₂— | | H | =C(H)— | 0 |
| Me | —CH₂CH₂CH₂CF₂— | | H | =C(H)— | 0 |
| Et | —CH₂CH₂CH₂CF₂— | | H | =C(H)— | 0 |
| Pr | —CH₂CH₂CH₂CF₂— | | H | =C(H)— | 0 |
| MeO | —CH₂CH₂CH₂CF₂— | | H | =C(H)— | 0 |
| EtO | —CH₂CH₂CH₂CF₂— | | H | =C(H)— | 0 |
| PrO | —CH₂CH₂CH₂CF₂— | | H | =C(H)— | 0 |
| CF₃CH₂O | —CH₂CH₂CH₂CF₂— | | H | =C(H)— | 0 |
| iPrO | —CH₂CH₂CH₂CF₂— | | H | =C(H)— | 0 |
| MeS | —CH₂CH₂CH₂CF₂— | | H | =C(H)— | 0 |
| EtS | —CH₂CH₂CH₂CF₂— | | H | =C(H)— | 0 |
| PrS | —CH₂CH₂CH₂CF₂— | | H | =C(H)— | 0 |
| CF₃CH₂S | —CH₂CH₂CH₂CF₂— | | H | =C(H)— | 0 |
| iPrS | —CH₂CH₂CH₂CF₂— | | H | =C(H)— | 0 |
| Ph | —CH₂CH₂CH₂CF₂— | | H | =C(H)— | 0 |
| 2-Py | —CH₂CH₂CH₂CF₂— | | H | =C(H)— | 0 |
| 3-Py | —CH₂CH₂CH₂CF₂— | | H | =C(H)— | 0 |
| 4-Py | —CH₂CH₂CH₂CF₂— | | H | =C(H)— | 0 |
| 1-Tz | —CH₂CH₂CH₂CF₂— | | H | =C(H)— | 0 |
| 1-Pz | —CH₂CH₂CH₂CF₂— | | H | =C(H)— | 0 |
| H | —OCH₂CH₂CF₂— | | H | =C(H)— | 0 |

TABLE 27

| R³ | R⁵ | R⁶ | R⁷ | A² | n |
|---|---|---|---|---|---|
| F | —OCH₂CH₂CF₂— | | H | =C(H)— | 0 |
| Cl | —OCH₂CH₂CF₂— | | H | =C(H)— | 0 |
| Br | —OCH₂CH₂CF₂— | | H | =C(H)— | 0 |
| I | —OCH₂CH₂CF₂— | | H | =C(H)— | 0 |
| Me | —OCH₂CH₂CF₂— | | H | =C(H)— | 0 |
| Et | —OCH₂CH₂CF₂— | | H | =C(H)— | 0 |
| Pr | —OCH₂CH₂CF₂— | | H | =C(H)— | 0 |
| MeO | —OCH₂CH₂CF₂— | | H | =C(H)— | 0 |
| EtO | —OCH₂CH₂CF₂— | | H | =C(H)— | 0 |
| PrO | —OCH₂CH₂CF₂— | | H | =C(H)— | 0 |
| CF₃CH₂O | —OCH₂CH₂CF₂— | | H | =C(H)— | 0 |
| iPrO | —OCH₂CH₂CF₂— | | H | =C(H)— | 0 |
| MeS | —OCH₂CH₂CF₂— | | H | =C(H)— | 0 |
| EtS | —OCH₂CH₂CF₂— | | H | =C(H)— | 0 |
| PrS | —OCH₂CH₂CF₂— | | H | =C(H)— | 0 |
| CF₃CH₂S | —OCH₂CH₂CF₂— | | H | =C(H)— | 0 |
| iPrS | —OCH₂CH₂CF₂— | | H | =C(H)— | 0 |
| Ph | —OCH₂CH₂CF₂— | | H | =C(H)— | 0 |
| 2-Py | —OCH₂CH₂CF₂— | | H | =C(H)— | 0 |
| 3-Py | —OCH₂CH₂CF₂— | | H | =C(H)— | 0 |
| 4-Py | —OCH₂CH₂CF₂— | | H | =C(H)— | 0 |
| 1-Tz | —OCH₂CH₂CF₂— | | H | =C(H)— | 0 |
| 1-Pz | —OCH₂CH₂CF₂— | | H | =C(H)— | 0 |

TABLE 28

| R³ | R⁵ | R⁶ | R⁷ | A² | n |
|---|---|---|---|---|---|
| CH₃OCH₂ | tBu | H | H | =C(H)— | 0 |
| CHF₂CH₂O | tBu | H | H | =C(H)— | 0 |
| MeS(O) | tBu | H | H | =C(H)— | 0 |
| MeS(O)₂ | tBu | H | H | =C(H)— | 0 |
| EtS(O) | tBu | H | H | =C(H)— | 0 |
| EtS(O)₂ | tBu | H | H | =C(H)— | 0 |
| PrS(O) | tBu | H | H | =C(H)— | 0 |
| PrS(O)₂ | tBu | H | H | =C(H)— | 0 |
| CHF₂CH₂S | tBu | H | H | =C(H)— | 0 |
| iPrS(O) | tBu | H | H | =C(H)— | 0 |
| iPrS(O)₂ | tBu | H | H | =C(H)— | 0 |
| CF₃ | tBu | H | H | =C(H)— | 0 |
| CH₃OCH₂ | CF₃ | H | H | =C(H)— | 0 |
| CHF₂CH₂O | CF₃ | H | H | =C(H)— | 0 |
| MeS(O) | CF₃ | H | H | =C(H)— | 0 |
| MeS(O)₂ | CF₃ | H | H | =C(H)— | 0 |

TABLE 28-continued

| R³ | R⁵ | R⁶ | R⁷ | A² | n |
|---|---|---|---|---|---|
| EtS(O) | CF₃ | H | H | =C(H)— | 0 |
| EtS(O)₂ | CF₃ | H | H | =C(H)— | 0 |
| PrS(O) | CF₃ | H | H | =C(H)— | 0 |
| PrS(O)₂ | CF₃ | H | H | =C(H)— | 0 |
| CHF₂CH₂S | CF₃ | H | H | =C(H)— | 0 |
| iPrS(O) | CF₃ | H | H | =C(H)— | 0 |
| iPrS(O)₂ | CF₃ | H | H | =C(H)— | 0 |
| CF₃ | CF₃ | H | H | =C(H)— | 0 |

TABLE 29

| R³ | R⁵ | R⁶ | R⁷ | A² | n |
|---|---|---|---|---|---|
| CH₃OCH₂ | CF₃O | H | H | =C(H)— | 0 |
| CHF₂CH₂O | CF₃O | H | H | =C(H)— | 0 |
| MeS(O) | CF₃O | H | H | =C(H)— | 0 |
| MeS(O)₂ | CF₃O | H | H | =C(H)— | 0 |
| EtS(O) | CF₃O | H | H | =C(H)— | 0 |
| EtS(O)₂ | CF₃O | H | H | =C(H)— | 0 |
| PrS(O) | CF₃O | H | H | =C(H)— | 0 |
| PrS(O)₂ | CF₃O | H | H | =C(H)— | 0 |
| CHF₂CH₂S | CF₃O | H | H | =C(H)— | 0 |
| iPrS(O) | CF₃O | H | H | =C(H)— | 0 |
| iPrS(O)₂ | CF₃O | H | H | =C(H)— | 0 |
| CF₃ | CF₃O | H | H | =C(H)— | 0 |
| CH₃OCH₂ | CF₃ | H | H | =N— | 0 |
| CHF₂CH₂O | CF₃ | H | H | =N— | 0 |
| MeS(O) | CF₃ | H | H | =N— | 0 |
| MeS(O)₂ | CF₃ | H | H | =N— | 0 |
| EtS(O) | CF₃ | H | H | =N— | 0 |
| EtS(O)₂ | CF₃ | H | H | =N— | 0 |
| PrS(O) | CF₃ | H | H | =N— | 0 |
| PrS(O)₂ | CF₃ | H | H | =N— | 0 |
| CHF₂CH₂S | CF₃ | H | H | =N— | 0 |
| iPrS(O) | CF₃ | H | H | =N— | 0 |
| iPrS(O)₂ | CF₃ | H | H | =N— | 0 |
| CF₃ | CF₃ | H | H | =N— | 0 |

TABLE 30

| R³ | R⁵ | R⁶ | R⁷ | A² | n |
|---|---|---|---|---|---|
| CH₃OCH₂ | H | tBu | H | =C(H)— | 0 |
| CHF₂CH₂O | H | tBu | H | =C(H)— | 0 |
| MeS(O) | H | tBu | H | =C(H)— | 0 |
| MeS(O)₂ | H | tBu | H | =C(H)— | 0 |
| EtS(O) | H | tBu | H | =C(H)— | 0 |
| EtS(O)2 | H | tBu | H | =C(H)— | 0 |
| PrS(O) | H | tBu | H | =C(H)— | 0 |
| PrS(O)₂ | H | tBu | H | =C(H)— | 0 |
| CHF₂CH₂S | H | tBu | H | =C(H)— | 0 |
| iPrS(O) | H | tBu | H | =C(H)— | 0 |
| iPrS(O)₂ | H | tBu | H | =C(H)— | 0 |
| CF₃ | H | tBu | H | =C(H)— | 0 |
| CH₃OCH₂ | H | CF₃ | H | =C(H)— | 0 |
| CHF₂CH₂O | H | CF₃ | H | =C(H)— | 0 |
| MeS(O) | H | CF₃ | H | =C(H)— | 0 |
| MeS(O)₂ | H | CF₃ | H | =C(H)— | 0 |
| EtS(O) | H | CF₃ | H | =C(H)— | 0 |
| EtS(O)₂ | H | CF₃ | H | =C(H)— | 0 |
| PrS(O) | H | CF₃ | H | =C(H)— | 0 |
| PrS(O)₂ | H | CF₃ | H | =C(H)— | 0 |
| CHF₂CH₂S | H | CF₃ | H | =C(H)— | 0 |
| iPrS(O) | H | CF₃ | H | =C(H)— | 0 |
| iPrS(O)₂ | H | CF₃ | H | =C(H)— | 0 |
| CF₃ | H | CF₃ | H | =C(H)— | 0 |

TABLE 31

| R³ | R⁵ | R⁶ | R⁷ | A² | n |
|---|---|---|---|---|---|
| CH₃OCH₂ | H | CF₃O | H | =C(H)— | 0 |
| CHF₂CH₂O | H | CF₃O | H | =C(H)— | 0 |
| MeS(O) | H | CF₃O | H | =C(H)— | 0 |
| MeS(O)₂ | H | CF₃O | H | =C(H)— | 0 |
| EtS(O) | H | CF₃O | H | =C(H)— | 0 |
| EtS(O)₂ | H | CF₃O | H | =C(H)— | 0 |
| PrS(O) | H | CF₃O | H | =C(H)— | 0 |
| PrS(O)₂ | H | CF₃O | H | =C(H)— | 0 |
| CHF₂CH₂S | H | CF₃O | H | =C(H)— | 0 |
| iPrS(O) | H | CF₃O | H | =C(H)— | 0 |
| iPrS(O)₂ | H | CF₃O | H | =C(H)— | 0 |
| CF₃ | H | CF₃O | H | =C(H)— | 0 |
| CH₃OCH₂ | tBu | H | H | =N— | 0 |
| CHF₂CH₂O | tBu | H | H | =N— | 0 |
| MeS(O) | tBu | H | H | =N— | 0 |
| MeS(O)₂ | tBu | H | H | =N— | 0 |
| EtS(O) | tBu | H | H | =N— | 0 |
| EtS(O)₂ | tBu | H | H | =N— | 0 |
| PrS(O) | tBu | H | H | =N— | 0 |
| PrS(O)₂ | tBu | H | H | =N— | 0 |
| CHF₂CH₂S | tBu | H | H | =N— | 0 |
| iPrS(O) | tBu | H | H | =N— | 0 |
| iPrS(O)₂ | tBu | H | H | =N— | 0 |
| CF₃ | tBu | H | H | =N— | 0 |

TABLE 32

| R³ | R⁵ | R⁶ | R⁷ | A² | n |
|---|---|---|---|---|---|
| H | tBu | H | H | =N— | 0 |
| F | tBu | H | H | =N— | 0 |
| Cl | tBu | H | H | =N— | 0 |
| Br | tBu | H | H | =N— | 0 |
| I | tBu | H | H | =N— | 0 |
| Me | tBu | H | H | =N— | 0 |
| Et | tBu | H | H | =N— | 0 |
| Pr | tBu | H | H | =N— | 0 |
| MeO | tBu | H | H | =N— | 0 |
| EtO | tBu | H | H | =N— | 0 |
| PrO | tBu | H | H | =N— | 0 |
| CF₃CH₂O | tButBu | H | H | =N— | 0 |
| iPrO | tBu | H | H | =N— | 0 |
| MeS | tBu | H | H | =N— | 0 |
| EtS | tBu | H | H | =N— | 0 |
| PrS | tBu | H | H | =N— | 0 |
| CF₃CH₂S | tBu | H | H | =N— | 0 |
| iPrS | tBu | H | H | =N— | 0 |
| CH₃OCH₂ | —CF₂OCF₂— | | H | =C(H)— | 0 |
| CHF₂CH₂O | —CF₂OCF₂— | | H | =C(H)— | 0 |
| MeS(O) | —CF₂OCF₂— | | H | =C(H)— | 0 |
| MeS(O)₂ | —CF₂OCF₂— | | H | =C(H)— | 0 |
| EtS(O) | —CF₂OCF₂— | | H | =C(H)— | 0 |
| EtS(O)₂ | —CF₂OCF₂— | | H | =C(H)— | 0 |

TABLE 33

| R³ | R⁵ | R⁶ | R⁷ | A² | n |
|---|---|---|---|---|---|
| PrS(O) | —CF₂OCF₂— | | H | =C(H)— | 0 |
| PrS(O)₂ | —CF₂OCF₂— | | H | =C(H)— | 0 |
| CHF₂CH₂S | —CF₂OCF₂— | | H | =C(H)— | 0 |
| iPrS(O) | —CF₂OCF₂— | | H | =C(H)— | 0 |
| iPrS(O)₂ | —CF₂OCF₂— | | H | =C(H)— | 0 |
| CF₃ | —CF₂OCF₂— | | H | =C(H)— | 0 |
| H | —OC(CH₃)₂CH₂— | | H | =C(H)— | 0 |
| F | —OC(CH₃)₂CH₂— | | H | =C(H)— | 0 |
| Cl | —OC(CH₃)₂CH₂— | | H | =C(H)— | 0 |
| Br | —OC(CH₃)₂CH₂— | | H | =C(H)— | 0 |
| I | —OC(CH₃)₂CH₂— | | H | =C(H)— | 0 |
| Me | —OC(CH₃)₂CH₂— | | H | =C(H)— | 0 |
| Et | —OC(CH₃)₂CH₂— | | H | =C(H)— | 0 |
| Pr | —OC(CH₃)₂CH₂— | | H | =C(H)— | 0 |
| CH₃OCH₂ | —OC(CH₃)₂CH₂— | | H | =C(H)— | 0 |

TABLE 33-continued

| R³ | R⁵ | R⁶ | R⁷ | A² | n |
|---|---|---|---|---|---|
| MeO | —OC(CH₃)₂CH₂— | | H | =C(H)— | 0 |
| EtO | —OC(CH₃)₂CH₂— | | H | =C(H)— | 0 |
| PrO | —OC(CH₃)₂CH₂— | | H | =C(H)— | 0 |
| CHF₂CH₂O | —OC(CH₃)₂CH₂— | | H | =C(H)— | 0 |
| CF₃CH₂O | —OC(CH₃)₂CH₂— | | H | =C(H)— | 0 |
| iPrO | —OC(CH₃)₂CH₂— | | H | =C(H)— | 0 |
| MeS | —OC(CH₃)₂CH₂— | | H | =C(H)— | 0 |
| MeS(O) | —OC(CH₃)₂CH₂— | | H | =C(H)— | 0 |
| MeS(O)₂ | —OC(CH₃)₂CH₂— | | H | =C(H)— | 0 |

TABLE 34

| R³ | R⁵ | R⁶ | R⁷ | A² | n |
|---|---|---|---|---|---|
| EtS | —OC(CH₃)₂CH₂— | | H | =C(H)— | 0 |
| EtS(O) | —OC(CH₃)₂CH₂— | | H | =C(H)— | 0 |
| EtS(O)₂ | —OC(CH₃)₂CH₂— | | H | =C(H)— | 0 |
| PrS | —OC(CH₃)₂CH₂— | | H | =C(H)— | 0 |
| PrS(O) | —OC(CH₃)₂CH₂— | | H | =C(H)— | 0 |
| PrS(O)₂ | —OC(CH₃)₂CH₂— | | H | =C(H)— | 0 |
| CHF₂CH₂S | —OC(CH₃)₂CH₂— | | H | =C(H)— | 0 |
| CF₃CH₂S | —OC(CH₃)₂CH₂— | | H | =C(H)— | 0 |
| iPr | —OC(CH₃)₂CH₂— | | H | =C(H)— | 0 |
| iPrS(O) | —OC(CH₃)₂CH₂— | | H | =C(H)— | 0 |
| iPrS(O)₂ | —OC(CH₃)₂CH₂— | | H | =C(H)— | 0 |
| CF₃ | —OC(CH₃)₂CH₂— | | H | =C(H)— | 0 |
| H | —CH₂C(CH₃)₂O— | | H | =C(H)— | 0 |
| F | —CH₂C(CH₃)₂O— | | H | =C(H)— | 0 |
| Cl | —CH₂C(CH₃)₂O— | | H | =C(H)— | 0 |
| Br | —CH₂C(CH₃)₂O— | | H | =C(H)— | 0 |
| I | —CH₂C(CH₃)₂O— | | H | =C(H)— | 0 |
| Me | —CH₂C(CH₃)₂O— | | H | =C(H)— | 0 |
| Et | —CH₂C(CH₃)₂O— | | H | =C(H)— | 0 |
| Pr | —CH₂C(CH₃)₂O— | | H | =C(H)— | 0 |
| CH₃OCH₂ | —CH₂C(CH₃)₂O— | | H | =C(H)— | 0 |
| MeO | —CH₂C(CH₃)₂O— | | H | =C(H)— | 0 |
| EtO | —CH₂C(CH₃)₂O— | | H | =C(H)— | 0 |
| PrO | —CH₂C(CH₃)₂O— | | H | =C(H)— | 0 |

TABLE 35

| R³ | R⁵ | R⁶ | R⁷ | A² | n |
|---|---|---|---|---|---|
| CHF₂CH₂O | —CH₂C(CH₃)₂O— | | H | =C(H)— | 0 |
| CF₃CH₂O | —CH₂C(CH₃)₂O— | | H | =C(H)— | 0 |
| iPrO | —CH₂C(CH₃)₂O— | | H | =C(H)— | 0 |
| MeS | —CH₂C(CH₃)₂O— | | H | =C(H)— | 0 |
| MeS(O) | —CH₂C(CH₃)₂O— | | H | =C(H)— | 0 |
| MeS(O)₂ | —CH₂C(CH₃)₂O— | | H | =C(H)— | 0 |
| EtS | —CH₂C(CH₃)₂O— | | H | =C(H)— | 0 |
| EtS(O) | —CH₂C(CH₃)₂O— | | H | =C(H)— | 0 |
| EtS(O)₂ | —CH₂C(CH₃)₂O— | | H | =C(H)— | 0 |
| PrS | —CH₂C(CH₃)₂O— | | H | =C(H)— | 0 |
| PrS(O) | —CH₂C(CH₃)₂O— | | H | =C(H)— | 0 |
| PrS(O)₂ | —CH₂C(CH₃)₂O— | | H | =C(H)— | 0 |
| CHF₂CH₂S | —CH₂C(CH₃)₂O— | | H | =C(H)— | 0 |
| CF₃CH₂S | —CH₂C(CH₃)₂O— | | H | =C(H)— | 0 |
| iPr | —CH₂C(CH₃)₂O— | | H | =C(H)— | 0 |
| iPrS(O) | —CH₂C(CH₃)₂O— | | H | =C(H)— | 0 |
| iPrS(O)₂ | —CH₂C(CH₃)₂O— | | H | =C(H)— | 0 |
| CF₃ | —CH₂C(CH₃)₂O— | | H | =C(H)— | 0 |

The compound represented by the following formula (1-B):

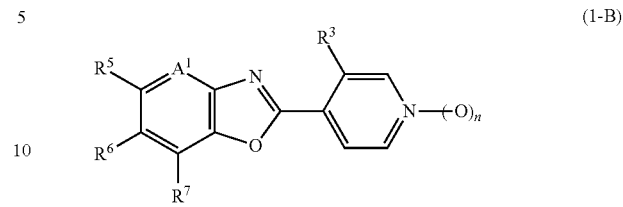

(1-B)

In the above formula (1-B), substituents used for $R^3$, $R^5$, $R^6$, $R^7$, $A^1$, and n are available in the combinations shown in the following (Table 36) to (Table 42).

TABLE 36

| R³ | R⁵ | R⁶ | R⁷ | A¹ | n |
|---|---|---|---|---|---|
| H | CH₃ | H | H | =N— | 0 |
| F | CH₃ | H | H | =N— | 0 |
| Cl | CH₃ | H | H | =N— | 0 |
| Br | CH₃ | H | H | =N— | 0 |
| I | CH₃ | H | H | =N— | 0 |
| Me | CH₃ | H | H | =N— | 0 |
| Et | CH₃ | H | H | =N— | 0 |
| Pr | CH₃ | H | H | =N— | 0 |
| CH₃OCH₂ | CH₃ | H | H | =N— | 0 |
| MeO | CH₃ | H | H | =N— | 0 |
| EtO | CH₃ | H | H | =N— | 0 |
| PrO | CH₃ | H | H | =N— | 0 |
| CHF₂CH₂O | CH₃ | H | H | =N— | 0 |
| CF₃CH₂O | CH₃ | H | H | =N— | 0 |
| iPrO | CH₃ | H | H | =N— | 0 |
| MeS | CH₃ | H | H | =N— | 0 |
| MeS(O) | CH₃ | H | H | =N— | 0 |
| MeS(O)₂ | CH₃ | H | H | =N— | 0 |
| EtS | CH₃ | H | H | =N— | 0 |
| EtS(O) | CH₃ | H | H | =N— | 0 |
| EtS(O)₂ | CH₃ | H | H | =N— | 0 |
| PrS | CH₃ | H | H | =N— | 0 |
| PrS(O) | CH₃ | H | H | =N— | 0 |
| PrS(O)₂ | CH₃ | H | H | =N— | 0 |

TABLE 37

| R³ | R⁵ | R⁶ | R⁷ | A¹ | n |
|---|---|---|---|---|---|
| CHF₂CH₂S | CH₃ | H | H | =N— | 0 |
| CF₃CH₂S | CH₃ | H | H | =N— | 0 |
| iPrS | CH₃ | H | H | =N— | 0 |
| iPrS(O) | CH₃ | H | H | =N— | 0 |
| iPrS(O)₂ | CH₃ | H | H | =N— | 0 |
| CF₃ | CH₃ | H | H | =N— | 0 |
| H | tBu | H | H | =N— | 0 |
| F | tBu | H | H | =N— | 0 |
| Cl | tBu | H | H | =N— | 0 |
| Br | tBu | H | H | =N— | 0 |
| I | tBu | H | H | =N— | 0 |
| Me | tBu | H | H | =N— | 0 |
| Et | tBu | H | H | =N— | 0 |
| Pr | tBu | H | H | =N— | 0 |
| CH₃OCH₂ | tBu | H | H | =N— | 0 |
| MeO | tBu | H | H | =N— | 0 |
| EtO | tBu | H | H | =N— | 0 |
| PrO | tBu | H | H | =N— | 0 |
| CHF₂CH₂O | tBu | H | H | =N— | 0 |
| CF₃CH₂O | tBu | H | H | =N— | 0 |
| iPrO | tBu | H | H | =N— | 0 |
| MeS | tBu | H | H | =N— | 0 |
| MeS(O) | tBu | H | H | =N— | 0 |
| MeS(O)₂ | tBu | H | H | =N— | 0 |

TABLE 38

| $R^3$ | $R^5$ | $R^6$ | $R^7$ | $A^1$ | n |
|---|---|---|---|---|---|
| EtS | tBu | H | H | =N— | 0 |
| EtS(O) | tBu | H | H | =N— | 0 |
| EtS(O)$_2$ | tBu | H | H | =N— | 0 |
| PrS | tBu | H | H | =N— | 0 |
| PrS(O) | tBu | H | H | =N— | 0 |
| PrS(O)$_2$ | tBu | H | H | =N— | 0 |
| CHF$_2$CH$_2$S | tBu | H | H | =N— | 0 |
| CF$_3$CH$_2$S | tBu | H | H | =N— | 0 |
| iPrS | tBu | H | H | =N— | 0 |
| iPrS(O) | tBu | H | H | =N— | 0 |
| iPrS(O)$_2$ | tBu | H | H | =N— | 0 |
| CF$_3$ | tBu | H | H | =N— | 0 |
| H | CF$_3$ | H | H | =N— | 0 |
| F | CF$_3$ | H | H | =N— | 0 |
| Cl | CF$_3$ | H | H | =N— | 0 |
| Br | CF$_3$ | H | H | =N— | 0 |
| I | CF$_3$ | H | H | =N— | 0 |
| Me | CF$_3$ | H | H | =N— | 0 |
| Et | CF$_3$ | H | H | =N— | 0 |
| Pr | CF$_3$ | H | H | =N— | 0 |
| CH$_3$OCH$_2$ | CF$_3$ | H | H | =N— | 0 |
| MeO | CF$_3$ | H | H | =N— | 0 |
| EtO | CF$_3$ | H | H | =N— | 0 |
| PrO | CF$_3$ | H | H | =N— | 0 |

TABLE 39

| $R^3$ | $R^5$ | $R^6$ | $R^7$ | $A^1$ | n |
|---|---|---|---|---|---|
| CHF$_2$CH$_2$O | CF$_3$ | H | H | =N— | 0 |
| CF$_3$CH$_2$O | CF$_3$ | H | H | =N— | 0 |
| iPrO | CF$_3$ | H | H | =N— | 0 |
| MeS | CF$_3$ | H | H | =N— | 0 |
| MeS(O) | CF$_3$ | H | H | =N— | 0 |
| MeS(O)$_2$ | CF$_3$ | H | H | =N— | 0 |
| EtS | CF$_3$ | H | H | =N— | 0 |
| EtS(O) | CF$_3$ | H | H | =N— | 0 |
| EtS(O)$_2$ | CF$_3$ | H | H | =N— | 0 |
| PrS | CF$_3$ | H | H | =N— | 0 |
| PrS(O) | CF$_3$ | H | H | =N— | 0 |
| PrS(O)$_2$ | CF$_3$ | H | H | =N— | 0 |
| CHF$_2$CH$_2$S | CF$_3$ | H | H | =N— | 0 |
| CF$_3$CH$_2$S | CF$_3$ | H | H | =N— | 0 |
| iPrS | CF$_3$ | H | H | =N— | 0 |
| iPrS(O) | CF$_3$ | H | H | =N— | 0 |
| iPrS(O)$_2$ | CF$_3$ | H | H | =N— | 0 |
| CF$_3$ | CF$_3$ | H | H | =N— | 0 |
| H | H | tBu | H | =N— | 0 |
| F | H | tBu | H | =N— | 0 |
| Cl | H | tBu | H | =N— | 0 |
| Br | H | tBu | H | =N— | 0 |
| I | H | tBu | H | =N— | 0 |
| Me | H | tBu | H | =N— | 0 |

TABLE 40

| $R^3$ | $R^5$ | $R^6$ | $R^7$ | $A^1$ | n |
|---|---|---|---|---|---|
| Et | H | tBu | H | =N— | 0 |
| Pr | H | tBu | H | =N— | 0 |
| CH$_3$OCH$_2$ | H | tBu | H | =N— | 0 |
| MeO | H | tBu | H | =N— | 0 |
| EtO | H | tBu | H | =N— | 0 |
| PrO | H | tBu | H | =N— | 0 |
| CHF$_2$CH$_2$O | H | tBu | H | =N— | 0 |
| CF$_3$CH$_2$O | H | tBu | H | =N— | 0 |
| iPrO | H | tBu | H | =N— | 0 |
| MeS | H | tBu | H | =N— | 0 |
| MeS(O) | H | tBu | H | =N— | 0 |
| MeS(O)$_2$ | H | tBu | H | =N— | 0 |
| EtS | H | tBu | H | =N— | 0 |
| EtS(O) | H | tBu | H | =N— | 0 |
| EtS(O)$_2$ | H | tBu | H | =N— | 0 |
| PrS | H | tBu | H | =N— | 0 |
| PrS(O) | H | tBu | H | =N— | 0 |
| PrS(O)$_2$ | H | tBu | H | =N— | 0 |
| CHF$_2$CH$_2$S | H | tBu | H | =N— | 0 |
| CF$_3$CH$_2$S | H | tBu | H | =N— | 0 |
| iPrS | H | tBu | H | =N— | 0 |
| iPrS(O) | H | tBu | H | =N— | 0 |
| iPrS(O)$_2$ | H | tBu | H | =N— | 0 |
| CF$_3$ | H | tBu | H | =N— | 0 |

TABLE 41

| $R^3$ | $R^5$ | $R^6$ | $R^7$ | $A^1$ | n |
|---|---|---|---|---|---|
| H | H | CF$_3$ | H | =N— | 0 |
| F | H | CF$_3$ | H | =N— | 0 |
| Cl | H | CF$_3$ | H | =N— | 0 |
| Br | H | CF$_3$ | H | =N— | 0 |
| I | H | CF$_3$ | H | =N— | 0 |
| Me | H | CF$_3$ | H | =N— | 0 |
| Et | H | CF$_3$ | H | =N— | 0 |
| Pr | H | CF$_3$ | H | =N— | 0 |
| CH$_3$OCH$_2$ | H | CF$_3$ | H | =N— | 0 |
| MeO | H | CF$_3$ | H | =N— | 0 |
| EtO | H | CF$_3$ | H | =N— | 0 |
| PrO | H | CF$_3$ | H | =N— | 0 |
| CHF$_2$CH$_2$O | H | CF$_3$ | H | =N— | 0 |
| CF$_3$CH$_2$O | H | CF$_3$ | H | =N— | 0 |
| iPrO | H | CF$_3$ | H | =N— | 0 |
| MeS | H | CF$_3$ | H | =N— | 0 |
| MeS(O) | H | CF$_3$ | H | =N— | 0 |
| MeS(O)$_2$ | H | CF$_3$ | H | =N— | 0 |
| EtS | H | CF$_3$ | H | =N— | 0 |
| EtS(O) | H | CF$_3$ | H | =N— | 0 |
| EtS(O)$_2$ | H | CF$_3$ | H | =N— | 0 |
| PrS | H | CF$_3$ | H | =N— | 0 |
| PrS(O) | H | CF$_3$ | H | =N— | 0 |
| PrS(O)$_2$ | H | CF$_3$ | H | =N— | 0 |

TABLE 42

| $R^3$ | $R^5$ | $R^6$ | $R^7$ | $A^1$ | n |
|---|---|---|---|---|---|
| CHF$_2$CH$_2$S | H | CF$_3$ | H | =N— | 0 |
| CF$_3$CH$_2$S | H | CF$_3$ | H | =N— | 0 |
| iPrS | H | CF$_3$ | H | =N— | 0 |
| iPrS(O) | H | CF$_3$ | H | =N— | 0 |
| iPrS(O)$_2$ | H | CF$_3$ | H | =N— | 0 |
| CF$_3$ | H | CF$_3$ | H | =N— | 0 |

The composition of the present invention comprises the present active compound as an active ingredient.

The composition of the present invention may comprise a single species of the present active compound, or two or more species of the present active compounds. The composition of the present invention preferably comprises one or more and three or less species of the present active compounds.

In general, the composition of the present invention comprises carriers and the like as described later, and they can be a preparation in the form of agrochemicals or animal drugs.

The composition of the present invention can be prepared, for example, as the following formulations according to known methods such as dissolution or dispersion of the present active compound in a suitable liquid carrier, mixing or adsorption of the present active compound with or on a suitable solid carrier or ointment base, or mixing or dispersion of the present active compound with or in a suitable gaseous carrier.

Examples of the formulations include an emulsion, an aqueous liquid agent, a microemulsion, a flowable agent, an oil agent, a wettable powder, a granulated wettable powder, a powder, a granule, a microgranule, a seed coating agent, a seed immersing agent, a fumigant, a tablet, a microcapsule, a spray, an aerosol, a carbon dioxide preparation, heated vaporization agents such as a mosquito coil, an electric mosquito mat or an electric mosquito liquid, an EW agent, an ointment, a toxic bait, a capsule, a pellet, a film, an injection, an embrocation, a resin preparation, and a shampoo.

During the preparation of the present composition, auxiliary agents for formulations such as an emulsifier, a suspending agent, a spreading agent, a penetrant, a wetting agent, a thickener, a stabilizer, a fixer, a binder, a dispersant, or a colorant may be added, as necessary.

The composition of the present invention generally comprises 0.01% to 95% by weight of the present active compound.

Examples of the liquid carrier include: the substances listed in the EPA list (List Nos. 4A and 4B); water; alcohols (e.g. methyl alcohol, ethyl alcohol, n-propyl alcohol, isopropyl alcohol, butyl alcohol, hexyl alcohol, benzyl alcohol, ethylene glycol, propylene glycol, phenoxyethanol, etc.); ketones (e.g. acetone, methyl ethyl ketone, methyl isobutyl ketone, cyclohexanone, etc.); ethers (e.g. diisopropyl ether, 1,4-dioxane, tetrahydrofuran, ethylene glycol monomethyl ether, ethylene glycol dimethyl ether, diethylene glycol monomethyl ether, propylene glycol monomethyl ether, dipropylene glycol monomethyl ether, 3-methoxy-3-methyl-1-butanol, etc.); aliphatic hydrocarbons (e.g. hexane, cyclohexane, kerosine, coal oil, burning oil, machine oil, etc.); aromatic hydrocarbons (e.g. toluene, xylene, ethylbenzene, dodecylbenzene, phenyl xylyl ethane, solvent naphtha, methylnaphthalene, etc.); halogenated hydrocarbons (e.g. dichloromethane, trichloroethane, chloroform, carbon tetrachloride, etc.); acid amides (e.g. N,N-dimethylformamide, N,N-dimethylacetamide, N-methylpyrrolidone, N-octylpyrrolidone, etc.); esters (e.g. butyl lactate, ethyl acetate, butyl acetate, isopropyl myristate, ethyl oleate, diisopropyl adipate, diisobutyl adipate, propylene glycol monomethyl ether acetate, fatty acid glycerin ester, γ-butyrolactone, etc.); nitriles (e.g. acetonitrile, isobutyronitrile, propionitrile, etc.); carbonates (e.g. propylene carbonate, etc.); and vegetable oils (e.g. soybean oil, olive oil, linseed oil, coconut oil, copra oil, peanut oil, wheat germ oil, almond oil, sesame oil, mineral oil, rosemary oil, geranium oil, rapeseed oil, cottonseed oil, corn oil, safflower oil, orange oil, etc.). In the above-mentioned preparation, only a single type of liquid carrier may be used, or two or more types of liquid carriers may also be used. Preferably, one or more types to three or less types of liquid carriers are used. When two or more types of the liquid carriers are used, the liquid carriers may be mixed at an appropriate ratio and may be then used, depending on intended use and the like.

Examples of the solid carrier (diluent/thickener) include: the substances listed in the EPA list (List Nos. 4A and 4B); and micropowders and grains such as vegetable flours (e.g. soybean flour, tobacco flour, wheat flour, wood flour, etc.); mineral powders (e.g. clay such as kaoline clay, Fubasami clay, bentonite or Japanese acid clay; talc such as talcum powder or Roseki powder; silica such as diatomaceous earth or mica powder; etc.); synthetic hydrated silicon oxide; alumina; talc; ceramic; other inorganic minerals (sericite, quarz, sulfur, activated carbon, calcium carbonate, hydrated silica, etc.); and chemical fertilizers (ammonium sulfate, ammonium phosphate, ammonium nitrate, urea, ammonium chloride). In the above-mentioned preparation, only a single type of the solid carrier may be used, or two or more types of the solid carriers may also be used. Preferably, one or more types to three or less types of the solid carriers are used. When two or more types of the solid carriers are used, the solid carriers may be mixed at an appropriate ratio and may be then used, depending on intended use and the like.

Examples of the gaseous carrier include the substances disclosed in the EPA list (List Nos. 4A and 4B), fluorocarbon, butane gas, LPG (liquefied petroleum gas), dimethyl ether, and carbon dioxide. In the above-mentioned preparation, only a single type of the gaseous carrier may be used, or two or more types of the gaseous carriers may also be used. Preferably, one or more types to three or less types of the gaseous carriers are used. When two or more types of the gaseous carriers are used, the gaseous carriers may be mixed at an appropriate ratio and may be then used, depending on intended use and the like. It may also be used in combination with the liquid carrier.

Examples of the ointment base include: the substances disclosed in the EPA list (List Nos. 4A and 4B); polyethylene glycol; pectin; polyhydric alcohol esters of higher fatty acids, such as glycerin monostearate; cellulose derivatives such as methylcellulose; sodium alginate; higher alcohol; polyhydric alcohol such as glycerin; Vaseline; white petrolatum; liquid paraffin; lard; various types of vegetable oils; lanolin; anhydrous lanolin; hydrogenated oil; and resins. In the above-mentioned preparation, only a single type of ointment base may be used, or two or more types of the ointment bases may also be used. Preferably, one or more types to three or less types of the ointment bases are used. When two or more types of the ointment bases are used, the ointment bases may be mixed at an appropriate ratio and may be then used, depending on intended use and the like. Otherwise, the surfactants as described below may be added to the medicament, and may be then used.

In the medicament, a surfactant may be used as an emulsifier, a spreading agent, a penetrant, a dispersant, or the like.

Examples of such surfactant include nonionic and anionic surfactants such as: soaps; polyoxyethylene alkyl aryl ethers [e.g. Noigen (product name), EA142 (product name), manufactured by Dai-Ich Kogyo Seiyaku Co., Ltd; Nonal (product name), manufactured by Toho Chemical Industry Co., Ltd.]; alkyl sulfates [e.g. Emal 10 (product name), Emal 40 (product name), manufactured by Kao Corporation]; alkylbenzene sulfonates [e.g. Neogen (product name), Neogen T (product name), manufactured by Dai-Ichi Kogyo Seiyaku Co., Ltd.; Neoperex, manufactured by Kao Corporation]; polyethylene glycol ethers [e.g. Nonipol 85 (product name), Nonipol 100 (product name), Nonipol 160 (product name), manufactured by Sanyo Chemical Industries Ltd.]; polyoxyethylene alkyl ethers [e.g. Noigen ET-135 (product name), manufactured by Dai-Ich Kogyo Seiyaku Co., Ltd.]; polyoxyethylene-polyoxypropylene block polymers [e.g. Newpol PE-64 (product name), Sanyo Chemical Industries Ltd.]; polyhydric alcohol esters [e.g. Tween 20 (product name), Tween 80 (product name), manufactured by Kao Corporation]; alkyl sulfosuccinates [e.g. Sanmorin OT20 (product name), Sanyo Chemical Industries Ltd.; Newkalgen EX70 (product name), Takemoto Yushi K.K.]; alkyl naphthalene sulfonates [e.g. Newkalgen WG-1 (product name), Takemoto Yushi K.K.]; and alkenyl sulfonates [e.g. Sorpol 5115 (product name), Toho Chemical Co., Ltd.]. One or more types of (preferably one or more types to three or less types of) such surfactants may be mixed at an appropriate ratio and may be then used.

Other specific examples of the auxiliary agent for the medicament include casein, gelatin, sugars (starch, gum Arabic, a cellulose derivative, alginic acid, etc.), a lignin derivative, bentonite, a synthetic water-soluble polymer (polyvinyl alcohol, polyvinylpyrrolidone, polyacrylic acids, etc.), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

The composition of the present invention may also comprise an insecticide, an acaricide, a nematicide, a microbicide, a plant hormone agent, a plant growth-control agent, a herbicide, a synergist or an antidote, in addition to the present active compound.

The content of the present active compound in the composition of the present invention is generally 0.01% to 95% by weight, preferably approximately 0.1% to 90% by weight, and more preferably approximately 5% to 70% by weight, based on the total amount of the composition of the present invention.

Specifically, when the composition of the present invention is in the form of an emulsion, a liquid agent, a wettable powder, or a granule wettable powder, the content of the present active compound is generally approximately 1% to 90% by weight, and preferably approximately 5% to 50% by weight, based on the total amount of the composition of the present invention. When the composition of the present invention is in the form of an oil agent or a powder agent, the content of the present active compound is generally approximately 0.1% to 50% by weight, and preferably approximately 0.1% to 20% by weight, based on the total amount of the composition of the present invention. When the composition of the present invention is in the form of a granule agent, the content of the present active compound is generally approximately 0.1% to 50% by weight, and preferably approximately 0.5% to 20% by weight, based on the total amount of the composition of the present invention.

The content of the other agricultural active ingredient (e.g. an insecticide, a herbicide, an acaricide and/or a microbicide) mixed into the composition of the present invention is preferably approximately 1% to 80% by weight, and more preferably approximately 1% to 20%, based on the total amount of the composition of the present invention.

The content of an additive other than the active ingredient differs depending on the type or content of an agricultural active ingredient, the formulation of a medicament, and the like. It is generally approximately 0.001% to 99.9% by weight, and preferably approximately 1% to 99% by weight, based on the total amount of the composition of the present invention. For example, a surfactant may be added at a percentage of generally approximately 1% to 20% by weight, and preferably approximately 1% to 15% by weight; a flowable agent may be added at a percentage of approximately 1% to 20% by weight; and a carrier may be added at a percentage of approximately 1% to 90% by weight, and preferably approximately 1% to 70% by weight, based on the total amount of the composition of the present invention. When the composition of the present invention is in the form of a liquid agent, a surfactant may be added at a percentage of generally 1% to 20% by weight, and preferably approximately 1% to 10% by weight, and water may be added at a percentage of approximately 20% to 90% by weight, based on the total amount of the composition of the present invention. Moreover, an emulsion, a wettable powder, a granule wettable powder, or the like may be appropriately extended with water or the like (for example, approximately 100 to 5,000 times) before use, and it may be then diffused.

Typical examples of the insecticide, acaricide, nematicide, microbicide, plant hormone agent, plant growth-control agent, herbicide, synergist, and antidote will be given below.

Examples of the insecticides include the following compounds:
(1) Organophosphorus Compounds
acephate, Aluminium phosphide, butathiofos, cadusafos, chlorethoxyfos, chlorfenvinphos, chlorpyrifos, chlorpyrifos-methyl, cyanophos: CYAP, diazinon, dichlorodiisopropyl ether, dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, cadusafos and the like;
(2) Carbamate Compounds
alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, aldicarb and the like;
(3) Synthetic Pyrethroid Compounds
acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzil (EZ)-(1RS,3RS;1RS,3SR)-2,2-dimethyl-3-prop-1-enylcyclopropanecarboxylate, 2,3,5,6-tetrafluoro-4-methylbenzyl (EZ)-(1RS,3RS;1RS,3SR)-2,2-dimethyl-3-prop-1-enylcyclopropanecarboxylate, 2,3,5,6-tetrafluoro-4-(methoxymethyl)benzil (1RS,3RS;1RS,3SR)-2,2-dimethyl-3-(2-methyl-1-propenyl)cyclopropanecarboxylate and the like;
(4) Nereistoxin compounds
cartap, bensultap, thiocyclam, monosultap, bisultap and the like;
(5) Neonicotinoid compounds
imidacloprid, nitenpyram, acetamiprid, thiamethoxam, thiacloprid, dinotefuran, clothianidin and the like;
(6) Benzoylurea compounds
chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron and the like;
(7) Phenylpyrazole compounds
acetoprole, ethiprole, fipronil, vaniliprole, pyriprole, pyrafluprole and the like;
(8) Bt toxin insecticides
Fresh spores derived from *Bacillus thuringiensis*, crystalline toxins generated therefrom, and the mixtures thereof;
(9) Hydrazine compounds
chromafenozide, halofenozide, methoxyfenozide, tebufenozide and the like;
(10) Organnochlorine compounds
aldrin, dieldrin, dienochlor, endosulfan, methoxychlor and the like;
(11) Natural insecticides
machine oil, nicotine-sulfate;
(12) Other types of insecticides
avermectin-B, bromopropylate, buprofezin, chlorphenapyr, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, Sulfur, metaflumizone, spirotetramat, pyrifluquinazone, spinetoram, chlorantraniliprole, tralopyril, and a compound represented by the following formula (A):

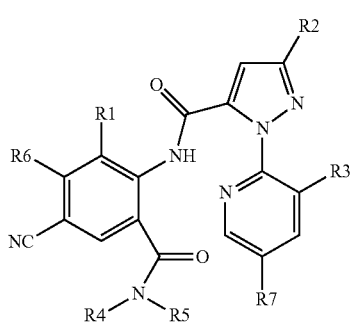

wherein R1 represents Me, Cl, Br, or F,
R2 represents F, Cl, Br, C1-C4 haloalkyl, or C1-C4 haloalkoxy,
R3 represents F, Cl, or Br,
R4 represents H, one or more halogen atoms, C1-C4 alkyl optionally substituted with CN, SMe, S(O)Me, S(O)$_2$Me and OMe, C3-C4 alkenyl, C3-C4 alkynyl, or C3-C5 cycloalkylalkyl,
R5 represents H or Me,
R6 represents H, F, or Cl, and
F7 represents H, F, or Cl.

Examples of the acaricides (acarcidal active ingredients) include
acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, cyenopyrafen and the like, and
examples of the nematicides (nematicidal active ingredients) include DCIP, fosthiazate, levamisol hydrochloride, methylisothiocyanate; morantel tartarate, and imicyafos.

Examples of the fungicides include:
azole-based fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;
cyclic amine-based fungicidal compounds such as fenpropimorph, tridemorph, and fenpropidin;
benzimidazole-based fungicidal compounds such as carbendezim, benomyl, thiabendazole, and thiophanate-methyl;
procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid, and proquinazid.

Examples of the herbicides include:
(1) Phenoxy fatty acid-based herbicidal compounds
such as 2,4-PA, MCP, MCPB, phenothiol, mecoprop, fluroxypyr, triclopyr, clomeprop, and naproanilide;
(2) Benzoic acid-based herbicidal compounds
such as 2,3,6-TBA, dicamba, clopyralid, picloram, aminopyralid, quinclorac, and quinmerac;
(3) Urea-based herbicidal compounds
such as diuron, linuron, chlortoluron, isoproturon, flumeturon, isouron, tebuthiuron, methabenzthiazuron,cumyluron, daimuron, and methyl-daimuron;
(4) Triazine-based herbicidal compounds
such as atrazine, ametoryn, cyanazine, simazine, propazine, simetryn, dimethametryn, prometryn, metribuzin, and triaziflam;
(5) Bipyridinium-based herbicidal compounds
such as paraquat and diquat;
(6) Hydroxybenzonitrile-based herbicidal compounds
such as bromoxynil and ioxynil;
(7) Dinitroaniline-based herbicidal compounds
such as pendimethalin, prodiamine, and trifluralin;
(8) Organic phosphorus-based herbicidal compounds
such as amiprofos-methyl, butamifos, bensulide, piperophos, anilofos, glyphosate, glufosinate, and bialaphos;
(9) Carbamate-based herbicidal compounds
such as di-allate, tri-allate, EPTC, butylate, benthiocarb, esprocarb, molinate, dimepiperate, swep, chlorpropham, phenmedipham, phenisopham, pyributicarb, and asulam;
(10) Acid amide-based herbicidal compounds
such as propanil, propyzamide, bromobutide, and etobenzanid;
(11) Chloroacetanilide-based herbicidal compounds
such as acetochlor, alachlor, butachlor, dimethenamid, propachlor, metazachlor, metolachlor, pretilachlor, thenylchlor, and pethoxamid;
(12) Diphenyl ether-based herbicidal compounds
such as acifluorfen-sodium, bifenox, oxyfluorfen, lactofen, fomesafen, chlomethoxynil, and aclonifen;
(13) Cyclic imide-based herbicidal compounds
such as oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, and benzfendizone;
(14) Pyrazole-based herbicidal compounds
such as benzofenap, pyrazolate, pyrazoxyfen, topramezone, and pyrasulfotole;
(15) Triketone-based herbicidal compounds
such as isoxaflutole, benzobicyclon, sulcotrione, mesotrione, tembotrione, and tefuryltrione;
(16) Aryloxyphenoxypropionic acid-based herbicidal compounds
such as clodinafop-propargyl, cyhalofop-butyl, diclofop-methyl, fenoxaprop-ethyl, fluazifop-butyl, haloxyfop-methyl, quizalofop-ethyl, and metamifop;
(17) Trione oxime-based herbicidal compounds
such as alloxydim-sodium, sethoxydim, butroxydim, clethodim, cloproxydim, cycloxydim, tepraloxydim, tralkoxydim, and profoxydim;
(18) Sulfonylurea-based herbicidal compounds
such as chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and 1-(2-chloro-6-propylimidazo[1,2-a]pyridazin-3-ylsulfonyl)-3-(4,6-dimethoxypyrimidin-2-yl)urea;

(19) Imidazolinone-based herbicidal compounds such as imazamethabenz-methyl, imazamethapyr, imazamox, imazapyr, imazaquin, and imazethapyr;

(20) Sulfonamide-based herbicidal compounds such as flumetsulam, metosulam, diclosulam, florasulam, cloransulam-methyl, penoxsulam, and pyroxsulam;

(21) Pyrimidinyloxybenzoic acid-based herbicidal compounds such as pyrithiobac-sodium, bispyribac-sodium, pyriminobac-methyl, pyribenzoxim, pyriftalid, and pyrimisulfan;

(22) Other herbicidal compounds such as bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, and thiencarbazone-methyl.

Examples of the plant growth regulators include:

hymexazol, paclobutrazol, uniconazole-P, inabenfide, prohexadione-calcium, aviglycine, 1-naphthylacetamide, abscisic acid, indolebutyric acid, ethychlozate ethyl, ethephon, cloxyfonac, chlormequat, dichlorprop, gibberellin, prohydrojasmon, benzylaminopurine, forchlorfenuron, maleic hydrazide, calcium peroxide, mepiquat-chloride, and 4-CPA (4-chlorophenoxyacetic acid).

Examples of the synergists include:

piperonyl butoxide, sesamex, sulfoxide, N-(2-ethylhexyl)-8,9,10-trinorborn-5-ene-2,3-dicarboximide (MGK 264), N-declyimidazole, WARF-antiresistant, TBPT, TPP, IBP, PSCP, methyl iodide ($CH_3I$), t-phenylbutenone, diethylmaleate, DMC, FDMC, ETP, and ETN.

Examples of the safeners include:

benoxacor, cloquintocet-mexyl, cyometrinil, daimuron, dichlormid, fenchlorazole-ethyl, fenclorim, flurazole, fluxofenim, furilazole, mefenpyr-diethyl, MG191 oxabetrinil, allidochlor, isoxadifen-ethyl, cyprosulfamide, fluxofenim, and 1,8-naphthalic anhydride.

The composition of the present invention or the present active compound can be used simultaneously with agents for controlling harmful organisms such as natural enemy organisms or natural enemy microorganisms.

Typical examples of such natural enemy organisms, natural enemy microorganisms, etc., will be given below.

staphylinidae, Braconidae, Ichneumonidae, Pseudanastatus, Tenthredinidae, Siricidae, Orussidae, Aphididae, Eulophidae, Franklinothrips, Lycosidae, Aphelinidae, Tessaratominae, Cecidomyiidae, Syrphidae, Anthocoridae, Phytoseiidae, Chrysopidae, Mantidae, Coccinelidae, Libellulidae, Harpalidae, Formicidae, *Beauveria*, *Verticillium*, *Paecilomyces*, muscardine fungi, nucleopolyhedrovirus, granulosis virus, Cytoplasmic polyhedrosis virus, entomophilic nematodes, and nematocidal fungi such as *Pasteuria* sp. and *Monacrosporium* sp.

An arthropod pest control method, which comprises applying an effective amount of the present active compound to arthropod pests or areas where arthropod pests live is also one embodiment of the present invention.

Examples of arthropod pests, on which the present active compound has an effect, include harmful insects and harmful acarids. Specific examples are given below:

Insect pests belonging to Hemiptera, including: Delphacidae such as *Laodelphax striatellus, Nilaparvata lugens*, or *Sogatella furcifera*; leafhoppers such as *Nephotettix cincticeps, Nephotettix virescens*, or *Empoasca onukii*; aphids such as *Aphis gossypii, Myzus persicae, Brevicoryne brassicae, Aphis spiraecola, Macrosiphum euphorbiae, Aulacorthum solani, Rhopalosiphum padi, Toxoptera citricidus*, or *Hyalopterus pruni*; Pentatomorpha such as *Nezara antennata, Riptortus clavetus, Leptocorisa chinensis, Eysarcoris parvus*, or *Halyomorpha mista*; white flies such as *Trialeurodes vaporariorum, Bemisia tabaci, Dialeurodes citri*, or *Aleurocanthus spiniferus*; scale insects such as *Aonidiella aurantii, Comstockaspis perniciosa, Unaspis citri, Ceroplastes rubens, Icerya purchasi, Planococcus kraunhiae, Pseudococcus longispinis*, or *Pseudaulacaspis pentagona*; tingis flies; bedbugs such as *Cimex lectularius*; psyllas; and others;

Insect pests belonging to Lepidoptera, including: pyralids such as *Chilo suppressalis, Tryporyza incertulas, Cnaphalocrocis medinalis, Notarcha derogata, Plodia interpunctella, Ostrinia furnacalis, Hellula undalis*, or *Pediasia teterrellus*; owlet moths such as *Spodoptera litura, Spodoptera exigua, Pseudaletia separata, Mamestra brassicae, Agrotis ipsilon, Plusia nigrisigna*, genus *Trichoplusia*, genus *Heliothis*, or genus *Helicoverpa*; cabbage butterflies such as *Pieris rapae*; tortrixes such as genus *Adoxopheys, Grapholita molesta, Leguminivora glycinivorella, Matsumuraeses azukivora, Adoxophyes orana fasciata, Adoxophyes honmai, Homona magnanima, Archips fuscocupreanus*, or *Cydia pomonella*; Gracillariidae such as *Caloptilia theivora* or *Phyllonorycter ringoneella*; Carposinidae such as *Carposina niponensis*; Lyonetiidae such as genus *Lyonetia*; Liparidae such as genus *Lymantria* or genus *Euproctis*; Yponomeutidae such as *Plutella xylostella*; Gelechiidae such as *Pectinophora gossypiella* or *Phthorimaea operculella*; Arctiidae such as *Hyphantria cunea*; Tineidae such as *Tinea translucens* or *Tineola bisselliella*; and others;

Insect pests belonging to Thysanoptera, including: thysanopterans such as *Frankliniella occidentalis, Thrips parmi, Scirtothrips dorsalis, Thrips tabaci*, or *Frankliniella intonsa*; and others;

Insect pests belonging to Diptera, including: *Culex* such as *Culex pipiens pallens, Culex tritaeniorhynchus*, or *Culex quinquefasciatus*; genus *Aedes* such as *Aedes aegypti* or *Aedes albopictus*; genus *Anopheles* such as *Anopheles sinensis; Chironomus*; Muscidae such as *Musca domestica* or *Muscina stabulans*; Calliphoridae; Sarcophagidae; Fanniidae; Anthomyiidae such as *Delia platura* or *Delia antiqua*; Agromyzidae such as *Agromyza oryzae, Hydrellia griseola, Liriomyza sativae, Liriomyza trifolii*, or *Chromatomyia horticola*; Carnoidea such as *Chlorops oryzae*; Tephritoidea such as *Dacus cucurbitae* or *Ceratitis capitata; Drosophila*; Phoridae such as *Megaselia spiracularis*; Psychodidae such as *Clogmia albipunctata*; Simuliidae; Tabanidae such as *Tabanus trigonus; Stomoxys*; and others;

Insect pests belonging to Coleoptera, including: Corn Rootworms such as *Diabrotica virgifera virgifera* or *Diabrotica undecimpunctata howardi*; Scarabaeidae such as *Anomala cuprea, Anomala rufocuprea*, or *Popillia japonica*; Curculionidae such as *Sitophilus zeamais, Lissorhoptrus oryzophilus, Callosobruchuys chienensis, Echinocnemus*

*squameus, Anthonomus grandis,* or *Sphenophorus venatus*; Tenebrionoidea such as *Tenebrio molitor* or *Tribolium castaneum*;

Chrysomelidae such as *Oulema oryzae, Aulacophora femoralis, Phyllotreta striolata,* or *Leptinotarsa decemlineata*; Dermestidae such as *Anthrenus verbasci* or *Dermestes maculates*; Anobiidae such as *Lasioderma serricorne*; *Epilachna* such as *Epilachna vigintioctopunctata*; Scolytidae such as *Lyctus brunneus* or *Tomicus piniperda*; Bostrichidae; Ptinidae; Cerambycidae such as *Anoplophora malasiaca; Agriotes* spp.; *Paederus fuscipes,* and others;

Insect pests belonging to Orthoptera, including: *Locusta migratoria, Gryllotalpa Africana, Oxya yezoensis, Oxya japonica,* Grylloidea; and others;

Insect pests belonging to Siphonaptera, including *Ctenocephalides felis, Ctenocephalides canis, Pulex irritans, Xenopsylla cheopis,* and others;

Insect pests belonging to Anoplura, including *Pediculus humanus corporis, Phthirus pubis, Haematopinus eurysternus, Dalmalinia ovis, Haematopinus suis,* and others;

Insect pests belonging to Hymenoptera, including: Formicidae such as *Monomorium pharaosis, Formica fusca japonica, Ochetellus glaber, Pristomyrmex pungens, Pheidole noda, Acromyrmex* spp., *Solenopsis* spp.; Vespidae; Bethylidae; Tenthredinidae such as *Athalia rosae* or *Athalia japonica*; and others;

Insect pests belonging to Blattariae, including: *Blattella germanica, Periplaneta fuliginosa, Periplaneta americana, Periplaneta brunnea, Blatta orientalis,* and others;

Insect pests belonging to Acarina, including: Tetranychidae such as *Tetranychus urticae, Tetranychus kanzawai, Panonychus citri, Panonychus ulmi,* or genus *Oligonicus*; Eriophyidae such as *Aculops pelekassi, Phyllocoptruta citri, Aculops lycopersici, Calacarus carinatus, Acaphylla theavagrans, Eriophyes chibaensis,* or *Aculus schlechtendali*; Tarsonemidae such as *Polyphagotarsonemus latus*; Tenuipalpidae such as *Brevipalpus phoenicis*; Tuckerellidae; Ixodidae such as *Haemaphysalis longicornis, Haemaphysalis flava, Dermacentor taiwanicus, Ixodes ovatus, Ixodes persulcatus, Ixodes scapularis, Boophilus microplus,* or *Rhipicephalus sanguineus*; Acaridae such as *Tyrophagus putrescentiae* or *Tyrophagus similis*; Epidermoptidae such as *Dermatophagoides farinae* or *Dermatophagoides ptrenyssnus*; Cheyletidae such as *Cheyletus eruditus, Cheyletus malaccensis,* or *Cheyletus moorei*; Dermanyssidae such as *Ornithonyssus bacoti, Ornithonyssus sylvairum,* or *Dermanyssus gallinae*; Trombiculidae such as *Leptotrombidium akamushi*; Arachnida such as *Chiracanthium japonicum* or *Latrodectus hasseltii*; and others;

Chilopoda including *Thereuonema hilgendorfi, Scolopendra subspinipes,* and others;

Diplopoda including *Oxidus gracilis, Nedyopus tambanus,* and others;

Isopoda including *Armadillidium vulgare,* and others; and

Gastropoda including *Limax marginatus, Limax flavus,* and others.

In the controlling method of the present invention, arthropod pests, on which the present active compound has a high effect, are insect pests belonging to Hemiptera.

Among the arthropod pests, an example of insect pest to timber products is Isoptera. Specific examples of such Isoptera will be given below.

Mastotermitidae, Termopsidae [genus *Zootermopsis*, genus *Archotermopsis*, genus *Hodotermopsis*, genus *Porotermes*, and genus *Stolotermes*], Kalotermitidae [genus *Kalotermes*, genus *Neotermes*, genus *Cryptotermes*, genus *Incistermes*, and genus *Glyptotermes*], Hodotermitidae [genus *Hodotermes*, genus *Microhodotermes,* and genus *Anacanthotermes*], Rhinotermitidae [genus *Reticulitermes,* genus *Heterotermes,* genus *Coptotermes,* and genus *Schedolinotermes*], Serritermitidae, and Termitidae {genus *Amitermes*, genus *Drepanotermes*, genus *Hopitalitermes*, genus *Trinervitermes*, genus *Macrotermes*, genus *Odontotermes,* genus *Microtermes*, genus *Nasutitermes*, genus *Pericapritermes*, and genus *Anoplotermes*}.

Of these, specific examples of Isoptera as a target to be controlled include *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Glyptotermes kodamai, Glyptotermes kushimensis, Hodotermopsis japonica, Coptotermes guangzhoensis, Reticulitermes miyatakei, Reticulitermes flaviceps amamianus, Reticulitermes* sp., *Nasutitermes takasagoensis, Pericapritermes nitobei, Sinocapritermes mushae, Reticulitermes flavipes, Reticulitermes hesperus, Reticulitermes virginicus, Reticulitermes tibialis, Heterotermes aureus,* and *Zootermopsis nevadensis.*

Insects other than Isoptera that are harmful to timber products include coleopteran insects such as Lyctidae, Bostrichidae, Anobiidae, and Cerambycidae.

The present active compound can be used to control arthropods internally or externally parasitizing in vertebrate animals such as a human, a bovine, a sheep, a goat, a swine, a fowl, a dog, a cat, and fish in the field of treatment of animal diseases and in the livestock industry, so as to maintain public health. Examples of such harmful organisms include: *Ixodes* spp. such as *Ixodes scapularis; Boophilus* spp. such as *Boophilus microplus; Amblyomma* spp.; *Hyalomma* spp.; *Rhipicephalus* spp. such as *Rhipicephalus sanguineus; Haemaphysalis* spp. such as *Haemaphysalis longicornis; Dermacentor* spp.; *Ornithodoros* spp. such as *Ornithodoros moubata; Dermahyssus gallinae; Ornithonyssus sylviarum; Sarcoptes* spp. such as *Sarcoptes scabiei; Psoroptes* spp.; *Chorioptes* spp.; *Demodex* spp.; *Eutrombicula* spp.; *Aedes* spp. such as *Aedes albopictus; Anopheles* spp.; *Culex* spp.; *Culicodes* spp.; *Musca* spp.; *Hypoderma* spp.; *Gasterophilus* spp.; *Haematobia* spp.; *Tabanus* spp.; *Simulium* spp.; *Triatoma* spp.; *Phthiraptera* such as *Damalinia* spp., *Linognathus* spp., or *Haematopinus* spp.; *Ctenocephalides* spp. such as *Ctenocephalides felis; Xenosylla* spp.; and *Monomorium pharaonis.*

According to the control method of the present invention, the present active compound may be directly applied without any other ingredients, or the present active compound may be applied in combination with the above-described other agents such as an insecticide, an acaricide, a nematicide, or a microbicide. Alternatively, the present active compound may also be applied in combination with natural enemy organisms or natural enemy microorganisms. Further, the composition of the present invention may be used as the present active compound.

Examples of the areas where the arthropod pests live include a paddy field, a dry field, a farm land, a tea garden, an orchard, a nonagricultural land, a house, a seedling-raising tray, a seedling-raising box, a seedling-raising soil, a seedling-raising mat, and a water culture medium in a hydroponic farm.

In the control method, the present active compound can be applied to arthropod pests or areas where arthropod pests live by allowing the compound to come into contact with the arthropod pests or causing the arthropod pests to ingest the compound, according to the same method as in the case of conventional arthropod pest control agents.

Examples of such application method include a spraying treatment, a soil treatment, a seed treatment, and a water culture medium treatment.

The spraying treatment is a treatment method, which comprises spraying an active ingredient (the present active compound) onto the surface of a plant body, for example, according to foliage spraying or truck spraying, or onto an arthropod pest itself, so as to exhibit a controlling effect on the arthropod pests.

The soil treatment is, for example, a treatment method, which comprises giving an active ingredient to the root portion of a crop to be protected so as to directly control arthropod pests, or penetrating such active ingredient into a plant body to control such arthropod pests.

Specific examples of the soil treatment include a planting hole treatment (planting hole spraying and planting hole-treated soil mixture), a seedling treatment (seedling spraying, seedling soil mixture, seedling irrigation, and a seedling treatment in the latter part of a seedling-raising period), a planting ditch treatment (planting ditch spraying and planting ditch soil mixture), a planting row treatment (planting row spraying, planting row soil mixture, and planting row spraying in a growing period), a planting row treatment during a seeding time (planting row spraying during a seeding time and planting row soil mixture during a seeding time), a total treatment (total soil spraying and total soil mixture), a side row treatment, a water surface treatment (water surface application and water surface application after flooding), other soil spraying treatments (the spraying of a granule agent onto leave during a growing period, the spraying of the agent to below the tree crown or around the main stem, the spraying of the agent onto the soil surface, soil surface mixture, planting hole spraying, furrow surface spraying, and the spraying of the agent to between stocks), other irrigation treatments (soil irrigation, irrigation in a seeding-raising period, an agent injection treatment, irrigation to a soil-contacting portion of plant, agent drip irrigation, and chemigation), a seedling-raising box treatment (seedling-raising box spraying, seedling-raising box irrigation, and the flooding of a seedling-raising box with an agent liquid), a seedling-raising tray treatment (seedling-raising tray spraying, seedling-raising tray irrigation, and the flooding of a seedling-raising tray with an agent liquid), a seedbed treatment (seedbed spraying, seedbed irrigation, flooded nursery seedbed spraying, and nursery immersion), a seedbed soil mixing treatment (seedbed soil mixing, seedbed soil mixture before seeding, spraying before cover soil in a seeding time, spraying after cover soil in a seeding time, and cover soil mixing), and other treatments (seeding soil mixture, plowing, surface soil mixture, the mixing of a rain-dropping portion of soil, a planting position treatment, the spraying of a granule agent to inflorescence, and paste fertilizer mixture).

The seed treatment is a treatment method, which comprises directly treating with an active ingredient, seeds, seed potatoes, bulbs, etc. of crops to be protected, or treating the neighborhood thereof with such active ingredient, so as to exhibit a control effect on arthropod pests. Specific examples of the seed treatment include a spraying treatment, a smearing treatment, an immersion treatment, an impregnation treatment, an application treatment, a film coating treatment, and a pellet coating treatment.

The water culture medium treatment is, for example, a treatment method, which comprises treating a water culture medium or the like with an active ingredient in order to infiltrate the active ingredient from the root portion of a crop to be protected to the internal portion thereof, so as to protect the crop from the damage caused by arthropod pests. Specific examples of the water culture medium treatment include water culture medium mixture and water culture medium incorporation.

The present active compound can be used as an arthropod pest control agent in agricultural or nonagricultural lands such as a farm land, a paddy field, a lawn, and an orchard.

When the present active compound is used to control arthropod pests in the agricultural field, the amount of application can be broadly altered depending on an application period, an application site, an application method, etc. It is generally 1 to 10,000 g per 10,000 m$^2$. When the present active compound is formulated to be an emulsion, a wettable powder, a flowable agent, etc., the active compound is diluted with water to a concentration of 0.01 to 10,000 ppm. A powder agent, a granule agent, or the like is generally applied as it is.

The present active compound or a water dilution thereof may be directly sprayed to arthropod pests or plants, or it may also be subjected to the soil treatment.

Otherwise, the present active compound may also applied using a resin preparation that is processed in the form of a sheet or a cord. The resin preparation comprising the present active compound may be twisted around crops, strung around the neighborhood of the crops, or spread on the planting soil.

In some cases, the present active compound may control insect pests in an agricultural land and the like, where the "crops" as described below and the like are cultivated, without giving harmful effects on the crops and the like.

Crops: corn, rice, wheat, barley, rye, oat, sorghum, cotton, soybean, peanut, buckwheat, sugarbeet, rapeseed, sunflower, sugarcane, tobacco, etc.

Vegetables: solanaceous vegetables (eggplant, tomato, pimento, pepper, potato, etc.), cucurbitaceous vegetables (cucumber, pumpkin, zucchini, watermelon, melon, etc.), brassicaceous vegetables (Japanese radish, turnip, horseradish, kohlrabi, Chinese cabbage, cabbage, leaf mustard, broccoli, cauliflower, etc.), asteraceous vegetables (burdock, *Chrysanthemum coronarium*, artichoke, lettuce, etc.), liliaceous vegetables (spring onion, onion, garlic, asparagus), umbelliferous vegetables (carrot, parsley, celery, parsnip, etc.), chenopodiaceous vegetables (spinach, silver beet, etc.), lamiaceous vegetables (Japanese basil, mint, basil, etc.), strawberry, sweet potato, *Dioscorea japonica*, colocasia antiquorum, and others.

Fruit trees; pome fleshy fruits (apple, pear, Japanese pear, amboyna, quince, etc.), stone fleshy fruits (peach, plum, nectarine, *Prunus mume, Prunus avium*, apricot, prune, etc.), citrus fruits (*Citrus unshiu*, orange, lemon, lime, grapefruit, etc.), nuts (malon, walnuts, hazelnuts, almond, pistachio, cashew nuts, macadamia nuts, etc.), sap fruits (blueberry, cranberry, blackberry, raspberry, etc.), grape, Japanese persimmon, olive, *Eriobotrya japonica*, banana, coffee, *Phoenix dactylifera, Cocos nucifera, Elaeis guineensis*, and others.

Trees other than fruit trees; tea tree, *Morus alba*, flowering plants, street trees (ash, birch, *Benthamidia florida*, Eucalyptus, *Ginkgo biloba*, lilac, maple, oak, poplar, Chinese redbud, Formosa sweet gum, plane tree, zelkova, Japanese arborvitae, fir, Japanese hemlock, needle juniper, pine, Japanese spruce, and Japanese yew), Jatropha, and others.

Lawns: lawn grasses (*Zoysia japonica, Zoysia tenuifolia*, etc.), Bermuda grasses (*Cynodon dactylon*, etc.), bent grasses (redtop grass, *Agrostis stolonifera L., Agrostis capillaris L.*, etc.), blue grasses (Kentucky bluegrass, *Poatrivialis L.*, etc.), festuca (*Festuca arundinacea* Schreb., *Festuca rubra.*, creeping red fescue, etc.), ryegrasses (Australian ryegrass, perennial ryegrass, etc.), rchard grass, timothy, and others.

Others; flowers, foliage plants, and others.

The "crops" include plants which have acquired resistance to herbicides including HPPD inhibitors such as isoxaflutole, ALS inhibitors such as imazethapyr and thifensulfuron methyl, EPSP synthetase inhibitors, glutamine synthetase inhibitors, acetyl-CoA carboxylase inhibitors, bromoxynil, and the like, according to classical breeding methods or gene recombination technology.

Examples of the "crops" which have acquired resistance according to classical breeding methods include: Clearfield [registered trademark] canola that is resistant to imidazolinone herbicides such as imazethapyr; and STS soybean that is resistant to sulfonylurea ALS inhibition-type herbicides such as thifensulfuron methyl.

Likewise, an example of the crops which have acquired resistance to acetyl-CoA carboxylase inhibitors such as trione oxime herbicides or aryloxyphenoxypropionic acid herbicides according to classical breeding methods is SR corn.

The crops which have acquired resistance to acetyl-CoA carboxylase inhibitors are disclosed in Proceedings of the National Academy of Sciences of the United States of America (Proc. Natl. Acad. Sci. USA), Vol. 87, pp. 7175-7179 (1990), and other publications. Moreover, a mutant acetyl-CoA carboxylase that is resistant to acetyl-CoA carboxylase inhibitors is disclosed in Weed Science, Vol. 53, pp. 728-746 (2005), and other publications. Such mutant acetyl-CoA carboxylase gene is introduced into a crop according to a gene recombination technology, or a mutation associated with addition of resistance is introduced into the acetyl-CoA carboxylase of a crop, so as to produce a crop that is resistant to acetyl-CoA carboxylase inhibitors.

Moreover, a base substitution mutation-introduced nucleic acid, which includes chimeraplasty technology (Gura T. 1999. Repairing the Genome's Spelling Mistakes. Science 285: 316-318) as a typical example, is introduced into the cells of a crop, so as to cause a site-directed amino acid substitution mutation to a crop (acetyl-CoA carboxylase/herbicide target) gene, thereby producing a crop resistant to (acetyl-CoA carboxylase inhibitor/herbicide).

Examples of such crop which has acquired resistance as a result of a gene recombination technology include corn varieties resistant to glyphosate and glufosinate. Such corn varieties have already been on sale with product names "RoundupReady" [registered trademark], "LibertyLink" [registered trademark], and the like.

The "crops" include plants which have become able to synthesize selective toxin and the like that are known in genus *Bacillus* using a gene recombination technology.

Examples of such toxin produced in such genetically modified plants include: insecticidal proteins derived from *Bacillus cereus* and *Bacillus popilliae*; insecticidal proteins derived from *Bacillus thuringiensis*, including δ-endotoxins such as Cry1Ab, Cry1Ac, Cry1F, Cry1Fa2, Cry2Ab, Cry3A, Cry3Bb1 or Cry9C, VIP1, VIP2, VIP3, VIP3A, or the like; insecticidal proteins derived from nematode; toxins produced by animals, such as scorpion toxin, spider toxin, bee toxin, or insect-specific neurotoxin; toxins of filamentous fungi; plant lectin; agglutinin; protease inhibitors such as a trypsin inhibitor, a serine protease inhibitor, patatin, cystatin, or a papain inhibitor; ribosome-inactivating proteins (RIP) such as ricin, corn-RIP, abrin, rufin, sapolin, or briodin; steroid metabolic enzymes such as 3-hydroxysteroid oxidase, ecdysteroid-UDP-glucosyltransferase, or cholesterol oxidase; ecdysone inhibitors; HMG-CoA reductase; ion channel inhibitors such as a sodium channel inhibitor or a calcium channel inhibitor; juvenile hormone esterase; diuretic hormone receptors; stilbene synthetase; bibenzyl synthetase; chitinase; and glucanase.

The toxins produced in such genetically modified crops also include hybrid toxins, partially deficient toxins and modified toxins of the above-described insecticidal proteins. The hybrid toxins are produced by a novel combination of the different domains of such a protein by adopting a recombination technique. As the partially deficient toxin, Cry1Ab, which is deficient in a part of the amino acid sequence, is known. In the modified toxins, one or more amino acids of a natural toxin have been replaced.

Examples of such toxins and genetically modified plants capable of synthesizing such toxins are disclosed in EP-A-0374753, WO 93/07278, WO 95/34656, EP-A-0427529, EP-A-0451878, WO 03/052073, etc.

The toxins contained in such genetically modified plants impart to the plants, resistance to, particularly, insect pests belonging to Coleoptera, insect pests belonging to Diptera, and insect pests belonging to Lepidoptera.

Genetically modified plants containing one or more insecticidal insect-resistant genes and capable of producing one or more toxins have already been known, and some of them are on the market. As these genetically modified plants, there are exemplified YieldGard [registered trademark] (a corn variety capable of producing Cry1Ab toxin), YieldGard Rootworm [registered trademark] (a corn variety capable of producing Cry3Bb1 toxin), YieldGard Plus [registered trademark] (a corn variety capable of producing Cry1Ab and Cry3Bb1 toxins), Herculex I [registered trademark] (a corn variety capable of producing phosphinotrysin N-acetyltransferase (PAT) for imparting resistance to Cry1Fa2 toxin and Glufosinate), NuCOTN33B [registered trademark] (a cotton variety capable of producing Cry1Ac toxin), Bollgard I [registered trademark] (a cotton variety capable of producing Cry1Ac toxin), Bollgard II [registered trademark] (a cotton variety capable of producing Cry1Ac and Cry2Ab toxins), VIPCOT [registered trademark] (a cotton variety capable of producing VIP toxin), NewLeaf [registered trademark] (a potato variety capable of producing Cry3A toxin), NatureGard [registered trademark], Agrisure [registered trademark], GT Advantage (GA21 glyphosate-resistant properties), Agrisure [registered trademark], CB Advantage (Bt11 corn borer (CB) properties), and Protecta [registered trademark].

The “crops” also include crops having an ability to produce an anti-pathogenic substance having selective action which has been imparted by a gene recombination technology.

Examples of such anti-pathogenic substance produced in genetically modified plants include: ion channel inhibitors such as sodium channel inhibitors and calcium channel inhibitors (for example, KP1, KP4 and KP6 toxins produced by viruses are known); stilbene synthases; bibenzyl synthases; chitinase; glucanase; PR proteins (PRPs, EP 0392225 A); and anti-pathogenic substances produced by microorganisms, such as peptide antibiotics, antibiotics having a heterocyclic ring, and protein factors associated with resistance to plant diseases (disclosed in WO 03/000906). Such anti-pathogenic substances and genetically modified plants producing such substances are disclosed in EP 0392225 A, WO 95/33818, EP 0353191 A, etc.

The “crops” also include crops having useful properties such as an oil ingredient-modifying property or an amino acid content-increasing property which has been imparted by a gene recombination technology. Examples of such crop having useful properties include: VISTIVE [registered trademark] (a low linoleic acid soybean containing a reduced amount of linoleic acid); and high-lysine (high-oil) corn (a corn containing an increased amount of lysine or oil).

The crops further include stack varieties, in which a plurality of the classical herbicide properties, a herbicide resistance gene, an insecticidal insect pest resistance gene, an anti-pathogenic substance-producing gene, and useful properties such as an oil ingredient-modifying property or an amino acid content-increasing property are combined.

When the present active compound is used to control arthropod pests that reside in a house (e.g. a fly, a mosquito, and a cockroach), the amount applied is generally 0.01 to 1,000 mg per m² of area to be treated, in the case of applying it to a floor. In the case of applying the active compound to a space, the amount applied is generally 0.01 to 500 mg per m³ of space to be treated. When the present active compound is formulated to an emulsion, a wettable powder, a flowable agent, etc., it is generally diluted with water to a concentration of 0.1 to 1,000 ppm. When the active compound is in the form of an oil agent, an aerosol, a fumigant, a toxic bait, etc., it is applied as it is.

EXAMPLES

Hereinafter, the present invention is described in more detail with reference to Production Examples, Reference Production Examples, and Test Examples. However, the present invention is not necessarily limited to these Examples.

Production Example 1

A mixture of 1.2 g of 2-amino-4-propylphenol, 0.98 g of isonicotinic acid and 32.8 g of polyphosphoric acid was stirred while heating at 190° C. for five hours. The mixture was cooled to room temperature and then poured into an ice-cooled aqueous solution of sodium hydroxide, followed by extraction with ethyl acetate three times. The combined organic layers were washed with water and a saturated sodium chloride solution, and dried over magnesium sulfate. Activated carbon was added thereto, which was filtered through Celite™. The filtrate was concentrated under reduced pressure. The residue was subjected to silica gel column chromatography to give 0.72 g of 5-propyl-2-(pyridin-4-yl)-benzoxazole (hereinafter, referred to as "active compound 1").

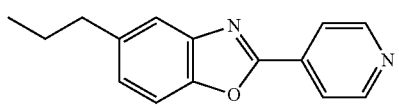

Active Compound 1
¹H-NMR (CDCl₃) δ: 8.81 (dd, J=4.6, 1.7 Hz, 2H), 8.08 (dd, J=4.5, 1.7 Hz, 2H), 7.62-7.60 (m, 1H), 7.54-7.50 (m, 1H), 7.27-7.23 (m, 1H), 2.74 (t, J=7.5 Hz, 2H), 1.76-1.66 (m, 2H), 1.31 (t, J=7.5 Hz, 3H)

Production Example 2

Production Example 2 was carried out according to the same manner as in Production Example 1, using 2-amino-4-methylphenol instead of 2-amino-4-propylphenol to give 5-methyl-2-(pyridin-4-yl)-benzoxazole (hereinafter, referred to as "active compound 2").

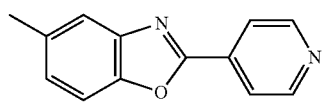

Active Compound 2
¹H-NMR (CDCl₃) δ: 8.81 (dd, J=4.5, 1.6 Hz, 2H), 8.07 (dd, J=4.5, 1.6 Hz, 2H), 7.62-7.59 (m, 1H), 7.52-7.48 (m, 1H), 7.25-7.22 (m, 1H), 2.51 (s, 3H)

Production Example 3

Production Example 3 was carried out according to the same manner as in Production Example 1, using 2-amino-4-ethylphenol instead of 2-amino-4-propylphenol to give 5-ethyl-2-(pyridin-4-yl)-benzoxazole (hereinafter, referred to as "active compound 3").

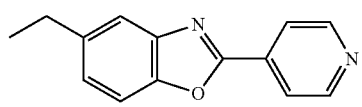

Active Compound 3
¹H-NMR (CDCl₃) δ: 8.81 (dd, J=4.6, 1.7 Hz, 2H), 8.07 (dd, J=4.4, 1.7 Hz, 2H), 7.64-7.62 (m, 1H), 7.52 (d, J=8.5 Hz, 1H), 7.27 (dd, J=8.5, 1.7 Hz, 1H), 2.80 (q, J=7.6 Hz, 2H), 1.31 (t, J=7.6 Hz, 3H)

Production Example 4

Production Example 4 was carried out according to the same manner as in Production Example 1, using 2-amino-4-butylphenol instead of 2-amino-4-propylphenol to give 5-butyl-2-(pyridin-4-yl)-benzoxazole (hereinafter, referred to as "active compound 4").

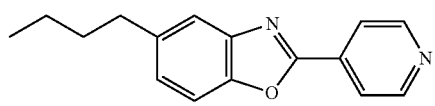

Active Compound 4
¹H-NMR (CDCl₃) δ: 8.81 (dd, J=4.4, 1.7 Hz, 2H), 8.08 (dd, J=4.6, 1.7 Hz, 2H), 7.62-7.61 (m, 1H), 7.53-7.50 (m, 1H), 7.27-7.23 (m, 1H), 2.76 (t, J=7.6 Hz, 2H), 1.71-1.62 (m, 2H), 1.44-1.33 (m, 2H), 0.95 (t, J=7.3 Hz, 3H)

Production Example 5

Production Example 5 was carried out according to the same manner as in Production Example 1, using 2-amino-4-isopropylphenol instead of 2-amino-4-propylphenol to give 5-isopropyl-2-(pyridin-4-yl)-benzoxazole (hereinafter, referred to as "active compound 5").

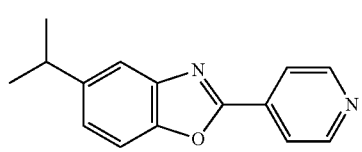

Active Compound 5

¹H-NMR (CDCl₃) δ: 8.82 (dd, J=4.5, 1.6 Hz, 2H), 8.08 (dd, J=4.5, 1.6 Hz, 2H), 7.68 (d, J=1.7 Hz, 1H), 7.53 (d, J=8.5 Hz, 1H), 7.31 (dd, J=8.4, 1.8 Hz, 1H), 3.11-3.04 (m, 1H), 1.33 (d, J=6.8 Hz, 6H)

Production Example 6

Production Example 6 was carried out according to the same manner as in Production Example 1, using 2-amino-4-tert-butylphenol instead of 2-amino-4-propylphenol to give 5-tert-butyl-2-(pyridin-4-yl)-benzoxazole (hereinafter, referred to as "active compound 6").

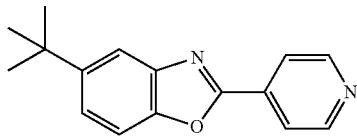

Active Compound 6

¹H-NMR (CDCl₃) δ: 8.83-8.80 (m, 2H), 8.09-8.06 (m, 2H), 7.86-7.83 (m, 1H), 7.56-7.48 (m, 2H), 1.41 (s, 9H)

Production Example 7

Production Example 7 was carried out according to the same manner as in Production Example 1, using 2-amino-5-methylphenol instead of 2-amino-4-propylphenol to give 6-methyl-2-(pyridin-4-yl)-benzoxazole (hereinafter, referred to as "active compound 7").

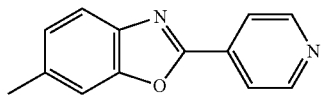

Active Compound 7

¹H-NMR (CDCl₃) δ: 8.81 (dd, J=4.5, 1.6 Hz, 2H), 8.07 (dd, J=4.5, 1.6 Hz, 2H), 7.69 (d, J=8.3 Hz, 1H), 7.43 (s, 1H), 7.23 (d, J=8.3 Hz, 1H), 2.53 (s, 3H)

Production Example 8

A mixture of 1.22 g of N-(4-tert-butyl-2-hydroxyphenyl) isonicotinamide, 15 ml of carbon tetrachloride, 3.55 g of triphenylphosphine and 1.37 g of triethylamine was heated to reflux for three hours. The mixture was cooled to room temperature, and then water was poured into the mixture, followed by extraction with ethyl acetate twice. The combined organic layers were washed with a saturated sodium chloride solution, dried over magnesium sulfate, and then concentrated under reduced pressure. The residue was subjected to silica gel column chromatography to give 0.30 g of 6-tert-butyl-2-(pyridin-4-yl)-benzoxazole (hereinafter, referred to as "active compound 8").

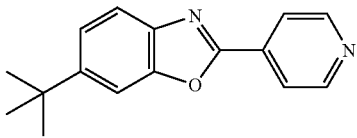

Active Compound 8

¹H-NMR (CDCl₃) δ: 8.81 (dd, J=4.6, 1.7 Hz, 2H), 8.07 (dd, J=4.4, 1.7 Hz, 2H), 7.74 (d, J=8.3 Hz, 1H), 7.65 (d, J=1.7 Hz, 1H), 7.48 (dd, J=8.5, 1.7 Hz, 1H), 1.41 (s, 9H)

Production Example 9

Production Example 9 was carried out according to the same manner as in Production Example 1, using 2-amino-4-chlorophenol instead of 2-amino-4-propylphenol to give 5-chloro-2-(pyridin-4-yl)-benzoxazole (hereinafter, referred to as "active compound 9").

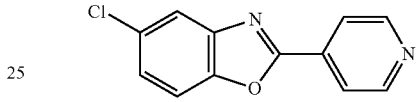

Active Compound 9

¹H-NMR (CDCl₃) δ: 8.84 (dd, J=4.4, 1.7 Hz, 2H), 8.07 (dd, J=4.4, 1.7 Hz, 2H), 7.80 (d, J=2.0 Hz, 1H), 7.56 (d, J=8.8 Hz, 1H), 7.41 (dd, J=8.8, 2.0 Hz, 1H)

Production Example 10

Production Example 10 was carried out according to the same manner as in Production Example 1, using 2-amino-4-bromophenol instead of 2-amino-4-propylphenol to give 5-bromo-2-(pyridin-4-yl)-benzoxazole (hereinafter, referred to as "active compound 10").

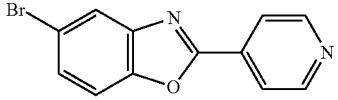

Active Compound 10

¹H-NMR (CDCl₃) δ: 8.83 (dd, J=4.4, 1.7 Hz, 2H), 8.07 (dd, J=4.4, 1.6 Hz, 2H), 7.96 (d, J=1.9 Hz, 1H), 7.55 (d, J=8.6, 1.8 Hz, 1H), 7.51 (dd, J=8.5 Hz, 1H)

Production Example 11

To a mixture of 1.17 g of N-(2-hydroxy-5-methoxyphenyl) isonicotinamide, 1.26 g of triphenylphosphine and 25 ml of tetrahydrofuran, a mixture of 0.85 g diethyl azodicarboxylate and 5 ml of tetrahydrofuran was added dropwise. The mixture was warmed to room temperature and stirred for four hours. Water was added to the reaction mixture, followed by extraction with ethyl acetate. The combined organic layers were washed with water and a saturated sodium chloride solution, and dried over magnesium sulfate. Activated carbon was added thereto, which was filtered through Celite™. The filtrate was concentrated under reduced pressure. The residue was subjected to silica gel column chromatography to give 0.11 g of 5-methoxy-2-(pyridin-4-yl)-benzoxazole (hereinafter, referred to as "active compound 11").

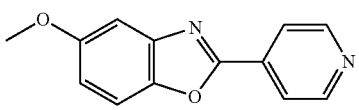

Active Compound 11

$^1$H-NMR (CDCl$_3$) δ: 8.81 (dd, J=4.4, 1.7 Hz, 2H), 8.07-8.05 (m, 2H), 7.51 (d, J=9.0 Hz, 1H), 7.29 (d, J=2.7 Hz, 1H), 7.04 (dd, J=9.0, 2.7 Hz, 1H), 3.89 (s, 3H)

Production Example 12

To a mixture of 1.96 g of N-[5-(trifluoromethoxy)-2-hydroxyphenyl]isonicotinamide, 35 ml of tetrahydrofuran and 1.73 g of triphenylphosphine, a mixture of 1.26 g of diethyl azodicarboxylate and 5 ml of THF was added dropwise at room temperature. The resultant mixture was stirred at room temperature for two hours. To the mixture, 1.73 g of triphenylphosphine and 3.15 g of 40% toluene solution of diethyl azodicarboxylate were added and stirred for one hour. Furthermore, to the mixture, 0.58 g of triphenylphosphine and 1.05 g of 40% toluene solution of diethyl azodicarboxylate were added and stirred for one hour. The mixture solution was poured into water, followed by extraction with ethyl acetate. The combined organic layers were washed with water and a saturated sodium chloride solution, and dried over magnesium sulfate. The reaction mixture was concentrated. The residue was subjected to silica gel column chromatography to give 2-(pyridin-4-yl)-5-(trifluoromethoxy)benzoxazole (hereinafter, referred to as "active compound 12").

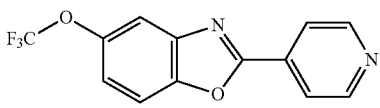

Active Compound 12

$^1$H-NMR (CDCl$_3$) δ: 8.86-8.84 (m, 2H), 8.10-8.07 (m, 2H), 7.73-7.70 (m, 1H), 7.64 (d, J=8.8 Hz, 1H), 7.35-7.30 (m, 1H)

Production Example 13

To a mixture of 1.69 g of N-(2-hydroxy-5-trifluoromethylphenyl)isonicotinamide, 25 ml of tetrahydrofuran and 2.36 g of triphenylphosphine, 3.91g of 40% toluene solution of diethyl azodicarboxylate was added dropwise at room temperature. After 1.3 hours, 0.6 g of triphenylphosphine and 1.0 g of 40% toluene solution of diethyl azodicarboxylate were added and stirred for further 40 minutes. Water was poured into the mixture, followed by extraction with ethyl acetate twice. The combined organic layers were washed with water and a saturated sodium chloride solution, dried over sodium sulfate, and then concentrated under reduced pressure. The residue was washed with diethyl ether, and 10 ml of methanol and 10 ml of 1 M aqueous solution of sodium hydroxide were added and stirred for two hours at room temperature. After concentrated hydrochloric acid was added to the reaction mixture while ice-cooling so as to make it acidic, the reaction mixture was washed with ethyl acetate. To the aqueous layer, 1 M aqueous solution of sodium hydroxide was added so as to make the solution alkaline, followed by extraction with ethyl acetate twice. The combined organic layers were washed with water and a saturated sodium chloride solution, and dried over magnesium sulfate and then concentrated under reduced pressure. The residue was subjected to silica gel column chromatography to give 0.44 g of 2-(pyridin-4-yl)-5-(trifluoromethyl)benzoxazole (hereinafter, referred to as "active compound 13").

Active Compound 13

$^1$H-NMR (CDCl$_3$) δ: 8.86 (dd, J=4.4, 1.7 Hz, 2H), 8.13-8.09 (m, 3H), 7.75 (d, J=8.5 Hz, 1H), 7.72 (dd, J=8.7, 1.6 Hz, 1H)

Production Example 14

To a mixture of 0.47 g of 2-(pyridin-4-yl)-5-(trifluoromethyl)benzoxazole and 5 ml of chloroform, 0.64 g of 65% m-chloroperbenzoic acid was added while ice-cooling. The reaction mixture was stirred while ice-cooling for 30 minutes, and then stirred at room temperature for 1.5 hours. The reaction mixture was diluted with chloroform, and washed with 5% aqueous solution of sodium hydroxide and a saturated sodium chloride solution. Organic layers were dried over anhydrous sodium sulfate, and then concentrated under reduced pressure to give 0.39 g of 4-[5-(trifluoromethyl)benzoxazole-2-yl]pyridine N-oxide (hereinafter, referred to as "active compound 14").

Active Compound 14

$^1$H-NMR (CDCl$_3$) δ: 8.34-8.31 (m, 2H), 8.13-8.10 (m, 2H), 8.08 (s, 1H), 7.73-7.68 (m, 2H)

Production Example 15

A mixture of 0.8 g of N-(2-hydroxy-4-trifluoromethylphenyl)isonicotinamide, 15 ml of carbon tetrachloride, 2.23 g of triphenylphosphine and 0.86 g of triethylamine was heated to reflux for five hours. The mixture was cooled to room temperature. Then, water was poured into the mixture, followed by extraction with ethyl acetate twice. The combined organic layers were washed with water and a saturated sodium chloride solution, dried over magnesium sulfate, and then concentrated under reduced pressure. The residue was subjected to silica gel column chromatography to give 0.25 g of 2-(pyridin-4-yl)-6-(trifluoromethyl)benzoxazole (hereinafter, referred to as "active compound 15").

Active Compound 15

$^1$H-NMR (CDCl$_3$) δ: 8.87 (dd, J=4.5, 1.6 Hz, 2H), 8.11 (dd, J=4.4, 1.5 Hz, 2H), 7.95-7.91 (m, 2H), 7.72-7.68 (m, 1H)

Production Example 16

To a mixture of 1.34 g of N-(1,1,3,3-tetrafluoro-6-hydroxy-1,3-dihydroisobenzofuran-5-yl)isonicotinamide, 10 ml of tetrahydrofuran and 1.07 g of triphenylphosphine, 2.67 g of 40% toluene solution of diethyl azodicarboxylate was added dropwise at room temperature. After 30 minutes, 1.07 g of triphenylphosphine was added, 2.67 g of 40% toluene solution of diethyl azodicarboxylate was added dropwise thereto and stirred for further two hours. Water was added thereto, followed by extraction with ethyl acetate twice. The combined organic layers were washed with water and a saturated sodium chloride solution, dried over magnesium sulfate, and concentrated under reduced pressure. The residue was subjected to silica gel column chromatography and the resultant solid was recrystallized to give 0.14 g of 5,5,7,7-tetrafluoro-2-pyridin-4-yl-5,7-dihydro-furo[3',4':4,5]benzo[1,2-d]oxazole (hereinafter, referred to as "active compound 16").

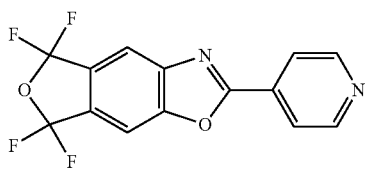

Active Compound 16
$^1$H-NMR (CDCl$_3$) δ: 8.91 (dd, J=4.4, 1.7 Hz, 2H), 8.12 (dd, J=4.5, 1.6 Hz, 2H), 8.08 (s, 1H), 7.91 (s, 1H)

Production Example 17

A mixture of 0.35 g of 3,5-dichloro-N-(2-hydroxy-5-trifluoromethylphenyl)isonicotinamide, 5 ml of carbon tetrachloride, 0.78 g of triphenylphosphine and 0.30 g of triethylamine was heated to reflux for three hours. The mixture was cooled to room temperature, and then water was added to the mixture, followed by extraction with ethyl acetate twice. The combined organic layers were washed with a saturated sodium chloride solution, dried over magnesium sulfate, and concentrated under reduced pressure. The residue was subjected to silica gel column chromatography to give 0.18 g of 2-(3,5-dichloropyridin-4-yl)-5-(trifluoromethyl)benzoxazole (hereinafter, referred to as "active compound 17").

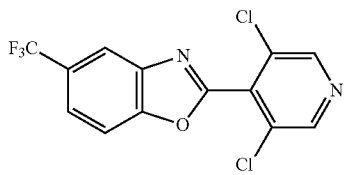

Active Compound 17
$^1$H-NMR (CDCl$_3$) δ: 8.72 (s, 2H), 8.21 (s, 1H), 7.79-7.77 (m, 2H)

Production Example 18

To a mixture of 0.71 g of 2-(3-chloropyridin-4-yl)methylideneamino-4-(trifluoromethyl)phenol and 10 ml of methanol, 0.80 g of iodobenzene diacetate was added at room temperature and stirred for 2.5 hours. The reaction mixture was concentrated under reduced pressure, and then water was added to the reaction mixture, followed by extraction with ethyl acetate. Organic layers were washed with a saturated sodium chloride solution, dried over anhydrous magnesium sulfate, and then concentrated under reduced pressure. The residue was subjected to silica gel column chromatography to give 0.14 g of 2-(3-chloropyridin-4-yl)-5-(trifluoromethyl)benzoxazole (hereinafter, referred to as "active compound 18").

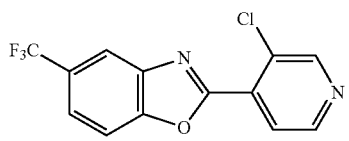

Active Compound 18
$^1$H-NMR (CDCl$_3$) δ: 8.86 (s, 1H), 8.70 (d, J=5.1 Hz, 1H), 8.20-8.18 (m, 1H), 8.10 (d, J=5.1 Hz, 1H), 7.78 (d, J=8.6 Hz, 1H), 7.75 (dd, J=8.5, 1.2 Hz, 1H)

Production Example 19

To a mixture of 1.74 g of 3-chloro-N-[2-hydroxy-5-(trifluoromethyl)phenyl]isonicotinamide, 15 ml of tetrahydrofuran and 1.73 g of triphenylphosphine, 2.87 g of 40% toluene solution of diethyl azodicarboxylate was added dropwise at room temperature. The reaction mixture was stirred at 50° C. for 30 minutes. After 30 minutes, 0.26 g of triphenylphosphine and 0.43 g of 40% toluene solution of diethyl azodicarboxylate were added and the reaction mixture was stirred at 50° C. for one hour. The reaction mixture was cooled to room temperature and then concentrated under reduced pressure. The residue was subjected to silica gel column chromatography to give 1.44 g of active compound 18.

Production Example 20

To a mixture of 0.45 g of 2-(3-chloropyridin-4-yl)-5-(trifluoromethyl)benzoxazole and 5 ml of chloroform, 0.53 g of 65% m-chloroperbenzoic acid was added while ice-cooling. The reaction mixture was stirred at room temperature for 5.5 hours, and was then diluted with chloroform, and washed with 5% aqueous solution of sodium hydroxide and a saturated sodium chloride solution, sequentially. Organic layers were dried over anhydrous sodium sulfate, and concentrated under reduced pressure. The residue was subjected to silica gel column chromatography to give 0.25 g of 3-chloro-4-[5-(trifluoromethyl)benzoxazole-2-yl]pyridine N-oxide (hereinafter, referred to as "active compound 19").

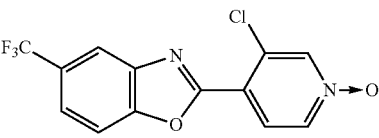

Active Compound 19
$^1$H-NMR (CDCl$_3$) δ: 8.40 (d, J=1.3 Hz, 1H), 8.21 (dd, J=7.1, 1.5 Hz, 1H), 8.17-8.14 (m, 2H), 7.77-7.72 (m, 2H)

Production Example 21

To a mixture of 0.49 g of 2-(3-chloropyridin-4-yl)methylideneamino-4-tert-butylphenol and 10 ml of methanol, 0.57 g of iodobenzene diacetate was added at room temperature and stirred for two hours. The reaction mixture was concentrated, and then water was added thereto, followed by extraction with ethyl acetate. The organic layer was washed with a saturated aqueous solution of sodium hydrogencarbonate and a saturated sodium chloride solution sequentially, and dried over anhydrous magnesium sulfate and concentrated under reduced pressure. The residue was subjected to silica gel column chromatography to give 0.21 g of 2-(3-chloropyridin-4-yl)-5-tert-butylbenzoxazole (hereinafter, referred to as "active compound 20").

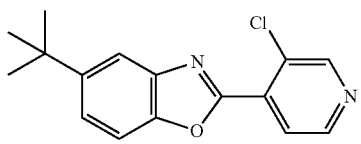

Active Compound 20
$^1$H-NMR (CDCl$_3$) δ: 8.81 (s, 1H), 8.65 (d, J=5.1 Hz, 1H), 8.07 (d, J=5.1 Hz, 1H), 7.92-7.91 (m 1H), 7.57 (dd, J=8.8, 0.7 Hz, 1H), 7.53 (dd, J=8.8, 1.8 Hz, 1H), 1.41 (s, 9H)

Production Example 22

To a mixture of 0.77 g of 2-chloro-N-[2-hydroxy-5-(trifluoromethyl)phenyl]isonicotinamide, 20 ml of tetrahydrofuran and 0.80 g of triphenylphosphine, 1.32 g of 40% toluene solution of diethyl azodicarboxylate was added dropwise at room temperature, and the mixture solution was stirred for 1.5 hours at room temperature and then 1.5 hours at 60° C. The reaction mixture was cooled to room temperature, and then concentrated under reduced pressure. The residue was subjected to silica gel column chromatography to give 0.60 g of 2-(2-chloropyridin-4-yl)-5-(trifluoromethyl)benzoxazole (hereinafter, referred to as "active compound 21").

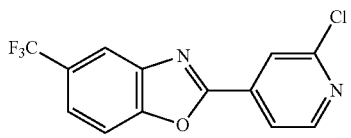

Active Compound 21
$^1$H-NMR (CDCl$_3$) δ: 8.63 (d, 1H), 8.17-8.12 (m, 2H), 8.05-8.03 (m, 1H), 7.77-7.72 (m, 2H)

Production Example 23

To a mixture of 0.40 g of 2-(2-chloropyridin-4-yl)-5-(trifluoromethyl)benzoxazole and 4 ml of chloroform, 0.53 g of 65% m-chloroperbenzoic acid was added while ice-cooling. The reaction mixture was stirred while ice-cooling for 30 minutes, then stirred at room temperature for three hours, and then stirred while heating at 50° C. for 1.5 hours. To the mixture, 0.53 g of 65% m-chloroperbenzoic acid and 2 ml of chloroform were added and stirred while heating at 60° C. for five hours. The reaction mixture was cooled to room temperature, then diluted with ethyl acetate, and washed with 5% aqueous solution of sodium hydroxide and a saturated sodium chloride solution, sequentially. The organic layer was dried over anhydrous sodium sulfate and then concentrated under reduced pressure to give 0.38 g of 2-chloro-4-[5-(trifluoromethyl)benzoxazole-2-yl]pyridine N-oxide (hereinafter, referred to as "active compod 22").

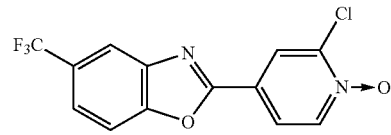

Active Compound 22
$^1$H-NMR (CDCl$_3$) δ: 8.45 (d, J=7.1 Hz, 1H), 8.36 (d, J=2.2 Hz, 1H), 8.10-8.08 (m, 1H), 8.04 (dd, J=7.1, 2.4 Hz, 1H), 7.73-7.72 (m, 2H)

Production Example 24

To a mixture of 0.38 g of N-[2-hydroxy-5-(trifluoromethyl)phenyl]-3-methylisonicotinamide, 5 ml of tetrahydrofuran and 0.42 g of triphenylphosphine, 0.69 g of 40% toluene solution of diethyl azodicarboxylate was added dropwise at room temperature and stirred while heating at 60° C. After three hours, 5 ml of 10% aqueous solution of sodium hydroxide was added and stirred while heating at 60° C. for two hours. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and then concentrated under reduced pressure. The residue was subjected to silica gel column chromatography to give 0.29 g of 2-(3-methylpyridin-4-yl)-5-(trifluoromethyl)benzoxazole (hereinafter, referred to as "active compound 23").

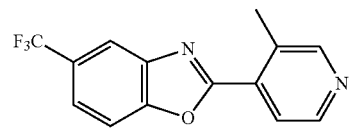

Active Compound 23
$^1$H-NMR (CDCl$_3$) δ: 8.69 (s, 1H), 8.66 (d, J=5.1 Hz, 1H), 8.16-8.14 (m, 1H), 8.04 (d, J=5.3 Hz, 1H), 7.75 (d, J=8.8 Hz, 1H), 7.71 (dd, J=8.8, 1.2 Hz, 1H), 2.83 (s, 3H)

Production Example 25

To a mixture of 0.20 g of 2-(3-methylpyridin-4-yl)-5-(trifluoromethyl)benzoxazole and 4 ml of chloroform, 0.30 g of 65% m-chloroperbenzoic acid was added while ice-cooling. The reaction mixture was stirred at room temperature for three hours, then diluted with ethyl acetate, and washed with 5% aqueous solution of sodium hydroxide and a saturated sodium chloride solution, sequentially. The organic layer was dried over anhydrous sodium sulfate, and concentrated under reduced pressure to give 0.17 g of 3-methyl-4-[5-(trifluoromethyl)benzoxazole-2-yl]pyridine N-oxide (hereinafter, referred to as "active compound 24").

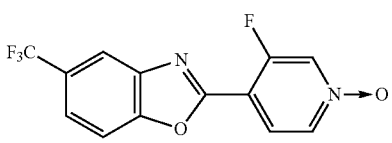

Active Compound 24
$^1$H-NMR (CDCl$_3$) δ: 8.22-8.21 (m, 1H), 8.19-8.16 (m, 1H), 8.12-8.09 (m, 2H), 7.72-7.69 (m, 2H), 2.81 (s, 3H)

Production Example 26

To a mixture of 0.51 g of 3-fluoro-N-[2-hydroxy-5-(trifluoromethyl)phenyl]isonicotinamide, 5 ml of tetrahydrofuran and 0.53 g of triphenylphosphine, 0.89 g of 40% toluene solution of diethyl azodicarboxylate was added dropwise at room temperature. The reaction mixture was stirred while heating at 50° C. for 1.5 hours. The reaction mixture was cooled to room temperature, and then concentrated under reduced pressure. The residue was subjected to silica gel column chromatography to give 0.46 g of 2-(3-fluoropyridin-4-yl)-5-(trifluoromethyl)benzoxazole (hereinafter, referred to as "active compound 25").

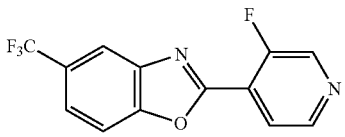

Active Compound 25
$^1$H-NMR (CDCl$_3$) δ: 8.76 (d, J=2.4 Hz, 1H), 8.66 (d, J=0.6 Hz, 1H), 8.17 (m, 1H), 8.15-8.12 (m, 1H), 7.78 (d, J=8.8 Hz, 1H), 7.75 (dd, J=8.8, 1.3 Hz, 1H)

Production Example 27

To a mixture of 0.34 g of 2-(3-fluoropyridin-4-yl)-5-(trifluoromethyl)benzoxazole and 6 ml of chloroform, 0.48 g of 65% m-chloroperbenzoic acid was added at room temperature. The solution was stirred while heating at 50° C. for 1.5 hours. The reaction mixture was cooled to room temperature, and diluted with ethyl acetate, and then washed with a saturated aqueous solution of sodium hydrogencarbonate twice and a saturated sodium chloride solution once, sequentially. The organic layer was dried over anhydrous sodium sulfate, and concentrated under reduced pressure. The residue was subjected to silica gel column chromatography to give 0.23 g of 3-fluoro-4-[5-(trifluoromethyl)benzoxazole-2-yl]pyridine N-oxide (hereinafter, referred to as "active compound 26").

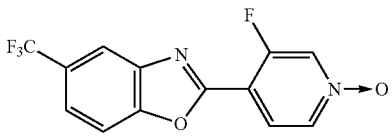

Active Compound 26
$^1$H-NMR (CDCl$_3$) δ: 8.32-8.29 (m, 1H), 8.17-8.12 (m, 3H), 7.76-7.71 (m, 2H)

Production Example 28

To a mixture of 0.29 g of 3-bromo-N-[2-hydroxy-5-(trifluoromethyl)phenyl]isonicotinamide, 4 ml of tetrahydrofuran and 0.25 g of triphenylphosphine, 0.42 g of 40% toluene solution of diethyl azodicarboxylate was added dropwise at room temperature. The reaction mixture was stirred while heating at 50° C. for 1.5 hours. The reaction mixture was cooled to room temperature, and then concentrated under reduced pressure. The residue was subjected to silica gel column chromatography to give 0.24 g of 2-(3-bromopyridin-4-yl)-5-(trifluoromethyl)benzoxazole (hereinafter, referred to as "active compound 27").

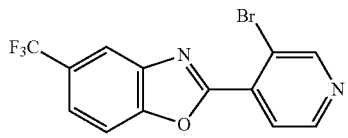

Active Compound 27
$^1$H-NMR (CDCl$_3$) δ: 9.00 (s, 1H), 8.73 (d, J=4.9 Hz, 1H), 8.20 (s, 1H), 8.06 (d, J=4.9 Hz, 1H), 7.78 (d, J=8.8 Hz, 1H), 7.75 (d, J=8.8 Hz, 1H)

Production Example 29

To a mixture of 0.50 g of 2-(3-bromopyridin-4-yl)-5-(trifluoromethyl)benzoxazole and 5 ml of chloroform, 0.58 g of 65% m-chloroperbenzoic acid was added. The reaction mixture was stirred while heating at 50° C. for 1.5 hours. The reaction mixture was cooled to room temperature, then diluted with ethyl acetate, and washed with a saturated aqueous solution of sodium hydrogencarbonate (twice) and a saturated sodium chloride solution, sequentially. The organic layer was dried over anhydrous sodium sulfate and concentrated under reduced pressure. The residue was subjected to silica gel column chromatography to give 0.37 g of 3-bromo-4-[5-(trifluoromethyl)benzoxazole-2-yl]pyridine N-oxide (hereinafter, referred to as "active compound 28").

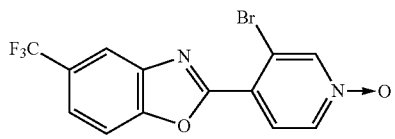

Active Compound 28
$^1$H-NMR (CDCl$_3$) δ: 8.56 (d, J=1.7 Hz, 1H), 8.24 (dd, J=7.1, 1.7 Hz, 1H), 8.16 (s, 1H), 8.13 (d, J=7.1 Hz, 1H), 7.76-7.72 (m, 2H)

Production Example 30

To a mixture of 1.81 g of N-[2-hydroxy-5-(trifluoromethyl)phenyl]-3-iodoisonicotinamide, 20 ml of tetrahydrofuran and 1.34 g of triphenylphosphine, 2.22 g of 40% toluene solution of diethyl azodicarboxylate was added dropwise at room temperature. The reaction mixture was stirred while heating at 50° C. for one hour. The reaction mixture was cooled to room temperature, and then the reaction mixture was concentrated under reduced pressure. The residue was subjected to silica gel column chromatography to give 1.40 g of 2-(3-iodopyridin-4-yl)-5-(trifluoromethyl)benzoxazole (hereinafter, referred to as "active compound 29").

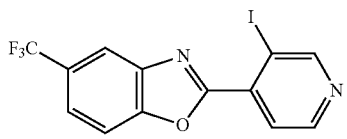

Active Compound 29

$^1$H-NMR (CDCl$_3$) δ: 9.26 (s, 1H), 8.73 (d, J=5.1 Hz, 1H), 8.21 (s, 1H), 8.01 (d, J=5.1 Hz, 1H), 7.78 (d, J=8.8 Hz, 1H), 7.75 (d, J=8.8 Hz, 1H)

Production Example 31

To a mixture of 0.30 g of 2-(3-iodopyridin-4-yl)-5-(trifluoromethyl)benzoxazole and 3 ml of chloroform, 0.26 g of 65% m-chloroperbenzoic acid was added while ice-cooling. The reaction mixture was stirred at room temperature for 30 minutes. The reaction mixture was stirred while heating at 50° C. for one hour. Then, 0.20 g of 65% m-chloroperbenzoic acid was added thereto and stirred while heating at 50° C. for further two hours. The reaction mixture was cooled to room temperature, and then diluted with ethyl acetate, and washed with a saturated aqueous solution of sodium hydrogencarbonate and a saturated sodium chloride solution, sequentially. The organic layer was dried over anhydrous sodium sulfate, and then concentrated under reduced pressure. The residue was subjected to silica gel column chromatography to give 0.09 g of 3-iode-4-[5-(trifluoromethyl)benzoxazole-2-yl]pyridine N-oxide (hereinafter, referred to as "active compound 30").

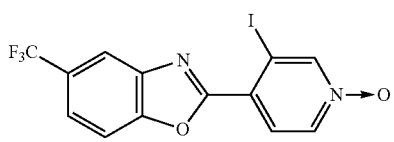

Active Compound 30

$^1$H-NMR (CDCl$_3$) δ: 8.83 (d, J=1.7 Hz, 1H), 8.25 (dd, J=7.1, 1.7 Hz, 1H), 8.18-8.15 (m, 1H), 8.04 (d, J=7.1 Hz, 1H), 7.75-7.72 (m, 2H)

Production Example 32

A mixture of 0.39 g of 2-(3-iodopyridin-4-yl)-5-(trifluoromethyl)benzoxazole, 0.18 g of copper (I) cyanide and 2 ml of 1-methyl-2-pyrrolidinone was stirred while heating at 80° C. for 2 hours. Water and ethyl acetate were poured into the reaction mixture, which was filtered through Celite™. The resultant filtrate was washed with a saturated sodium chloride solution, dried over anhydrous sodium sulfate, and concentrated under reduced pressure. The residue was subjected to silica gel column chromatography to give 0.11 g of 2-(3-cyanopyridin-4-yl)-5-(trifluoromethyl)benzoxazole (hereinafter, referred to as "active compound 31").

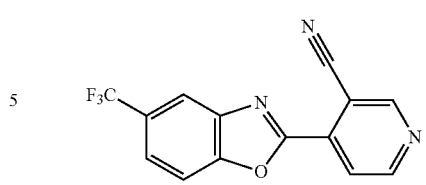

Active Compound 31

$^1$H-NMR (CDCl$_3$) δ: 9.14 (s, 1H), 9.02 (d, J=5.4 Hz, 1H), 8.29 (d, J=5.1 Hz, 1H), 8.25-8.22 (m, 1H), 7.83 (d, J=8.8 Hz, 1H), 7.79 (d, J=8.8, 1.3 Hz, 1H)

Production Example 33

To a mixture of 0.78 g of 2-(3-iodopyridin-4-yl)-5-(trifluoromethyl)benzoxazole, 0.27 g of phenylboronic acid, 5 ml of tetrahydrofuran and 0.14 g of dichlorobis(triphenylphosphine)palladium (II), 3 ml of 10% aqueous solution of sodium hydroxide was added and heated to reflux for three hours. Water was added to the reaction mixture, followed by extraction with ethyl acetate twice. The combined organic layers were washed with water and a saturated sodium chloride solution, dried over anhydrous magnesium sulfate, and concentrated under reduced pressure. The residue was subjected to silica gel column chromatography to give 0.18 g of 2-(3-phenyl pyridin-4-yl)-5-(trifluoromethyl)benzoxazole (hereinafter, referred to as "active compound 32").

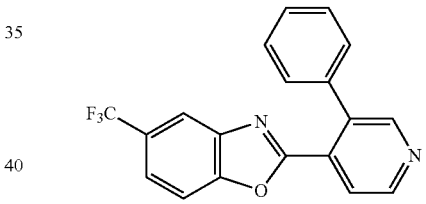

Active Compound 32

$^1$H-NMR (CDCl$_3$) δ: 8.81 (d, J=5.1 Hz, 1H), 8.80 (s, 1H), 8.05-8.02 (m, 2H), 7.62-7.59 (m, 1H), 7.45-7.38 (m, 4H), 7.35-7.30 (m, 2H)

Production Example 35

A mixture of 1.17 g of 2-(3-iodopyridin-4-yl)-5-(trifluoromethyl)benzoxazole, 0.40 g of (trimethylsilyl)acetylene, 0.03 g of copper (I) iodide, 0.11 g of dichlorobis(triphenylphosphine)palladium (II), 2.5 ml of triethylamine and 10 ml of tetrahydrofuran was stirred while heating at 50° C. for two hours. The reaction solution was cooled to room temperature, to which tert-butyl methyl ether was added. The reaction mixture was washed with a saturated aqueous solution of sodium hydrogencarbonate and a saturated sodium chloride solution sequentially. The organic layer was dried over anhydrous magnesium sulfate, and concentrated under reduced pressure. The residue was subjected to silica gel column chromatography to give 0.50 g of 5-(trifluoromethyl)2-[3-(trimethylsilyl)ethynyl-4-yl]-benzoxazole.

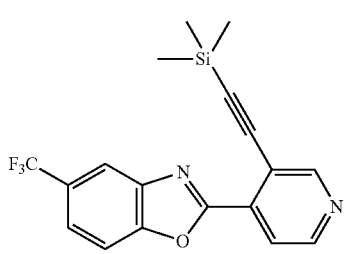

¹H-NMR (CDCl₃) δ: 8.93 (d, J=0.7 Hz, 1H), 8.71 (d, J=5.3 Hz, 1H), 8.13-8.11 (m, 1H), 8.10 (dd, J=5.3, 0.7 Hz, 1H), 7.73-7.72 (m, 2H), 0.35 (s, 9H)

To a mixture of 0.74 g of 5-(trifluoromethyl)2-[3-(trimethylsilyl)ethynyl-4-yl]-benzoxazole and 6 ml of methanol, 0.20 g of potassium carbonate was added. The reaction mixture was stirred at room temperature for one hour. Water was added to the reaction mixture, which was extracted with ethyl acetate. The organic layer was washed with a saturated sodium chloride solution, then dried over anhydrous magnesium sulfate, and concentrated under reduced pressure. The residue was subjected to silica gel column chromatography to give 0.46 g of 2-(3-ethynylpyridin-4-yl)-5-(trifluoromethyl)benzoxazole (hereinafter, referred to as "active compound 34").

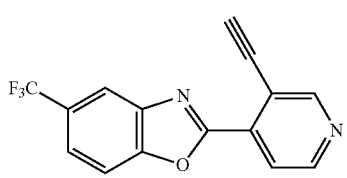

Active Compound 34
¹H-NMR (CDCl₃) δ: 8.97 (s, 1H), 8.76 (d, J=5.1 Hz, 1H), 8.19-8.17 (m, 1H), 8.10 (d, J=5.1 Hz, 1H), 7.76 (d, J=8.6 Hz, 1H), 7.73 (dd, J=8.5, 1.2 Hz, 1H), 3.63 (s, 1H)

Production Example 36

A mixture of 0.34 g of 2-(3-ethynylpyridin-4-yl)-5-(trifluoromethyl)benzoxazole, 0.10 g of 5% palladium on carbon and 8 ml of ethyl acetate was stirred under about one atmosphere of hydrogen at room temperature for two hours. The reaction mixture was filtered through Celite™. The filtrate was concentrated under reduced pressure. The residue was subjected to silica gel column chromatography to give 0.33 g of 2-(3-ethylpyridin-4-yl)-5-(trifluoromethyl)benzoxazole (hereinafter, referred to as "active compound 35").

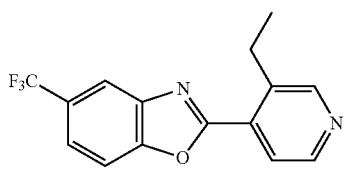

Active Compound 35
¹H-NMR (CDCl₃) δ: 8.71 (s, 1H), 8.66 (d, J=5.1 Hz, 1H), 8.16-8.14 (m, 1H), 8.01 (d, J=5.1 Hz, 1H), 7.74 (d, J=8.5 Hz, 1H), 7.71 (dd, J=8.8, 1.3 Hz, 1H), 3.29 (q, J=7.6 Hz, 2H), 1.35 (t, J=7.6 Hz, 3H)

Production Example 37

To a mixture of 1.78 g of 3-tert-butoxycarbonylamino-N-[2-hydroxy-5-(trifluoromethyl)phenyl]isonicotinamide, 20 ml of tetrahydrofuran and 1.29 g of triphenylphosphine, 2.15 g of 40% toluene solution of diethyl azodicarboxylate was added dropwise at room temperature. The reaction mixture was stirred at room temperature for one hour and then stirred while heating at 50° C. for 30 minutes. The reaction mixture was cooled to room temperature, and then concentrated under reduced pressure. The residue was subjected to silica gel column chromatography to give 0.69 g of 2-(3-tert-butoxycarbonylamino pyridin-4-yl)-5-(trifluoromethyl)benzoxazole (hereinafter, referred to as "active compound 36").

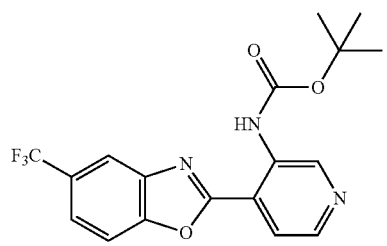

Active Compound 36
¹H-NMR (CDCl₃) δ: 10.57 (s, 1H), 9.88 (s, 1H), 8.45 (d, J=5.1 Hz, 1H), 8.17 (s, 1H), 7.99 (d, J=5.1 Hz, 1H), 7.78-7.73 (m, 2H), 1.62 (s, 9H)

Production Example 38

A mixture of 0.28 g of 2-(3-fluoropyridin-4-yl)-5-(trifluoromethyl)benzoxazole, 0.27 g of potassium carbonate and 3 ml of methanol was stirred while heating at 60° C. for two hours. The reaction mixture was concentrated under reduced pressure. Water was added thereto, which followed by extraction with ethyl acetate twice. The combined organic layers were washed with water and a saturated sodium chloride solution, dried over anhydrous magnesium sulfate, and concentrated under reduced pressure. The residue was subjected to silica gel column chromatography to give 0.21 g of 2-(3-methoxypyridin-4-yl)-5-(trifluoromethyl)benzoxazole (hereinafter, referred to as "active compound 37").

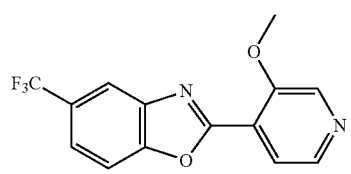

Active Compound 37
¹H-NMR (CDCl₃) δ: 8.60 (s, 1H), 8.46 (d, J=4.9 Hz, 1H), 8.16-8.14 (m, 1H), 8.02 (d, J=4.9 Hz, 1H), 7.74 (d, J=8.5 Hz, 1H), 7.69 (dd, J=8.5, 1.1 Hz, 1H), 4.16 (s, 3H)

Production Example 39

A mixture of 0.28 g of 2-(3-fluoropyridin-4-yl)-5-(trifluoromethyl)benzoxazole, 0.15 g of phenol, 0.55 g of potassium carbonate and 2 ml of DMF was stirred at room temperature for one hour, and then stirred while heating at 50° C. for four hours. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and then concentrated under reduced pressure. The residue was subjected to silica gel column chromatography to give 0.24 g of 2-(3-phenoxypyridin-4-yl)-5-(trifluoromethyl)benzoxazole (hereinafter, referred to as "active compound 38").

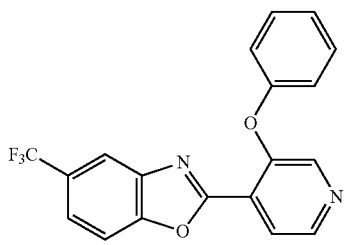

Active Compound 38
$^1$H-NMR (CDCl$_3$) δ: 8.57 (d, J=4.9 Hz, 1H), 8.47 (s, 1H), 8.14 (d, J=4.9 Hz, 1H), 8.11 (s, 1H), 7.69-7.65 (m, 2H), 7.41-7.37 (m, 2H), 7.20-7.16 (m, 1H), 7.13-7.09 (m, 2H)

Production Example 40

A mixture of 0.06 g of 55% sodium hydride (in oil) and 2 ml of DMF was stirred at room temperature. To the mixture, a mixture solution of 0.13g of 2,2,2-trifluoroethanol and 0.5 ml of DMF was added. The mixture solution was stirred at the same temperature for 15 minutes, and then 0.28 g of 2-(3-fluoropyridin-4-yl)-5-(trifluoromethyl)benzoxazole was stirred at room temperature for one hour. Water was added to the reaction mixture, which followed by extraction with ethyl acetate twice. The combined organic layers were washed with a saturated sodium chloride solution, dried over anhydrous magnesium sulfate, and then concentrated under reduced pressure. The residue was subjected to silica gel column chromatography to give 0.27 g of 2-[3-(2,2,2-trifluoroethyl)oxypyridin-4-yl]-5-(trifluoromethyl)benzoxazole (hereinafter, referred to as "active compound 39").

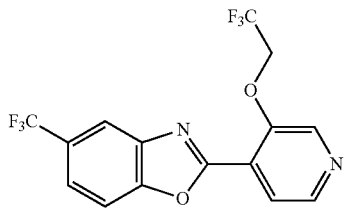

Active Compound 39
$^1$H-NMR (CDCl$_3$) δ: 8.61 (s, 1H), 8.59 (d, J=4.9 Hz, 1H), 8.15-8.14 (m, 1H), 8.11 (d, J=5.1 Hz, 1H), 7.76-7.71 (m, 2H), 4.67 (q, J=8.0 Hz, 2H)

Production Example 41

A mixture of 0.28 g of 2-(3-fluoropyridin-4-yl)-5-(trifluoromethyl)benzoxazole, 0.14 g of methyl mercaptan sodium salt and 2 ml of DMF was stirred while heating at 50° C. for two hours. The reaction mixture was cooled to room temperature, and then water was added to the reaction mixture, followed by extraction with ethyl acetate. The organic layer was washed with a saturated sodium chloride solution, dried over anhydrous magnesium sulfate, and concentrated under reduced pressure. The resultant residue was subjected to silica gel column chromatography to give 0.21 g of 2-[3-(methylthio)pyridin-4-yl]-5-(trifluoromethyl)benzoxazole (hereinafter, referred to as "active compound 40").

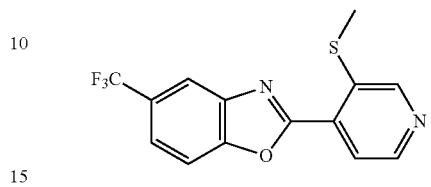

Active Compound 40
$^1$H-NMR (CDCl$_3$) δ: 8.68 (s, 1H), 8.56 (d, J=5.1 Hz, 1H), 8.22-8.20 (m, 1H), 8.02 (d, J=5.1 Hz, 1H), 7.74 (d, J=8.5 Hz, 1H), 7.71 (dd, J=8.8, 1.4 Hz, 1H), 2.68 (s, 3H)

Production Example 42

A mixture of 0.28 g of 2-(3-fluoropyridin-4-yl)-5-(trifluoromethyl)benzoxazole, 0.20 g of ethyl mercaptan sodium salt and 2 ml of DMF was stirred at room temperature for one hour. Water was added to the reaction mixture, and was extracted with ethyl acetate. The organic layer was washed with a saturated sodium chloride solution, dried over anhydrous magnesium sulfate, and concentrated under reduced pressure. The residue was subjected to silica gel column chromatography to give 0.28 g of 2-(3-ethylthio pyridin-4-yl)-5-(trifluoromethyl)benzoxazole (hereinafter, referred to as "active compound 41").

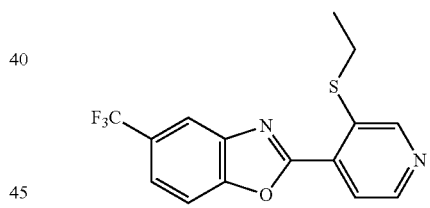

Active Compound 41
$^1$H-NMR (CDCl$_3$) δ: 8.72 (s, 1H), 8.55 (d, J=5.1 Hz, 1H), 8.21 (s, 1H), 8.01 (d, J=5.1 Hz, 1H), 7.76-7.70 (m, 2H), 3.20 (q, J=7.5 Hz, 2H), 1.48 (t, J=7.5 Hz, 3H)

Production Example 43

A mixture of 0.28 g of 2-(3-fluoropyridin-4-yl)-5-(trifluoromethyl)benzoxazole, 0.15 g of 1-propanethiol, 0.40 g of potassium carbonate and 2 ml of DMF was stirred while heating at 50° C. for one hour. The reaction mixture was cooled to room temperature, and then water was added to the reaction mixture, which was extracted with ethyl acetate. The organic layer was washed with a saturated sodium chloride solution, dried over anhydrous magnesium sulfate, and concentrated under reduced pressure. The residue was subjected to silica gel column chromatography to give 0.30 g of 2-(3-propylthiopyridin-4-yl)-5-(trifluoromethyl)benzoxazole (hereinafter, referred to as "active compound 42").

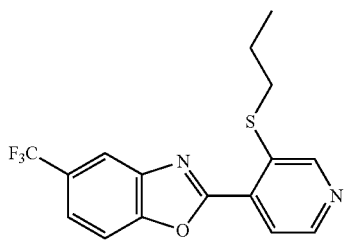

Active Compound 42

¹H-NMR (CDCl₃) δ: 8.72 (s, 1H), 8.55 (d, J=5.1 Hz, 1H), 8.23-8.21 (m, 1H), 8.01 (d, J=5.1 Hz, 1H), 7.75 (d, J=8.8 Hz, 1H), 7.71 (dd, J=8.8, 1.5 Hz, 1H), 3.12 (t, J=7.6 Hz, 2H), 1.87-1.80 (m, 2H), 1.13 (t, J=7.6 Hz, 3H)

Production Example 44

To a mixture of 0.28 g of 2-(3-fluoropyridin-4-yl)-5-(trifluoromethyl)benzoxazole, 0.50 g of potassium carbonate and 2 ml of DMF, a mixture of 0.15 g of 2-propanethiol and 0.5 ml of DMF was added. The reaction mixture was stirred while heating at 60° C. for two hours. The reaction mixture was cooled to room temperature, and then water was added to the reaction mixture, which was extracted with ethyl acetate. The organic layer was washed with 5% aqueous solution of potassium carbonate and a saturated sodium chloride solution, sequentially, dried over anhydrous magnesium sulfate, and concentrated under reduced pressure. The residue was subjected to silica gel column chromatography to give 0.26 g of 2-(3-isopropylthiopyridin-4-yl)-5-(trifluoromethyl)benzoxazole (hereinafter, referred to as "active compound 43").

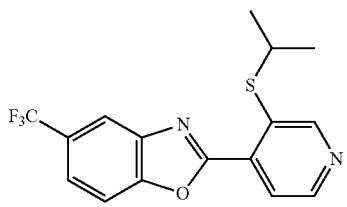

Active Compound 43

¹H-NMR (CDCl₃) δ: 8.79 (s, 1H), 8.57 (d, J=5.1 Hz, 1H), 8.22-8.20 (m, 1H), 7.99 (d, J=5.1 Hz, 1H), 7.75 (d, J=8.8 Hz, 1H), 7.71 (dd, J=8.8, 1.4 Hz, 1H), 3.78 (sep, J=6.6 Hz, 1H), 1.45 (d, J=6.6 Hz, 6H)

Production Example 45

Production Example 45 was carried out according to the same manner as in Production Example 43, using tert-butyl mercaptan instead of 2-propanethiol. Thus, 2-(3-tert-butylthiopyridin-4-yl)-5-(trifluoromethyl)benzoxazole (hereinafter, referred to as "active compound 44") was obtained.

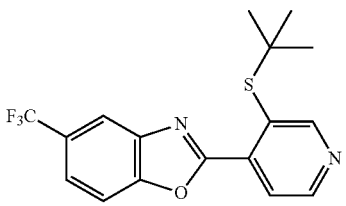

Active Compound 44

¹H-NMR (CDCl₃) δ: 8.99 (d, J=0.7 Hz, 1H), 8.77 (d, J=5.1 Hz, 1H), 8.18-8.16 (m, 1H), 7.93 (dd, J=5.1, 0.7 Hz, 1H), 7.77 (d, J=8.8 Hz, 1H), 7.73 (dd, J=8.8, 1.5 Hz, 1H), 1.24 (s, 9H)

Production Example 46

Production Example 46 was carried out according to the same manner as in Production Example 43, using 1-pentanethiol instead of 2-propanethiol. Thus, 2-(3-pentylthiopyridin-4-yl)-5-(trifluoromethyl)benzoxazole (hereinafter, referred to as "active compound 45") was obtained.

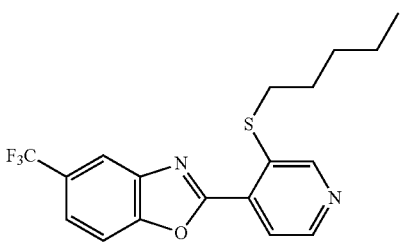

Active Compound 45

¹H-NMR (CDCl₃) δ: 8.72 (s, 1H), 8.55 (d, J=5.2 Hz, 1H), 8.23-8.21 (m, 1H), 8.00 (d, J=5.1, 1H), 7.75 (d, J=8.6 Hz, 1H), 7.71 (dd, J=8.8, 1.6 Hz, 1H), 3.13 (t, J=7.6 Hz, 2H), 1.81 (m, 2H), 1.50 (m, 2H), 1.38 (m, 2H), 0.92 (t, J=7.5 Hz, 3H)

Production Example 47

To a mixture of 0.28 g of 2-(3-fluoropyridin-4-yl)-5-(trifluoromethyl)benzoxazole, 0.50 g of potassium carbonate and 2 ml of DMF, 0.15 g of 2,2,2-trifluoroethanethiol was added. The reaction mixture was stirred at room temperature for 1.2 hours. Water was added to reaction mixture, which followed by extraction with ethyl acetate twice. The combined organic layers were washed with saturated sodium chloride solution, dried over anhydrous magnesium sulfate, and concentrated under reduced pressure. The residue was subjected to silica gel column chromatography to give 0.32 g of 2-[3-(2,2,2-trifluoroethylthio)pyridin-4-yl]-5-(trifluoromethyl)benzoxazole (hereinafter, referred to as "active compound 46").

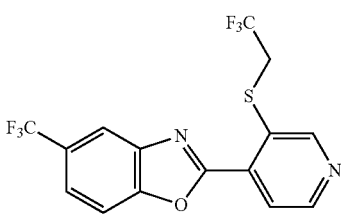

Active Compound 46

¹H-NMR (CDCl₃) δ: 8.94 (s, 1H), 8.74 (d, J=5.1 Hz, 1H), 8.22-8.21 (m, 1H), 8.06 (d, J=5.1 Hz, 1H), 7.78-7.73 (m, 2H), 3.76 (q, J=9.5 Hz, 2H)

Production Example 48

Production Example 48 was carried out according to the same manner as in Production Example 43 except for using benzyl mercaptan instead of 2-propanethiol. Thus, 2-(3-benzylthiopyridin-4-yl)-5-(trifluoromethyl)benzoxazole (hereinafter, referred to as "active compound 47") was obtained.

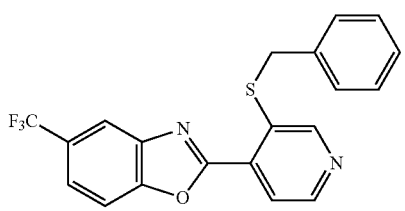

Active Compound 47

¹H-NMR (CDCl₃) δ: 8.75 (s, 1H), 8.56 (d, J=5.2 Hz, 1H), 8.19-8.18 (m, 1H), 8.00 (dd, J=5.2, 0.8 Hz, 1H), 7.74 (d, J=8.6 Hz, 1H), 7.70 (dd, J=8.8, 1.5 Hz, 1H), 7.43-7.40 (m, 2H), 7.35-7.27 (m, 3H), 4.36 (s, 2H)

Production Example 49

Production Example 49 was carried out according to the method as in Production Example 43 except for using 4-chlorobenzyl mercaptan instead of 2-propanethiol. Thus, 2-[3-(4-chlorobenzylthio)pyridin-4-yl]-5-(trifluoromethyl)benzoxazole (hereinafter, referred to as "active compound 48") was obtained.

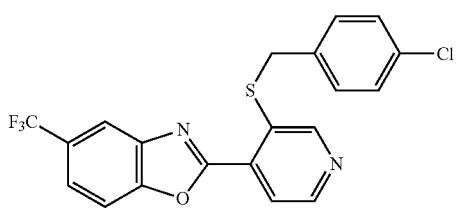

Active Compound 48

¹H-NMR (CDCl₃) δ: 8.71 (s, 1H), 8.58 (d, J=5.1 Hz, 1H), 8.20-8.18 (m, 1H), 8.00 (d, J=5.1 Hz, 1H), 7.75-7.70 (m, 2H), 7.35-7.32 (m, 2H), 7.29-7.26 (m, 2H), 4.32 (s, 2H)

Production Example 50

To a mixture of 0.28 g of 2-(3-fluoropyridin-4-yl)-5-(trifluoromethyl)benzoxazole, 0.40 g of potassium carbonate and 2 ml of DMF, a mixture of 0.17 g of thiophenol and 0.5 ml of DMF was added. The reaction mixture was stirred at room temperature for one hour. Water was added to the reaction mixture, which was extracted with ethyl acetate. The organic layer was washed with a saturated sodium chloride solution, dried over anhydrous magnesium sulfate, and concentrated under reduced pressure. The residue was subjected to silica gel column chromatography to give 0.30 g of 2-[3-(phenylthio)pyridin-4-yl]-5-(trifluoromethyl)benzoxazole (hereinafter, referred to as "active compound 49").

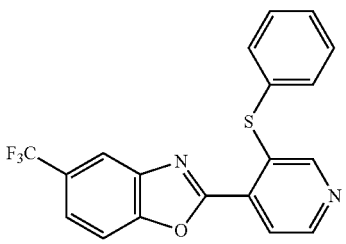

Active Compound 49

¹H-NMR (CDCl₃) δ: 8.51 (d, J=5.1 Hz, 1H), 8.23 (s, 1H), 8.20 (s, 1H), 8.02 (d, J=5.1 Hz, 1H), 7.76 (d, J=8.8 Hz, 1H), 7.74 (dd, J=8.8, 1.4 Hz, 1H), 7.65-7.61 (m, 2H), 7.48-7.45 (m, 3H)

Production Example 51

Production Example 51 was carried out according to the same manner as in Production Example 50 except for using 4-chlorothiophenol instead of thiophenol. Thus, 2-[3-(4-chloro-phenylthio)pyridin-4-yl]-5-(trifluoromethyl)benzoxazole (hereinafter, referred to as "active compound 50") was obtained.

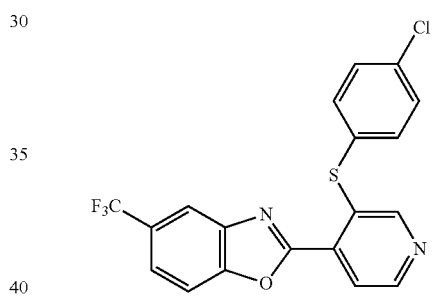

Active Compound 50

¹H-NMR (CDCl₃) δ: 8.54 (d, J=5.1 Hz, 1H), 8.23-8.22 (m, 1H), 8.20 (s, 1H), 8.03 (d, J=5.1 Hz, 1H), 7.77 (d, J=8.8 Hz, 1H), 7.74 (dd, J=8.8, 1.2 Hz, 1H), 7.57-7.54 (m, 2H), 7.46-7.43 (m, 2H)

Production Example 53

A mixture of 1.41 g of 2-(3-fluoropyridin-4-yl)-5-(trifluoromethyl)benzoxazole, 1.85 g of phthalimide potassium and 8 ml of DMF was stirred while heating at 120° C. After six hours, 0.92 g of phthalimide potassium was added and stirred while heating at 140° C. for further one hour. The reaction mixture was cooled to room temperature, and then water was added to the reaction mixture, which followed by extraction with ethyl acetate twice. The combined organic layers were washed with water and a saturated sodium chloride solution, sequentially, dried over anhydrous magnesium sulfate, and concentrated under reduced pressure. The residue was subjected to silica gel column chromatography to give 1.26 g of N-{4-[5-(trifluoromethyl)benzoxazole-2-yl]pyridin-3-yl} phthalimide.

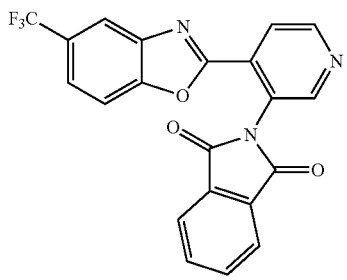

$^1$H-NMR (CDCl$_3$) δ: 8.95 (d, J=5.1 Hz, 1H), 8.82 (s, 1H), 8.27 (d, J=5.1 Hz, 1H), 8.04-7.99 (m, 2H), 7.92-7.88 (n, 2H), 7.73-7.70 (m, 1H), 7.64 (dd, J=8.8, 1.2 Hz, 1H), 7.57 (d, J=8.8 Hz, 1H)

To a mixture of 0.41 g of N-{4-[5-(trifluoromethyl)benzoxazole-2-yl]pyridin-3-yl}phthalimide and 5 ml of ethanol, 0.3 ml of hydrazine monohydrate was added and stirred at room temperature for 1.5 hours. To the reaction mixture, ethanol was added and filtrated, and the filtrate was concentrated. The residue was diluted with ethyl acetate, and washed with water and then with a saturated sodium chloride solution. The organic layer was dried over anhydrous magnesium sulfate, and then concentrated under reduced pressure. The residue was subjected to silica gel column chromatography to give 0.19 g of 2-(3-aminopyridin-4-yl)-5-(trifluoromethyl)benzoxazole (hereinafter, referred to as "active compound 52").

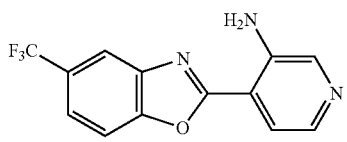

Active Compound 52

$^1$H-NMR (CDCl$_3$) δ: 8.34 (d, J=0.5 Hz, 1H), 8.08-8.06 (m, 2H), 7.83 (d, J=5.4 Hz, 1H), 7.72 (d, J=8.8 Hz, 1H), 7.68 (dd, J=8.8, 1.5 Hz, 1H), 6.14 (br s, 2H)

Production Example 54

A mixture of 0.31 g of 2-(3-fluoropyridin-4-yl)-5-(trifluoromethyl)benzoxazole, 0.21 g of pyrrolidine, 0.55 g of potassium carbonate and 2 ml of DMF was stirred while heating at 60° C. for one hour. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and then concentrated under reduced pressure. The residue was subjected to silica gel column chromatography to give 0.37 g of 2-[3-(pyrrolidine-1-yl)pyridin-4-yl]-5-(trifluoromethyl)benzoxazole (hereinafter, referred to as "active compound 53").

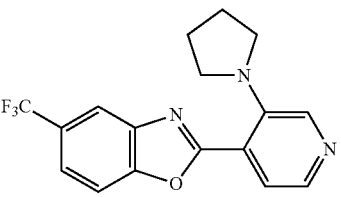

Active Compound 53

$^1$-NMR (CDCl$_3$) δ: 8.40 (s, 1H), 8.10 (d, J=4.9 Hz, 1H), 8.09-8.07 (m, 1H), 7.71 (d, J=8.5 Hz, 1H), 7.69 (dd, J=8.6, 1.7 Hz, 1H), 7.56 (d, J=5.1 Hz, 1H), 3.28-3.24 (m, 4H), 1.97-1.93 (m, 4H)

Production Example 55

A mixture of 0.28 g of 2-(3-fluoropyridin-4-yl)-5-(trifluoromethyl)benzoxazole, 0.17 g of piperidine, 0.55 g of potassium carbonate and 2 ml of DMF was stirred while heating at 50° C. for two hours, and then at 80° C. for 1.3 hours. Water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.34 g of 2-[3-(piperidine-1-yl)pyridin-4-yl]-5-(trifluoromethyl)benzoxazole (hereinafter, referred to as "active compound 54").

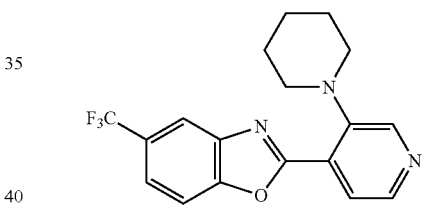

Active Compound 54

$^1$H-NMR (CDCl$_3$) δ: 8.54 (s, 1H), 8.36 (d, J=5.1 Hz, 1H), 8.12-8.11 (m, 1H), 7.89 (d, J=5.1 Hz, 1H), 7.73 (d, J=8.7 Hz, 1H), 7.69 (dd, J=8.8, 1.6 Hz, 1H), 3.11-3.09 (m, 4H), 1.81-1.75 (m, 4H), 1.66-1.59 (m, 2H)

Production Example 56

Production Example 56 was carried out according to the same manner as in Production Example 55, using morpholine instead of piperidine. Thus, 2-[3-(morpholin-4-yl)pyridin-4-yl]-5-(trifluoromethyl)benzoxazole (hereinafter, referred to as "active compound 55") was obtained.

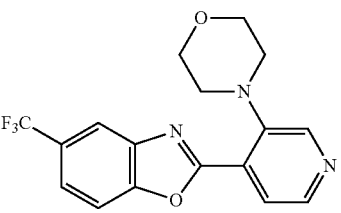

Active Compound 55

$^1$H-NMR (CDCl$_3$) δ: 8.57 (s, 1H), 8.46 (d, 5=4.9 Hz, 1H), 8.13-8.11 (m, 1H), 7.97 (d, J=4.9 Hz, 1H), 7.74 (d, J=8.6 Hz, 1H), 7.71 (dd, J=8.7, 1.7 Hz, 1H), 3.96-3.93 (m, 4H), 3.21-3.18 (m, 4H)

Production Example 57

A mixture of 0.31 g of 2-(3-fluoropyridin-4-yl)-5-(trifluoromethyl)benzoxazole, 0.14 g of imidazole, 0.55 g of potassium carbonate and 2 ml of DMF was stirred while heating at room temperature for 1.5 hours, and then at 60° C. for 1.5 hours. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.31 g of 2-[3-(imidazole-1-yl)pyridin-4-yl]-5-(trifluoromethyl)benzoxazole (hereinafter, referred to as "active compound 56").

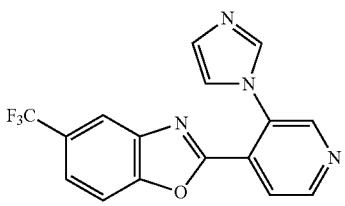

Active Compound 56

$^1$H-NMR (CDCl$_3$) δ: 8.93 (d, J=5.1 Hz, 1H), 8.82 (s, 1H), 8.23 (d, J=5.1 Hz, 1H), 8.08-8.06 (m, 1H), 7.72-7.71 (m, 1H), 7.69 (dd, J=8.5, 1.3 Hz, 1H), 7.59 (d, J=8.5 Hz, 1H), 7.29-7.28 (m, 1H), 7.13-7.11 (m, 1H)

Production Example 58

A mixture of 0.28 g of 2-(3-fluoropyridin-4-yl)-5-(trifluoromethyl)benzoxazole, 0.18 g of 4-(trifluoromethyl)-1H-imidazole, 0.55 g of potassium carbonate and 2 ml of DMF was stirred while heating at 50° C. for 1.5 hours. Then, the reaction mixture was cooled to room temperature. Water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.40 g of 2-{3-[4-(trifluoromethyl)imidazole-1-yl]pyridin-4-yl}-5-(trifluoromethyl)benzoxazole (hereinafter, referred to as "active compound 57").

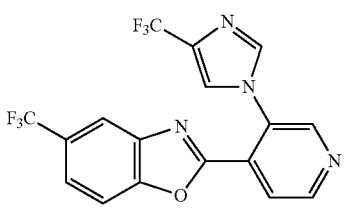

Active Compound 57

$^1$H-NMR (CDCl$_3$) δ: 9.00 (d, J=5.2 Hz, 1H), 8.84 (s, 1H), 8.31 (d, J=5.1 Hz, 1H), 8.06-8.04 (m, 1H), 7.77-7.75 (m, 1H), 7.74-7.70 (m, 1H), 7.62 (d, J=8.6 Hz, 1H), 7.52-7.50 (m, 1H)

Production Example 59

A mixture of 0.24 g of 2-(3-fluoropyridin-4-yl)-5-(trifluoromethyl)benzoxazole, 0.14 g of pyrazole, 0.69 g of potassium carbonate and 4 ml of DMF was stirred while heating at 50° C. for two hours. Water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.22 g of 2-[3-(pyrazole-1-yl)pyridin-4-yl]-5-(trifluoromethyl)benzoxazole (hereinafter, referred to as "active compound 58").

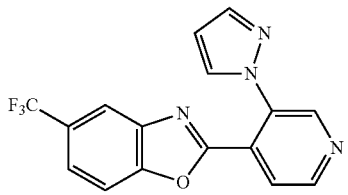

Active Compound 58

$^1$H-NMR (CDCl$_3$) δ: 8.93 (s, 1H), 8.87 (d, J=5.1 Hz, 1H), 8.10 (d, J=5.1 Hz, 1H), 8.08-8.06 (m, 1H), 7.77 (d, J=2.2 Hz, 1H), 7.72 (d, J=1.7 Hz, 1H), 7.66 (dd, J=8.6, 1.3 Hz, 1H), 7.53 (d, J=8.8 Hz, 1H), 6.55-6.53 (m, 1H)

Production Example 60

A mixture of 0.28 g of 2-(3-fluoropyridin-4-yl)-5-(trifluoromethyl)benzoxazole, 0.19 g of 3-bromopyrazole, 0.55 g of potassium carbonate and 2 ml of DMF was stirred while heating at 50° C. for 1.5 hours. Then, the reaction mixture was cooled to room temperature. Water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.31 g of 2-[3-(3-bromopyrazole-1-yl)pyridin-4-yl]-5-(trifluoromethyl)benzoxazole (hereinafter, referred to as "active compound 59").

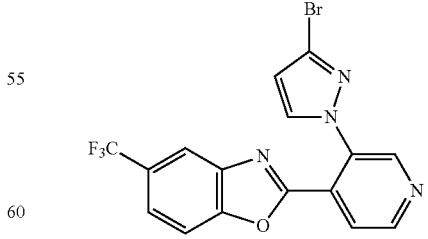

Active Compound 59

$^1$H-NMR (CDCl$_3$) δ: 8.92 (s, 1H), 8.89 (d, J=5.1 Hz, 1H), 8.16 (d, J=5.1 Hz, 1H), 8.08-8.07 (m, 1H), 7.69 (dd, J=8.8, 1.2 Hz, 1H), 7.66 (d, J=2.4 Hz, 1H), 7.59 (d, J=8.8 Hz, 1H), 6.57 (d, J=2.4 Hz, 1H)

Production Example 61

A mixture of 0.28 g of 2-(3-fluoropyridin-4-yl)-5-(trifluoromethyl)benzoxazole, 0.18 g of 3-trifluoromethylpyrazole, 0.55 g of potassium carbonate and 3 ml of DMF was stirred while heating at 60° C. for one hour. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and then concentrated under reduced pressure. The residue was subjected to silica gel column chromatography to give 0.34 g of 2-[3-(3-trifluoromethylpyrazole-1-yl)pyridin-4-yl]-5-(trifluoromethyl)benzoxazole (hereinafter, referred to as "active compound 60").

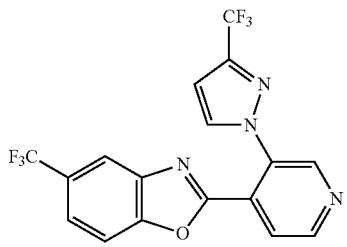

Active Compound 60
$^1$H-NMR (CDCl$_3$) δ: 8.95 (d, J=5.2 Hz, 1H), 8.94 (s, 1H), 8.22 (dd, J=5.2, 0.7 Hz, 1H), 8.05-8.03 (m, 1H), 7.84-7.82 (m, 1H), 7.68 (dd, J=8.8, 1.3 Hz, 1H), 7.54 (d, J=8.8 Hz, 1H), 6.83 (d, J=2.2 Hz, 1H)

Production Example 62

A mixture of 0.28 g of 2-(3-fluoropyridin-4-yl)-5-(trifluoromethyl)benzoxazole, 0.11 g of 4-methylpyrazole, 0.55 g of potassium carbonate and 3 ml of DMF was stirred while heating at 60° C. for 1.5 hours. To the mixture, 0.05 g of 4-methylpyrazole was added and further stirred while heating at 60° C. for 1.5 hours. Then, the reaction mixture was cooled to room temperature. Water was added to the reaction mixture, followed by extraction with ethyl acetate twice. The combined organic layers were washed with a saturated sodium chloride solution, dried over anhydrous magnesium sulfate, and then concentrated under reduced pressure. The residue was subjected to silica gel column chromatography to give 0.25 g of 2-[3-(4-methylpyrazole-1-yl)pyridin-4-yl]-5-(trifluoromethyl)benzoxazole (hereinafter, referred to as "active compound 61").

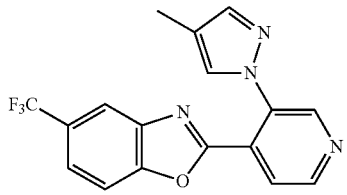

Active Compound 61
$^1$H-NMR (CDCl$_3$) δ: 8.89 (d, J=0.5 Hz, 1H), 8.81 (d, J=5.1 Hz, 1H), 8.08-8.07 (m, 1H), 8.04 (dd, J=5.1, 0.6 Hz, 1H), 7.67-7.65 (m, 1H), 7.57-7.54 (m, 2H), 7.51 (s, 1H), 2.19 (s, 3H)

Production Example 63

A mixture of 0.28 g of 2-(3-fluoropyridin-4-yl)-5-(trifluoromethyl)benzoxazole, 0.18 g of 4-(trifluoromethyl)pyrazole, 0.55 g of potassium carbonate and 2 ml of DMF was stirred while heating at 50° C. for 1.5 hours. The reaction mixture was cooled to room temperature. Water was added to the reaction mixture, followed by extraction with ethyl acetate twice. The combined organic layers were washed with a saturated sodium chloride solution, dried over anhydrous magnesium sulfate, and then concentrated under reduced pressure. The residue was subjected to silica gel column chromatography to give 0.36 g of 2-{3-[4-(trifluoromethyl)pyrazole-1-yl]pyridin-4-yl}-5-(trifluoromethyl)benzoxazole (hereinafter, referred to as "active compound 62").

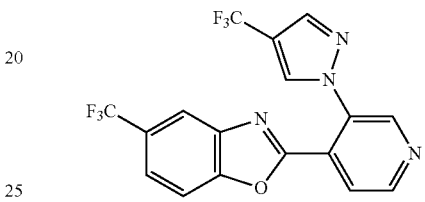

Active Compound 62
$^1$H-NMR (CDCl$_3$) δ: 8.96 (d, J=5.1 Hz, 1H), 8.93 (d, J=0.5 Hz, 1H), 8.21 (dd, J=5.1, 0.5 Hz, 1H), 8.13-8.11 (m, 1H), 8.05-8.04 (m, 1H), 7.95 (s, 1H), 7.71-7.68 (m, 1H), 7.56 (d, J=8.8 Hz, 1H)

Production Example 64

A mixture of 0.28 g of 2-(3-fluoropyridin-4-yl)-5-(trifluoromethyl)benzoxazole, 0.10 g of 1H-1,2,4-triazole, 0.55 g of potassium carbonate and 2 ml of DMF was stirred while heating at 50° C. for 1.5 hours. Then, the reaction mixture was cooled to room temperature. Water was added to the reaction mixture, followed by extraction with ethyl acetate twice. The combined organic layers were washed with a saturated sodium chloride solution, dried over anhydrous magnesium sulfate, and then concentrated under reduced pressure. The residue was subjected to silica gel column chromatography to give 0.26 g of 2-[3-(1,2,4-triazole-1-yl)pyridin-4-yl]-5-(trifluoromethyl)benzoxazole (hereinafter, referred to as "active compound 63").

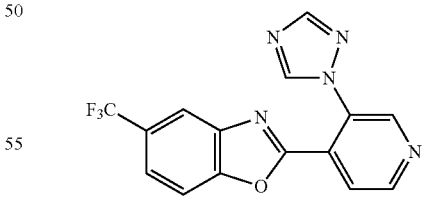

Active Compound 63
$^1$H-NMR (CDCl$_3$) δ: 8.99 (d, J=5.3 Hz, 1H), 8.92 (d, J=0.8 Hz, 1H), 8.52 (s, 1H), 8.25 (dd, J=5.3, 0.6 Hz, 1H), 8.19 (s, 1H), 8.05-8.04 (m, 1H), 7.71-7.69 (m, 1H), 7.61-7.59 (m, 1H)

Production Example 65

To a mixture of 0.42 g of N-[3-chloro-5-(trifluoromethyl)-2-hydroxyphenyl]isonicotinamide, 5 ml of tetrahydrofuran and 0.38 g of triphenylphosphine, 0.64 g of 40% toluene solution of diethyl azodicarboxylate was added dropwise at room temperature. The reaction mixture was stirred while heating at room temperature for one hour and then at 50° C. for 2.5 hours. The reaction mixture was cooled to room temperature, and then concentrated under reduced pressure. The residue was subjected to silica gel column chromatography to give 2-(pyridin-4-yl)-7-chloro-5-(trifluoromethyl)benzoxazole (hereinafter, referred to as "active compound 64").

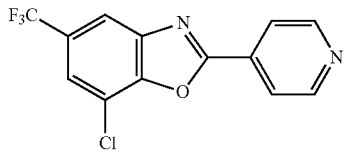

Active Compound 64
¹H-NMR (CDCl₃) δ: 8.89-8.88 (m, 2H), 8.16-8.13 (m, 2H), 8.02-8.01 (m 1H), 7.72-7.71 (m, 1H)

Production Example 66

To a mixture of 0.49 g of N-[2-hydroxy-5-(pentafluoroethyl)phenyl]isonicotinamide, 5 ml of tetrahydrofuran and 0.46 g of triphenylphosphine, 0.77 g of 40% toluene solution of diethyl azodicarboxylate was added dropwise at room temperature. The reaction mixture was stirred for 1.8 hours. The reaction mixture was concentrated under reduced pressure. The residue was subjected to silica gel column chromatography to give 0.41 g of 5-(pentafluoroethyl)-2-(pyridin-4-yl)-benzoxazole (hereinafter, referred to as "active compound 65").

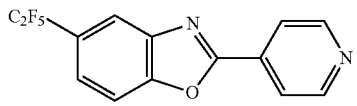

Active Compound 65
¹H-NMR (CDCl₃) δ: 8.88-8.86 (m, 2H), 8.12-8.10 (m, 3H), 7.77 (d, J=8.8 Hz, 1H), 7.70-7.67 (m, 1H)

Production Example 67

To a mixture of 0.24 g of 3-chloro-N-[2-hydroxy-5-(pentafluoroethyl)phenyl]isonicotinamide, 4 ml of tetrahydrofuran and 0.21 g of triphenylphosphine, 0.34 g of 40% toluene solution of diethyl azodicarboxylate was added dropwise at room temperature. The reaction mixture was stirred for 1.8 hours. The reaction mixture was concentrated under reduced pressure. The residue was subjected to silica gel column chromatography to give 0.19 g of 2-(3-chloropyridin-4-yl)-5-(pentafluoroethyl)benzoxazole (hereinafter, referred to as "active compound 66").

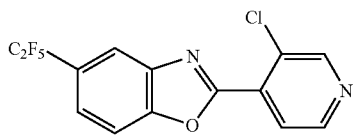

Active Compound 66
¹H-NMR (CDCl₃) δ: 8.86 (s, 1H), 8.71 (d, J=5.1 Hz, 1H), 8.18 (s, 1H), 8.10 (d, J=5.1 Hz, 1H), 7.80 (d, J=8.5 Hz, 1H), 7.72 (d, J=8.8 Hz, 1H)

Production Example 68

To a mixture of 0.79 g of N-[2-hydroxy-5-(heptafluoroisopropyl)phenyl]isonicotinamide, 8 ml of tetrahydrofuran and 0.60 g of triphenylphosphine, 0.99 g of 40% toluene solution of diethyl azodicarboxylate was added dropwise at room temperature. The reaction mixture was stirred for 2.3 hours. The reaction mixture was concentrated under reduced pressure. The residue was subjected to silica gel column chromatography to give 2-(pyridin-4-yl)-5-(heptafluoroisopropyl)benzoxazole (hereinafter referred to as "active compound 67").

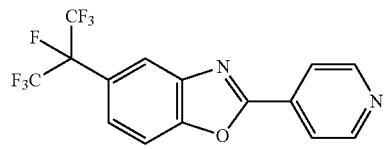

Active Compound 67
¹H-NMR (CDCl₃) δ: 8.88-8.86 (m, 2H), 8.14 (s, 1H), 8.12-8.10 (m, 2H), 7.78 (d, J=8.8 Hz, 1H), 7.71 (d, J=8.8 Hz, 1H)

Production Example 69

To a mixture of 0.90 g of 3-chloro-N-[2-hydroxy-5-(heptafluoroisopropyl)phenyl]isonicotinamide, 10 ml of tetrahydrofuran and 0.68 g of triphenylphosphine, 1.13 g of 40% toluene solution of diethyl azodicarboxylate was added dropwise at room temperature. The reaction mixture was stirred for 1.2 hours. The reaction mixture was concentrated under reduced pressure. The residue was subjected to silica gel column chromatography to give 0.58 g of 2-(3-chloropyridin-4-yl)-5-(heptafluoroisopropyl)benzoxazole (hereinafter, referred to as "active compound 68").

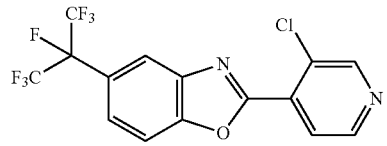

Active Compound 68
¹H-NMR (CDCl₃) δ: 8.86 (s, 1H), 8.71 (d, J=5.1 Hz, 1H), 8.21 (s, 1H), 8.09 (d, J=4.9 Hz, 1H), 7.81 (d, J=8.8 Hz, 1H), 7.74 (d, J=8.7 Hz, 1H)

Production Example 70

A mixture of 0.28 g of 2-(3-fluoropyridin-4-yl)-5-(trifluoromethyl)benzoxazole, 0.27 g of potassium carbonate and 3 ml of ethanol was stirred while heating at 60° C. for two hours and then at 90° C. for 2.5 hours. The reaction mixture was cooled to room temperature, and then concentrated under reduced pressure. Water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.18 g of 2-(3-ethoxypyridin-4-yl)-5-(trifluoromethyl)benzoxazole (hereinafter, referred to as "active compound 69").

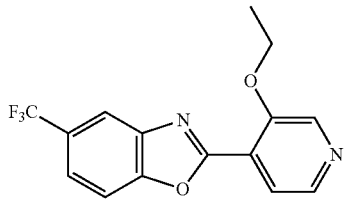

Active Compound 69

$^1$H-NMR (CDCl$_3$) δ: 8.57 (s, 1H), 8.43 (d, J=4.8 Hz, 1H), 8.14-8.12 (m, 1H), 8.00 (d, J=4.8 Hz, 1H), 7.75-7.67 (m, 2H), 4.39 (q, J=7.0 Hz, 2H), 1.58 (t, J=7.0 Hz, 3H)

Production Example 71

To a mixture of 0.28 g of 2-(3-fluoropyridin-4-yl)-5-(trifluoromethyl)benzoxazole and 3 ml of 2-propanol, 52 mg of 60% sodium hydride (in oil) was added while ice-cooling. The mixture was stirred for 1.5 hours and then heated to room temperature and stirred for 1.5 hours. Water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.12 g of 2-(3-isopropoxypyridin-4-yl)-5-(trifluoromethyl)benzoxazole (hereinafter, referred to as "active compound 70").

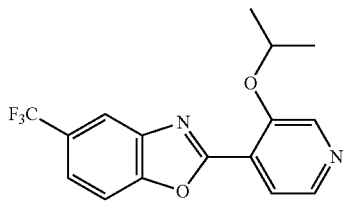

Active Compound 70

$^1$H-NMR (CDCl$_3$) δ: 8.57 (s, 1H), 8.41 (d, J=5.1 Hz, 1H), 8.13-8.12 (m, 8.00 (d, J=5.1 Hz, 1H), 7.74-7.67 (m, 2H), 4.87-4.78 (m, 1H), 1.49 (d, J=6.0 Hz, 6H)

Production Example 72

A mixture of 0.28 g of 2-(3-fluoropyridin-4-yl)-5-(trifluoromethyl)benzoxazole, 0.27 g of potassium carbonate, and 3 ml of propanol was heated to reflux while stirring for six hours. The reaction mixture was cooled to room temperature, and then concentrated under reduced pressure. Water was added the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.25 g of 2-(3-propoxypyridin-4-yl)-5-(trifluoromethyl)benzoxazole (hereinafter, referred to as "active compound 71").

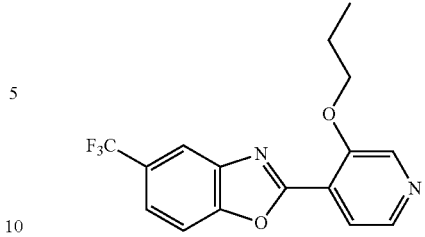

Active Compound 71

$^1$H-NMR (CDCl$_3$) δ: 8.56 (s, 1H), 8.43 (d, J=5.0 Hz, 1H), 8.13-8.11 (m, 1H), 8.01 (d, J=5.1 Hz, 1H), 7.74-7.67 (m, 2H), 4.27 (t, J=6.5, 2H), 2.02-1.92 (m, 2H), 1.15 (t, J=7.5 Hz, 3H)

Production Example 73

A mixture of 0.28 g of 2-(3-fluoropyridin-4-yl)-5-(trifluoromethyl)benzoxazole, 0.27 g of potassium carbonate and 3 ml of butanol was stirred while heating at 100° C. for six hours. To the mixture, 0.14 g of potassium carbonate was added, and the reaction mixture was stirred while heating at 100° C. for further four hours. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.24 g of 2-(3-butoxypyridin-4-yl)-5-(trifluoromethyl)benzoxazole (hereinafter, referred to as "active compound 72").

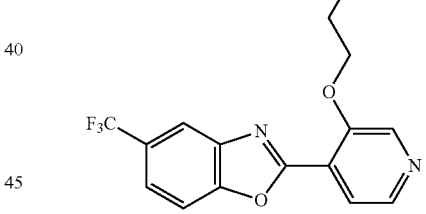

Active Compound 72

$^1$H-NMR (CDCl$_3$) δ: 8.57 (s, 1H), 8.42 (d, J=4.8 Hz, 1H), 8.13-8.11 (m, 1H), 8.01 (d, J=4.8 Hz, 1H), 7.73-7.67 (m, 2H), 4.31 (t, J=6.5 Hz, 2H), 1.97-1.88 (m, 2H), 1.67-1.55 (m, 2H), 1.03 (t, J=7.5 Hz, 3H)

Production Example 74

A mixture of 0.28 g of 2-(3-fluoropyridin-4-yl)-5-(trifluoromethyl)benzoxazole, 0.27 g of potassium carbonate and 3 ml of 2-propyne-1-ol was stirred while heating at 100° C. for two hours. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.20 g of 2-(3-(2-propyne-1-yloxy)pyridin-4-yl)-5-(trifluoromethyl)benzoxazole (hereinafter, referred to as "active compound 73").

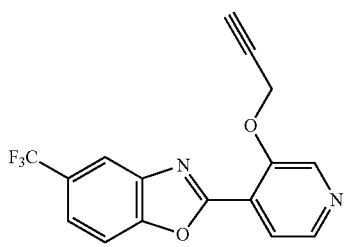

Active Compound 73

$^1$H-NMR (CDCl$_3$) δ: 8.75 (s, 1H), 8.51 (d, J=4.8 Hz, 1H), 8.16-8.14 (m, 1H), 8.05 (d, J=5.1 Hz, 1H), 7.77-7.69 (m, 2H), 5.05-5.03 (m, 2H), 2.64-2.62 (m, 1H)

Production Example 75

A mixture of 0.28 g of 2-(3-fluoropyridin-4-yl)-5-(trifluoromethyl)benzoxazole, 0.27 g of potassium carbonate and 3 ml of allyl alcohol was stirred while heating at 100° C. for two hours. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.24 g of 2-(3-allyloxypyridin-4-yl)-5-(trifluoromethyl)benzoxazole (hereinafter, referred to as "active compound 74").

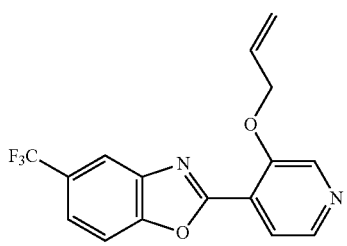

Active Compound 74

$^1$H-NMR (CDCl$_3$) δ: 8.57 (s, 1H), 8.45 (d, J=4.9 Hz, 1H), 8.15-8.13 (m, 1H), 8.03 (d, J=4.9 Hz, 1H), 7.75-7.68 (m, 2H), 6.19-6.09 (m, 1H), 5.70-5.62 (m, 1H), 5.44-5.38 (m, 1H), 4.92-4.86 (m, 2H)

Production Example 76

A mixture of 0.28 g of 2-(3-fluoropyridin-4-yl)-5-(trifluoromethyl)benzoxazole, 0.27 g of potassium carbonate and 3 ml of 2,2,3,3,3-pentafluoropropanol was heated to reflux while stirring for 5.5 hours. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.33 g of 2-[3-(2,2,3,3,3-pentafluoropropoxy)pyridin-4-yl]-5-(trifluoromethyl)benzoxazole (hereinafter, referred to as "active compound 75").

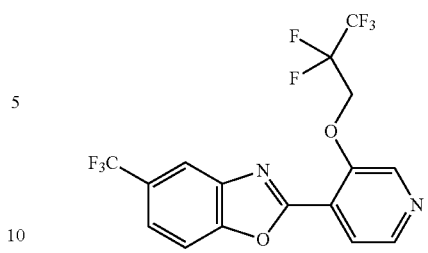

Active Compound 75

$^1$H-NMR (CDCl$_3$) δ: 8.61-8.58 (m, 2H), 8.14-8.11 (m, 2H), 7.73-7.72 (m, 2H), 4.77-4.70 (m, 2H)

Production Example 77

To a mixture of 0.69 g of N-[2-hydroxy-5-(trifluoromethylthio)phenyl]isonicotinamide, 9 ml of tetrahydrofuran, and 0.63 g of triphenylphosphine, 1.05 g of 40% toluene solution of diethyl azodicarboxylate was added dropwise at room temperature and stirred for three hours. To the mixture, 0.21 g of triphenylphosphine and 0.35 g of 40% toluene solution of diethyl azodicarboxylate were added. The reaction mixture was stirred for further two hours. The reaction mixture was concentrated under reduced pressure. The residue was subjected to silica gel column chromatography and the resultant crystals were washed with methanol to give 0.17 g of 2-(pyridin-4-yl)-5-(trifluoromethylthio)benzoxazole (hereinafter, referred to as "active compound 76").

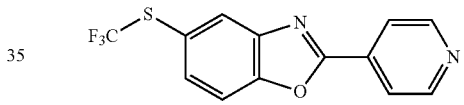

Active Compound 76

$^1$H-NMR (CDCl$_3$) δ: 8.86 (dd, J=4.3, 1.7 Hz, 2H), 8.17-8.16 (m, 1H), 8.10 (dd, J=4.3, 1.7 Hz, 2H), 7.74 (dd, J=8.7, 1.4 Hz, 1H), 7.69 (d, J=8.5 Hz, 1H)

Production Example 78

To a mixture of 0.64 g of 3-chloro-N-[2-hydroxy-5-(trifluoromethylthio)phenyl]isonicotinamide, 6 ml of tetrahydrofuran and 0.53 g of triphenylphosphine, 0.87 g of 40% toluene solution of diethyl azodicarboxylate was added dropwise at room temperature and stirred for 1.5 hours. The reaction mixture was concentrated under reduced pressure. The residue was subjected to silica gel column chromatography to give 0.57 g of 2-(3-chloropyridin-4-yl)-5-(trifluoromethylthio)benzoxazole (hereinafter, referred to as "active compound 77").

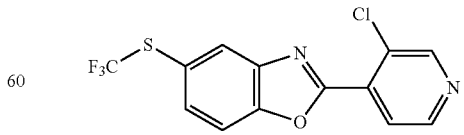

Active Compound 77

$^1$H-NMR (CDCl$_3$) δ: 8.85 (s, 1H), 8.70 (d, J=5.1 Hz, 1H), 8.24 (d, J=1.7 Hz, 1H), 8.09 (d, J=5.1 Hz, 1H), 7.78 (dd, J=8.5, 1.7 Hz, 1H), 7.72 (d, J=8.5 Hz, 1H)

Production Example 79

To a mixture of 0.55 g of N-[5-chloro-2-hydroxy-4-(trifluoromethyl)phenyl]isonicotinamide, 6 ml of tetrahydrofuran and 0.50 g of triphenylphosphine, 0.83 g of 40% toluene solution of diethyl azodicarboxylate was added dropwise at room temperature. The reaction mixture was stirred for 1.5 hours. The reaction mixture was concentrated under reduced pressure. The residue was subjected to silica gel column chromatography, and the resultant crystals were washed with methanol to give 0.11 g of 5-chloro-2-(pyridin-4-yl)-6-(trifluoromethyl)benzoxazole (hereinafter, referred to as "active compound 78").

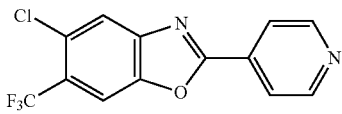

Active Compound 78
$^1$H-NMR (CDCl$_3$) δ: 8.88 (dd, J=4.3, 1.7 Hz, 2H), 8.10 (dd, J=4.5, 1.7 Hz, 2H), 8.01 (s, 1H), 7.97 (s, 1H)

Production Example 80

To a mixture of 0.67 g of 3-chloro-N-[5-chloro-2-hydroxy-4-(trifluoromethyl)phenyl]isonicotinamide, 7 ml of tetrahydrofuran and 0.55 g of triphenylphosphine, 0.91 g of 40% toluene solution of diethyl azodicarboxylate was added dropwise at room temperature. The reaction mixture was stirred for 1.5 hours. To the mixture, 0.14 g of triphenylphosphine and 0.23 g of 40% toluene solution of diethyl azodicarboxylate were added and stirred for further one hour. The reaction mixture was concentrated under reduced pressure. The residue was subjected to silica gel column chromatography, and the resultant crystals were washed with isopropanol and hexane to give 0.37 g of 5-chloro-2-(3-chloropyridin-4-yl)-6-(trifluoromethyl)benzoxazole (hereinafter, referred to as "active compound 79").

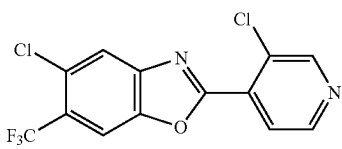

Active Compound 79
$^1$H-NMR (CDCl$_3$) δ: 8.87 (s, 1H), 8.72 (d, J=5.1 Hz, 1H), 8.09 (d, J=5.1 Hz, 1H), 8.06 (s, 1H), 8.03 (s, 1H)

Production Example 81

To a mixture of 1.01 g of N-[4-chloro-2-hydroxy-5-(trifluoromethyl)phenyl]isonicotinamide, 10 ml of tetrahydrofuran and 0.92 g of triphenylphosphine, 1.53 g of 40% toluene solution of diethyl azodicarboxylate was added dropwise at room temperature, and the reaction mixture was stirred for two hours. The reaction mixture was concentrated under reduced pressure. The residue was subjected to silica gel column chromatography and the resultant crystals washed with methanol to give 0.66 g of 6-chloro-2-(pyridin-4-yl)-5-(trifluoromethyl)benzoxazole (hereinafter, referred to as "active compound 80").

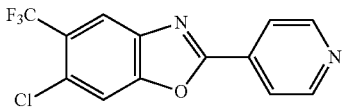

Active Compound 80
$^1$H-NMR (CDCl$_3$) δ: 8.87 (dd, J=4.3, 1.7 Hz, 2H), 8.18 (s, 1H), 8.08 (dd, J=4.3, 1.7 Hz, 2H), 7.81 (s, 1H)

Production Example 82

To a mixture of 0.46 g of 3-chloro-N-[4-chloro-2-hydroxy-5-(trifluoromethyl)phenyl]isonicotinamide, 5 ml of tetrahydrofuran and 0.38 g of triphenylphosphine, 0.63 g of 40% toluene solution of diethyl azodicarboxylate was added dropwise at room temperature, and the reaction mixture was stirred for two hours. The reaction mixture was concentrated under reduced pressure. The residue was subjected to silica gel column chromatography to give 0.39 g of 6-chloro-2-(3-chloropyridin-4-yl)-5-(trifluoromethyl)benzoxazole (hereinafter, referred to as "active compound 81").

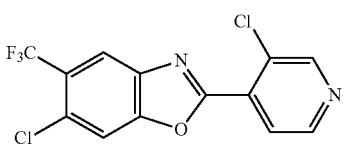

Active Compound 81
$^1$H-NMR (CDCl$_3$) δ: 8.86 (s, 1H), 8.71 (d, J=5.1 Hz, 1H), 8.26 (s, 1H), 8.08 (d, J=5.1 Hz, 1H), 7.86 (s, 1H)

Production Example 83

A mixture of 0.28 g of 2-(3-aminopyridin-4-yl)-5-(trifluoromethyl)benzoxazole and 3 ml of acetic anhydride was stirred while heating at 60° C. for two hours. The reaction mixture was cooled to room temperature, and then water was added to the reaction mixture, followed by extraction with ethyl acetate twice. The combined organic layers were washed with a saturated aqueous solution of sodium hydrogencarbonate and a saturated sodium chloride solution, dried over anhydrous magnesium sulfate, and concentrated under reduced pressure. The residue was washed with ethyl acetate to give 0.17 g of N-[4-(5-trifluoromethylbenzoxazole-2-yl)pyridin-3-yl]acetamide (hereinafter, referred to as "active compound 82").

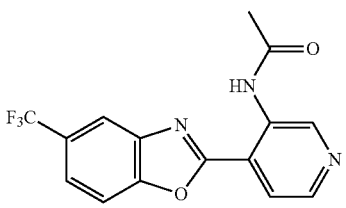

Active Compound 82
$^1$H-NMR (DMSO-d$_6$) δ: 10.92 (br s, 1H), 9.52 (s, 1H), 8.57 (d, J=5.1 Hz, 1H), 8.44-8.42 (m, 1H), 8.12 (d, J=8.7 Hz, 1H), 8.09-8.07 (m, 1H), 7.93-7.90 (m, 1H), 2.26 (s, 3H)

Production Example 84

A mixture of 0.28 g of 2-(3-fluoropyridin-4-yl)-5-(trifluoromethyl)benzoxazole, 0.55 g of potassium carbonate, 0.14 g of methylamine hydrochloride, and 3 ml of DMF was stirred while heating at 60° C. for three hours. To the mixture, 0.55 g of potassium carbonate and 0.14 g of methylamine hydrochloride were added, and the reaction mixture was stirred while heating for further two hours. Water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography, and resultant crystals were washed with diethyl ether to give 0.13 g of methyl-[4-(5-trifluoromethylbenzoxazole-2-yl)pyridin-3-yl]amine (hereinafter, referred to as "active compound 83").

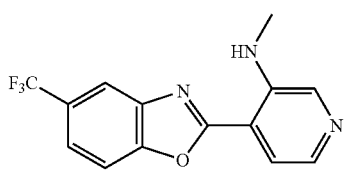

Active Compound 83
$^1$H-NMR (CDCl$_3$) δ: 8.35 (s, 1H), 8.08-8.04 (m, 2H), 7.94-7.87 (br m, 1H), 7.84 (d, J=5.1 Hz, 1H), 7.71 (d, J=8.7 Hz, 1H), 7.69-7.65 (m, 1H), 3.16 (d, J=5.1 Hz, 3H)

Production Example 85

A mixture of 0.28 g of 2-(3-fluoropyridin-4-yl)-5-(trifluoromethyl)benzoxazole, 0.55 g of potassium carbonate, 0.16 g of ethylamine hydrochloride and 3 ml of DMF was stirred while heating at 80° C. for 4.5 hours. To the mixture, 0.55 g of potassium carbonate, 0.16 g of ethylamine hydrochloride and 2 ml of DMF were added, and the reaction mixture was stirred while heating for further three hours. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.19 g of ethyl-[4-(5-trifluoromethylbenzoxazole-2-yl)pyridin-3-yl]amine (hereinafter, referred to as "active compound 84").

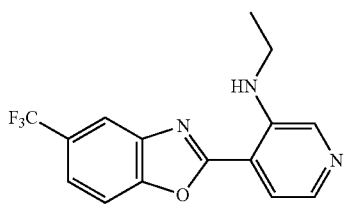

Active Compound 84
$^1$H-NMR (CDCl$_3$) δ: 8.35 (s, 1H), 8.08-8.06 (m, 1H), 8.04 (d, J=5.1 Hz, 1H), 7.92-7.87 (br m, 1H), 7.85 (d, J=5.1 Hz, 1H), 7.71 (d, J=8.7 Hz, 1H), 7.69-7.65 (m, 1H), 3.54-3.45 (m, 2H), 1.46 (t, J=7.1 Hz, 3H)

Production Example 86

A mixture of 0.28 g of 2-(3-fluoropyridin-4-yl)-5-(trifluoromethyl)benzoxazole, 0.69 g of potassium carbonate, 0.30 g of isopropylamine and 3 ml of DMF was stirred while heating at 50° C. for 1.5 hours and at 80° C. for 4 hours. To the mixture, 0.30 g of isopropylamine was added and stirred while heating for further three hours. To the reaction mixture, water was added, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.21 g of isopropyl-[4-(5-trifluoromethylbenzoxazole-2-yl)pyridin-3-yl]amine (hereinafter, referred to as "active compound 85").

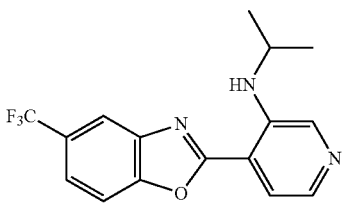

Active Compound 85
$^1$H-NMR (CDCl$_3$) δ: 8.36 (s, 1H), 8.09-8.07 (m, 1H), 8.00 (d, J=5.1 Hz, 1H), 7.95-7.89 (br m, 1H), 7.85 (d, J=5.1 Hz, 1H), 7.70 (d, J=8.5 Hz, 1H), 7.69-7.65 (m, 1H), 4.03-3.94 (m, 1H), 1.42 (d, J=6.3 Hz, 6H)

Production Example 87

To a mixture of 0.68 g of 3-chloro-N-(1,1,3,3-tetrafluoro-6-hydroxy-1,3-dihydroisobenzofuran-5-yl)isonicotinamide, 8 ml of tetrahydrofuran and 0.55 g of triphenylphosphine, 0.90 g of 40% toluene solution of diethyl azodicarboxylate was added dropwise at room temperature, and the reaction mixture was stirred for 1.5 hours. The reaction mixture was concentrated under reduced pressure. The residue was subjected to silica gel column chromatography to give 0.55 g of 2-(3-chloropyridin-4-yl)-5,5,7,7-tetrafluoro-5,7-dihydro-furo[3',4':4,5]benzo[1,2-d]oxazole (hereinafter, referred to as "active compound 86").

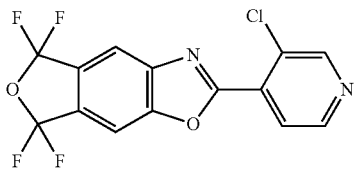

Active Compound 86
$^1$H-NMR (CDCl$_3$) δ: 8.89 (s, 1H), 8.74 (d, J=5.1 Hz, 1H), 8.16 (s, 1H), 8.11 (d, J=5.1 Hz, 1H), 7.96 (s, 1H)

Production Example 88

To a mixture of 1.46 g of 3-fluoro-N-(1,1,3,3-tetrafluoro-6-hydroxy-1,3-dihydroisobenzofuran-5-yl)isonicotinamide, 10 ml of tetrahydrofuran and 2.02 g of triphenylphosphine, 0.90 g of 40% toluene solution of diethyl azodicarboxylate was added dropwise at room temperature, and the reaction mixture was stirred for one hour. The reaction mixture was concentrated under reduced pressure. The residue was subjected to silica gel column chromatography to give 1.09 g of 5,5,7,7-tetrafluoro-2-(3-fluoropyridin-4-yl)-5,7-dihydro-furo[3',4':4,5]benzo[1,2-d]oxazole (hereinafter, referred to as "active compound 87").

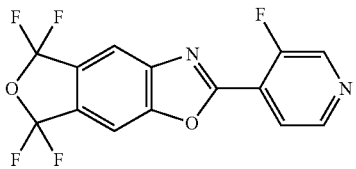

Active Compound 87
¹H-NMR (CDCl₃) δ: 8.80-8.78 (m, 1H), 8.71-8.68 (m, 1H), 8.17-8.12 (m, 2H), 7.96-7.94 (m, 1H)

Production Example 89

A mixture of 0.28 g of 5,5,7,7-tetrafluoro-2-(3-fluoropyridin-4-yl)-5,7-dihydro-furo[3',4':4,5]benzo[1,2-d]oxazole, 0.24 g of potassium carbonate and 3 ml of methanol was stirred while heating at 60° C. for 3.5 hours. Water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.13 g of 5,5,7,7-tetrafluoro-2-(3-methoxypyridin-4-yl)-5,7-dihydro-furo[3',4':4,5]benzo[1,2-d]oxazole (hereinafter, referred to as "active compound 88").

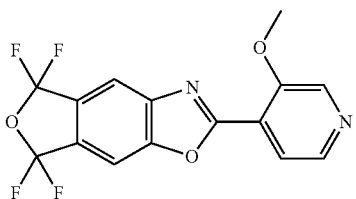

Active Compound 88
¹H-NMR (CDCl₃) δ: 8.63 (s, 1H), 8.49 (d, J=4.9 Hz, 1H), 8.10 (s, 1H), 8.03 (d, J=4.9 Hz, 1H), 7.91 (s, 1H), 4.17 (s, 3H)

Production Example 90

A mixture of 44 mg of 60% sodium hydride (in oil) and 2 ml of DMF was stirred at room temperature. To the mixture, a mixture solution of 0.11 g of 2,2,2-trifluoroethanol and 0.5 ml of DMF was added. The mixture solution was stirred for 15 minutes, and then, 0.28 g of 5,5,7,7-tetrafluoro-2-(3-fluoropyridin-4-yl)-5,7-dihydro-furo[3',4':4,5]benzo[1,2-d]oxazole was added and stirred at room temperature for one hour. Water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.25 g of 5,5,7,7-tetrafluoro-2-[3-(2,2,2-trifluoroethoxy)pyridin-4-yl]-5,7-dihydro-furo[3',4':4,5]benzo[1,2-d]oxazole (hereinafter, referred to as "active compound 89").

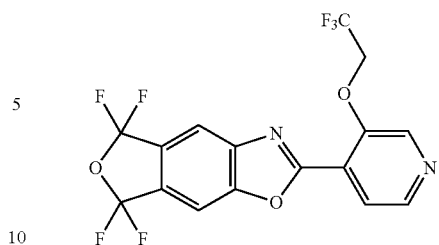

Active Compound 89
¹H-NMR (CDCl₃) δ: 8.63-8.61 (m, 2H), 8.12 (d, J=4.9 Hz, 1H), 8.11 (s, 1H), 7.91 (s, 1H), 4.69 (q, J=7.8 Hz, 2H)

Production Example 91

To a mixture of 2.08 g of 3-fluoro-N-[4-chloro-2-hydroxy-5-(trifluoromethyl)phenyl]isonicotinamide, 13 ml of tetrahydrofuran and 1.79 g of triphenylphosphine, 2.98 g of 40% toluene solution of diethyl azodicarboxylate was added dropwise at room temperature. The reaction mixture was stirred for one hour. The reaction mixture was concentrated under reduced pressure. The residue was subjected to silica gel column chromatography to give 1.74 g of 6-chloro-2-(3-fluoropyridin-4-yl)-5-(trifluoromethyl)benzoxazole (hereinafter, referred to as "active compound 90").

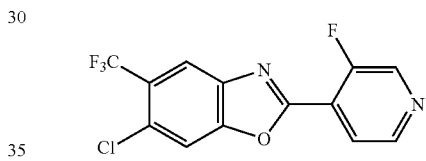

Active Compound 90
¹H-NMR (CDCl₃) δ: 8.77-8.75 (m, 1H), 8.68-8.65 (m, 1H), 8.24 (s, 1H), 8.13-8.08 (m, 1H), 7.85 (s, 1H)

Production Example 92

A mixture of 0.28 g of 6-chloro-2-(3-fluoropyridin-4-yl)-5-(trifluoromethyl)benzoxazole, 0.24 g of potassium carbonate and 3 ml of methanol was stirred while heating at 60° C. for two hours. Water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.13 g of 6-chloro-2-(3-methoxypyridin-4-yl)-5-(trifluoromethyl)benzoxazole (hereinafter, referred to as "active compound 91").

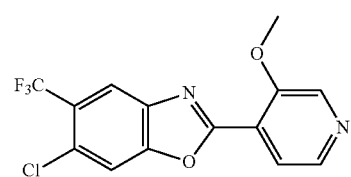

Active Compound 91
¹H-NMR (CDCl₃) δ: 8.60 (s, 1H), 8.47 (d, J=4.9 Hz, 1H), 8.21 (s, 1H), 7.99 (d, J=4.9 Hz, 1H), 7.81 (s, 1H), 4.16 (s, 3H)

Production Example 93

A mixture of 46 mg of 60% sodium hydride (in oil) and 2 ml of DMF was stirred at room temperature, to which a mixture solution of 0.12 g of 2,2,2-trifluoroethanol and 0.5 ml of DMF was added. After 15 minutes, 0.28 g of 6-chloro-2-(3-fluoropyridin-4-yl)-5-(trifluoromethyl)benzoxazole was added and stirred at room temperature for one hour. Water was added to the reaction mixture, followed by extraction with ethyl acetate twice. The combined organic layers were washed with a saturated sodium chloride solution, dried over anhydrous magnesium sulfate, and then concentrated under reduced pressure. The residue was subjected to silica gel column chromatography to give 0.26 g of 6-chloro-2-[3-(2,2,2-trifluoroethoxy)pyridin-4-yl]-5-(trifluoromethyl)benzoxazole (hereinafter, referred to as "active compound 92").

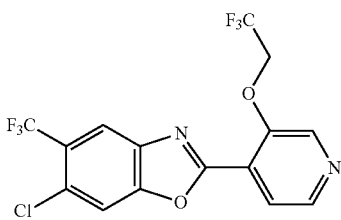

Active Compound 92
$^1$H-NMR (CDCl$_3$) δ: 8.60 (s, 1H), 8.59 (d, J=4.9 Hz, 1H), 8.21 (s, 1H), 8.08 (d, J=5.1 Hz, 1H), 7.81 (s, 1H), 4.66 (q, J=8.0 Hz, 2H)

Production Example 94

Production Example 94 was carried out according to the same manner as in Production Example 78, using N-[4-chloro-2-hydroxy-5-(trifluoromethyl)phenyl]-3-ethyl isonicotinamide instead of 3-chloro-N-[2-hydroxy-5-(trifluoromethylthio)phenyl]isonicotinamide, and thus 0.17 g of 6-chloro-2-(3-ethylpyridin-4-yl)-5-(trifluoromethyl)benzoxazole (hereinafter, referred to as "active compound 93") was obtained.

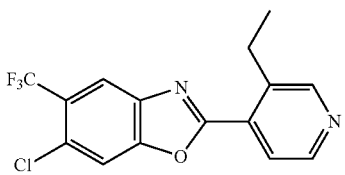

Active Compound 93
$^1$H-NMR (CDCl$_3$) δ: 8.72 (s, 1H), 8.67 (d, J=5.1 Hz, 1H), 8.21 (s, 1H), 7.98 (d, J=5.1 Hz, 1H), 7.81 (s, 1H), 3.27 (q, J=7.5 Hz, 2H), 1.34 (t, J=7.4 Hz, 3H)

Production Example 95

Production Example 95 was carried out according to the same manner as in Production Example 22, using 3-chloro-N-[4-fluoro-2-hydroxy-5-(trifluoromethyl)phenyl]isonicotinamide instead of 2-chloro-N-[2-hydroxy-5-(trifluoromethyl)phenyl]isonicotinamide, and thus 0.63 g of 2-(3-chloropyridin-4-yl)-6-fluoro-5-(trifluoromethyl)benzoxazole (hereinafter, referred to as "active compound 94") was obtained.

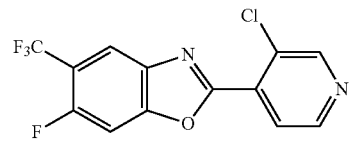

Active Compound 94
$^1$H-NMR (CDCl$_3$) δ: 8.86 (s, 1H), 8.70 (d, J=5.1 Hz, 1H), 8.17 (d, J=6.3 Hz, 1H), 8.06 (d, J=5.1 Hz, 1H), 7.54 (d, J=9.0 Hz, 1H)

Production Example 96

Production Example 96 was carried out according to the same manner as in Production Example 78, using 3-chloro-N-[2-fluoro-6-hydroxy-3-(trifluoromethyl)phenyl]isonicotinamide instead of 3-chloro-N-[2-hydroxy-5-(trifluoromethylthio)phenyl]isonicotinamide, and thus 56 mg of 2-(3-chloropyridin-4-yl)-4-fluoro-5-(trifluoromethyl)benzoxazole (hereinafter, referred to as "active compound 95") was obtained.

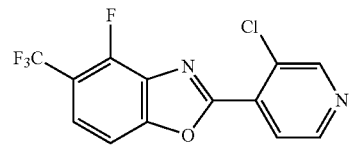

Active Compound 95
$^1$H-NMR (CDCl$_3$) δ: 8.86 (s, 1H), 8.71 (d, J=5.1 Hz, 1H), 8.12 (d, J=5.1 Hz, 7.73 (dd, J=8.5, 6.3 Hz, 1H), 7.57 (d, J=8.6 Hz, 1H)

Production Example 97

Production Example 97 was carried out according to the same manner as in Production Example 78, using N-[2-chloro-6-hydroxy-3-(trifluoromethyl)phenyl]isonicotinamide instead of 3-chloro-N-[2-hydroxy-5-(trifluoromethylthio)phenyl]isonicotinamide, and thus 91 mg of 4-chloro-2-(pyridin-4-yl)-5-(trifluoromethyl)benzoxazole (hereinafter, referred to as "active compound 96") was obtained.

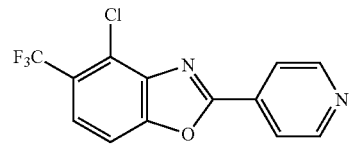

Active Compound 96
$^1$H-NMR (CDCl$_3$) δ: 8.88 (dd, J=4.4, 1.7 Hz, 2H), 8.15 (dd, J=4.5, 1.6 Hz, 2H), 7.80 (d, J=8.8 Hz, 1H), 7.63 (d, J=8.8 Hz, 1H)

Production Example 98

Production Example 98 was carried out according to the same manner as in Production Example 22, using 3-isopropoxy-N-(1,1,3,3-tetrafluoro-6-hydroxy-1,3-dihydroisobenzofuran-5-yl)isonicotinamide instead of 2-chloro-N-[2-hydroxy-5-(trifluoromethyl)phenyl]isonicotinamide, and thus 0.12 g of 5,5,7,7-tetrafluoro-2-(3-isopropoxypyridin-4-yl)-5,7-dihydro-furo[3',4':4,5]benzo[1,2-d]oxazole (hereinafter, referred to as "active compound 97") was obtained.

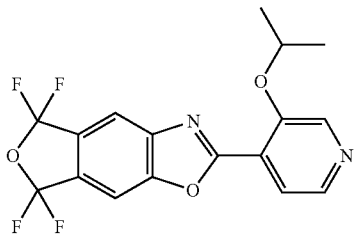

Active Compound 97

$^1$H-NMR (CDCl$_3$) δ: 8.59 (s, 1H), 8.42 (d, J=5.1 Hz, 1H), 8.08 (s, 1H), 8.01 (d, J=5.1 Hz, 1H), 7.89 (s, 1H), 4.92-4.82 (m, 1H), 1.50 (d, J=6.1 Hz, 6H)

Production Example 99

Production Example 99 was carried out according to the same manner as in Production Example 78, using 3-ethyl-N-(1,1,3,3-tetrafluoro-6-hydroxy-1,3-dihydroisobenzofuran-5-yl)isonicotinamide instead of 3-chloro-N-[2-hydroxy-5-(trifluoromethylthio)phenyl]isonicotinamide and thus 0.40 g of 2-(3-ethylpyridin-4-yl)-5,5,7,7-tetrafluoro-5,7-dihydro-furo[3',4':4,5]benzo[1,2-d]oxazole (hereinafter, referred to as "active compound 98") was obtained.

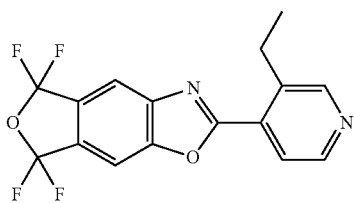

Active Compound 98

$^1$H-NMR (CDCl$_3$) δ: 8.75 (s, 1H), 8.70 (d, J=5.0 Hz, 1H), 8.11 (s, 1H), 8.02 (d, J=5.1 Hz, 1H), 7.91 (s, 1H), 3.29 (q, J=7.5 Hz, 2H), 1.35 (t, J=7.5 Hz, 3H)

Production Example 100

Production Example 100 was carried out according to the same manner as in Production Example 78, using N-(5-tert-butyl-2-hydroxyphenyl)-3-fluoro isonicotinamide instead of 3-chloro-N-[2-hydroxy-5-(trifluoromethylthio)phenyl] isonicotinamide, and thus 3.1 g of 5-tert-butyl-2-(3-fluoropyridin-4-yl)benzoxazole (hereinafter, referred to as "active compound 99") was obtained.

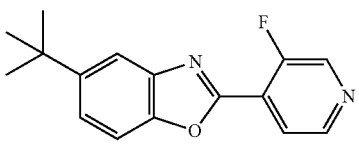

Active Compound 99

$^1$H-NMR (CDCl$_3$) δ: 8.72-8.70 (m, 1H), 8.62-8.59 (m, 1H), 8.12-8.09 (m, 1H), 7.91-7.89 (m, 1H), 7.59-7.51 (m, 2H), 1.41 (s, 9H)

Production Example 101

Production Example 101 was carried out according to the same manner as in Production Example 38, using 5-tert-butyl-2-(3-fluoropyridin-4-yl)benzoxazole instead of 2-(3-fluoropyridin-4-yl)-5-(trifluoromethyl)benzoxazole, and thus 0.27 g of 5-tert-butyl-2-(3-methoxypyridin-4-yl)benzoxazole (hereinafter, referred to as "active compound 100") was obtained.

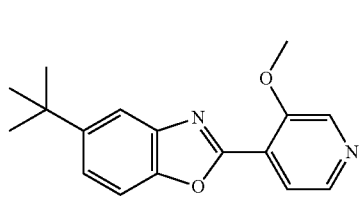

Active Compound 100

$^1$H-NMR (CDCl$_3$) δ: 8.56 (s, 1H), 8.43 (d, J=4.9 Hz, 1H), 8.00 (d, J=4.9 Hz, 1H), 7.89 (d, J=1.8 Hz, 1H), 7.54 (d, J=8.5 Hz, 1H), 7.48 (dd, J=8.8, 2.0 Hz, 1H), 4.15 (s, 3H), 1.40 (s, 9H)

Production Example 102

Production Example 102 was carried out according to the same manner as in Production Example 40, using 5-tert-butyl-2-(3-fluoropyridin-4-yl)benzoxazole instead of 2-(3-fluoropyridin-4-yl)-5-(trifluoromethyl)benzoxazole to give 0.33 g of 5-tert-butyl-2-[3-(2,2,2-trifluoroethoxy)pyridin-4-yl]benzoxazole (hereinafter, referred to as "active compound 101") was obtained.

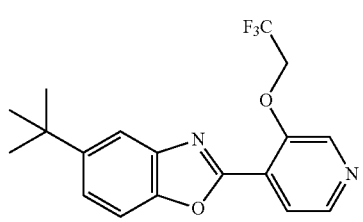

Active Compound 101

$^1$H-NMR (CDCl$_3$) δ: 8.59 (s, 1H), 8.56 (d, J=4.9 Hz, 1H), 8.08 (d, J=4.9 Hz, 1H), 7.86 (d, J=1.7 Hz, 1H), 7.55 (d, J=8.8 Hz, 1H), 7.51 (dd, J=8.7, 1.8 Hz, 1H), 4.65 (q, J=8.0 Hz, 2H), 1.41 (s, 9H)

Production Example 103

A mixture of 2.07 g of 5-tert-butyl-2-(3-fluoropyridin-4-yl)benzoxazole, 4.23 g of potassium carbonate and 8 ml of benzyl alcohol was stirred while heating at 100° C. for 8.5 hours. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 2.2 g of 2-(3-benzyloxypyridin-4-yl)-5-tert-butylbenzoxazole (hereinafter, referred to as "active compound 102").

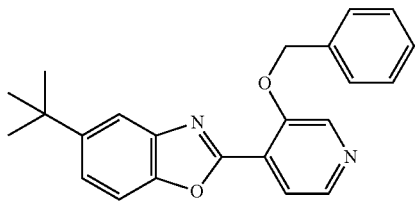

Active Compound 102

$^1$H-NMR (CDCl$_3$) δ: 8.56 (s, 1H), 8.41 (d, J=4.9 Hz, 1H), 8.03 (d, J=4.9 Hz, 1H), 7.88-7.86 (m, 1H), 7.59-7.55 (m, 2H), 7.54-7.47 (m, 2H), 7.43-7.37 (m, 2H), 7.36-7.30 (m, 1H), 5.42 (s, 2H), 1.41 (s, 9H)

Production Example 104

A mixture of 2.1 g of 2-(3-benzyloxypyridin-4-yl)-5-tert-butylbenzoxazole, 0.58 g of 5% palladium on carbon and 50 ml of acetic acid was stirred under about one atmosphere of hydrogen at room temperature for six hours. The reaction mixture was filtered through Celite™. The filtrate was concentrated under reduced pressure. The residue was subjected to silica gel column chromatography to give 1.3 g of 4-(5-tert-butylbenzoxazole-2-yl)pyridin-3-ol (hereinafter, referred to as "active compound 103").

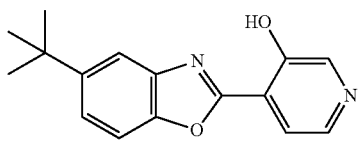

Active Compound 103

$^1$H-NMR (CDCl$_3$) δ: 11.21 (br s, 1H), 8.60 (s, 1H), 8.31 (d, J=4.9 Hz, 1H), 7.83-7.80 (m, 2H), 7.58 (d, J=8.5 Hz, 1H), 7.53 (dd, J=8.7, 1.8 Hz, 1H), 1.42 (s, 9H)

Production Example 105

To a mixture of 0.30 g of 4-(5-tert-butylbenzoxazole-2-yl)pyridin-3-ol, 0.17 g of potassium carbonate and 3 ml of DMF, 0.21 g of isopropyl iodide was added at room temperature. The reaction mixture was stirred while heating at 60° C. for two hours. The mixture was cooled to room temperature, and then water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.21 g of 5-tert-butyl-2-(3-isopropoxypyridin-4-yl)benzoxazole (hereinafter, referred to as "active compound 104").

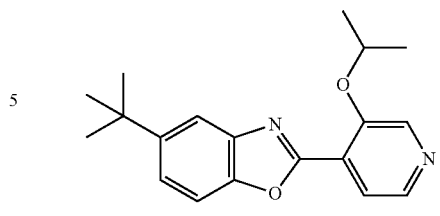

Active Compound 104

$^1$H-NMR (CDCl$_3$) δ: 8.53 (s, 1H), 8.38 (d, J=4.9 Hz, 1H), 7.98 (d, J=5.0 Hz, 1H), 7.86-7.84 (m, 1H), 7.55-7.46 (m, 2H), 4.81-4.70 (m, 1H), 1.47 (d, J=6.1 Hz, 6H), 1.41 (s, 9H)

Production Example 106

Production Example 106 was carried out according to the same manner as in Production Example 78, using N-(5-tert-butyl-2-hydroxyphenyl)-3-ethyl isonicotinamide instead of 3-chloro-N-[2-hydroxy-5-(trifluoromethylthio)phenyl]isonicotinamide, and thus 0.19 g of 5-tert-butyl-2-(3-ethylpyridin-4-yl)benzoxazole (hereinafter, referred to as "active compound 105") was obtained.

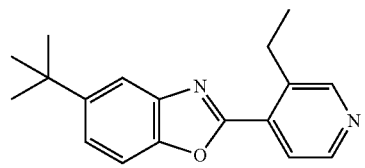

Active Compound 105

$^1$H-NMR (CDCl$_3$) δ: 8.67 (s, 1H), 8.61 (d, J=5.1 Hz, 1H), 7.99 (d, J=5.1 Hz, 1H), 7.87-7.85 (m, 1H), 7.56-7.47 (m, 2H), 3.29 (q, J=7.5 Hz, 2H), 1.41 (s, 9H), 1.34 (t, J=7.5 Hz, 3H)

Production Example 107

Production Example 106 was carried out according to the same manner as in Production Example 78, using N-(5-tert-butyl-2-hydroxyphenyl)-2-chloro-5-trifluoromethylisonicotinamide instead of 3-chloro-N-[2-hydroxy-5-(trifluoromethylthio)phenyl]isonicotinamide, and thus 0.59 g of 5-tert-butyl-2-[2-chloro-5-(trifluoromethyl)pyridin-4-yl]benzoxazole (hereinafter, referred to as "active compound 106") was obtained.

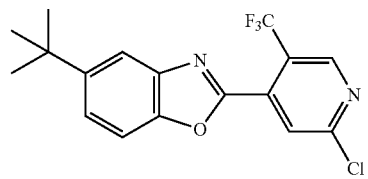

Active Compound 106

$^1$H-NMR (CDCl$_3$) δ: 8.89 (s, 1H), 8.23 (s, 1H), 7.90-7.88 (m, 1H), 7.58-7.57 (m, 2H), 1.41 (s, 9H)

Production Example 108

A mixture of 0.40 g of 5-tert-butyl-2-(2-chloro-5-trifluoromethylpyridin-4-yl)benzoxazole, 0.59 g of 5% palladium on carbon and 25 ml of acetic acid was stirred under about one atmosphere of hydrogen at room temperature for 15 hours. The reaction mixture was filtered through Celite™. The filtrate was concentrated under reduced pressure. The residue was subjected to silica gel column chromatography to give 0.19 g of 5-tert-butyl-2-(3-trifluoromethylpyridin-4-yl)benzoxazole (hereinafter, referred to as "active compound 107").

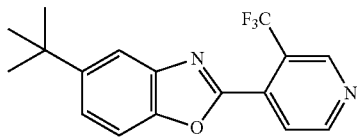

Active Compound 107
$^1$H-NMR (CDCl$_3$) δ: 9.13 (s, 1H), 8.98 (d, J=5.1 Hz, 1H), 8.14 (d, J=5.1 Hz, 1H), 7.89 (dd, J=1.7, 0.7 Hz, 1H), 7.58 (d, J=8.6, 0.7 Hz, 1H), 7.54 (dd, J=8.8, 1.8 Hz, 1H), 1.41 (s, 9H)

Production Example 109

Production Example 109 was carried out according to the same manner as in Production Example 78, using 3-chloro-N-(2-hydroxy-5-trifluoromethoxyphenyl)isonicotinamide instead of 3-chloro-N-[2-hydroxy-5-(trifluoromethylthio)phenyl]isonicotinamide, and thus 0.32 g of 2-(3-chloropyridin-4-yl)-5-(trifluoromethoxyl)benzoxazole (hereinafter, referred to as "active compound 108") was obtained.

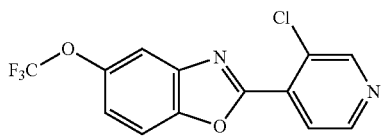

Active Compound 108
$^1$H-NMR (CDCl$_3$) δ: 8.85-8.84 (m, 1H), 8.69 (d, J=5.1 Hz, 1H), 8.09-8.07 (m, 1H), 7.79-7.77 (m, 1H), 7.69-7.66 (m, 1H), 7.38-7.34 (m, 1H)

Production Example 110

Production Example 110 was carried out according to the same manner as in Production Example 22, using 3-ethyl-N-[2-hydroxy-5-(trifluoromethoxy)phenyl]isonicotinamide instead of 2-chloro-N-[2-hydroxy-5-(trifluoromethyl)phenyl]isonicotinamide, and thus 0.32 g of 2-(3-ethylpyridin-4-yl)-5-(trifluoromethoxy)benzoxazole (hereinafter, referred to as "active compound 109") was obtained.

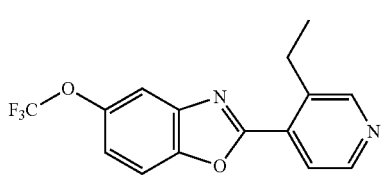

Active Compound 109
$^1$H-NMR (CDCl$_3$) δ: 8.70 (s, 1H), 8.65 (d, J=5.1 Hz, 1H), 7.99 (d, J=5.1 Hz, 1H), 7.74-7.72 (m, 1H), 7.65-7.62 (m, 1H), 7.34-7.30 (m, 1H), 3.28 (q, J=7.5 Hz, 2H), 1.34 (t, J=7.5 Hz, 3H)

Production Example 111

Production Example 111 was carried out according to the same manner as in Production Example 40, using 2,2-difluoroethanol instead of 2,2,2-trifluoroethanol, and thus 0.24 g of 2-[3-(2,2-difluoroethoxy)pyridin-4-yl]-5-(trifluoromethyl)benzoxazole (hereinafter, referred to as "active compound 110") was obtained.

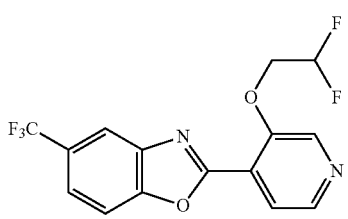

Active Compound 110
$^1$H-NMR (CDCl$_3$) δ: 8.59 (s, 1H), 8.55 (d, J=4.9 Hz, 1H), 8.14 (s, 1H), 8.07 (d, J=4.9 Hz, 1H), 7.76-7.70 (m, 2H), 6.28 (tt, J=54.9, 4.0 Hz, 1H), 4.51 (td, J=12.8, 4.0 Hz, 2H)

Production Example 112

Production Example 112 was carried out according to the same manner as in Production Example 40, using 1,1,1-trifluoro-2-propanol instead of 2,2,2-trifluoroethanol, and thus 0.31 g of 2-[3-(1-methyl-2,2,2-trifluoroethoxy)pyridin-4-yl]-5-(trifluoromethyl)benzoxazole (hereinafter, referred to as "active compound 111") was obtained.

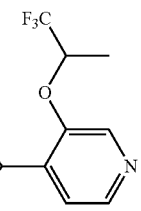

Active Compound 111
$^1$H-NMR (CDCl$_3$) δ: 8.61 (s, 1H), 8.55 (d, J=4.9 Hz, 1H), 8.14-8.12 (m, 1H), 8.09 (d, J=4.9 Hz, 1H), 7.76-7.70 (m, 2H), 4.97-4.87 (m, 1H), 1.69 (d, J=6.6 Hz, 3H)

Production Example 113

Production Example 113 was carried out according to the same manner as in Production Example 40, using 2,2,3,3-tetrafluoropropanol instead of 2,2,2-trifluoroethanol, and thus 0.34 g of 2-[3-(2,2,3,3-tetrafluoropropoxy)pyridin-4-yl]-5-(trifluoromethyl)benzoxazole (hereinafter, referred to as "active compound 112") was obtained.

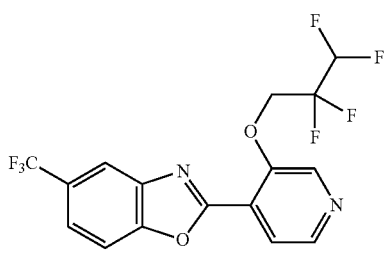

Active Compound 112
¹H-NMR (CDCl₃) δ: 8.58 (d, J=5.1 Hz, 1H), 8.56 (s, 1H), 8.13-8.12 (m, 1H), 8.10 (d, J=4.9 Hz, 1H), 7.74-7.73 (m, 2H), 6.75-6.44 (m, 1H), 4.71-4.63 (m, 2H)

Production Example 114

Production Example 114 was carried out according to the same manner as in Production Example 103, using 2-(3-fluoropyridin-4-yl)-5-(trifluoromethyl)benzoxazole instead of 5-tert-butyl-2-(3-fluoropyridin-4-yl)benzoxazole, and thus 4.6 g of 2-(3-benzyloxypyridin-4-yl)-5-(trifluoromethyl)benzoxazole (hereinafter, referred to as "active compound 113") was obtained.

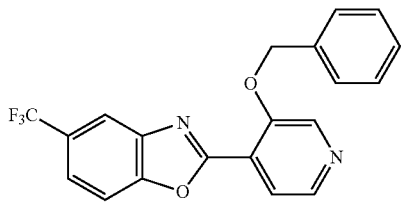

Active Compound 113
¹H-NMR (CDCl₃) δ: 8.62 (s, 1H), 8.45 (d, J=4.9 Hz, 1H), 8.15-8.13 (m, 1H), 8.05 (d, J=5.0 Hz, 1H), 7.73-7.67 (m, 2H), 7.60-7.54 (m, 2H), 7.45-7.39 (m, 2H), 7.38-7.33 (m, 1H), 5.44 (s, 2H)

Production Example 115

A mixture of 4.69 g of 2-(3-benzyloxypyridin-4-yl)-5-(trifluoromethyl)benzoxazole, 1.0 g of 5% palladium on carbon and 70 ml of acetic acid was stirred under about one atmosphere of hydrogen at room temperature for nine hours. The reaction mixture was filtered through Celite™. The filtrate was concentrated under reduced pressure. The residue was subjected to silica gel column chromatography to give 3.44 g of 4-[5-(trifluoromethyl)benzoxazole-2-yl]pyridin-3-ol (hereinafter, referred to as "active compound 114").

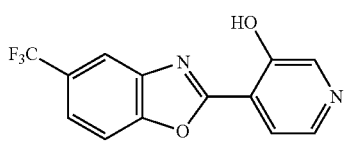

Active Compound 114
¹H-NMR (CDCl₃) δ: 10.84 (br s, 1H), 8.63 (s, 1H), 8.35 (d, J=4.9 Hz, 1H), 8.12-8.09 (m, 1H), 7.86 (d, J=5.1 Hz, 1H), 7.79 (d, J=8.8 Hz, 1H), 7.76 (dd, J=8.5, 1.7 Hz, 1H)

Production Example 116

To a mixture of 0.28 g of 4-[5-(trifluoromethyl)benzoxazole-2-yl]pyridin-3-ol, 0.28 g of potassium carbonate and 2 ml of DMF, a mixture of 0.29 g of cyclopentyl bromide and 2 ml of DMF was added at room temperature. The reaction mixture was stirred while heating at 60° C. for four hours. The reaction mixture was cooled to room temperature, and then water was added to the reaction mixture, followed by extraction with ethyl acetate twice. The combined organic layers were washed with water and a saturated sodium chloride solution, dried over anhydrous magnesium sulfate, and concentrated under reduced pressure. The residue was subjected to silica gel column chromatography to give 0.29 g of 2-(3-cyclopentyloxypyridin-4-yl)-5-(trifluoromethyl)benzoxazole (hereinafter, referred to as "active compound 115").

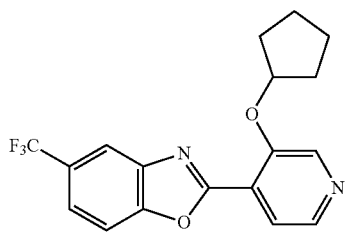

Active Compound 115
¹H-NMR (CDCl₃) δ: 8.56 (s, 1H), 8.39 (d, J=4.9 Hz, 1H), 8.13-8.10 (m, 1H), 8.00 (d, J=4.9 Hz, 1H), 7.73-7.66 (m, 2H), 5.13-5.06 (m, 1H), 2.08-1.99 (m, 4H), 1.96-1.84 (m, 2H), 1.77-1.65 (m, 2H)

Production Example 117

Production Example 117 was carried out according to the same manner as in Production Example 72, using isobutyl alcohol instead of propanol, and thus 0.24 g of 2-(3-isobutoxypyridin-4-yl)-5-(trifluoromethyl)benzoxazole (hereinafter, referred to as "active compound 116") was obtained.

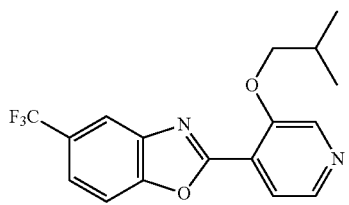

Active Compound 116
¹H-NMR (CDCl₃) δ: 8.55 (s, 1H), 8.42 (d, J=5.1 Hz, 1H), 8.12-8.11 (m, 1H), 8.02 (d, J=5.1 Hz, 1H), 7.73-7.67 (m, 2H), 4.06 (d, J=6.3 Hz, 2H), 2.32-2.20 (m, 1H), 1.14 (d, J=6.6 Hz, 6H)

Production Example 118

Production Example 118 was carried out according to the same manner as in Production Example 72, using 2,2-dimethyl-1-propanol instead of propanol, and thus 0.23 g of 2-[3-(2,2-dimethylpropoxy)pyridin-4-yl]-5-(trifluoromethyl)benzoxazole (hereinafter, referred to as "active compound 117") was obtained.

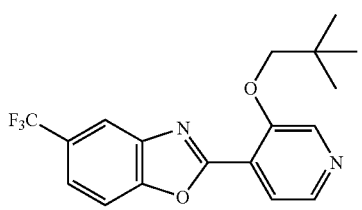

Active Compound 117
¹H-NMR (CDCl₃) δ: 8.53 (s, 1H), 8.42 (d, J=4.9 Hz, 1H), 8.12-8.10 (m, 1H), 8.04 (d, J=4.9 Hz, 1H), 7.72-7.66 (m, 2H), 3.93 (s, 2H), 1.15 (s, 9H)

Production Example 119

Production Example 119 was carried out according to the same manner as in Production Example 72, using cyclopropane methanol instead of propanol, and thus 0.23 g of 2-[3-(cyclopropylmethoxy)pyridin-4-yl]-5-(trifluoromethyl)benzoxazole (hereinafter, referred to as "active compound 118") was obtained.

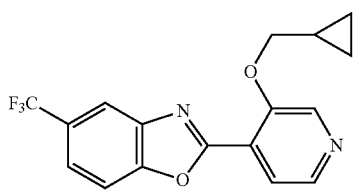

Active Compound 118
¹H-NMR (CDCl₃) δ: 8.57 (s, 1H), 8.44 (d, J=5.1 Hz, 1H), 8.14-8.12 (m, 1H), 8.01 (d, J=5.0 Hz, 1H), 7.75-7.68 (m, 2H), 4.19 (d, J=6.5 Hz, 2H), 1.45-1.34 (m, 1H), 0.73-0.65 (m, 2H), 0.51-0.45 (m, 2H)

Production Example 120

Production Example 120 was carried out according to the same manner as in Production Example 116, using 2-bromobutane instead of cyclopentyl bromide, and thus 0.14 g of 2-(3-sec-butoxypyridin-4-yl)-5-(trifluoromethyl)benzoxazole (hereinafter, referred to as "active compound 119") was obtained.

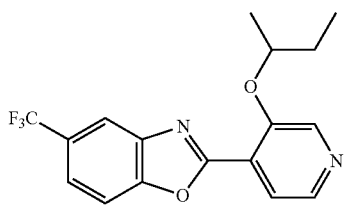

Active Compound 119
¹H-NMR (CDCl₃) δ: 8.56 (s, 1H), 8.39 (d, J=5.1 Hz, 1H), 8.13-8.11 (m, 1H), 8.00 (d, J=5.1 Hz, 1H), 7.73-7.66 (m, 2H), 4.68-4.58 (m, 1H), 1.96-1.73 (m, 2H), 1.45 (d, J=6.1 Hz, 3H), 1.07 (t, J=7.4 Hz, 3H)

Production Example 121

A mixture of 0.28 g of 2-(3-fluoropyridin-4-yl)-5-(trifluoromethyl)benzoxazole, 0.27 g of potassium carbonate and 3 ml of 2-methoxyethanol was stirred while heating at 80° C. for 2.5 hours. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.23 g of 2-[3-(2-methoxyethoxy)pyridin-4-yl]-5-(trifluoromethyl)benzoxazole (hereinafter, referred to as "active compound 120").

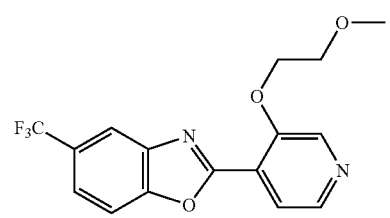

Active Compound 120
¹H-NMR (CDCl₃) δ: 8.61 (s, 1H), 8.46 (d, J=4.9 Hz, 1H), 8.13-8.11 (m, 1H), 8.02 (d, J=4.9 Hz, 1H), 7.73-7.67 (m, 2H), 4.48-4.42 (m, 2H), 3.94-3.87 (m, 2H), 3.50 (s, 3H)

Production Example 122

Production Example 122 was carried out according to the same manner as in Production Example 121, using 3-methoxy-1-propanol instead of 2-methoxyethanol, and thus 0.23 g of 2-[3-(3-methoxypropoxy)pyridin-4-yl]-5-(trifluoromethyl)benzoxazole (hereinafter, referred to as "active compound 121") was obtained.

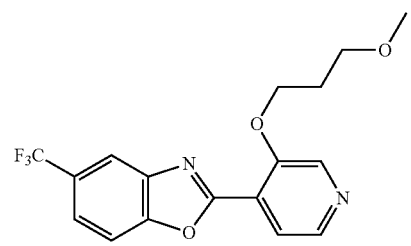

Active Compound 121
¹H-NMR (CDCl₃) δ: 8.59 (s, 1H), 8.43 (d, J=5.0 Hz, 1H), 8.13-8.10 (m, 1H), 8.01 (d, J=4.9 Hz, 1H), 7.74-7.67 (m, 2H), 4.40 (t, J=6.2 Hz, 2H), 3.69 (t, J=6.1 Hz, 2H), 3.37 (s, 3H), 2.23-2.17 (m, 2H)

Production Example 123

Production Example 123 was carried out according to the same manner as in Production Example 116, using 2-bromoethyl ethyl ether instead of cyclopentyl bromide, and thus 0.10 g of 2-[3-(2-ethoxy ethoxy)pyridin-4-yl]-5-(trifluoromethyl)benzoxazole (hereinafter, referred to as "active compound 122") was obtained.

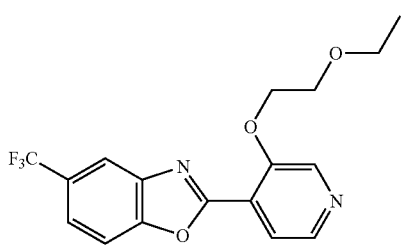

Active Compound 122
$^1$H-NMR (CDCl$_3$) δ: 8.62 (s, 1H), 8.45 (d, J=4.9 Hz, 1H), 8.12-8.10 (m, 1H), 8.01 (d, J=4.9 Hz, 1H), 7.73-7.67 (m, 2H), 4.48-4.43 (m, 2H), 3.96-3.91 (m, 2H), 3.66 (q, J=7.1 Hz, 2H), 1.24 (t, J=7.1 Hz, 3H)

Production Example 124

Production Example 124 was carried out according to the same manner as in Production Example 72, using pentanol instead of propanol, and thus 0.29 g of 2-(3-pentyloxypyridin-4-yl)-5-(trifluoromethyl)benzoxazole (hereinafter, referred to as "active compound 123") was obtained.

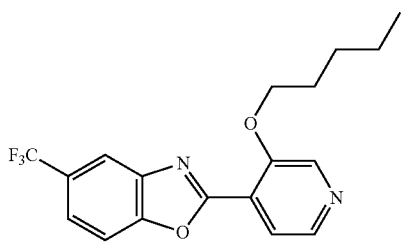

Active Compound 123
$^1$H-NMR (CDCl$_3$) δ: 8.56 (s, 1H), 8.42 (d, J=4.9 Hz, 1H), 8.13-8.10 (m, 1H), 8.01 (d, J=4.9 Hz, 1H), 7.73-7.67 (m, 2H), 4.29 (t, J=6.5 Hz, 2H), 1.99-1.90 (m, 2H), 1.62-1.52 (m, 2H), 1.49-1.37 (m, 2H), 0.96 (t, J=7.2 Hz, 3H)

Production Example 125

Production Example 125 was carried out according to the same manner as in Production Example 72, using hexanol instead of propanol, and thus 0.23 g of 2-(3-hexyloxypyridin-4-yl)-5-(trifluoromethyl)benzoxazole (hereinafter, referred to as "active compound 124") was obtained.

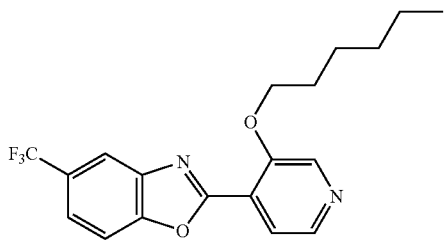

Active Compound 124
$^1$H-NMR (CDCl$_3$) δ: 8.56 (s, 1H), 8.42 (d, J=5.0 Hz, 1H), 8.15-8.09 (m, 1H), 8.01 (d, J=5.1 Hz, 1H), 7.74-7.68 (m, 2H), 4.32-4.27 (m, 2H), 1.98-1.88 (m, 2H), 1.61-1.52 (m, 2H), 1.42-1.31 (m, 4H), 0.95-0.88 (m, 3H)

Production Example 126

Production Example 126 was carried out according to the same manner as in Production Example 78, using N-[2-hydroxy-5-(trifluoromethyl)phenyl]-3-(trifluoromethyl)isonicotinamide instead of 3-chloro-N-[2-hydroxy-5-(trifluoromethylthio)phenyl]isonicotinamide, an thus 0.55 g of 5-trifluoromethyl-2-[3-(trifluoromethyl)pyridin-4-yl]-benzoxazole (hereinafter, referred to as "active compound 125") was obtained.

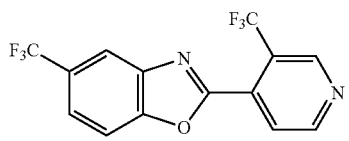

Active Compound 125
$^1$H-NMR (CDCl$_3$) δ: 9.18 (s, 1H), 9.04 (d, J=4.9 Hz, 1H), 8.20-8.18 (m, 1H), 8.16 (d, J=5.1 Hz, 1H), 7.81-7.74 (m, 2H)

Production Example 127

A mixture of 0.50 g of 4-[5-(trifluoromethyl)benzoxazole-2-yl]pyridin-3-ol, 1.23 g of potassium carbonate and 14 ml of DMF was stirred while heating at 70° C. for three hours with chlorodifluoromethane gas injected. By stopping injection of gas, the mixture was cooled to room temperature and allowed to stand overnight. Water was added to the reaction mixture, followed by extraction with ethyl acetate twice. The combined organic layers were washed with water and a saturated sodium chloride solution, dried over anhydrous magnesium sulfate, and concentrated under reduced pressure. The residue was subjected to silica gel column chromatography to give 0.11 g of 2-(3-difluoromethoxypyridin-4-yl)-5-(trifluoromethyl)benzoxazole (hereinafter, referred to as "active compound 126").

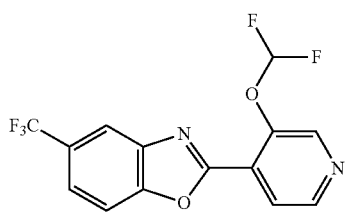

Active Compound 126
$^1$H-NMR (CDCl$_3$) δ: 8.80 (s, 1H), 8.74 (d, J=5.1 Hz, 1H), 8.18-8.16 (m, 1H), 8.15 (d, J=5.1 Hz, 1H), 7.79-7.72 (m, 2H), 6.82 (t, J=73.0 Hz, 1H)

Production Example 128

Production Example 128 was carried out according to the same manner as in Production Example 39, using 3-hydroxy pyridine instead of phenol, and thus 0.30 g of 2-[3-(pyridin-3-yloxy)-pyridin-4-yl]-5-(trifluoromethyl)benzoxazole (hereinafter, referred to as "active compound 127") was obtained.

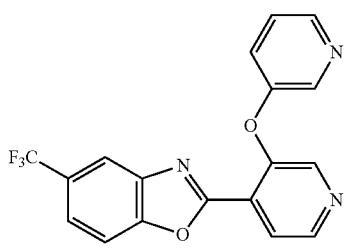

Active Compound 127

¹H-NMR (CDCl₃) δ: 8.67 (d, J=5.1 Hz, 1H), 8.54 (s, 1H), 8.53-8.52 (m, 1H), 8.45-8.42 (m, 1H), 8.20-8.18 (m, 1H), 8.10-8.08 (m, 1H), 7.71-7.65 (m, 2H), 7.40-7.36 (m, 1H), 7.35-7.30 (m, 1H)

Production Example 129

To a mixture of 0.40 g of 2-(3-iodopyridin-4-yl)-5-(trifluoromethyl)benzoxazole, 0.21 g of 3-pyridine boronic acid, 8 ml of 1,4-dioxane and 0.07 g of dichlorobis(triphenylphosphine)palladium (II), a mixture of 0.40 g of sodium carbonate and 3 ml of water was added and heated to reflux for two hours. The reaction mixture was cooled to room temperature, and then water was added to the reaction mixture, followed by extraction with ethyl acetate. The combined organic layers were washed with water and a saturated sodium chloride solution, dried over anhydrous magnesium sulfate, and concentrated under reduced pressure. The residue was subjected to silica gel column chromatography to give 0.36 g of 4-(5-trifluoromethyl-benzoxazole-2-yl)-[3,3']bipyridinyl (hereinafter, referred to as "active compound 128").

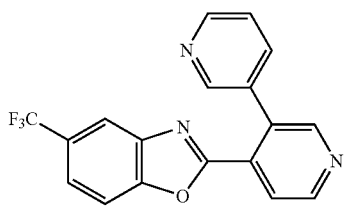

Active Compound 128

¹H-NMR (CDCl₃) δ: 8.89 (d, J=5.1 Hz, 1H), 8.77 (s, 1H), 8.74-8.69 (m, 1H), 8.68-8.62 (m, 1H), 8.18-8.13 (m, 1H), 8.04-7.99 (m, 1H), 7.73-7.68 (m, 1H), 7.67-7.62 (m, 1H), 7.54-7.47 (m, 1H), 7.43-7.36 (m, 1H)

Production Example 130

Production Example 130 was carried out according to the same manner as in Production Example 129, using 4-pyridine boronic acid instead of 3-pyridine boronic acid, and thus 0.20 g of 4-(5-trifluoromethyl-benzoxazole-2-yl)-[3,4']bipyridinyl (hereinafter, referred to as "active compound 129") was obtained.

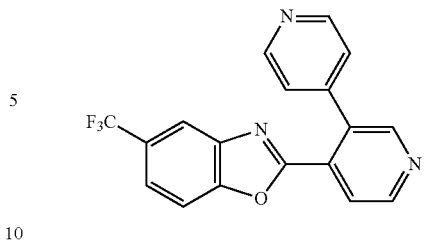

Active Compound 129

¹H-NMR (CDCl₃) δ: 8.90 (d, J=5.1 Hz, 1H), 8.75 (s, 1H), 8.70 (dd, J=4.4, 1.7 Hz, 2H), 8.14-8.12 (m, 1H), 8.03-8.02 (m, 1H), 7.67-7.63 (m, 1H), 7.50 (d, J=8.5 Hz, 1H), 7.28 (dd, J=4.4, 1.7, 2H)

Production Example 131

A mixture of 0.30 g of 2-(3-aminopyridin-4-yl)-5-(trifluoromethyl)benzoxazole and 3 ml of trifluoroacetic anhydride was stirred while heating at 60° C. for 15 minutes. The reaction mixture was cooled to room temperature, and then water and a saturated aqueous solution of sodium hydrogencarbonate were added to the reaction mixture. The precipitated crystals were filtered. The resultant crystals were dissolved in ethyl acetate. The resultant solution was washed with a saturated sodium chloride solution, dried over anhydrous magnesium sulfate, and concentrated under reduced pressure. The residue was subjected to silica gel column chromatography to give 0.32 g of 2,2,2-trifluoro-N-[4-(5-trifluoromethylbenzoxazole-2-yl)pyridin-3-yl]acetamide (hereinafter, referred to as "active compound 130").

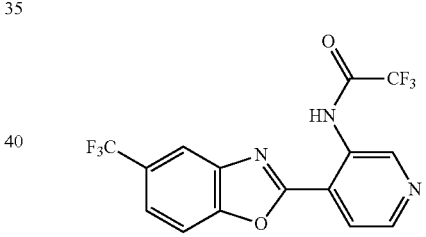

Active Compound 130

¹H-NMR (DMSO-d₆) δ: 12.66 (br s, 1H), 10.11 (s, 1H), 8.71 (d, J=5.1 Hz, 1H), 8.15-8.14 (m, 1H), 8.12 (d, J=5.1 Hz, 1H), 7.85-7.79 (m, 2H)

Production Example 132

To a mixture of 0.28 g of 2-(3-fluoropyridin-4-yl)-5-(trifluoromethyl)benzoxazole, 0.14 g of potassium carbonate and 3 ml of DMF, 3 ml of a THF solution of dimethylamine was added and stirred while heating at 60° C. for 3.3 hours. The reaction mixture was cooled to room temperature, and then water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography, and the resultant crystals were washed with diethyl ether to give 0.27 g of dimethyl-{4-[5-(trifluoromethyl)benzoxazole-2-yl]pyridin-3-yl}amine (hereinafter, referred to as "active compound 131").

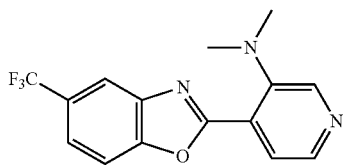

Active Compound 131
¹H-NMR (CDCl₃) δ: 8.53 (s, 1H), 8.28 (d, J=5.1 Hz, 1H), 8.13-8.11 (m, 1H), 7.79 (d, J=5.1 Hz, 1H), 7.74-7.71 (m, 1H), 7.70-7.67 (m, 1H), 2.93 (s, 6H)

Production Example 133

Production Example 133 was carried out according to the same manner as in Production Example 86, using N-isopropylmethylamine instead of isopropylamine, and thus 0.17 g of isopropyl-methyl-{4-[5-(trifluoromethyl)benzoxazole-2-yl]pyridin-3-yl}amine (hereinafter, referred to as "active compound 132") was obtained.

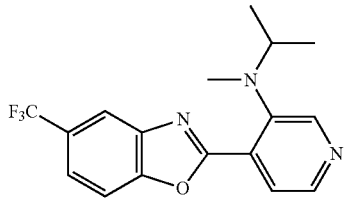

Active Compound 132
¹H-NMR (CDCl₃) δ: 8.53 (s, 1H), 8.29 (d, J=4.9 Hz, 1H), 8.11-8.09 (m, 1H), 7.79 (d, J=4.9 Hz, 1H), 7.73-7.66 (m, 2H), 3.57-3.45 (m, 1H), 2.82 (s, 3H), 1.15 (d, J=6.6 Hz, 6H Production Example 134

To a mixture of 0.60 g of 2-(3-ethylthio pyridin-4-yl)-5-(trifluoromethyl)benzoxazole and 8 ml of chloroform, 0.64 g of 70% m-chloroperbenzoic acid was added while ice-cooling and stirred at 0° C. for one hour. The reaction mixture was diluted with chloroform, washed with 5% aqueous solution of sodium hydroxide and a saturated sodium chloride solution, dried over anhydrous magnesium sulfate, and concentrated under reduced pressure. The residue was subjected to silica gel column chromatography to give 0.21 g of 2-[3-(ethanesulfonyl)pyridin-4-yl]-5-(trifluoromethyl)benzoxazole (hereinafter, referred to as "active compound 133") and 0.30 g of 2-[3-(ethanesulfinyl)pyridin-4-yl]-5-(trifluoromethyl) benzoxazole (hereinafter, referred to as "active compound 134").

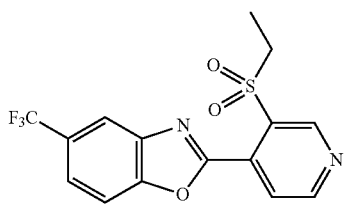

Active Compound 133
¹H-NMR (CDCl₃) δ: 9.44-9.43 (m, 1H), 9.09 (d, J=4.9 Hz, 1H), 8.17-8.14 (m, 1H), 7.96-7.94 (m, 1H), 7.78-7.75 (m, 2H), 3.93 (q, J=7.5 Hz, 2H), 1.46 (t, J=7.6 Hz, 3H)

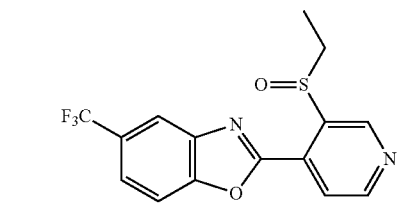

Active Compound 134
¹H-NMR (CDCl₃) δ: 9.45-9.44 (m, 1H), 8.99 (d, J=5.1 Hz, 1H), 8.18-8.17 (m, 1H), 8.13-8.11 (m, 1H), 7.81-7.76 (m, 2H), 3.53-3.41 (m, 1H), 3.15-3.04 (m, 1H), 1.45 (t, J=7.4 Hz, 3H)

Production Example 135

Production Example 135 was carried out according to the same manner as in Production Example 134, using 2-(3-methylthiopyridin-4-yl)-5-(trifluoromethyl)benzoxazole instead of 2-(3-ethylthiopyridin-4-yl)-5-(trifluoromethyl)benzoxazole, and thus 0.26 g of 2-[3-(methanesulfonyl)pyridin-4-yl]-5-(trifluoromethyl)benzoxazole (hereinafter, referred to as "active compound 135") and 0.37 g of 2-[3-(methanesulfinyl)pyridin-4-yl]-5-(trifluoromethyl)benzoxazole (hereinafter, referred to as "active compound 136") were obtained.

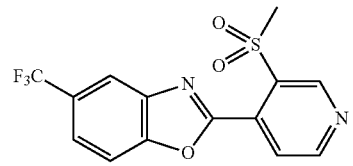

Active Compound 135
¹H-NMR (CDCl₃) δ: 9.51 (s, 1H), 9.11 (d, J=4.9 Hz, 1H), 8.19-8.16 (m, 1H), 7.97 (d, J=5.0 Hz, 1H), 7.80-7.76 (m, 2H), 3.72 (s, 3H)

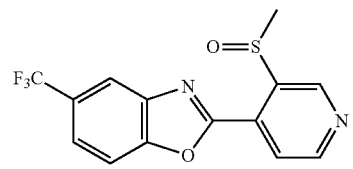

Active Compound 136
¹H-NMR (CDCl₃) δ: 9.55 (s, 1H), 9.01 (d, J=5.1 Hz, 1H), 8.21-8.19 (m, 1H), 8.12-8.10 (m, 1H), 7.82-7.76 (m, 2H), 3.13 (s, 3H)

Production Example 136

Production Example 136 was carried out according to the same manner as in Production Example 78, using N-[2-hydroxy-5-(trifluoromethyl)phenyl]-3-(methoxymethyl)isonicotinamide instead of 3-chloro-N-[2-hydroxy-5-(trifluoromethylthio)phenyl]isonicotinamide, and thus 0.26 g of 2-[3-(methoxymethyl)pyridin-4-yl]-5-(trifluoromethyl)benzoxazole (hereinafter, referred to as "active compound 137") was obtained.

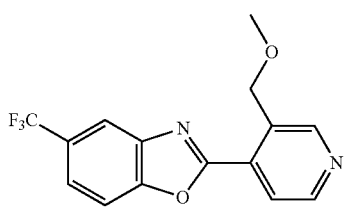

Active Compound 137
¹H-NMR (CDCl₃) δ: 9.02-9.01 (m, 1H), 8.78 (d, J=5.1 Hz, 1H), 8.17-8.15 (m, 1H), 8.08-8.05 (m, 1H), 7.77-7.71 (m, 2H), 5.12 (s, 2H), 3.57 (s, 3H)

Production Example 137

Production Example 137 was carried out according to the same manner as in Production Example 22, using N-[2-hydroxy-5-(trifluoromethyl)pyridin-3-yl]isonicotinamide instead of 2-chloro-N-[2-hydroxy-5-(trifluoromethyl)phenyl]isonicotinamide, and thus 0.32 g of 2-pyridin-4-yl-6-(trifluoromethyl)oxazolo[5,4-b]pyridine (hereinafter, referred to as "active compound 138") was obtained.

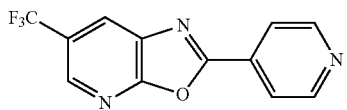

Active Compound 138
¹H-NMR (CDCl₃) δ: 8.90 (dd, J=4.5, 1.6 Hz, 2H), 8.76-8.74 (m, 1H), 8.40-8.38 (m, 1H), 8.14 (dd, J=4,4, 1.7 Hz, 2H)

Production Example 138

Production Example 138 was carried out according to the same manner as in Production Example 22, using 3-chloro-N-[2-hydroxy-5-(trifluoromethyl)pyridin-3-yl]isonicotinamide instead of 2-chloro-N-[2-hydroxy-5-(trifluoromethyl)phenyl]isonicotinamide, and thus 0.72 g of 2-(3-chloropyridin-4-yl)-6-(trifluoromethyl)oxazolo[5,4-b]pyridine (hereinafter, referred to as "active compound 139") was obtained.

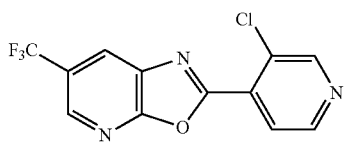

Active Compound 139
¹H-NMR (CDCl₃) δ: 8.89 (s, 1H), 8.80-8.77 (m, 1H), 8.74 (d, J=5.1 Hz, 1H), 8.48-8.46 (m, 1H), 8.13 (d, J=5.1 Hz, 1H)

Production Example 139

To a mixture of 0.45 g of 2-(3-chloropyridin-4-yl)-6-(trifluoromethyl)oxazolo[5,4-b]pyridine and 5 ml of chloroform, 0.48 g of 70% m-chloroperbenzoic acid was added in ice-cooling and stirred while heating at room temperature for four hours and at 50° C. for two hours. The reaction mixture was cooled to room temperature, then diluted with chloroform, and washed with 5% aqueous solution of sodium hydroxide and a saturated sodium chloride solution, sequentially. The organic layer was dried over anhydrous magnesium sulfate, and then concentrated under reduced pressure. The residue was subjected to silica gel column chromatography to give 0.36 g of 2-(3-chloro-1-oxypyridin-4-yl)-6-(trifluoromethyl)oxazolo[5,4-b]pyridine (hereinafter, referred to as "active compound 140").

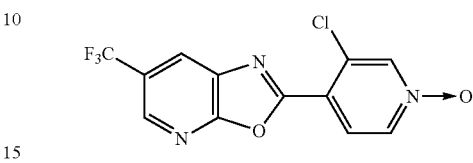

Active Compound 140
¹H-NMR (CDCl₃) δ: 8.77-8.74 (m, 1H), 8.43-8.42 (m, 1H), 8.41 (d, J=1.7 Hz, 1H), 8.23 (dd, J=7.0, 1.6 Hz, 1H), 8.19 (d, J=6.9 Hz, 1H)

Production Example 140

Production Example 140 was carried out according to the same manner as in Production Example 22, using 3-fluoro-N-[2-hydroxy-5-(trifluoromethyl)pyridin-3-yl]isonicotinamide instead of 2-chloro-N-[2-hydroxy-5-(trifluoromethyl)phenyl]isonicotinamide, and thus 1.72 g of 2-(3-fluoropyridin-4-yl)-6-(trifluoromethyl)oxazolo[5,4-b]pyridine (hereinafter referred to as "active compound 141") was obtained.

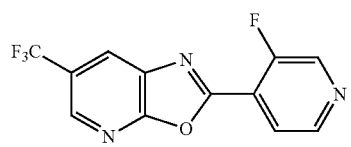

Active Compound 141
¹H-NMR (CDCl₃) δ: 8.81-8.76 (m, 2H), 8.70 (d, J=5.1 Hz, 1H), 8.46-8.43 (m, 1H), 8.17-8.13 (m, 1H)

Production Example 141

Production Example 141 was carried out according to the same manner as in Production Example 22, using N-[2-hydroxy-5-(trifluoromethyl)pyridin-3-yl]-3-methylisonicotinamide instead of 2-chloro-N-[2-hydroxy-5-(trifluoromethyl)phenyl]isonicotinamide, and thus 0.23 g of 2-(3-methylpyridin-4-yl)-6-(trifluoromethyl)oxazolo[5,4-b]pyridine (hereinafter, referred to as "active compound 142") was obtained.

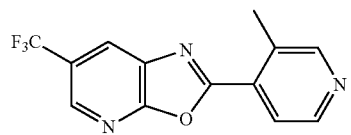

Active Compound 142
¹H-NMR (CDCl₃) δ: 8.76-8.74 (m, 1H), 8.72 (s, 1H), 8.70 (d, J=5.1 Hz, 1H), 8.43-8.41 (m, 1H), 8.09 (d, J=5.1 Hz, 1H), 2.84 (s, 3H)

Production Example 142

Production Example 142 was carried out according to the same manner as in Production Example 22, using 3-ethyl-N-[2-hydroxy-5-(trifluoromethyl)pyridin-3-yl]isonicotinamide instead of 2-chloro-N-[2-hydroxy-5-(trifluoromethyl)phenyl]isonicotinamide, and thus 0.16 g of 2-(3-ethylpyridin-4-yl)-6-(trifluoromethyl)oxazolo[5,4-b]pyridine (hereinafter, referred to as "active compound 143") was obtained.

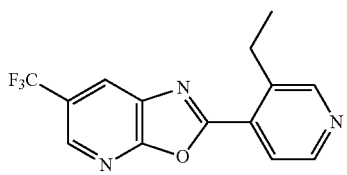

Active Compound 143
$^{1}$H-NMR (CDCl$_3$) δ: 8.76-8.73 (m, 2H), 8.70 (d, J=5.1 Hz, 1H), 8.43-8.41 (m, 1H), 8.07 (d, J=5.1 Hz, 1H), 3.30 (q, J=7.5 Hz, 2H), 1.36 (t, J=7.5 Hz, 3H)

Production Example 143

Production Example 143 was carried out according to the same manner as in Production Example 22, using N-[2-hydroxy-5-(trifluoromethyl)pyridin-3-yl]-3-(trifluoromethyl)isonicotinamide instead of 2-chloro-N-[2-hydroxy-5-(trifluoromethyl)phenyl]isonicotinamide, and thus 0.22 g of 6-trifluoromethyl-2-[3-(trifluoromethyl)pyridin-4-yl]-oxazolo[5,4-b]pyridine (hereinafter, referred to as "active compound 144") was obtained.

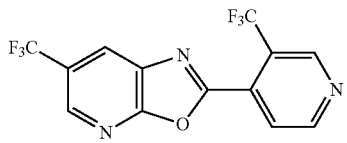

Active Compound 144
$^{1}$H-NMR (CDCl$_3$) δ: 9.21 (s, 1H), 9.08 (d, J=5.1 Hz, 1H), 8.81-8.79 (m, 1H), 8.49-8.47 (m, 1H), 8.17 (d, J=5.1 Hz, 1H)

Production Example 144

Production Example 144 was carried out according to the same manner as in Production Example 78, using N-[2-hydroxy-5-(trifluoromethyl)pyridin-3-yl]-3-methoxyisonicotinamide instead of 3-chloro-N-[2-hydroxy-5-(trifluoromethylthio)phenyl]isonicotinamide, and thus 0.27 g of 2-(3-methoxypyridin-4-yl)-6-(trifluoromethyl)oxazolo[5,4-b]pyridine (hereinafter, referred to as "active compound 145") was obtained.

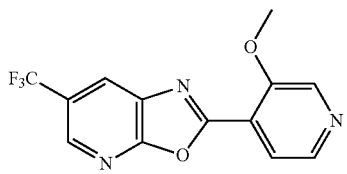

Active Compound 145
$^{1}$H-NMR (CDCl$_3$) δ: 8.75-8.72 (m, 1H), 8.63 (s, 1H), 8.49 (d, J=4.9 Hz, 1H), 8.41-8.40 (m, 1H), 8.06-8.04 (m, 1H), 4.18 (s, 3H)

Production Example 145

Production Example 145 was carried out according to the same manner as in Production Example 78, using N-[2-hydroxy-5-(trifluoromethyl)pyridin-3-yl]-3-methylthioisonicotinamide instead of 3-chloro-N-[2-hydroxy-5-(trifluoromethylthio)phenyl]isonicotinamide, and thus 1.07 g of 2-(3-methylthiopyridin-4-yl)-6-(trifluoromethyl)oxazolo[5,4-b]pyridine (hereinafter, referred to as "active compound 146") was obtained.

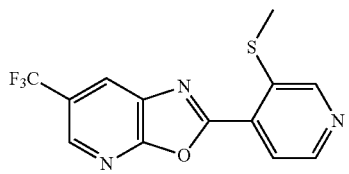

Active Compound 146
$^{1}$H-NMR (CDCl$_3$) δ: 8.76-8.74 (m, 1H), 8.71 (s, 1H), 8.60 (d, J=5.1 Hz, 1H), 8.48-8.46 (m, 1H), 8.09 (d, J=5.1 Hz, 1H), 2.70 (s, 3H)

Production Example 146

Production Example 146 was carried out according to the same manner as in Production Example 134, using 2-(3-methylthiopyridin-4-yl)-6-trifluoromethyl-oxazolo[5,4-b]pyridine instead of 2-(3-ethylthiopyridin-4-yl)-5-(trifluoromethyl)benzoxazole, and thus 0.20 g of 2-[3-(methanesulfonyl)pyridin-4-yl]-6-(trifluoromethyl)oxazolo[5,4-b]pyridine (hereinafter, referred to as "active compound 147") and 0.29 g of 2-[3-(methanesulfinyl)pyridin-4-yl]-6-(trifluoromethyl)oxazolo[5,4-b]pyridine (hereinafter, referred to as "active compound 148") were obtained.

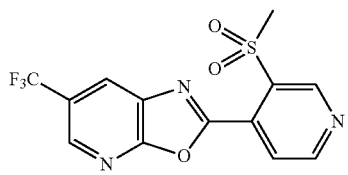

Active Compound 147
$^{1}$H-NMR (CDCl$_3$) δ: 9.52 (d, J=0.5 Hz, 1H), 9.14 (t, J=5.1 Hz, 1H), 8.81-8.79 (m, 1H), 8.47-8.46 (m, 1H), 8.00 (dd, J=5.0, 0.6 Hz, 1H), 3.69 (s, 3H)

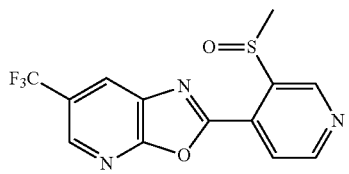

Active Compound 148

¹H-NMR (CDCl₃) δ: 9.59 (s, 1H), 9.07-9.05 (m, 1H), 8.82-8.80 (m, 1H), 8.51-8.19 (m, 1H), 8.19-8.16 (m, 1H), 3.12 (s, 3H)

Production Example 147

Production Example 147 was carried out according to the same manner as in Production Example 78, using N-[2-hydroxy-5-(trifluoromethyl)pyridin-3-yl]-3-ethylthioisonicotinamide instead of 3-chloro-N-[2-hydroxy-5-(trifluoromethylthio)phenyl]isonicotinamide, and thus 1.06 g of 2-(3-ethylthiopyridin-4-yl)-6-(trifluoromethyl)oxazolo[5,4-b]pyridine (hereinafter, referred to as "active compound 149") was obtained.

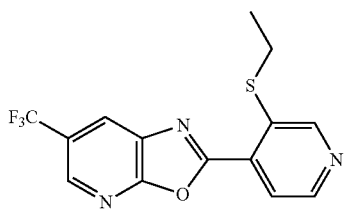

Active Compound 149

¹H-NMR (CDCl₃) δ: 8.77-8.73 (m, 2H), 8.59 (d, J=5.1 Hz, 1H), 8.48-8.47 (m, 1H), 8.08-8.06 (m, 1H), 3.21 (q, J=7.4 Hz, 2H), 1.49 (t, J=7.3 Hz, 3H)

Production Example 148

Production Example 148 was carried out according to the same manner as in Production Example 134, using 2-(3-ethylthiopyridin-4-yl)-6-trifluoromethyl-oxazolo[5,4-b]pyridine instead of 2-(3-ethylthiopyridin-4-yl)-5-(trifluoromethyl)benzoxazole, and thus 0.29 g of 2-[3-(ethanesulfonyl)pyridin-4-yl]-6-(trifluoromethyl)oxazolo[5,4-b]pyridine (hereinafter, referred to as "active compound 150") and 0.20 g of 2-[3-(ethanesulfinyl)pyridin-4-yl]-6-(trifluoromethyl)oxazolo[5,4-b]pyridine (hereinafter, referred to as "active compound 151") were obtained.

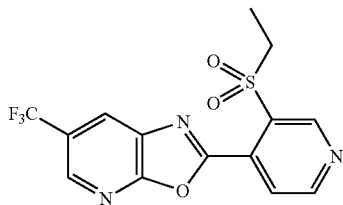

Active Compound 150

¹H-NMR (CDCl₃) δ: 9.46-9.45 (m, 1H), 9.14 (d, J=4.9 Hz, 1H), 8.80-8.79 (m, 1H), 8.46-8.44 (m, 1H), 7.99-7.97 (m, 1H), 3.88 (q, J=7.5 Hz, 2H), 1.48 (t, J=7.3 Hz, 3H)

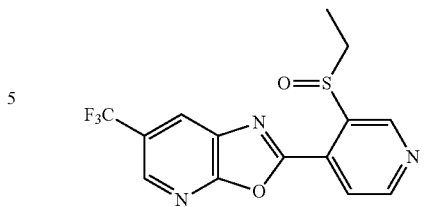

Active Compound 151

¹H-NMR (CDCl₃) δ: 9.48 (s, 1H), 9.04 (d, J=5.1 Hz, 1H), 8.82-8.80 (m, 1H), 8.49-8.47 (m, 1H), 8.19-8.17 (m, 1H), 3.51-3.39 (m, 1H), 3.14-3.04 (m, 1H), 1.44 (t, J=7.4 Hz, 3H)

Production Example 149

Production Example 149 was carried out according to the same manner as in Production Example 78, using N-[2-hydroxy-5-(trifluoromethyl)pyridin-3-yl]-3-(methoxymethyl)isonicotinamide instead of 2-chloro-N-[2-hydroxy-5-(trifluoromethyl)phenyl]isonicotinamide, and thus 0.29 g of 2-[3-(methoxymethyl)pyridin-4-yl]-6-(trifluoromethyl)oxazolo[5,4-b]pyridine (hereinafter, referred to as "active compound 152") was obtained.

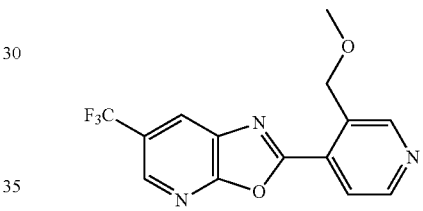

Active Compound 152

¹H-NMR (CDCl₃) δ: 9.04 (s, 1H), 8.82 (d, J=5.1 Hz, 1H), 8.77-8.75 (m, 1H), 8.44-8.42 (m, 1H), 8.12 (d, J=5.1 Hz, 1H), 5.11 (s, 2H), 3.56 (s, 3H)

Production Example 150

Production Example 150 was carried out according to the same manner as in Production Example 22, using N-[2-hydroxy-6-(trifluoromethyl)pyridin-3-yl]-isonicotinamide instead of 2-chloro-N-[2-hydroxy-5-(trifluoromethyl)phenyl]isonicotinamide, and thus 0.27 g of 2-(pyridin-4-yl)-5-(trifluoromethyl)oxazolo[5,4-b]pyridine (hereinafter, referred to as "active compound 153") was obtained.

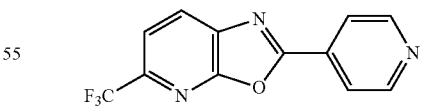

Active Compound 153

¹H-NMR (CDCl₃) δ: 8.91 (dd, J=4.4, 1.7 Hz, 2H), 8.30 (d, J=8.0 Hz, 1H), 8.14 (dd, J=4.4, 1.7 Hz, 2H), 7.85 (d, J=8.0 Hz, 1H)

Production Example 151

Production Example 151 was carried out according to the same manner as in Production Example 78, using 3-chloro- N-[2-hydroxy-6-(trifluoromethyl)pyridin-3-yl]-isonicotinamide instead of 3-chloro-N-[2-hydroxy-5-(trifluoromethylthio)phenyl]isonicotinamide, and thus 0.42 g of 2-(3-chloropyridin-4-yl)-5-(trifluoromethyl)oxazolo[5,4-b]pyridine (hereinafter, referred to as "active compound 154") was obtained.

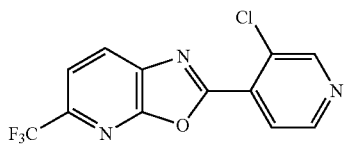

Active Compound 154
¹H-NMR (CDCl₃) δ: 8.89 (s, 1H), 8.74 (d, J=5.1 Hz, 1H), 8.38 (d, J=8.0 Hz, 1H), 8.14-8.12 (m, 1H), 7.88 (d, J=8.0 Hz, 1H)

Production Example 152

Production Example 152 was carried out according to the same manner as in Production Example 139, using 2-(3-chloropyridin-4-yl)-5-trifluoromethyl-oxazolo[5,4-b]pyridine instead of 2-(3-chloropyridin-4-yl)-6-trifluoromethyl-oxazolo[5,4-b]pyridine, and thus 0.14 g of 2-(3-chloro-1-oxypyridin-4-yl)-5-(trifluoromethyl)oxazolo[5,4-b]pyridine (hereinafter, referred to as "active compound 155") was obtained.

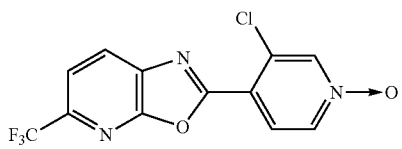

Active Compound 155
¹H-NMR (CDCl₃) δ: 8.41 (d, J=1.7 Hz, 1H), 8.33 (d, J=8.0 Hz, 1H), 8.23 (dd, J=7.1, 1.7 Hz, 1H), 8.19 (d, J=7.1 Hz, 1H), 7.86 (d, J=8.1 Hz, 1H)

Production Example 153

Production Example 153 was carried out according to the same manner as in Production Example 1, using 2-amino-6-methylpyridin-3-ol instead of 2-amino-4-propylphenol, and thus 0.62 g of 5-methyl-2-pyridin-4-yl-oxazolo[4,5-b]pyridine (hereinafter, referred to as "active compound 156") was obtained.

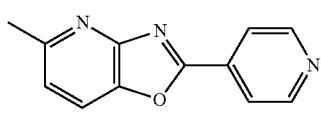

Active Compound 156
¹H-NMR (CDCl₃) δ: 8.85 (dd, J=4.5, 1.6 Hz, 2H), 8.13 (dd, J=4.5, 1.6 Hz, 2H), 7.82 (d, J=8.5 Hz, 1H), 7.24 (d, J=8.5 Hz, 1H), 2.72 (s, 3H)

Production Example 154

Production Example 154 was carried out according to the same manner as in Production Example 1, using 2-amino-6-methylpyridin-3-ol and 3-chloroisonicotinic acid instead of 2-amino-4-propylphenol and isonicotinic acid, and thus 0.44 g of 2-(3-chloropyridin-4-yl)-5-methyl-oxazolo[4,5-b]pyridine (hereinafter, referred to as "active compound 157") was obtained.

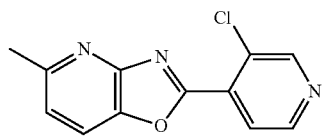

Active Compound 157
¹H-NMR (CDCl₃) δ: 8.83 (s, 1H), 8.69 (d, J=5.1 Hz, 1H), 8.16 (d, J=5.1 Hz, 1H), 7.86 (d, J=8.5 Hz, 1H), 7.28 (d, J=8.4 Hz, 1H), 2.74 (s, 3H)

Production Example 155

Production Example 154 was carried out according to the same manner as in Production Example 22, using 3-benzyloxy-N-[2-hydroxy-5-(trifluoromethyl)pyridin-3-yl]-isonicotinamide instead of 2-chloro-N-[2-hydroxy-5-(trifluoromethyl)phenyl]isonicotinamide, and thus 2.23 g of 2-[3-(benzyloxy)pyridin-4-yl]-6-trifluoromethyl-oxazolo[5,4-b]pyridine (hereinafter, referred to as "active compound 158") was obtained.

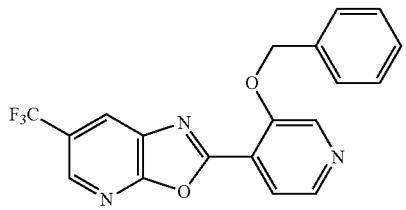

Active Compound 158
¹H-NMR (CDCl₃) δ: 8.75-8.73 (m, 1H), 8.63 (s, 1H), 8.47 (d, J=4.9 Hz, 1H), 8.40-8.38 (m, 1H), 8.06 (d, J=4.9 Hz, 1H), 7.60-7.56 (m, 2H), 7.45-7.40 (m, 2H), 7.38-7.32 (m, 1H), 5.47 (s, 2H)

Production Example 156

A mixture of 1.7 g of 2-[3-(benzyloxy)pyridin-4-yl]-6-trifluoromethyl-oxazolo[5,4-b]pyridine, 40 ml of ethyl acetate and 10% palladium on carbon was reacted under the conditions of 40 bar and 40° C. for two hours. The reaction solution was concentrated under reduced pressure. The residue was subjected to silica gel column chromatography to give 1.0 g of 4-(6-trifluoromethyl-oxazolo[5,4-b]pyridin-2-yl)pyridin-3-ol (hereinafter, referred to as "active compound 159").

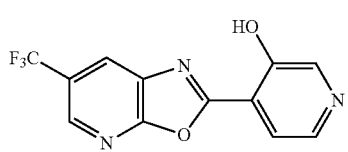

Active Compound 159

$^1$H-NMR (CDCl$_3$) δ: 10.57 (s, 1H), 8.79-8.78 (m, 1H), 8.67 (s, 1H), 8.41-8.39 (m, 2H), 7.91 (d, J=5.1 Hz, 1H)

Production Example 157

To a mixture of 0.26 g of 4-(6-trifluoromethyl-oxazolo[5,4-b]pyridin-2-yl)pyridin-3-ol, 0.14 g of potassium carbonate and 3 ml of DMF, 0.17 g of isopropyl iodide was added at room temperature and stirred while heating at 60° C. for 1.5 hours. To the reaction solution, 38 mg of potassium carbonate and 47 mg of isopropyl iodide were added, and the reaction solution was stirred while heating at 60° C. for two hours. The reaction solution was cooled to room temperature, and then water was added to the reaction mixture, followed by extraction with ethyl acetate twice. The combined organic layers were washed with water and a saturated sodium chloride solution, dried over anhydrous magnesium sulfate, and concentrated under reduced pressure. The residue was subjected to silica gel column chromatography to give .16 g of 2-(3-isopropoxypyridin-4-yl)-6-trifluoromethyl-oxazolo[5,4-b]pyridine (hereinafter, referred to as "active compound 160").

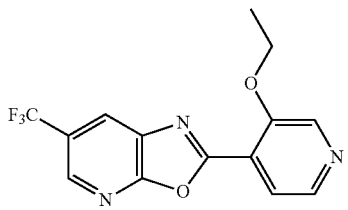

Active Compound 161

$^1$H-NMR (CDCl$_3$) δ: 8.74-8.72 (m, 1H), 8.60 (s, 1H), 8.45 (d, J=4.9 Hz, 1H), 8.40-8.38 (m, 1H), 8.04-8.02 (m, 1H), 4.41 (q, J=6.9 Hz, 2H), 1.60 (t, J=7.0 Hz, 3H)

Production Example 159

To a mixture of 0.31 g of 4-(6-trifluoromethyl-oxazolo[5,4-b]pyridin-2-yl)pyridin-3-ol, 0.23 g of potassium carbonate and 3 ml of DMF, a mixture of 0.50 g of trifluoromethanesulfonate(2,2-difluoroethyl)ester and 7 ml of DMF was added at room temperature, and then stirred while heating at 60° C. for six hours. The reaction mixture was cooled to room temperature, and then water was added to the reaction mixture, followed by extraction with ethyl acetate twice. The combined organic layers were washed with water and a saturated sodium chloride solution, dried over anhydrous magnesium sulfate, and concentrated under reduced pressure. The residue was subjected to silica gel column chromatography to give 0.10 g of 2-[3-(2,2-difluoroethoxy)pyridin-4-yl]-6-trifluoromethyl-oxazolo[5,4-b]pyridine (hereinafter, referred to as "active compound 162").

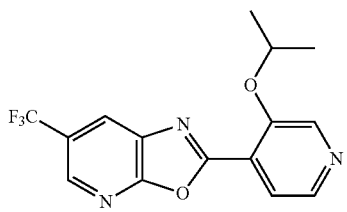

Active Compound 160

$^1$H-NMR (CDCl$_3$) δ: 8.73-8.71 (m, 1H), 8.60 (s, 1H), 8.43-8.41 (m, 1H), 8.39-8.38 (m, 1H), 8.02 (d, J=5.1 Hz, 1H), 4.94-4.83 (m, 1H), 1.52 (d, J=6.1 Hz, 6H)

Production Example 158

To a mixture of 0.25 g of 4-(6-trifluoromethyl-oxazolo[5,4-b]pyridin-2-yl)pyridin-3-ol, 0.14 g of potassium carbonate and 3 ml of DMF, a mixture of 0.15 g of ethyl iodide and 1 ml of DMF was added at room temperature and stirred while heating at 60° C. for 1.5 hours. To the reaction mixture, 70 mg of potassium carbonate and 53 mg of iodoethane were added, and the reaction solution was stirred while heating at 60° C. for 3.5 hours. The reaction solution was cooled to room temperature, and then water was added to the reaction mixture, followed by extraction with ethyl acetate twice. The combined organic layers were washed with water and a saturated sodium chloride solution, dried over anhydrous magnesium sulfate, and concentrated under reduced pressure. The residue was subjected to silica gel column chromatography to give 60 mg of 2-(3-ethoxypyridin-4-yl)-6-trifluoromethyl-oxazolo[5,4-b]pyridine (hereinafter, referred to as "active compound 161").

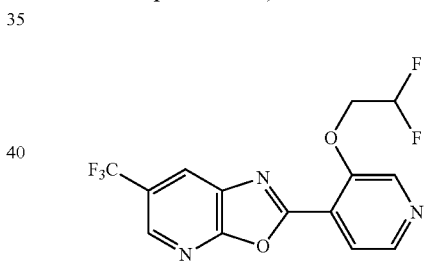

Active Compound 162

$^1$H-NMR (CDCl$_3$) δ: 8.76-8.74 (m, 1H), 8.62 (s, 1H), 8.57 (d, J=5.1 Hz, 1H), 8.41-8.40 (m, 1H), 8.09 (d, J=5.1 Hz, 1H), 6.30 (tt, J=54.8, 4.0 Hz, 1H), 4.53 (td, J=12.7, 4.1 Hz, 2H)

Next, Production Examples for producing production intermediates of the above-mentioned active compounds are described.

Reference Production Example 1

To a mixture of 5.0 g of 4-propylphenol and 35 ml of acetic acid, a mixture of 3.80 g of 61% nitric acid and 10 ml of acetic acid was added dropwise with the temperature kept at 10-15° C., which was stirred for four hours. The reaction mixture was poured into ice water and extracted with ethyl acetate, The combined organic layers were washed with water, a saturated aqueous solution of sodium hydrogencarbonate and a saturated sodium chloride solution, dried over magnesium sulfate, and then concentrated under reduced pressure to give 6.65 g of 4-propyl-2-nitrophenol.

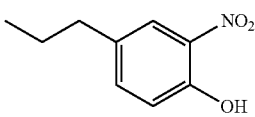

¹H-NMR (CDCl₃) δ: 10.46 (s, 1H), 7.89 (d, J=2.2 Hz, 1H), 7.40 (dd, J=8.5, 2.2 Hz, 1H) 7.08 (d, J=8.5 Hz, 1H), 2.58 (t, J=7.8 Hz, 2H), 1.69-1.59 (m, 2H), 0.94 (t, J=7.3 Hz, 3H)

A mixture of 6.65 g of 4-propyl-2-nitrophenol, 55 ml of ethyl acetate and 1.0 g of 5% palladium on carbon was stirred under about one atmosphere of hydrogen at room temperature for two hours. The mixture was filtered through Celite™. The filtrate was concentrated under reduced pressure to give 5.17 g of 2-amino-4-propylphenol.

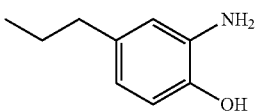

¹H-NMR (CDCl₃) δ: 6.64 (d, J=7.9 Hz, 1H), 6.59 (d, J=2.0 Hz, 1H), 6.49 (dd, J=8.0, 2.0 Hz, 1H), 3.74 (br s, 2H), 2.44 (t, J=7.8 Hz, 2H), 1.63-1.52 (m, 2H), 0.91 (t, J=7.3 Hz, 3H)

Reference Production Example 2

4-butyl-2-nitrophenol was obtained according to the same manner as that of Reference Production Example 1 using 4-butylphenol instead of 4-propylphenol.

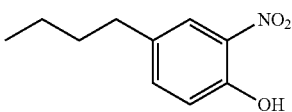

¹H-NMR (CDCl₃) δ: 10.46 (s, 1H), 7.89 (d, J=2.2 Hz, 1H), 7.41 (dd, J=8.5, 2.2 Hz, 1H), 7.07 (d, J=8.5 Hz, 1H), 2.60 (t, J=7.6 Hz, 2H), 1.65-1.53 (m, 2H), 1.41-1.30 (m, 2H), 0.93 (t, J=7.3 Hz, 3H)

2-amino-4-butylphenol was obtained according to the same manner as that of Reference Production Example 1, using 4-butyl-2-nitrophenol instead of 4-propyl-2-nitrophenol.

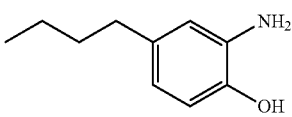

¹H-NMR (CDCl₃) δ: 6.64 (d, J=8.0 Hz, 1H), 6.59 (d, J=2.0 Hz, 1H), 6.49 (dd, J=8.0, 2.0 Hz, 1H), 3.60 (br s, 2H), 2.47 (t, J=7.6 Hz, 2H), 1.59-1.49 (m, 2H), 1.38-1.27 (m, 2H), 0.91 (t, J=7.3 Hz, 3H)

Reference Production Example 3

A mixture of 7 g of 4-methoxy-2-nitrophenol, 50 ml of ethyl acetate and 1.3 g of 5% palladium on carbon was stirred under about one atmosphere of hydrogen at room temperature for 3.3 hours. The reaction mixture was filtered through Celite™. The filtrate was concentrated under reduced pressure to give 2-amino-4-methoxyphenol. This is used in the following reaction without purification.

A mixture of 2.5 g of a crude product of 2-amino-4-methoxyphenol, 3.2 g of isonicotinic acid chloride hydrochloride and 20 ml of pyridine was heated to reflux for 12 hours. The reaction mixture was poured into ice water, and precipitated deposits are collected by filtration. The obtained solid was dissolved in ethyl acetate, washed with water and a saturated sodium chloride solution, and dried over magnesium sulfate. Activated carbon was added thereto, followed by filtration through Celite™. The filtrate was concentrated under reduced pressure to give N-(2-hydroxy-5-methoxyphenyl) isonicotinamide.

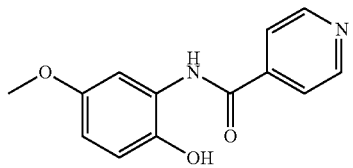

¹H-NMR (DMSO-d₆) δ: 9.50 (br s, 1H), 8.79-8.75 (m, 2H), 7.89-7.83 (m, 2H), 7.36-7.30 (m, 1H), 6.87-6.81 (m, 1H), 6.70-6.64 (m, 1H), 3.69 (s, 3H)

Reference Production Example 4

4-ethyl-2-nitrophenol was obtained according to the same manner as that of Reference Production Example 1, using 4-ethylphenol instead of 4-propylphenol.

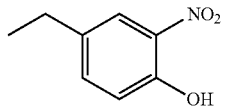

¹H-NMR (CDCl₃) δ: 10.46 (s, 1H), 7.91 (d, J=2.1 Hz, 1H), 7.43 (dd, J=8.5, 2.2 Hz, 1H), 7.08 (d, J=8.7 Hz, 1H), 2.64 (q, J=7.8 Hz, 2H), 1.25 (t, J=7.8 Hz, 3H)

2-amino-4-ethylphenol was obtained according to the same manner as that of Reference Production Example 1, using 4-ethyl-2-nitrophenol instead of 4-propyl-2-nitrophenol.

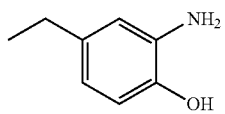

¹H-NMR (CDCl₃) δ: 6.65 (d, J=8.0 Hz, 1H), 6.61 (d, J=2.1 Hz, 1H), 6.53-6.49 (m, 1H), 3.84 (br s, 2H), 2.51 (q, J=7.6 Hz, 2H), 1.18 (t, J=7.6 Hz, 3H)

Reference Production Example 5

4-isopropyl-2-nitrophenol was obtained according to the same manner as that of Reference Production Example 1, using 4-isopropylphenol instead of 4-propylphenol.

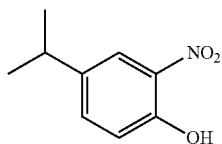

$^1$H-NMR (CDCl$_3$) δ: 10.46 (s, 1H), 7.93 (d, J=2.1 Hz, 1H), 7.47 (dd, J=8.5, 2.2 Hz, 1H), 7.09 (d, J=8.6 Hz, 1H), 2.97-2.86 (m, 1H), 1.25 (d, J=7.0 Hz, 6H)

2-amino-4-isopropylphenol was obtained according to the same manner as that of Reference Production Example 1, using 4-isopropyl-2-nitrophenol instead of 4-propyl-2-nitrophenol.

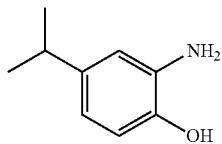

$^1$H-NMR (CDCl$_3$) δ: 6.66 (d, J=8.2 Hz, 1H), 6.64 (d, J=2.1 Hz, 1H), 6.54 (dd, J=8.0, 2.2 Hz, 1H), 4.60 (br s, 1H), 3.58 (br s, 2H), 2.84-2.70 (m, 1H), 1.19 (d, J=7.0 Hz, 6H)

Reference Production Example 6

4-tert-butyl-2-nitrophenol was obtained according to the same manner as that of Reference Production Example 1, using 4-tert-butylphenol instead of 4-propylphenol.

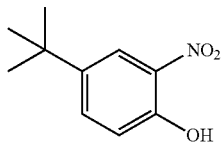

$^1$H-NMR (CDCl$_3$) δ: 10.47 (s, 1H), 8.07 (d, J=2.4 Hz, 1H), 7.64 (dd, J=8.8, 2.4 Hz, 1H), 7.10 (d, J=8.8 Hz, 1H), 1.33 (s, 9H)

2-amino-4-tert-butylphenol was obtained according to the same manner as that of Reference Production Example 1, using 4-tert-butyl-2-nitrophenol instead of 4-propyl-2-nitrophenol.

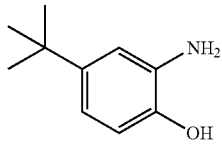

$^1$H-NMR (CDCl$_3$) δ: 6.80 (d, J=2.2 Hz, 1H), 6.70 (dd, J=8.2, 2.2 Hz, 1H), 6.66 (d, J=8.2 Hz, 1H), 3.59 (br s, 2H), 1.26 (s, 9H)

Reference Production Example 7

2-amino-4-trifluoromethylphenol was obtained according to the same manner as that of Reference Production Example 1, using 2-nitro-4-trifluoromethylphenol instead of 4-propyl-2-nitrophenol.

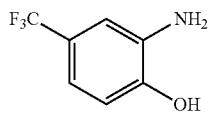

$^1$H-NMR (CDCl$_3$) δ: 6.98 (d, J=2.2 Hz, 1H), 6.95-6.92 (m, 1H), 6.76 (d, J=8.3, 1H), 5.33 (br s, 1H), 3.80 (br s, 2H)

A mixture of 2.84 g of 2-amino-4-trifluoromethylphenol, 1.97 g of isonicotinic acid, 3.69 g of WSC [1-ethyl-3-(3-dimethylaminopropyl)carbodiimide hydrochloride] and 20 ml of pyridine was stirred while heating at 80° C. for four hours. The reaction mixture was cooled to room temperature, and then water was poured, followed by extraction with ethyl acetate twice. The combined organic layers were washed with water and a saturated sodium chloride solution, dried over magnesium sulfate, and then concentrated under reduced pressure. The residue was washed with an ethyl acetate-hexane mixture solvent to give 1.69 g of N-(2-hydroxy-5-trifluoromethylphenyl)isonicotinamide.

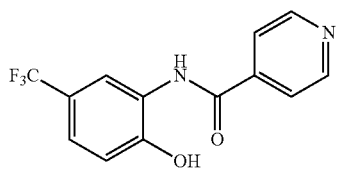

$^1$H-NMR (DMSO-d$_6$) δ: 10.82 (br s, 1H), 9.94 (br s, 1H), 8.80-8.78 (m, 2H), 8.05 (d, J=2.0 Hz, 1H), 7.88-7.86 (m, 2H), 7.43 (dd, J=8.5, 2.0 Hz, 1H), 7.10 (d, J=8.6 Hz, 1H)

Reference Production Example 8

To a mixture of 5 g of 3-tert-butylphenol and 30 ml of acetic acid, a mixture of 3.0 g of 70% nitric acid and 10 ml of acetic acid was added dropwise with the temperature kept at 10-15° C. and stirred for two hours. The reaction mixture was poured into ice water and extracted with ethyl acetate twice. The combined organic layers were washed with water, a saturated aqueous solution of sodium hydrogencarbonate and a saturated sodium chloride solution, dried over magnesium sulfate, and then concentrated under reduced pressure. The residue was subjected to silica gel column chromatography to give 1.82 g of 5-tert-butyl-2-nitrophenol.

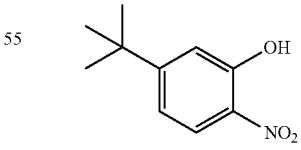

$^1$H-NMR (CDCl$_3$) δ: 10.60 (s, 1H), 8.01 (d, J=9.0 Hz, 1H), 7.13 (d, J=2.2, 1H), 7.01 (dd, J=9.0, 2.0 Hz, 1H), 1.33 (s, 9H)

2-amino-5-tert-butylphenol was obtained according to the same manner as that of Reference Production Example 1, using 5-tert-butyl-2-nitrophenol instead of 4-propyl-2-nitrophenol.

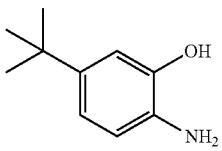

A mixture of 1.44 g of 2-amino-5-tert-butylphenol, 1.07 g of isonicotinic acid, 2.17 g of WSC and 15 ml of pyridine was stirred while heating at 80° C. for five hours. The reaction mixture was cooled to room temperature, and then water was poured. Precipitated solid was filtered and washed with water and diethyl ether to give 1.22 g of N-(4-tert-butyl-2-hydroxyphenyl)isonicotinamide.

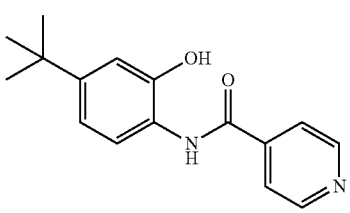

$^1$H-NMR (CDCl$_3$+DMSO-d$_6$) δ: 9.32 (br s, 1H), 9.12 (br s, 1H), 8.81-8.77 (m, 2H), 7.85-7.78 (m, 3H), 7.03 (d, J=1.9, 1H), 6.93 (dd, J=8.5, 1.9 Hz, 1H), 1.31 (s, 9H)

Reference Production Example 9

To 7.5 g of 3-trifluoromethylphenol, 9 ml of 70% nitric acid was added dropwise at room temperature and the reaction mixture was stirred for one hour. The reaction mixture was poured into an ice-cooled saturated aqueous solution of sodium hydrogencarbonate, followed by extraction with ethyl acetate twice. The combined organic layers washed with water and a saturated sodium chloride solution, dried over magnesium sulfate, and concentrated under reduced pressure. The residue was subjected to silica gel column chromatography to give 1.56 g of 2-nitro-5-trifluoromethylphenol.

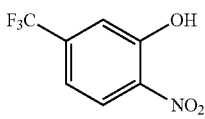

$^1$H-NMR (CDCl$_3$) δ: 10.59 (s, 1H), 8.25 (d, J=8.8 Hz, 1H), 7.48-7.46 (m, 1H), 7.27-7.23 (m, 1H)

2-amino-5-trifluoromethylphenol was obtained according to the same manner as that of Reference Production Example 1, using 2-nitro-5-trifluoromethylphenol instead of 4-propyl-2-nitrophenol.

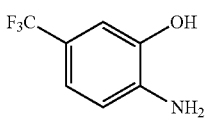

$^1$H-NMR (CDCl$_3$+DMSO-d$_6$) δ: 9.03 (br s, 1H), 7.01 (d, J=1.8 Hz, 1H), 6.95-6.91 (m, 1H), 6.71-6.66 (m, 1H), 4.13 (br s, 2H)

A mixture of 1.30 g of 2-amino-5-trifluoromethylphenol, 0.9 g of isonicotinic acid, 1.83 g of WSC and 15 ml of pyridine was stirred while heating at 80° C. for three hours. The mixture was cooled to room temperature, and then water was poured. Precipitated solid was filtered and washed with water, and then dried under reduced pressure to give 1.5 g of N-(2-hydroxy-4-trifluoromethylphenyl)isonicotinamide.

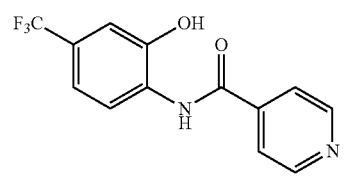

$^1$H-NMR (DMSO-d$_6$) δ: 8.82-8.76 (m, 2H), 7.98-7.93 (m, 1H), 7.89-7.85 (m, 2H), 7.23-7.17 (m, 2H)

Reference Production Example 10

A mixture of 6.8 g of 1,1,3,3-tetrafluoro-5-hydroxy-6-nitro-1,3-dihydroisobenzofuran and 20 ml of acetic acid was added dropwise to a mixture, which was heated to 80° C., of 7.8 g of electrolytic iron, 20 ml of acetic acid and 20 ml of water, and then the reaction mixture was stirred for one hour. The mixture was cooled to room temperature, and then water was added, followed by extraction with ethyl acetate twice. The combined organic layers were washed with water, a saturated aqueous solution of sodium hydrogencarbonate, and a saturated sodium chloride solution, and dried over magnesium sulfate. Activated carbon was added, followed by filtration through Celite™. The filtrates were concentrated under reduced pressure to give 4.43 g of 6-amino-1,1,3,3-tetrafluoro-5-hydroxy-1,3-dihydroisobenzofuran.

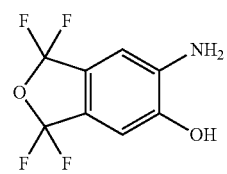

$^1$H-NMR (DMSO-d$_6$) δ: 10.65 (br s, 1H), 6.90 (s, 1H), 6.84 (s, 1H), 5.70 (br s, 2H)

A mixture of 2.0 g of 6-amino-1,1,3,3-tetrafluoro-5-hydroxy-1,3-dihydroisobenzofuran, 1.1 g of isonicotinic acid, 2.23 g of WSC and 15 ml of pyridine was stirred while heating at 80° C. for three hours. The reaction mixture was cooled to room temperature, and then water was poured into the reaction mixture. Precipitated solid was filtered and washed with water and dried under reduced pressure to give 1.34 g of N-(1,1,3,3-tetrafluoro-6-hydroxy-1,3-dihydroisobenzofuran-5-yl)isonicotinamide.

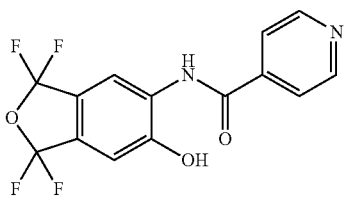

¹H-NMR (DMSO-d₆) δ: 10.07 (br s, 1H), 8.80 (dd, J=4.4, 1.5 Hz, 2H), 8.36 (s, 1H), 7.87 (dd, J=4.4, 1.5 Hz, 2H), 7.28 (s, 1H)

Reference Production Example 11

A mixture of 1 g of 3,5-dichloroisonicotinic acid and 5 ml of thionyl chloride was heated to reflux for seven hours. Then, the mixture was cooled to room temperature, and then concentrated under reduced pressure. The residue was dissolved in 3 ml of DMF, which was added dropwise to a mixture of 2-amino-4-trifluoromethylphenol, 5 ml of DMF and 1.05 g of triethylamine at 0° C. The reaction mixture was stirred at room temperature for two hours, and then water was added thereto, followed by extraction with ethyl acetate twice. The combined organic layers were washed with water and a saturated sodium chloride solution, dried over magnesium sulfate, and concentrated under reduced pressure. The residue was washed with diethyl ether to give 0.75 g of 3,5-dichloro-N-(2-hydroxy-5-trifluoromethylphenyl)isonicotinamide.

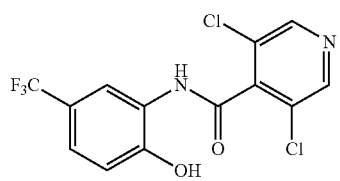

¹H-NMR (CDCl₃+DMSO-d₆) δ: 9.03 (br s, 1H), 8.59 (s, 2H), 8.45 (d, J=2.0 Hz, 1H), 7.30 (dd, J=8.5, 2.2 Hz, 1H), 7.04 (d, J=8.5 Hz, 1H)

Reference Production Example 12

A mixture of 0.89 g of 2-amino-4-(trifluoromethyl)phenol, 0.71 g of 3-chloro-4-pyridinecarboxyaldehyde and 5 ml of ethanol was heated to reflux for three hours. The reaction mixture was concentrated and the residue was washed with an ethyl acetate-hexane mixture solvent to give 0.71 g of 2-(3-chloropyridin-4-yl)methylideneamino-4-(trifluoromethyl)phenol.

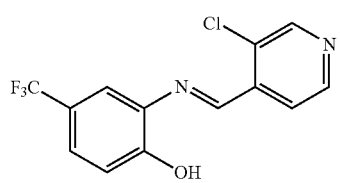

¹H-NMR (CDCl₃) δ: 9.14 (s, 1H), 8.76 (s, 1H), 8.65 (d, J=5.1 Hz, 1H), 8.01 (d, J=5.1 Hz, 1H), 7.62 (m, 1H), 7.56 (d, J=8.6 Hz, 1H), 7.35 (br s, 1H), 7.14 (d, J=8.6 Hz, 1H)

Reference Production Example 13

To a mixture of 1.77 g of 2-amino-4-(trifluoromethyl)phenol, 1.58 g of 3-chloroisonicotinic acid and 15 ml of pyridine, 2.70 g of WSC was added and stirred while heating at 60° C. for four hours. The reaction mixture was cooled to room temperature, and then concentrated under reduced pressure. Water was added to the residue, followed by extraction with ethyl acetate twice. The combined organic layers were washed with a saturated sodium chloride solution, dried over anhydrous sodium sulfate, and then concentrated under reduced pressure. The residue was washed with a mixture solvent of tert-butyl methyl ether and hexane to give 1.80 g of 3-chloro-N-[2-hydroxy-5-(trifluoromethyl)phenyl]isonicotinamide.

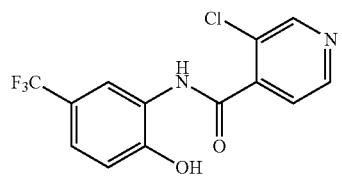

¹H-NMR (DMSO-d₆) δ: 10.89 (br s, 1H), 10.19 (br s, 1H), 8.75 (s, 1H), 8.64 (d, J=4.9 Hz, 1H), 8.32 (d, J=2.0 Hz, 1H), 7.63 (d, J=4.9 Hz, 1H), 7.40 (dd, J=8.5, 2.1 Hz, 1H), 7.08 (d, J=8.5 Hz, 1H)

Reference Production Example 14

To a mixture of 0.71 g of 2-amino-4-(trifluoromethyl)phenol, 0.63 g of 2-chloroisonicotinic acid and 7 ml of pyridine, 1.05 g of WSC was added and stirred while heating at 60° C. for four hours. The reaction mixture was cooled to room temperature, and then concentrated under reduced pressure. Water was added to the residue, followed by extraction with ethyl acetate twice. The combined organic layers were washed with a saturated sodium chloride solution, dried over anhydrous sodium sulfate, and then concentrated under reduced pressure. The residue was subjected to silica gel column chromatography to give 0.77 g of 2-chloro-N-[2-hydroxy-5-(trifluoromethyl)phenyl]isonicotinamide.

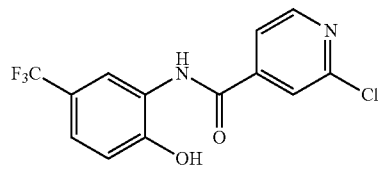

¹H-NMR (DMSO-d₆) δ: 10.12 (br s, 1H), 8.62 (d, J=5.1 Hz, 1H), 8.03-7.97 (m, 2H), 7.87 (dd, J=5.2, 1.3 Hz, 1H), 7.46-7.43 (m, 1H), 7.10 (d, J=8.2 Hz, 1H)

Reference Production Example 15

A mixture of 0.62 g of 2-amino-4-(trifluoromethyl)phenol, 0.48 g of 3-methyl isonicotinic acid, 0.86 g of WSC and 5 ml of pyridine was stirred while heating at 60° C. for three hours. The reaction mixture was cooled to room temperature, and then the reaction mixture was concentrated. Water was poured into the residue, followed by extraction with ethyl acetate. The organic layer was washed with water and a saturated sodium chloride solution, sequentially. The organic layer was dried over anhydrous sodium sulfate, and then concentrated under reduced pressure. The residue was washed with a mixture solvent of tert-butyl methyl ether and hexane to give 0.38 g of N-[2-hydroxy-5-(trifluoromethyp-phenyl]-3-methylisonicotinamide.

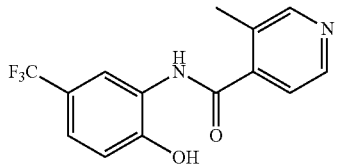

$^1$H-NMR (DMSO-d$_6$) δ: 9.83 (br s, 1H), 8.55 (s, 1H), 8.52 (d, J=5.1 Hz, 1H), 8.18 (s, 1H), 7.47 (d, J=5.1 Hz, 1H), 7.40 (dd, J=8.8, 1.9 Hz, 1H), 7.06 (d, J=8.8 Hz, 1H), 2.39 (s, 3H)

Reference Production Example 16

While a mixture of 3.54 g of diisopropylamine and 50 ml of tetrahydrofuran was cooled in a dry ice-acetone bath, 20 ml of 1.6 M hexane solution of n-butyllithium was added while stirring so that the temperature of the reaction mixture did not exceed –40° C. Thereafter, the reaction mixture was stirred for 30 minutes. Then, a mixture of 2.91 g of 3-fluoropyridine and 3 ml of tetrahydrofuran was added so that the temperature of the reaction mixture did not exceed –60° C. The mixture was further stirred for 30 minutes. After crushed dry ice was added to the reaction mixture, cooling was stopped. Then, the reaction mixture was stirred until the temperature returned to room temperature. Water was added to the reaction mixture, and most part of hexane and tetrahydrofuran was removed under reduced pressure. The residue was washed with tert-butyl methyl ether, and the aqueous layers were collected. To the collected aqueous layer, concentrated hydrochloric acid was added while ice-cooling, and pH of the mixture was made to be 3 and stirred for one hour. Precipitates were collected by filtration and dried under reduced pressure to give 3.59 g of 3-fluoroisonicotinic acid.

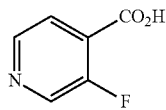

$^1$H-NMR (DMSO-d$_6$) δ: 8.74 (d, J=2.4 Hz, 1H), 8.58 (d, J=4.9 Hz, 1H), 7.80-7.77 (m, 1H)

Reference Production Example 17

A mixture of 0.49 g of 3-fluoroisonicotinic acid, 0.62 g of 2-amino-4-(trifluoromethyl)phenol, 1.00 g of WSC and 6 ml of pyridine was stirred while heating at 80° C. for two hours. The reaction mixture was cooled to room temperature, and then concentrated. Water was poured into the residue, followed by extraction with ethyl acetate. The organic layer was washed with a saturated sodium chloride solution. The organic layer was dried over anhydrous sodium sulfate, and then concentrated under reduced pressure. The residue was washed with a tert-butyl methyl ether-hexane mixture solvent to give 0.51 g of 3-fluoro-N-[2-hydroxy-5-(trifluoromethyl)phenyl]isonicotinamide.

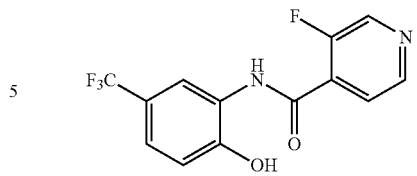

$^1$H-NMR (DMSO-d$_6$) δ: 11.09 (s, 1H), 9.98 (br s, 1H), 8.76 (m, 1H), 8.60 (d, J=4.6 Hz, 1H), 8.39 (d, J=2.2 Hz, 1H), 7.78-7.75 (m 1H), 7.41 (dd, J=8.6, 2.2 Hz, 1H), 7.09 (d, J=8.6 Hz, 1H)

Reference Production Example 18

A mixture of 3.54 g of diisopropylamine and 50 ml of tetrahydrofuran was stirred while cooling in a dry ice-acetone bath. To the reaction mixture, 20 ml of 1.6 M hexane solution of n-butyllithium was added so that the temperature of the reaction mixture did not exceed –40° C. The reaction mixture was stirred for 30 minutes. Then, a mixture of 4.74 g of 3-bromopyridine and 5 ml of tetrahydrofuran was added so that the temperature of the reaction mixture did not exceed –60° C. The reaction mixture was stirred for further 30 minutes. Crushed dry ice was added to the reaction mixture and then cooling was stopped. The reaction mixture was stirred until the temperature retuned to room temperature. Water was added thereto, most of hexane and tetrahydrofuran was removed under reduced pressure. The residue was washed with tert-butyl methyl ether, and the aqueous layers were collected. To the collected aqueous layers, concentrated hydrochloric acid was added while ice-cooling so that pH of the mixture was made to be 3 and stirred for one hour, followed by extraction with ethyl acetate three times. The combined organic layers were washed with a saturated sodium chloride solution, dried over anhydrous sodium sulfate, and concentrated under reduced pressure to give 0.69 g of 3-bromo isonicotinic acid.

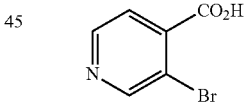

$^1$H-NMR (DMSO-d$_6$) δ: 8.74 (s, 1H), 8.67 (d, J=4.9 Hz, 1H), 7.69 (d, J=4.9 Hz, 1H)

Reference Production Example 19

A mixture of 0.69 g of 3-bromo isonicotinic acid, 0.60 g of 2-amino-4-(trifluoromethyl)phenol, 1.00 g of WSC and 6 ml of pyridine was stirred while heating at 80° C. for two hours. The reaction mixture was cooled to room temperature, and then concentrated. Water was added to the residue, followed by extraction with ethyl acetate. The organic layer was washed with a saturated sodium chloride solution, then dried over anhydrous sodium sulfate, and concentrated under reduced pressure. The residue was washed with a mixture solvent of ethyl acetate and hexane to give 0.29 g of 3-bromo-N-[2-hydroxy-5-(trifluoromethyl)phenyl]isonicotinamide.

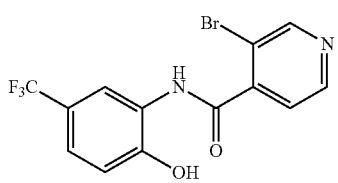

Reference Production Example 20

Water was added to 3.20 g of sodium hydroxide to make 30 ml of aqueous solution in total. To the solution, 5.83 g of 3-iodo-isonicotinic acid methyl ester (U.S. Pat. No. 6,277,871B1, O'Conner et al.) was added. The mixture solution was stirred while heating at 60° C. for three hours. The reaction mixture was cooled in ice, to which concentrated hydrochloric acid was added to adjust pH to 2-3. Precipitates were collected by filtration and dried under reduced pressure to give 5.21 g of 3-iodo-isonicotinic acid.

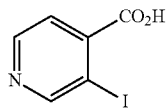

$^1$H-NMR (DMSO-$d_6$) δ: 9.04 (s, 1H), 8.64 (d, J=5.1 Hz, 1H), 7.65 (d, J=5.1 Hz, 1H)

Reference Production Example 21

A mixture of 1.78 g of 3-iodo-isonicotinic acid, 1.38 g of WSC and 12 ml of pyridine was stirred while heating at 50° C. for 15 minutes. Then, 1.15 g of 2-amino-4-(trifluoromethyl)phenol was added to the reaction mixture. The reaction mixture was stirred while heating at 80° C. for two hours. The reaction mixture was returned to room temperature, and concentrated under reduced pressure. Water was added to the residue, followed by extraction with ethyl acetate. The organic layer was washed with a saturated sodium chloride solution, dried over anhydrous sodium sulfate, and then concentrated under reduced pressure to give 1.81 g of N-[2-hydroxy-5-(trifluoromethyl)phenyl]-3iodo isonicotinamide.

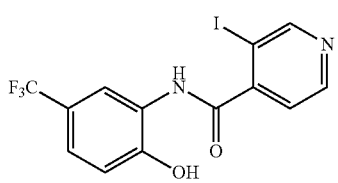

$^1$H-NMR (DMSO-$d_6$) δ: 10.85 (br s, 1H), 10.09 (br s, 1H), 8.97 (s, 1H), 8.64-8.62 (m, 1H), 8.29-8.27 (m, 1H), 7.54-7.51 (m 1H), 7.42-7.38 (m, 1H), 7.07 (d, J=8.5 Hz, 1H)

Reference Production Example 22

To a mixture of 3.69 g of nicotinic acid and 30 ml of toluene, 3.64 g of diisopropylethylamine, then 8.67 g of diphenylphosphoryl azide was added. The reaction mixture was stirred at room temperature for 30 minutes. To the reaction mixture, 4 ml of tert-butyl alcohol was added. The reaction mixture was stirred while heating at 80° C. for six hours. The reaction mixture was cooled to room temperature, then the reaction mixture was diluted with ethyl acetate, washed with water and then with a saturated sodium chloride solution, dried over anhydrous sodium sulfate, and concentrated under reduced pressure. The residue was washed with a mixture solvent of ethyl acetate and hexane to give 4.07 g of 3-(tert-butoxycarbonyl amino)pyridine.

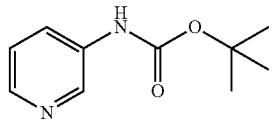

$^1$H-NMR (CDCl$_3$) δ: 8.46 (d, J=2.7 Hz, 1H), 8.28 (dd, J=4.9, 1.2 Hz, 1H), 8.03-7.96 (m, 1H), 7.25-7.21 (m, 1H), 7.04 (br s, 1H), 1.53 (s, 9H)

While a mixture of 1.16 g of 3-(tert-butoxycarbonyl amino)pyridine and 25 ml of tetrahydrofuran was cooled in a dry ice-acetone bath, 8.5 ml of 1.65 M hexane solution of n-butyllithium was added so that the temperature of the reaction mixture did not exceed −60° C. The reaction mixture was stirred for 15 minutes. Cooling was stopped. Then, the reaction mixture was stirred until the temperature became 0° C. The reaction mixture was cooled in a dry ice-acetone bath again. After injection of carbon dioxide, cooling was stopped, and the reaction mixture was stirred at room temperature for two hours. After water was added, most of tetrahydrofuran and hexane was removed by concentration under reduced pressure. The residue was ice-cooled and 3N hydrochloric acid was added so as to adjust pH to about 3. Extraction with a mixture solvent (4:1) of ethyl acetate to tetrahydrofuran was carried out several times. The combined organic layers were washed with a saturated sodium chloride solution, dried over anhydrous sodium sulfate, and concentrated under reduced pressure to give 0.53 g of 3-(tent-butoxycarbonyl amino) isonicotinic acid.

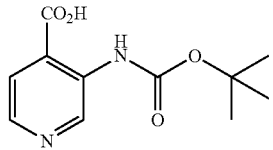

$^1$H-NMR (DMSO-$d_6$) δ: 10.07 (s, 1H), 9.37 (s, 1H), 8.35 (d, J=5.1 Hz, 1H), 7.76 (d, J=5.1 Hz, 1H), 1.49 (s, 9H)

To a mixture of 1.15 g of WSC and 8 ml of pyridine, 1.43 g of 3-tert-butoxycarbonylamino isonicotinic acid was added and stirred at room temperature for 15 minutes. To the reaction mixture, 1.06 g of 2-amino-4-(trifluoromethyl)phenol was added and stirred while heating at 60° C. for two hours. Thereafter, the mixture reaction was cooled to room temperature, and then concentrated under reduced pressure. Water was added to the residue, followed by extraction with ethyl acetate twice. The combined organic layers were washed with a saturated sodium chloride solution, dried over anhydrous sodium sulfate, and then concentrated under reduced pressure to give 1.79 g of 3-tert-butoxycarbonylamino-N-[2-hydroxy-5-(trifluoromethyl)phenyl]isonicotinamide.

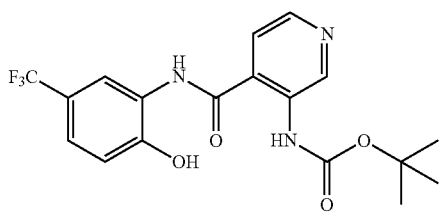

Reference Production Example 23

To a mixture of 5.0 g of 60% sodium hydride (in oil) and 70 ml of DMF, a mixture of 4-iodophenol and 25 ml of DMF was added dropwise while ice-cooling, and stirred for one hour. The temperature was increased to room temperature, a mixture of 12.9 g of chloromethyl ethyl ether and 10 ml of DMF was added dropwise, and stirred for further one hour. The reaction mixture was poured into ice water, and extracted with ethyl acetate three times. The combined organic layers was washed with water and a saturated sodium chloride solution, dried over anhydrous magnesium sulfate, and concentrated under reduced pressure to give 32 g of a crude product of 1-ethoxymethoxy-4-iodobenzene. The crude product was used for the next reaction without purification.

A mixture of 7.5 g of crude product of 1-ethoxymethoxy-4-iodobenzene, 10.0 g of sodium pentafluoropropionate salt, 10.27 g of copper (I) iodide, 120 ml of DMF and 45 ml of toluene was stirred while heating at 140 to 150° C. for one hour to remove about 40 ml of toluene. The reaction mixture was heated to reflux at 160 to 170° C. for further five hours, and then cooled to room temperature and poured into ice water. To the reaction mixture, 200 ml of diethyl ether was added. The reaction mixture was filtered through Celite™. The filtrate was extracted with diethyl ether. The combined organic layers were washed with water and a saturated sodium chloride solution, dried over anhydrous magnesium sulfate, and concentrated under reduced pressure to give 5.45 g of 1-ethoxymethoxy-4-pentafluoroethyl benzene.

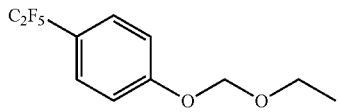

$^1$H-NMR (CDCl$_3$) δ: 7.51 (d, J=8.9 Hz, 2H), 7.13 (d, J=8.9 Hz, 2H), 5.27 (s, 2H), 3.73 (q, J=7.0 Hz, 2H), 1.23 (t, J=7.0, 3H)

7.39 g of 1-ethoxymethoxy-4-pentafluoroethyl benzene, 30 ml of acetone and 30 ml of 6 M hydrochloric acid were stirred while heating at 50° C. for 2.5 hours. The reaction mixture was cooled to room temperature, and then poured into water, followed by extraction with ethyl acetate. The combined organic layers were washed with water and a saturated sodium chloride solution, dried over anhydrous magnesium sulfate, and concentrated under reduced pressure. The residue was subjected to silica gel column chromatography to give 4-(pentafluoroethyl)phenol.

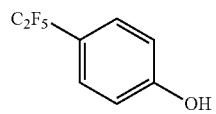

$^1$H-NMR (CDCl$_3$) δ: 7.47 (d, 8.5 Hz, 2H), 6.93 (d, 8.5 Hz, 2H), 5.74 (br s, 1H)

To a mixture of 1.70 g of 4-(pentafluoroethyl)phenol, 6 ml of acetic acid and 2.0 ml of concentrated sulfuric acid, a mixture of 0.80 g of 69% nitric acid and 1 ml of acetic acid was added dropwise while ice-cooling, and stirred at room temperature for three hours. The reaction mixture was poured into ice water, followed by extraction with ethyl acetate three times. The combined organic layers were washed with water and a saturated sodium chloride solution, dried over sodium sulfate, and concentrated under reduced pressure. The residue was subjected to silica gel column chromatography to give 1.40 g of 4-(pentafluoroethyl)-2-nrophenol.

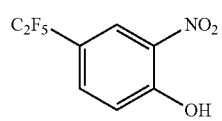

$^1$H-NMR (CDCl$_3$) δ: 10.02 (s, 1H), 8.40 (d, J=2.0 Hz, 1H), 7.79 (dd, J=9.0, 2.0 Hz, 1H), 7.32 (d, J=9.0 Hz, 1H)

A mixture of 1.38 g of 4-(pentafluoroethyl)-2-nitrophenol, 15 ml of ethyl acetate and 0.15 g of 5% palladium on carbon was stirred under about one atmosphere of hydrogen at room temperature for four hours. The reaction mixture was filtered through Celite™. The filtrate was concentrated under reduced pressure. The residue was washed with hexane to give 1.02 g of 2-amino-4-(pentafluoroethyl)phenol.

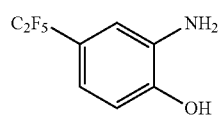

$^1$H-NMR (CDCl$_3$) δ: 6.94 (s, 1H), 6.91 (d, J=8.3 Hz, 1H), 6.78 (d, J=8.3 Hz, 1H), 5.34 (br s, 1H), 3.82 (br s, 2H)

To a mixture of 0.44 g of WSC and 4 ml of pyridine, 0.28 g of isonicotinic acid was added, and the reaction mixture was stirred at room temperature for 15 minutes. To the reaction mixture, 0.45 g of 2-amino-4-(pentafluoroethyl)phenol that had been obtained in the above-mentioned reaction was added and stirred while heating at 60° C. for two hours. The reaction mixture was cooled to room temperature, and the concentrated under reduced pressure. Water was added to the residue, followed by extraction with ethyl acetate twice. The combined organic layers were washed with water and a saturated sodium chloride solution, dried over anhydrous sodium sulfate, and then concentrated under reduced pressure. The residue was subjected to silica gel column chromatography to give 0.50 g of N-[2-hydroxy-5-(pentafluoroethyl)phenyl] isonicotinamide.

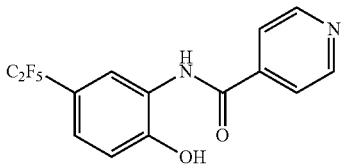

¹H-NMR (DMSO-d₆) δ: 10.89 (br s, 1H), 9.93 (br s, 1H), 8.79 (d, J=5.4 Hz, 2H), 8.03 (d, J=2.0 Hz, 1H), 7.88 (d, J=5.6 Hz, 2H), 7.39 (dd, J=8.5, 2.0 Hz, 1H), 7.14 (d, J=8.6 Hz, 1H)

Reference Production Example 24

To a mixture of 0.44 g of WSC and 4 ml of pyridine, 0.36 g of 3-chloroisonicotinic acid was added. The reaction mixture was stirred at room temperature for 15 minutes. To the reaction mixture, 0.45 g of 2-amino-4-(pentafluoroethyl)phenol was added and stirred while heating at 60° C. for two hours. The reaction mixture was cooled to room temperature, and then concentrated under reduced pressure. Water was added to the residue, followed by extraction with ethyl acetate twice. The combined organic layers were washed with water and a saturated sodium chloride solution, dried over anhydrous sodium sulfate, and concentrated under reduced pressure. The residue was subjected to silica gel column chromatography to give 0.25 g of 3-chloro-N-[2-hydroxy-5-(pentafluoroethyl)phenyl]isonicotinamide.

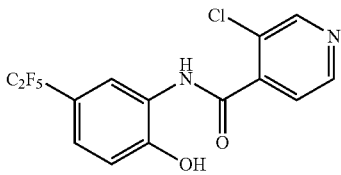

¹H-NMR (DMSO-d₆) δ: 10.99 (br s, 1H), 10.20 (br s, 1H), 8.75 (s, 1H), 8.64 (d, J=4.9 Hz, 1H), 8.31 (d, J=2.2 Hz, 1H), 7.64 (d, J=4.6 Hz, 1H), 7.36 (dd, J=8.6, 2.1 Hz, 1H), 7.11 (d, J=8.6 Hz, 1H)

Reference Production Example 25

To a mixture of 3.92 g of 4-(heptafluoroisopropyl)aniline, 20 ml of acetic acid, 3.0 g of concentrated sulfuric acid and 3 ml of water, an aqueous solution of 1.14 g of sodium nitrite was gradually added dropwise while ice-cooling, and stirred for 30 minutes while ice-cooling, and the stirred while heating at 80° C. for one hour. The reaction mixture was cooed to room temperature, and then the reaction mixture was poured into water, followed by extraction with ethyl acetate three times. The combined organic layers were washed with a saturated sodium chloride solution, dried over anhydrous sodium sulfate, and then concentrated under reduced pressure. The residue was subjected to silica gel column chromatography to give 3.60 g of mixture containing 4-(heptafluoroisopropyl)phenol.

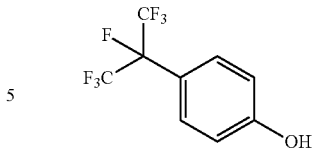

¹H-NMR (CDCl₃) δ: 7.48 (d, J=8.9 Hz, 2H), 6.96-6.92 (m, 2H), 5.64 (br s, 1H)

To a mixture of 3.60 g of mixture containing 4-(heptafluoroisopropyl)phenol, 8 ml of acetic acid, and 2.5 g of concentrated sulfuric acid, a mixture of 1.05 g of 69% nitric acid and 1 ml of acetic acid was added dropwise while ice-cooling, and then stirred at room temperature for two hours. The reaction mixture was poured into water, and extracted with ethyl acetate three times. The combined organic layers were washed with a saturated sodium chloride solution, dried over anhydrous sodium sulfate, and concentrated under reduced pressure. The residue was subjected to silica gel column chromatography to give 2.96 g of 4-(heptafluoroisopropyl)-2-nitrophenol.

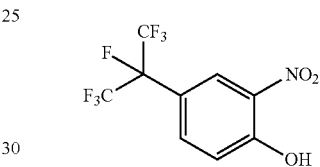

¹H-NMR (CDCl₃) δ: 10.76 (s, 1H), 8.42 (d, J=2.4 Hz, 1H), 7.79 (dd, J=9.0, 2.0 Hz, 1H), 7.34 (d, J=9.0 Hz, 1H)

A mixture of 2.95 g of 4-(heptafluoroisopropyl)-2-nitrophenol, 20 ml of ethyl acetate and 0.30 g of 5% palladium on carbon was stirred in a hydrogen atmosphere at room temperature for four hours. The reaction mixture was filtered through Celite™. The filtrate was concentrated under reduced pressure. The residue was subjected to silica gel column chromatography to give 2.08 g of 2-amino-4-(heptafluoroisopropyl)phenol.

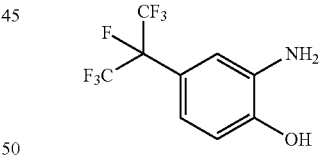

¹H-NMR (CDCl₃) δ: 6.96 (s, 1H), 6.89 (d, J=8.6 Hz, 1H), 6.78 (d, J=8.6 Hz, 1H), 5.38 (br s, 1H), 3.84 (br s, 2H)

To a mixture of 0.58 g of WSC and 5 ml of pyridine, 0.37 g of isonicotinic acid was added. The reaction mixture was stirred at room temperature for 25 minutes. To the reaction mixture, 0.75 g of 2-amino-4-(heptafluoroisopropyl)phenol was added and was stirred while heating at 60° C. for three hours. The mixture was cooled to room temperature, and then concentrated under reduced pressure. Then, water was added to the residue, followed by extraction with ethyl acetate twice. The combined organic layers were washed with water and a saturated sodium chloride solution, dried over anhydrous sodium sulfate, and concentrated under reduced pressure. The residue was subjected to silica gel column chromatography to give 0.79 g of N-[2-hydroxy-5-(heptafluoroisopropyl)phenyl]isonicotinamide.

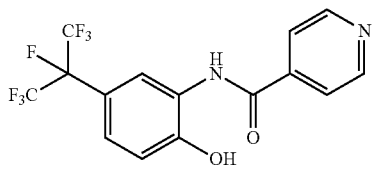

¹H-NMR (DMSO-d₆) δ: 10.83 (br s, 1H), 9.92 (br s, 1H), 8.80-8.78 (m, 2H), 8.06 (br s, 1H), 7.88-7.86 (m, 2H), 7.36 (dd, J=8.8, 2.0 Hz, 1H), 7.15 (d, J=8.8 Hz, 1H)

Reference Production Example 26

To a mixture of 0.58 g of WSC and 5 ml of pyridine 5m1, 0.48 g of 3-chloroisonicotinic acid was added. The reaction mixture was stirred at room temperature for 25 minutes. To the reaction mixture, 0.75 g of 2-amino-4-(heptafluoroisopropyl)phenol was added and was stirred while heating at 60° C. for three hours. The reaction mixture was cooled to room temperature, the 0.24 g of 3-chloroisonicotinic acid and 0.29 g of WSC was added and stirred while heating at 60° C. for 1.5 hours and then at 80° C. for 1.3 hours. The mixture reaction was cooled to room temperature, and then concentrated under reduced pressure. Then, water was added to the residue, followed by extraction with ethyl acetate twice. The combined organic layers were washed with a saturated sodium chloride solution, was dried over anhydrous sodium sulfate, and concentrated under reduced pressure. The residue was subjected to silica gel column chromatography to give 0.90 g of 3-chloro-N-[2-hydroxy-5-(heptafluoroisopropyl)phenyl] isonicotinamide.

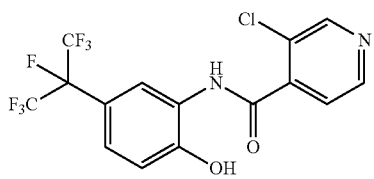

(DMSO-d₆) δ: 10.19 (br s, 1H), 8.75 (s, 1H), 8.63 (d, J=4.9 Hz, 1H), 8.36 (d, J=1.9 Hz, 1H), 7.65 (d, J=4.9 Hz, 1H), 7.32 (dd, J=8.8, 2.0 Hz, 1H), 7.12 (d, J=8.8 Hz, 1H)

Reference Production Example 27

To a mixture of 3.78 g of 2-chloro-4-(trifluoromethyl)phenol, 12 ml of acetic acid and 3 ml of concentrated sulfuric acid, a mixture of 21.5 g of 69% nitric acid and 2 ml of acetic acid was added while ice-cooling. The reaction mixture was stirred while heating at room temperature for 30 minutes and then at 60° C. for two hours. After the reaction mixture was cooled to room temperature, then the reaction mixture was poured into water, and extracted with ethyl acetate three times. The combined organic layers were washed with saturated sodium chloride solution, dried over anhydrous sodium sulfate, and concentrated under reduced pressure. The residue was subjected to silica gel column chromatography to give 5.01 g of a mixture containing 2-chloro-6-nitro-4-(trifluoromethyl)phenol.

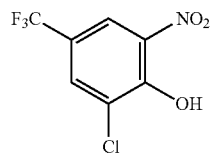

¹H-NMR (CDCl₃) δ: 11.26 (br s, 1H), 8.36 (m, 1H), 7.95 (d, J=2.2 Hz, 1H)

A mixture of 5.01 g of a mixture containing 2-chloro-4-(trifluoromethyl)-6-nitrophenol, 15 ml of ethyl acetate and 1.0 g of 5% palladium on carbon was stirred under about one atmosphere of hydrogen at room temperature for 15 hours. The mixture was filtered through Celite™. The filtrate was concentrated under reduced pressure. The residue was subjected to silica gel column chromatography to give 2.78 g of 2-amino-6-chloro-4-(trifluoromethyl)phenol.

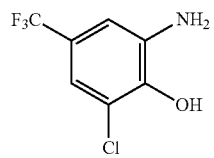

¹H-NMR (CDCl₃) δ: 7.00 (m, 1H), 6.84 (d, J=2.2 Hz, 1H), 5.80 (br s, 1H), 4.05 (br s, 2H)

To a mixture of 0.58 g of WSC and 5 ml pyridine, 0.37 g of isonicotinic acid was added. The reaction mixture was stirred at room temperature for 15 minutes. To the reaction mixture, 0.63 g of 2-amino-6-chloro-4-(trifluoromethyl)phenol that had been obtained in the above-mentioned reaction was added. The reaction mixture was stirred while heating at 60° C. for three hours. The reaction mixture was cooled to room temperature, and then concentrated under reduced pressure. Water was added to the residue, followed by extraction with ethyl acetate twice. The combined organic layers were washed with a saturated sodium chloride solution, then dried over anhydrous sodium sulfate, and concentrated under reduced pressure. The residue was washed with a mixture solvent of tert-butyl methyl ether and hexane to give 0.42 g of N-[3-chloro-5-(trifluoromethyl)-2-hydroxyphenyl]isonicotinamide.

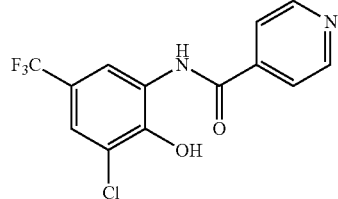

¹H-NMR (DMSO-d₆) δ: 10.27 (br s, 1H), 8.81-8.79 (m, 2H), 7.90-7.88 (m, 2H), 7.86 (d, J=2.0 Hz, 1H), 7.68-7.67 (m, 1H)

Reference Production Example 28

To a mixture of 4.0 g of 4-trifluoromethoxy phenol and 25 ml of acetic acid, a mixture of 2.02 g of 70% nitric acid and 10 ml of acetic acid was added dropwise with the temperature kept at 10-15° C. The reaction mixture was stirred for five hours. The reaction mixture was poured into ice water and extracted with ethyl acetate. The combined organic layers were washed with water, a saturated aqueous solution of sodium hydrogencarbonate and a saturated sodium chloride solution, dried over sodium sulfate, and then concentrated under reduced pressure to give 4.53 g of 4-trifluoromethoxy-2-nitrophenol.

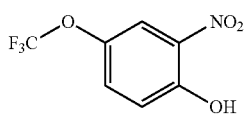

$^1$H-NMR (CDCl$_3$) δ: 10.50 (s, 1H), 8.02-7.99 (m, 1H), 7.50-7.45 (m, 1H), 7.22 (d, J=9.1 Hz, 1H)

A mixture of 4.53 g of 4-trifluoromethoxy-2-nitrophenol, 35 ml of ethyl acetate and 1.0 g of 5% palladium on carbon was stirred under about one atmosphere of hydrogen at room temperature for 1.7 hours. The mixture was filtered through Celite™. The filtrate was concentrated under reduced pressure to give 3.92 g of 2-amino-4-trifluoromethoxy phenol.

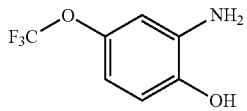

To a mixture of 2.5 g of 2-amino-4-trifluoromethoxy phenol, 2.62 g of triethylamine and 15 ml of DMF, 2.31 g of 4-isonicotinic acid chloride hydrochloride was added while ice-cooling. The reaction mixture was stirred for 3.3 hours. The reaction mixture was poured into water and precipitated crystals were filtered and dried under reduced pressure to give 2.19 g of N-[5-(trifluoromethoxy)-2-hydroxyphenyl]isonicotinamide.

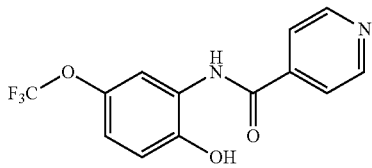

$^1$H-NMR (DMSO-d$_6$) δ: 8.78 (dd, J=4.4, 1.7 Hz, 2H), 7.86 (dd, J=4.4, 1.6 Hz, 2H), 7.80-7.77 (m, 1H), 7.10-7.05 (m, 1H), 6.99 (d, J=8.7 Hz, 1H)

Reference Production Example 29

A mixture of 0.41 g of 2-amino-4-tert-butylphenol, 0.35 g of 3-chloro-4-pyridinecarboxyaldehyde and 2.5 ml of ethanol was heated to reflux for three hours. The reaction mixture was concentrated. The residue was subjected to silica gel column chromatography to give 0.50 g of 2-(3-chloropyridin-4-yl)methylideneamino-4-tert-butylphenol.

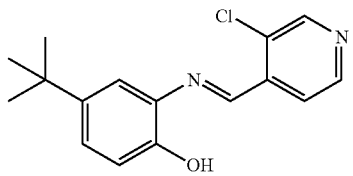

$^1$H-NMR (CDCl$_3$) δ: 9.07 (s, 1H), 8.71 (s, 1H), 8.60 (d, J=5.1 Hz, 1H), 8.01 (d, J=5.1 Hz, 1H), 7.36-7.33 (m, 2H), 7.02 (s, 1H), 7.00-6.97 (m, 1H), 1.35 (s, 9H)

Reference Production Example 30

To a mixture of 4.8 g of 4-(trifluoromethylthio)phenol and 20 ml of acetic acid, a mixture of 2.5 g of 70% nitric acid and 1 ml of acetic acid and then 1.5 ml of concentrated sulfuric acid were added dropwise with the internal temperature kept at 10-15° C. The reaction mixture was stirred for three hours. The reaction mixture was poured into ice water and extracted with ethyl acetate. The combined organic layers were washed with water, a saturated aqueous solution of sodium hydrogencarbonate and a saturated sodium chloride solution, dried over magnesium sulfate, and then concentrated under reduced pressure to give 5.94 g of 2-nitro-4-(trifluoromethylthio)phenol.

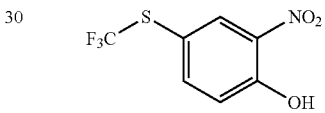

$^1$H-NMR (CDCl$_3$) δ: 10.78 (br s, 1H), 8.44 (s, 1H), 7.83 (d, J=8.8, 1H), 7.24 (d, J=8.8 Hz, 1H)

A mixture of 5.49 g of 2-nitro-4-(trifluoromethylthio)phenol and 10 ml of ethyl acetate was added dropwise to a mixture, which was heated to 80° C., of 6.4 g of electrolytic iron, 10 ml of acetic acid and 20 ml of water. The reaction mixture was stirred for 30 minutes. The mixture was cooled to room temperature, and then water was added, followed by extraction with ethyl acetate twice. The combined organic layers were washed with water, a saturated aqueous solution of sodium hydrogencarbonate and a saturated sodium chloride solution, dried over magnesium sulfate, and then concentrated under reduced pressure. The residue was subjected to silica gel column chromatography to give 2.0 g of 2-amino-4-(trifluoromethylthio)phenol.

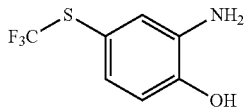

$^1$H-NMR (CDCl$_3$) δ: 7.04 (d, J=2.0 Hz, 1H), 6.97 (dd, J=8.0, 2.0 Hz, 1H), 6.73 (d, J=8.0 Hz, 1H), 5.16(br s, 1H), 3.74(br s, 2H)

A mixture of 0.70 g of 2-amino-4-(trifluoromethylthio)phenol, 0.83 g of WSC, 0.41 g of isonicotinic acid and 7 ml of pyridine was stirred while heating at 80° C. for three hours. The reaction mixture was cooled to room temperature, and then water was poured into the reaction mixture, followed by extraction with ethyl acetate three times. The combined organic layers were washed with water and a saturated sodium chloride solution, dried over anhydrous magnesium sulfate, and then concentrated under reduced pressure. The residue was subjected to silica gel column chromatography to give 0.42 g of N-[2-hydroxy-5-(trifluoromethylthio)phenyl]isonicotinamide.

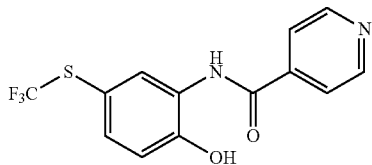

¹H-NMR (DMSO-d₆) δ: 9.89 (br s, 1H), 8.78 (dd, J=4.3, 1.7 Hz, 2H), 8.05 (d, J=2.2 Hz, 1H), 7.87 (dd, J=4.3, 1.7 Hz, 2H), 7.42 (dd, J=8.5, 2.2 Hz, 1H), 7.05 (d, J=8.5 Hz, 1H)

Reference Production Example 31

A mixture of 0.60 g of 2-amino-4-(trifluoromethylthio)phenol, 0.45 g of 3-chloroisonicotinic acid, 0.71 g of WSC and 6 ml of pyridine was stirred while heating at 80° C. for three hours. The reaction mixture was cooled to room temperature, and then water was added to the reaction mixture, followed by extraction with ethyl acetate three times. The combined organic layers were washed with water and a saturated sodium chloride solution, dried over anhydrous magnesium sulfate, and then concentrated under reduced pressure. The residue was subjected to silica gel column chromatography to give 0.63 g of 3-chloro-N-[2-hydroxy-5-(trifluoromethylthio)phenyl]isonicotinamide.

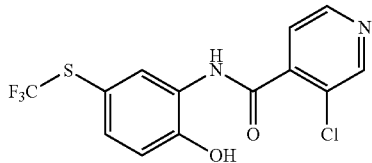

¹H-NMR (DMSO-d₆) δ: 10.89 (br s, 1H), 10.14 (br s, 1H), 8.74 (s, 1H), 8.63 (d, J=4.8 Hz, 1H), 8.31 (d, J=2.2 Hz, 1H), 7.63 (d, J=4.8 Hz, 1H), 7.39 (dd, J=8.5, 2.2 Hz, 1H), 7.03 (d, J=8.5 Hz, 1H)

Reference Production Example 32

To a mixture of 5.0 g of 4-chloro-3-trifluoromethylphenol and 20 ml of acetic acid, 1.5 ml of concentrated sulfuric acid and then 2.6 g of 69% nitric acid were added dropwise while ice-cooling. To the reaction mixture, 3 ml of concentrated sulfuric acid was added dropwise at room temperature, and stirred for three hours. The reaction mixture was poured into ice water, and extracted with ethyl acetate. The combined organic layers were washed with water, a saturated aqueous solution of sodium hydrogencarbonate and a saturated sodium chloride solution, dried over magnesium sulfate, and then concentrated under reduced pressure. The residue was subjected to silica gel column chromatography to give 2.3 g of 4-chloro-2-nitro-5-trifluoromethylphenol, 1.57 g of 4-chloro-2-nitro-3-trifluoromethylphenol.

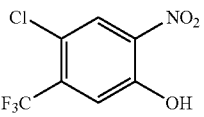

¹H-NMR (CDCl₃) δ: 10.43 (s, 1H), 8.27 (s, 1H), 7.57 (s, 1H)

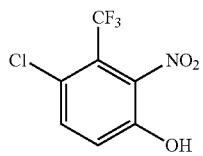

¹H-NMR (CDCl₃) δ: 7.53 (d, J=9.0 Hz, 1H), 7.24 (d, J=9.0 Hz, 1H)

A mixture of 2.3 g of 4-chloro-2-nitro 5-trifluoromethylphenol and 10 ml of ethyl acetate was added dropwise to a mixture, which was heated to 80° C., of 2.6 g of electrolytic iron, 10 ml of acetic acid and 20 ml of water, and then the reaction mixture was stirred for one hour. The mixture was cooled to room temperature, and then water was added, followed by extraction with ethyl acetate. The combined organic layers were washed with water, a saturated aqueous solution of sodium hydrogencarbonate and a saturated sodium chloride solution, dried over magnesium sulfate, and then concentrated under reduced pressure. The residue was subjected to silica gel column chromatography to give 1.7 g of 2-amino-4-chloro-5-trifluoromethylphenol.

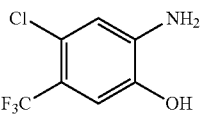

¹H-NMR (CDCl₃) δ: 6.99 (s, 1H), 6.77 (s, 1H), 5.01 (br s, 1H), 4.09 (br s, 2H)

A mixture of 0.70 g of 2-amino-4-chloro-5-trifluoromethylphenol, 0.79 g of WSC, 0.39 g of isonicotinic acid and 6 ml of pyridine was stirred while heating at 80° C. for three hours. The reaction mixture was cooled to room temperature, and then water was added, followed by extraction with ethyl acetate three times. The combined organic layers were washed with water and a saturated sodium chloride solution, dried over anhydrous magnesium sulfate, and then concentrated under reduced pressure. The residue was subjected to silica gel column chromatography to give 0.54 g of N-[5-chloro-2-hydroxy-4-trifluoromethylphenyl]isonicotinamide.

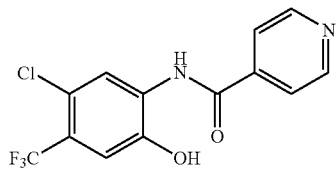

¹H-NMR (DMSO-d₆) δ: 10.08 (br s, 1H), 8.80 (dd, J=4.3, 1.7 Hz, 2H), 8.13 (s, 1H), 7.86 (dd, J=4.3, 1.7 Hz, 2H), 7.32 (s, 1H)

Reference Production Example 33

A mixture of 0.60 g of 2-amino-4-chloro-5-trifluoromethylphenol, 0.43 g of 3-chloroisonicotinic acid, 0.67 g of WSC and 5 ml of pyridine was stirred while heating at 80° C. for three hours. The reaction mixture was cooled to room temperature, and then water was added, followed by extraction with ethyl acetate three times. The combined organic layers were washed with water and a saturated sodium chloride solution, dried anhydrous magnesium sulfate, and then concentrated under reduced pressure. The residue was subjected to silica gel column chromatography to give 0.67 g of 3-chloro-N-[5-chloro-2-hydroxy-4-trifluoromethylphenyl]isonicotinamide.

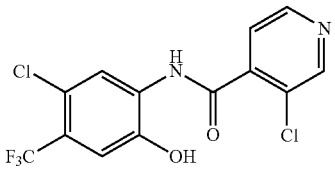

$^1$H-NMR (DMSO-d$_6$) δ: 8.75 (s, 1H), 8.64 (d, J=4.8 Hz, 1H), 8.36 (s, 1H), 7.62 (d, J=4.8 Hz, 1H), 7.28 (s, 1H)

Reference Production Example 34

A mixture of 1.57 g of 4-chloro-2-nitro-3-trifluoromethylphenol and 5 ml of ethyl acetate was added dropwise to a mixture, which was heated to 80° C., of 1.8 g of electrolytic iron, 7 ml of acetic acid and 7 ml of water, which was stirred for 30 minutes. The mixture was cooled to room temperature, and then water was added, followed by extraction with ethyl acetate. The combined organic layers were washed with water, a saturated aqueous solution of sodium hydrogencarbonate and a saturated sodium chloride solution, dried over magnesium sulfate, and then concentrated under reduced pressure. The residue was subjected to silica gel column chromatography to give 1.1 g of 2-amino-4-chloro-3-trifluoromethylphenol.

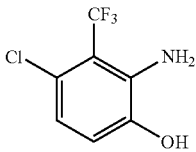

$^1$H-NMR (CDCl$_3$) δ: 6.72 (d, J=8.3 Hz, 1H), 6.68 (d, J=8.3 Hz, 1H), 5.48 (br s, 1H), 4.67 (br s, 2H)

A mixture of 0.75 g of 2-amino-4-chloro-3-trifluoromethylphenol, 0.84 g of WSC, 0.42 g of isonicotinic acid and 5 ml of pyridine was stirred while heating at 80° C. for three hours. To the reaction mixture, 0.1 g of isonicotinic acid was added, and the reaction mixture was stirred while heating for further three hours. The reaction mixture was cooled to room temperature, and then water was added, followed by extraction with ethyl acetate three times. The combined organic layers were washed with water and a saturated sodium chloride solution, dried over anhydrous magnesium sulfate, and then concentrated under reduced pressure. The residue was subjected to silica gel column chromatography to give 0.54 g of N-[3-chloro-6-hydroxy-2-trifluoromethylphenyl]isonicotinamide.

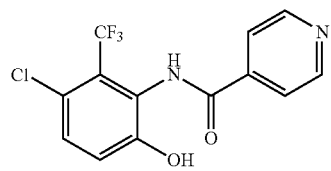

$^1$H-NMR (DMSO-d$_6$) δ: 10.47 (br s, 1H), 10.20 (br s, 1H), 8.80 (dd, J=4.6, 1.4 Hz, 2H), 7.85 (dd, J=4.6, 1.4 Hz, 2H), 7.51 (d, J=8.9 Hz, 1H), 7.22 (d, J=8.9 Hz, 1H)

Reference Production Example 35

A mixture of 10 g of 2,4-dichloro-5-nitrobenzotrifluoride, 4.15 g of potassium acetate and 60 ml of DMF was stirred while heating at 60° C. for one hour and at 80° C. for three hours. To the reaction mixture, 4.15 g of potassium acetate was added. The reaction mixture was stirred while heating at 80° C. for further one hour. The reaction mixture was cooled to room temperature, and 1 M hydrochloric acid was added thereto, followed by extraction with ethyl acetate. The combined organic layers were washed with water and a saturated sodium chloride solution, dried over magnesium sulfate, and then concentrated under reduced pressure. The residue was subjected to silica gel column chromatography to give 7.55 g of 5-chloro-2-nitro-4-trifluoromethylphenol.

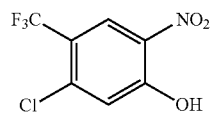

$^1$H-NMR (CDCl$_3$) δ: 10.81 (s, 1H), 8.49 (s, 1H), 7.37 (s, 1H)

A mixture of 7.55 g of 5-chloro-2-nitro-4-trifluoromethylphenol and 10 ml of ethyl acetate was added dropwise to a mixture, which was heated to 80° C., of 8.7 g of electrolytic iron, 30 ml of acetic acid and 50 ml of water, and then the reaction mixture was stirred at the same temperature for 30 minutes. The mixture was cooled to room temperature, and then water was added, followed by extraction with ethyl acetate. The combined organic layers were washed with water, a saturated aqueous solution of sodium hydrogencarbonate and a saturated sodium chloride solution, dried over magnesium sulfate, and then concentrated under reduced pressure. The residue was subjected to silica gel column chromatography to give 5.4 g of 2-amino-5-chloro-4-trifluoromethylphenol.

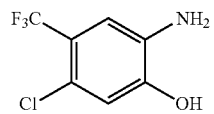

$^1$H-NMR (CDCl$_3$) δ: 7.03 (s, 1H), 6.84 (s, 1H), 5.93 (br s, 1H), 3.81 (br s, 2H)

A mixture of 1.2 g of 2-amino-5-chloro-4-trifluoromethylphenol, 1.35 g of WSC, 0.67 g of isonicotinic acid and 10 ml of pyridine was stirred while heating at 80° C. for three hours. The reaction mixture was cooled to room temperature, and then water was added, followed by extraction with ethyl acetate three times. The combined organic layers were washed with water and a saturated sodium chloride solution, dried over anhydrous magnesium sulfate, and then concentrated under reduced pressure. The residue was subjected to silica gel column chromatography to give 1.01 g of N-[4-chloro-2-hydroxy-5-trifluoromethylphenyl]isonicotinamide.

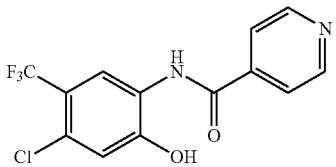

¹H-NMR (DMSO-d₆) δ: 10.03 (br s, 1H), 8.79 (dd, J=4.3, 1.7 Hz, 2H), 8.14 (s, 1H), 7.86 (dd, J=4.3, 1.7 Hz, 2H), 7.16 (s, 1H)

Reference Production Example 36

A mixture of 0.50 g of 2-amino-5-chloro-4-trifluoromethylphenol, 0.36 g of 3-chloroisonicotinic acid, 0.56 g of WSC and 5 ml of pyridine was stirred while heating at 80° C. for three hours. The reaction mixture was cooled to room temperature, and then water was added, followed by extraction with ethyl acetate three times. The combined organic layers were washed with water and a saturated sodium chloride solution, dried over anhydrous magnesium sulfate, and then concentrated under reduced pressure. The residue was subjected to silica gel column chromatography to give 0.46 g of 3-chloro-N-[4-chloro-2-hydroxy-5-trifluoromethylphenyl]isonicotinamide.

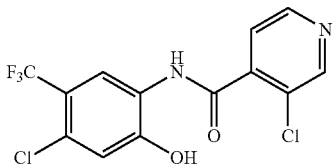

¹H-NMR (DMSO-d₆) δ: 10.32 (br s, 1H), 8.75 (s, 1H), 8.64 (d, J=4.8 Hz, 1H), 8.43 (s, 1H), 7.63 (d, J=4.8 Hz, 1H), 7.13 (s, 1H)

Reference Production Example 37

A mixture of 0.68 g of 6-amino-1,1,3,3-tetrafluoro-5-hydroxy-1,3-dihydroisobenzofuran, 0.48 g of 3-chloroisonicotinic acid, 0.76 g of WSC and 7 ml of pyridine was stirred while heating at 80° C. for three hours. The reaction mixture was cooled to room temperature, and then water was added, followed by extraction with ethyl acetate three times. The combined organic layers were washed with water and a saturated sodium chloride solution, then dried over anhydrous magnesium sulfate, and then concentrated under reduced pressure. The residue was subjected to silica gel column chromatography to give 0.68 g of 3-chloro-N-(1,1,3,3-tetrafluoro-6-hydroxy-1,3-dihydroisobenzofuran-5-yl)isonicotinamide.

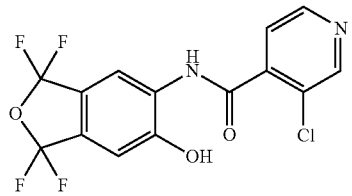

¹H-NMR (DMSO-d₆) δ: 10.47 (br s, 1H), 8.76 (s, 1H), 8.65 (d, J=4.6 Hz, 1H), 8.55 (s, 1H), 7.64 (d, J=4.8 Hz, 1H), 7.27 (s, 1H)

Reference Production Example 38

A mixture of 1.5 g of 6-amino-1,1,3,3-tetrafluoro-5-hydroxy-1,3-dihydroisobenzofuran, 0.95 g of 3-fluoroisonicotinic acid, 1.68 g of WSC and 13 ml of pyridine was stirred while heating at 80° C. for two hours. The reaction mixture was cooled to room temperature, and then water was added, followed by extraction with ethyl acetate three times. The combined organic layers were washed with water and a saturated sodium chloride solution, dried over anhydrous magnesium sulfate, and then concentrated under reduced pressure. The residue was subjected to silica gel column chromatography to give 1.46 g of 3-fluoro-N-(1,1,3,3-tetrafluoro-6-hydroxy-1,3-dihydroisobenzofuran-5-yl)isonicotinamide.

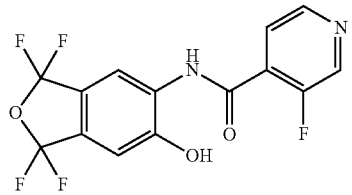

¹H-NMR (DMSO-d₆) δ: 10.21 (br s, 1H), 8.79-8.77 (m, 1H), 8.63-8.58 (m, 2H), 7.81-7.76 (m, 1H), 7.30 (s, 1H)

Reference Production Example 39

A mixture of 2.0 g of 2-amino-5-chloro-4-trifluoromethylphenol, 1.33 g of 3-fluoroisonicotinic acid, 2.36 g of WSC and 15 ml of pyridine was stirred while heating at 80° C. for 3.5 hours. The reaction mixture was cooled to room temperature, and then water was added, followed by extraction with ethyl acetate three times. The combined organic layers were washed with water and a saturated sodium chloride solution, then dried over anhydrous magnesium sulfate, and then concentrated under reduced pressure. The residue was subjected to silica gel column chromatography to give 2.08 g of 3-fluoro-N-[4-chloro-2-hydroxy-5-trifluoromethylphenyl]isonicotinamide.

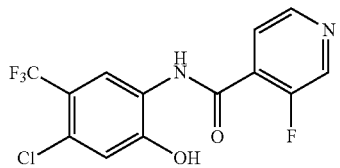

¹H-NMR (DMSO-d₆) δ: 11.57 (br s, 1H), 10.08 (br s, 1H), 8.77-8.75 (m, 1H), 8.61-8.58 (m, 1H), 8.48 (s, 1H), 7.78-7.73 (m, 1H), 7.15 (s, 1H)

Reference Production Example 40

A mixture of 0.62 g of 3-ethyl isonicotinic acid 4 ml of thionyl chloride was heated to reflux for 2.5 hours. The reaction mixture was cooled to room temperature, the reaction mixture was concentrated under reduced pressure to give 3-ethyl isonicotinic acid chloride. A mixture of the resultant 3-ethyl isonicotinic acid chloride and 3 ml of DMF was added dropwise to a mixture of 0.87 g of 2-amino-5-chloro-4-trifluoromethylphenol, 0.83 g of triethylamine and 3 ml of DMF while ice-cooling. The reaction mixture was stirred at room temperature for two hours, and then water was added to the reaction mixture, followed by extraction with ethyl acetate twice. The combined organic layers were washed with water and a saturated sodium chloride solution, dried over anhydrous magnesium sulfate, and then concentrated under reduced pressure. The residue was subjected to silica gel column chromatography to give 0.23 g of N-[4-chloro-2-hydroxy-5-(trifluoromethyl)phenyl]-3-ethyl isonicotinamide.

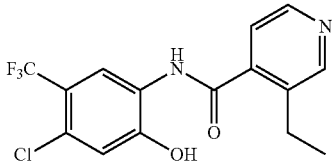

¹H-NMR (DMSO-d₆) δ: 9.98 (br s, 1H), 8.58-8.56 (m, 1H), 8.53 (d, J=4.8 Hz, 1H), 8.25 (s, 1H), 7.45 (d, J=4.9 Hz, 1H), 7.11 (s, 1H), 2.76 (q, J=7.6 Hz, 2H), 1.19 (t, J=7.6 Hz, 3H)

Reference Production Example 41

A mixture of 0.69 g of 3-chloroisonicotinic acid, 5 ml of thionyl chloride and 30 mg of DMF was heated to reflux for 3.5 hours. The reaction mixture was cooled to room temperature, and then the reaction mixture was concentrated under reduced pressure to give 3-chloroisonicotinic acid chloride. A mixture of the resultant 3-chloroisonicotinic acid chloride and 4 ml of DMF was added dropwise to a mixture of 0.85 g of 2-amino-5-fluoro-4-trifluoromethylphenol, 0.88 g of triethylamine and 4 ml of DMF while ice-cooling. Thereafter, the reaction mixture was stirred at room temperature for one hour and at 50° C. for one hour. The reaction mixture was cooled to room temperature, and then water was added, followed by extraction with ethyl acetate twice. The combined organic layers wee washed with water and a saturated sodium chloride solution, then dried over anhydrous magnesium sulfate, and then concentrated under reduced pressure. The resultant solid was washed with diethyl ether to give 0.77 g of 3-chloro-N-[4-fluoro-2-hydroxy-5-(trifluoromethyl)phenyl]-isonicotinamide.

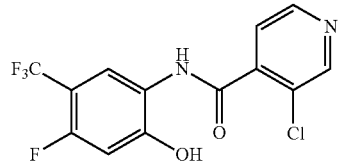

¹H-NMR (DMSO-d₆) δ: 10.20 (br s, 1H), 8.75 (s, 1H), 8.64 (d, J=4.8 Hz, 1H), 8.23 (d, J=8.5 Hz, 1H), 7.62 (d, J=4.8 Hz, 1H), 6.91-6.85 (m, 1H)

Reference Production Example 42

3-chloro-N-[2-fluoro-6-hydroxy-3-(trifluoromethyl)phenyl]-isonicotinamide was obtained according to the same manner as that of Reference Production Example 41 using 2-amino-3-fluoro-4-trifluoromethylphenol instead of 2-amino-5-fluoro-4-trifluoromethylphenol.

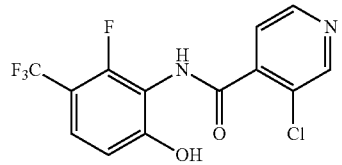

¹H-NMR (DMSO-d₆) δ: 11.15 (br s, 1H), 10.22 (br s, 1H), 8.79 (s, 1H), 8.67 (d, J=4.6 Hz, 1H), 7.62 (d, J=4.6 Hz, 1H), 7.58-7.52 (m, 1H), 6.92 (d, J=8.8 Hz, 1H)

Reference Production Example 43

A mixture of 0.17 g of 2-amino-3-chloro-4-trifluoromethylphenol, 0.99 g of isonicotinic acid, 0.19 g of WSC and 3 ml of pyridine was stirred while heating at 80° C. for two hours. The mixture was cooled to room temperature, and then water was poured, followed by extraction with ethyl acetate three times. The combined organic layers were washed with water and a saturated sodium chloride solution, dried over anhydrous magnesium sulfate, and concentrated under reduced pressure. The residue was subjected to silica gel column chromatography to give 0.15 g of N-[2-chloro-6-hydroxy-3-(trifluoromethyl)phenyl]isonicotinamide.

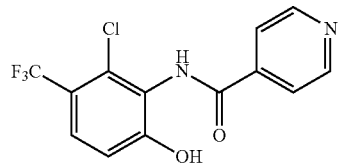

¹H-NMR (DMSO-d₆) δ: 10.98 (br s, 1H), 10.24 (br s, 1H), 8.82-8.79 (m, 2H), 7.94-7.85 (m, 2H), 7.67 (d, J=8.8 Hz, 1H), 7.06 (d, J=8.9 Hz, 1H)

Reference Production Example 44

3-ethyl-N-(1,1,3,3-tetrafluoro-6-hydroxy-1,3-dihydroisobenzofuran-5-yl)isonicotinamide was obtained according to the same manner as that of Reference Production Example 40 using 6-amino-1,1,3,3-tetrafluoro-5-hydroxy-1,3-dihydroisobenzofuran instead of 2-amino-5-chloro-4-trifluoromethylphenol.

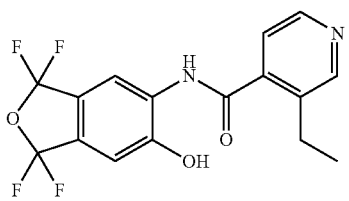

¹H-NMR (DMSO-d₆) δ: 10.10 (br s, 1H), 8.60-8.58 (m, 1H), 8.54 (d, J=4.9 Hz, 1H), 1H), 8.44 (s, 1H), 7.45 (d, J=4.9 Hz, 1H), 7.26 (s, 1H), 2.77 (q, J=7.6 Hz, 2H), 1.20 (t, J=7.6 Hz, 3H)

Reference Production Example 45

A mixture of 1.5 g of 3-fluoroisonicotinic acid, 5 ml of thionyl chloride and 50 mg of DMF was heated to reflux for two hours. The reaction mixture was cooled to room temperature, and then the reaction mixture was concentrated under reduced pressure to give 3-fluoroisonicotinic acid chloride. A mixture of the resultant 3-fluoroisonicotinic acid chloride and 5 ml of DMF was added dropwise to a mixture of 1.76 g of 2-amino-4-tert-butylphenol, 2.18 g of triethylamine and 10 ml of DMF while ice-cooling. The reaction mixture was stirred at room temperature for 1.5 hours and at 50° C. for 30 minutes. The reaction mixture was cooled to room temperature, and then water was added. Precipitated crystals were collected by filtration. The resultant crystals were dissolved in ethyl acetate, washed with water and a saturated sodium chloride solution, dried over anhydrous magnesium sulfate, concentrated under reduced pressure to give 2.41 g of N-(5-tert-butyl-2-hydroxyphenyl)-3-fluoroisonicotinamide.

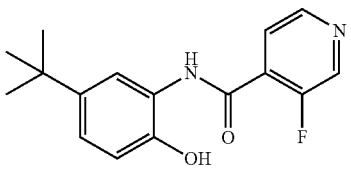

¹H-NMR (DMSO-d₆) δ: 9.73 (br s, 1H), 8.76-8.74 (m, 1H), 8.61-8.58 (m, 1H), 7.99 (d, J=2.4 Hz, 1H), 7.80-7.76 (m, 1H), 7.06 (dd, J=8.5, 2.4 Hz, 1H), 6.84 (d, J=8.5 Hz, 1H), 1.26 (s, 9H)

Reference Production Example 46

N-(5-tert-butyl-2-hydroxyphenyl)-3-ethyl isonicotinamide was obtained according to the same manner as that of Reference Production Example 40 using 2-amino-4-tert-butylphenol instead of 2-amino-5-chloro-4-trifluoromethylphenol.

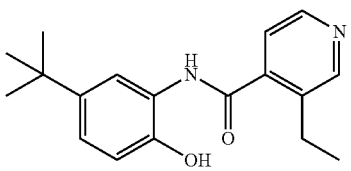

¹H-NMR (DMSO-d₆) δ: 9.66 (br s, 1H), 9.51 (br s, 1H), 8.58-8.56 (m, 1H), 8.52 (d, J=4.9 Hz, 1H), 7.65 (d, J=2.4 Hz, 1H), 7.45 (d, J=4.9 Hz, 1H), 7.07 (dd, J=8.5, 2.4 Hz, 1H), 6.83 (d, J=8.5 Hz, 1H), 2.79 (q, J=7.6 Hz, 2H), 1.21 (t, J=7.6 Hz, 3H)

Reference Production Example 47

A mixture of 0.66 g of 2-chloro-5-trifluoromethyl isonicotinic acid and 4 ml of thionyl chloride was heated to reflux for 2.5 hours. The reaction mixture was cooled to room temperature, and concentrated under reduced pressure to give 2-chloro-5-trifluoromethyl isonicotinic acid chloride. A mixture of the resultant 2-chloro-5-trifluoromethyl isonicotinic acid chloride and 4 ml of DMF was added dropwise to a mixture of 0.48 g of 2-amino-4-tert-butylphenol, 0.59 g of triethylamine and 4 ml of DMF while ice-cooling. The reaction mixture was stirred at room temperature for one hour, and stirred while heating at 50° C. for one hour. The mixture was cooled to room temperature, and water was added to the reaction mixture, followed by extraction with ethyl acetate twice. The combined organic layers were washed with water and a saturated sodium chloride solution, dried over anhydrous magnesium sulfate, and concentrated under reduced pressure. The residue was subjected to silica gel column chromatography to give 0.75 g of N-(5-tert-butyl-2-hydroxyphenyl)-2-chloro-5-trifluoromethylisonicotinamide.

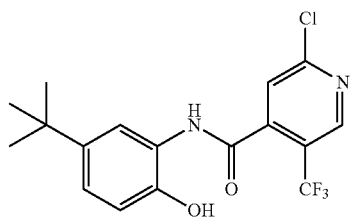

¹H-NMR (DMSO-d₆) δ: 8.92 (s, 1H), 7.98 (s, 1H), 7.84 (d, J=2.4 Hz, 1H), 7.06 (dd, J=8.5, 2.4 Hz, 1H), 6.83 (d, J=8.5 Hz, 1H), 1.25 (s, 9H)

Reference Production Example 48

A mixture of 0.35 g of 2-amino-4-trifluoromethoxy phenol, 0.29 g of 3-chloroisonicotinic acid, 1.04 g of (benzotriazole-1-yloxy)tris(dimethylamino)phosphonium hexafluorophosphate (hereinafter, referred to as a BOP reagent), 0.24 g of triethylamine and 5 ml of DMF was stirred at room temperature for two hours. Water was added to the reaction mixture, precipitated solid was collected by filtration. The resultant solid was dissolved in ethyl acetate. Then, the organic layer was washed with a saturated sodium chloride solution, dried over anhydrous magnesium sulfate, and concentrated under reduced pressure. The residue was subjected to silica gel column chromatography to give 0.43 g of 3-chloro-N-[2-hydroxy-5-(trifluoromethoxy)phenyl]isonicotinamide.

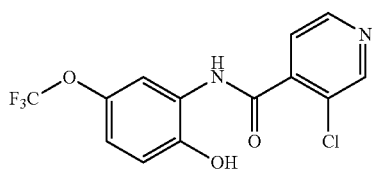

$^1$H-NMR (DMSO-d$_6$) δ: 10.37 (br s, 1H), 10.15 (br s, 1H), 8.75-8.73 (m, 1H), 8.64-8.61 (m, 1H), 8.04-8.01 (m, 1H), 7.63-7.60 (m, 1H), 7.07-7.02 (m, 1H), 6.98-6.94 (m, 1H)

Reference Production Example 49

A mixture of 0.72 g of 3-trifluoromethyl isonicotinic acid and 4 ml of thionyl chloride was heated to reflux for 1.5 hours. The reaction mixture was cooled to room temperature, and the reaction mixture was concentrated under reduced pressure to give 3-trifluoromethyl isonicotinic acid chloride. A mixture of the resultant 3-trifluoromethyl isonicotinic acid chloride and 4 ml of DMF was added dropwise to a mixture of 0.66 g of 2-amino-4-trifluoromethylphenol, 0.76 g of triethylamine, 4 ml of DMF while ice-cooling. The reaction mixture was stirred at room temperature for one hour and stirred while heating at 50° C. for 2.5 hours. The reaction mixture was cooled to room temperature, and then water was added to the reaction mixture, followed by extraction with ethyl acetate twice. The combined organic layers were washed with water and a saturated sodium chloride solution, dried over anhydrous magnesium sulfate, and concentrated under reduced pressure. The residue was washed with diethyl ether to give 0.62 g of N-[2-hydroxy-5-(trifluoromethyl)phenyl]-3-(trifluoromethyl)isonicotinamide.

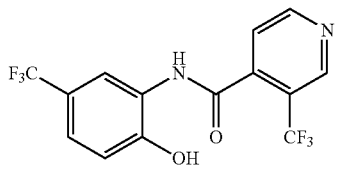

$^1$H-NMR (DMSO-d$_6$) δ: 9.06-9.04 (m, 1H), 8.98 (d, J=5.1 Hz, 1H), 8.28-8.25 (m, 1H), 7.74 (d, J=4.9 Hz, 1H), 7.41-7.37 (m, 1H), 7.06 (d, J=8.8 Hz, 1H)

Reference Production Example 50

To a mixture of 10.0 g of 3-hydroxymethylpyridine and 200 ml of THF, 3.7 g of 60% sodium hydride (in oil) was added in small portions at room temperature and then stirred for 15 minutes. To the reaction mixture, 13.0 g of methyl iodide was added dropwise, and the reaction mixture was stirred at room temperature for three hours. To the reaction mixture, 25 ml of water was added. Then, the reaction mixture was concentrated under reduced pressure. To the residue, 25 ml of water was added, followed by extraction with ethyl acetate three times. The combined organic layers were washed with a saturated sodium chloride solution, dried over anhydrous magnesium sulfate, and concentrated under reduced pressure. The residue was subjected to silica gel column chromatography to give 8.17 g of 3-methoxymethylpyridine.

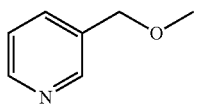

$^1$H-NMR (CDCl$_3$) δ: 8.59-8.57 (m, 1H), 8.56-8.54 (m, 1H), 7.70-7.66 (m, 1H), 7.31-7.27 (m, 1H), 4.47 (s, 2H), 3.41 (s, 3H)

Reference Production Example 51

A mixture of 7.74 g of 3-methoxymethylpyridine, 60 ml of acetic acid and 7.5 g of 30% hydrogen peroxide solution was stirred while heating at 80° C. for four hours. The reaction mixture was cooled to room temperature, and then sodium carbonate was added in small portions. The reaction mixture was subjected to filtration, and washed with ethyl acetate. The resultant filtrate was washed with a saturated aqueous solution of sodium hydrogensulfite and a saturated sodium chloride solution, and dried over anhydrous sodium carbonate. Activated carbon was added, followed by filtration through Celite™. The filtrate was concentrated under reduced pressure to give 2.66 g of 3-methoxymethylpyridine N-oxide.

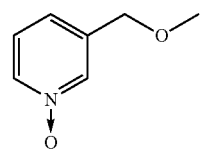

$^1$H-NMR (CDCl$_3$) δ: 8.24-8.21 (m, 1H), 8.16-8.13 (m, 1H), 7.29-7.22 (m, 2H), 4.43 (s, 2H), 3.43 (s, 3H)

Reference Production Example 52

A mixture of 2.66 g of 3-methoxymethylpyridine N-oxide and 9.0 g of iodoethane was stirred while heating at 60° C. for one hour. The reaction mixture was cooled to room temperature, diethyl ether was added thereto. Precipitated crystals were collected by filtration. To a mixture of the resultant solid and 20 ml of water, a mixture of 1.80 g of sodium cyanide and 7 ml of water was added dropwise at 50° C., and the reaction mixture was stirred while heating at the same temperature for one hour. The reaction mixture was cooled to room temperature, followed by extraction with diethyl ether three times. The combined organic layers were washed with a saturated sodium chloride solution, dried over anhydrous magnesium sulfate, and concentrated under reduced pressure. The residue was subjected to silica gel column chromatography to give 0.89 g of 3-methoxymethyl isonicotinonitrile.

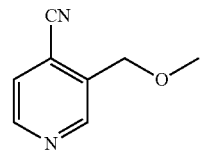

$^1$H-NMR (CDCl$_3$) δ: 8.86 (d, J=0.7 Hz, 1H), 8.73 (d, J=4.9 Hz, 1H), 7.53 (dd, J=4.9, 0.7 Hz, 1H), 4.66 (s, 2H), 3.51 (s, 3H)

Reference Production Example 53

A mixture of 0.89 g of 3-methoxymethyl isonicotinonitrile, 0.72 g of sodium hydroxide, 6 ml of ethanol and 6 ml of water was heated to reflux for three hours. The reaction mixture was cooled to room temperature, and concentrated under reduced pressure. 3 M hydrochloric acid was added so that pH of the resultant residue became about 3. The reaction mixture was concentrated under reduced pressure. To the resultant solid, 40 ml of ethanol was added. The mixture was heated to reflux for five minutes, and subjected to hot filtration. The solid collected by filtration was subjected to the same operation twice by using 40 ml each of ethanol. Combined filtrates were concentrated to give 1.0 g of 3-methoxy isonicotinic acid.

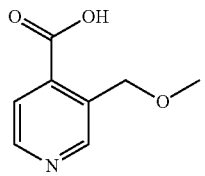

$^1$H-NMR (DMSO-$d_6$) δ: 8.77-8.75 (m, 1H), 8.67 (d, J=5.1 Hz, 1H), 7.72-7.69 (m, 1H), 4.75 (s, 2H), 3.35 (s, 3H)

Reference Production Example 54

A mixture of 0.40 g of 2-amino-4-(trifluoromethyl)phenol, 0.38 g of 3-methoxymethyl isonicotinic acid, 1.30 g of BOP reagent, 0.30 g of triethylamine, and 20 ml of DMF was stirred at room temperature for four hours. Water was added to the reaction mixture, and the reaction mixture was extracted with ethyl acetate twice. The combined organic layers were washed with a saturated sodium chloride solution, dried over anhydrous magnesium sulfate, and concentrated under reduced pressure. The residue was subjected to silica gel column chromatography to give 0.64 g of N-[2-hydroxy-5-(trifluoromethyl)phenyl]-3(methoxymethyl)isonicotinamide.

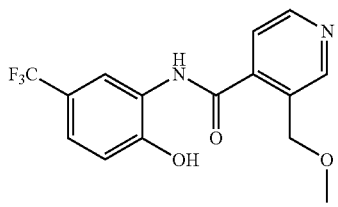

$^1$H-NMR (DMSO-$d_6$) δ: 10.89 (br s, 1H), 10.00 (br s, 1H), 8.70 (s, 1H), 8.69 (d, J=4.9 Hz, 1H), 8.32-8.30 (m, 1H), 7.60 (d, J=4.9 Hz, 1H), 7.42-7.38 (m, 1H), 7.08 (d, J=8.5 Hz, 1H), 4.63 (s, 2H), 3.33 (s, 3H)

Reference Production Example 55

A mixture of 3.13 g of 2-hydroxy-3-nitro-5-trifluoromethylpyridine, 40 ml of methanol and 0.85 g of 5% palladium on carbon was stirred under about one atmosphere of hydrogen at room temperature for two hours. The reaction mixture was filtered through Celite™. The filtrate was concentrated under reduced pressure to give 2.66 g of 3-amino-2-hydroxy-5-trifluoromethylpyridine.

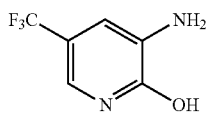

$^1$H-NMR (DMSO-$d_6$) δ: 11.83 (br s, 1H), 7.11-7.08 (m, 1H), 6.49-6.48 (m, 1H), 5.50 (br s, 2H)

Reference Production Example 56

A mixture of 1.0 g of 3-amino-2-hydroxy-5-trifluoromethylpyridine, 0.69 g of isonicotinic acid, 1.40 g of WSC and 7 ml of pyridine was stirred while heating at 80° C. for two hours. The reaction mixture was cooled to room temperature, and then water was added to the reaction mixture, followed by extraction with ethyl acetate three times. The combined organic layers were washed with water and a saturated sodium chloride solution, dried over anhydrous magnesium sulfate, and concentrated under reduced pressure. The residue was subjected to silica gel column chromatography to give 1.22 g of N-[2-hydroxy-5-(trifluoromethyl)pyridin-3-yl]isonicotinamide.

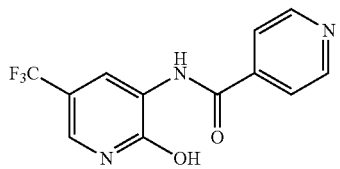

$^1$H-NMR (DMSO-$d_6$) δ: 12.76 (br s, 1H), 9.76 (s, 1H), 8.79 (dd, J=4.5, 1.6 Hz, 2H), 8.44 (d, J=2.4 Hz, 1H), 7.85-7.81 (m, 3H)

Reference Production Example 57

A mixture of 0.88 g of 3-chloroisonicotinic acid, 5 ml of thionyl chloride and 20 mg of DMF was heated to reflux for three hours. After the reaction mixture was cooled to room temperature, it was concentrated under reduced pressure to give 3-chloroisonicotinic acid chloride. The resultant 3-chloroisonicotinic acid chloride and 4 ml of DMF was added dropwise to a mixture of 1.0 g of 3-amino-2-hydroxy-5-trifluoromethylpyridine, 1.14 g of triethylamine and 8 ml of DMF while ice-cooling. The reaction mixture was stirred at room temperature for one hour, and then stirred while heating at 50° C. for 30 minutes. The reaction mixture was cooled to room temperature, and then water was added to the reaction mixture, followed by extraction with ethyl acetate twice. The combined organic layers were washed with water and a saturated sodium chloride solution, dried over anhydrous magnesium sulfate, and concentrated under reduced pressure. The residue was subjected to silica gel column chromatography to give 0.87 g of 3-chloro-N-[2-hydroxy-5-(trifluoromethyl)pyridin-3-yl]isonicotinamide.

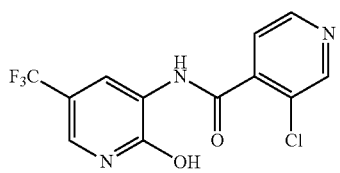

$^1$H-NMR (CDCl$_3$) δ: 12.59 (br s, 1H), 9.18 (br s, 1H), 8.85-8.83 (m, 1H), 8.77 (s, 1H), 8.69 (d, J=4.9 Hz, 1H), 7.69 (d, J=4.9 Hz, 1H), 7.55-7.53 (m, 1H)

Reference Production Example 58

3-fluoro-N-[2-hydroxy-5-(trifluoromethyl)pyridin-3-yl]isonicotinamide was obtained according to the same manner as that of Reference Production Example 57 using 3-fluoroisonicotinic acid instead of 3-chloroisonicotinic acid.

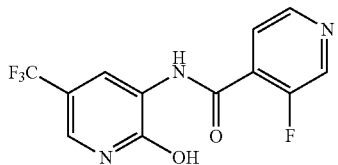

¹H-NMR (DMSO-d₆) δ: 12.78 (br s, 1H), 10.10 (d, J=5.6 Hz, 1H), 8.78 (d, J=2.2 Hz, 1H), 8.61 (d, J=4.8 Hz, 1H), 8.53 (d, J=2.4 Hz, 1H), 7.84-7.82 (m, 1H), 7.80-7.77 (m, 1H)

Reference Production Example 59

N-[2-hydroxy-5-(trifluoromethyppyridin-3-yl]-3-methyl-isonicotinamide was obtained according to the same manner as that of Reference Production Example 578 using methyl isonicotinic acid instead of 3-chloroisonicotinic acid.

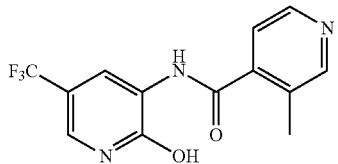

¹H-NMR (CDCl₃) δ: 12.79 (br s, 1H), 8.81-8.79 (m, 1H), 8.73-8.70 (m, 1H), 8.63-8.60 (m, 2H), 7.56-7.54 (m, 1H), 7.43-7.41 (m, 1H), 2.53 (s, 3H)

Reference Production Example 60

3-ethyl-N-[2-hydroxy-5-(trifluoromethyl)pyridin-3-yl]isonicotinamide was obtained according to the same manner as that of Reference Production Example 57 using 3-ethyl isonicotinic acid instead of 3-chloroisonicotinic acid.

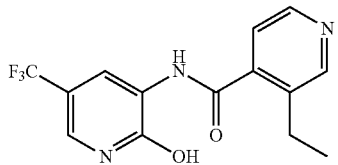

¹H-NMR (DMSO-d₆) δ: 12.67 (br s, 1H), 9.87 (br s, 1H), 8.57 (s, 1H), 8.52 (d, J=4.8 Hz, 1H), 8.45 (d, J=2.4 Hz, 1H), 7.82-7.79 (m, 1H), 7.41 (d, J=4.8 Hz, 1H), 2.73 (q, J=7.6 Hz, 2H), 1.18 (t, J=7.6 Hz, 3H)

Reference Production Example 61

N-(2-hydroxy-5-trifluoromethylpyridin-3-yl)-3-trifluoromethylisonicotinamide was obtained according to the same manner as that of Reference Production Example 57 using 3-trifluoromethyl isonicotinic acid instead of 3-chloroisonicotinic acid.

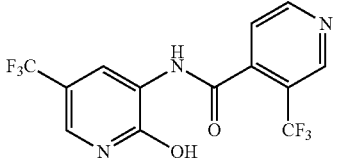

¹H-NMR (DMSO-d₆) δ: 12.67 (br s, 1H), 10.54 (br s, 1H), 9.02 (s, 1H), 8.95 (d, J=5.1 Hz, 1H), 8.48 (d, J=2.7 Hz, 1H), 7.83-7.80 (m, 1H), 7.69 (d, J=5.1 Hz, 1H)

Reference Production Example 62

A mixture of 1.73 g of 3-methoxyisonicotinonitrile, 1.03 g of sodium hydroxide and 20 ml of ethanol was heated to reflux for 20 hours. The mixture was cooled to room temperature, and then concentrated under reduced pressure. 3 M hydrochloric acid was added so that pH of the resultant residue became about 3, and the residue was concentrated under reduced pressure again. To the resultant solid, 40 ml of ethanol was added. The reaction mixture was heated to reflux for five minutes, and subjected to hot filtration. The solid collected by filtration was subjected to the same operation twice by using 40 ml each of ethanol. The combined filtrates were concentrated to give 1.97 g of 3-methoxy isonicotinic acid.

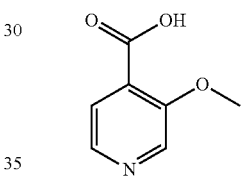

¹H-NMR (DMSO-d₆) δ: 8.55 (s, 1H), 8.30 (d, J=4.9 Hz, 1H), 7.53 (d, J=4.7 Hz, 1H), 3.94 (s, 3H)

Reference Production Example 63

N-[2-hydroxy-5-(trifluoromethyl)pyridin-3-yl]-3-methoxyisonicotinamide was obtained according to the same manner as that of Reference Production Example 57 using 3-methoxy isonicotinic acid instead of 3-chloroisonicotinic acid.

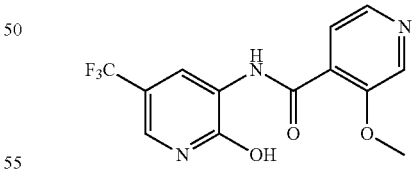

¹H-NMR (DMSO-d₆) δ: 12.74 (br s, 1H), 10.83 (br s, 1H), 8.73 (s, 1H), 8.57-8.55 (m, 1H), 8.44 (d, J=4.9 Hz, 1H), 7.89 (d, J=4.9 Hz, 1H), 7.81-7.77 (m, 1H), 4.18 (s, 3H)

Reference Production Example 64

To a mixture of 2.0 g of 3-chloroisonicotinonitrile and 8 ml of DMF, 1.02 g of sodium thiomethoxide was added while ice-cooling. The reaction mixture was stirred at 0° C. for one hour. The reaction mixture was concentrated under reduced pressure, to which ethyl acetate was added for filtering out insoluble matters. Filtrates were concentrated under reduced pressure, and the resultant residue was subjected to silica gel column chromatography to give 2.11 g of 3-methylthioisonicotinonitrile.

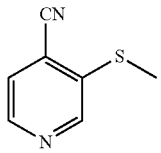

¹H-NMR (CDCl₃) δ: 8.65 (s, 1H), 8.53 (d, J=5.1 Hz, 1H), 7.46-7.44 (m, 1H), 2.66 (s, 3H)

Reference Production Example 65

3-methylthioisonicotinic acid was obtained according to the same manner as that of Reference Production Example 62 using 3-methylthioisonicotinonitrile instead of 3-methoxyisonicotinonitrile.

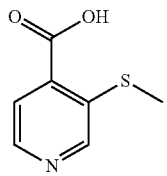

¹H-NMR (DMSO-d₆) δ: 13.73 (br s, 1H), 8.62 (s, 1H), 8.46 (d, J=5.1 Hz, 1H), 7.70 (d, J=5.0 Hz, 1H), 2.54 (s, 3H)

Reference Production Example 66

N-[2-hydroxy-5-(trifluoromethyl)pyridin-3-yl]-3-methylthio isonicotinamide was obtained according to the same manner as that of Reference Production Example 57 using 3-methylthioisonicotinic acid instead of 3-chloroisonicotinic acid.

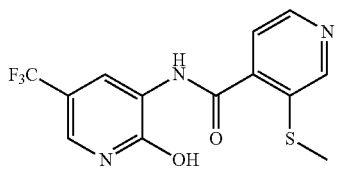

¹H-NMR (DMSO-d₆) δ: 12.68 (br s, 1H), 10.00 (br s, 1H), 8.65 (s, 1H), 8.49 (d, J=4.9 Hz, 1H), 8.47-8.45 (m, 1H), 7.82-7.78 (m, 1H), 7.50-7.48 (m, 1H), 2.55 (s, 3H)

Reference Production Example 67

3-ethylthioisonicotinonitrile was obtained according to the same manner as that of Reference Production Example 64 using sodium thioethoxide instead of sodium thiomethoxide.

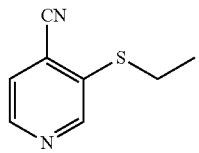

¹H-NMR (CDCl₃) δ: 8.73 (s, 1H), 8.56 (d, J=4.8 Hz, 1H), 7.47 (d, J=4.8 Hz, 1H), 3.13 (q, J=7.2 Hz, 2H), 1.39 (t, J=7.3 Hz, 3H)

Reference Production Example 68

3-ethylthio isonicotinic acid was obtained according to the same manner as that of Reference Production Example 62 using 3-ethylthioisonicotinonitrile instead of 3-methoxyisonicotinonitrile.

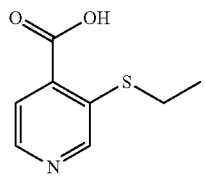

¹H-NMR (DMSO-d₆) δ: 13.72 (br s, 1H), 8.65 (s, 1H), 8.45 (d, J=5.1 Hz, 1H), 7.67 (d, J=5.0 Hz, 1H), 3.09 (q, J=7.3 Hz, 2H), 1.27 (t, J=7.4 Hz, 3H)

Reference Production Example 69

N-[2-hydroxy-5-(trifluoromethyl)pyridin-3-yl]-3-ethylthio isonicotinamide was obtained according to the same manner as that of Reference Production Example 57 using 3-ethylthio isonicotinic acid instead of 3-chloroisonicotinic acid.

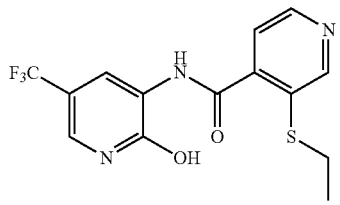

¹H-NMR (DMSO-d₆) δ: 12.67 (br s, 1H), 10.11 (br s, 1H), 8.70 (s, 1H), 8.52 (d, J=4.9 Hz, 1H), 8.49-8.47 (m, 1H), 7.82-7.79 (m, 1H), 7.50 (d, J=5.0 Hz, 1H), 3.04 (q, J=7.4 Hz, 2H), 1.21 (t, J=7.3 Hz, 3H)

Reference Production Example 70

A mixture of 0.51 g of 3-amino-2-hydroxy-5-trifluoromethylpyridine, 0.48 g of 3-methoxymethyl isonicotinic acid, 1.65 g of BOP reagent, 0.38 g of triethylamine and 6 ml of DMF was stirred at room temperature for one hour, and further stirred while heating at 50° C. for two hours. Water was added to the reaction mixture, followed by extraction with ethyl acetate twice. The combined organic layers were washed with a saturated sodium chloride solution, dried over anhydrous magnesium sulfate, and concentrated under reduced pressure. The residue was subjected to silica gel column chromatography to give 0.58 g of N-[2-hydroxy-5-(trifluoromethyl)pyridin-3-yl]-3-(methoxymethyl)isonicotinamide.

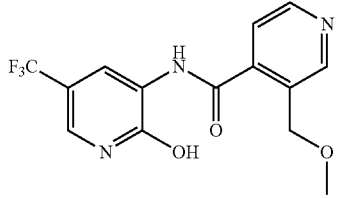

$^1$H-NMR (DMSO-d$_6$) δ: 12.67 (br s, 1H), 10.18 (br s, 1H), 8.71-8.67 (m, 2H), 8.54-8.51 (m, 1H), 7.80 (s, 1H), 7.58 (d, J=4.8 Hz, 1H), 4.58 (s, 2H), 3.33 (s, 3H)

Reference Production Example 71

To a mixture of 0.80 g of 3-amino-2-hydroxy-6-trifluoromethylpyridine, 1.14 g of triethylamine and 10 ml of DMF, 0.88 g of isonicotinic acid chloride hydrochloride was added while ice-cooling. The reaction mixture was stirred at room temperature for one hour and further stirred while heating at 50° C. for one hour. To the reaction mixture, 0.88 g of isonicotinic acid chloride hydrochloride and 1.1 g of triethylamine were added, and the reaction mixture was stirred while heating at 50° C. for further 1.5 hours. The reaction mixture was cooled to room temperature, and water was added to the reaction mixture. Precipitated crystals were collected by filtration. The resultant solid was dissolved in ethyl acetate, then washed with a saturated sodium chloride solution, dried over anhydrous magnesium sulfate, and concentrated under reduced pressure. The residue was subjected to silica gel column chromatography to give 0.91 g of N-[2-hydroxy-6-(trifluoromethyl)pyridin-3-yl]-isonicotinamide.

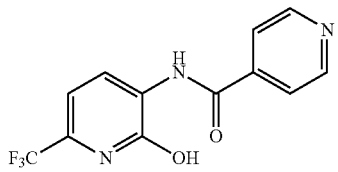

$^1$H-NMR (DMSO-d$_6$) δ: 9.98 (br s, 1H), 8.79 (dd, J=4.4, 1.5 Hz, 2H), 8.39 (d, J=7.8 Hz, 1H), 7.85 (dd, J=4.5, 1.6 Hz, 2H), 7.40-7.19 (m, 1H)

Reference Production Example 72

N-[2-hydroxy-6-(trifluoromethyl)pyridin-3-yl]-3-chloroisonicotinamide was obtained according to the same manner as that of Reference Production Example 57 using 3-amino-2-hydroxy-6-trifluoromethylpyridine instead of 3-amino-2-hydroxy-5-trifluoromethylpyridine.

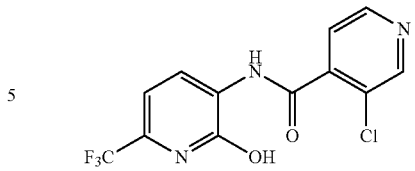

$^1$H-NMR (DMSO-d$_6$) δ: 10.47 (br s, 1H), 8.74 (s, 1H), 8.63 (d, J=4.9 Hz, 1H), 8.57 (s, 1H), 7.60 (d, J=4.8 Hz, 1H), 7.51-7.31 (m, 1H)

Reference Production Example 73

2-amino-6-methylpyridin-3-ol was obtained according to the same manner as that of Reference Production Example 1 using 6-methyl-2-nitropyridin-3-ol instead of 4-propyl-2-nitrophenol.

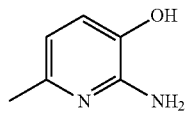

$^1$H-NMR (DMSO-d$_6$) δ: 9.11 (br s, 1H), 6.71 (d, J=7.5 Hz, 1H), 6.21 (d, J=7.5 Hz, 1H), 5.30 (br s, 2H), 2.14 (s, 3H)

Reference Production Example 74

A mixture of 0.59 g of 60% sodium hydride (in oil) and 5 ml of DMF was stirred while ice-cooling. To the reaction mixture, 1.59 g of benzyl alcohol was added. The reaction mixture was stirred at the same temperature for 10 minutes. To the reaction mixture, 2.0 g of 3-chloroisonicotinonitrile was added, and the reaction mixture was stirred at the same temperature for 30 minutes and at room temperature for 1.5 hours. The reaction mixture was concentrated under reduced pressure, and then to ethyl acetate was added to the reaction mixture, followed by filtration of insoluble matters. The filtrate was concentrated under reduced pressure and the resultant residue was subjected to silica gel column chromatography to give 2.64 g of 3-benzyloxy isonicotinonitrile.

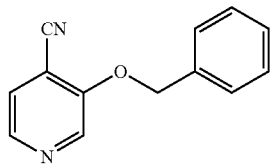

$^1$H-NMR (CDCl$_3$) δ: 8.52 (s, 1H), 8.36 (d, J=4.6 Hz, 1H), 7.48-7.33 (m, 6H), 5.33 (s, 2H)

Reference Production Example 75

3-benzyloxy isonicotinic acid was obtained according to the same manner as that of Reference Production Example 62 using 3-benzyloxy isonicotinonitrile instead of 3-methoxy isonicotinonitrile.

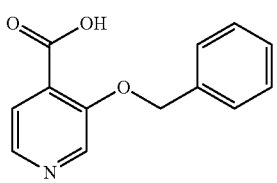

¹H-NMR (DMSO-d₆) δ: 13.41 (br s, 1H), 8.59 (s, 1H), 8.29 (d, J=4.6 Hz, 1H), 7.53 (d, J=4.6 Hz, 1H), 7.51-7.46 (m, 2H), 7.44-7.37 (m, 2H), 7.36-7.30 (m, 1H), 5.34 (s, 2H)

Reference Production Example 76

3-benzyloxy-N-[2-hydroxy-5-(trifluoromethyl)pyridin-3-yl]-isonicotinamide was obtained according to the same manner as that of Reference Production Example 70 using 3-benzyloxy isonicotinic acid instead of 3-methoxymethyl isonicotinic acid.

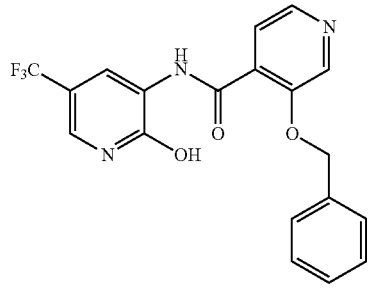

¹H-NMR (DMSO-d₆) δ: 12.76 (br s, 1H), 10.80 (br s, 1H), 8.76 (s, 1H), 8.57-8.55 (m, 1H), 8.38 (d, J=4.9 Hz, 1H), 7.85 (d, J=4.9 Hz, 1H), 7.79 (s, 1H), 7.63-7.58 (m, 2H), 7.41-7.29 (m, 3H), 5.61 (s, 2H)

Reference Production Example 77

A mixture of 10.0 g of 3-ethylpyridine, 60 ml of acetic acid and 12 ml of 30% hydrogen peroxide solution was stirred while heating at 80° C. for 2.5 hours. To the reaction mixture, 7 ml of 30% hydrogen peroxide solution was added, and the reaction mixture was stirred while heating at 80° C. for further seven hours. The reaction mixture was cooled to room temperature, and sodium carbonate was added to the reaction mixture in small portions. The reaction mixture was filtered, and washed with ethyl acetate. The resultant filtrate was washed with a saturated aqueous solution of sodium hydrogen sulfite and a saturated sodium chloride solution, dried over anhydrous water sodium carbonate. Activated carbon was added, followed by filtration through Celite™. The filtrate was concentrated under reduced pressure to give 6.0 g of 3-ethylpyridine N-oxide.

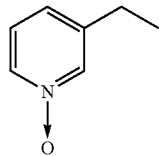

¹H-NMR (CDCl₃) δ: 8.12 (s, 1H), 8.10-8.08 (m, 1H), 7.23-7.18 (m, 1H), 7.16-7.12 (m, 1H), 2.64 (q, J=7.6 Hz, 2H), 1.26 (t, J=7.7 Hz, 3H)

Reference Production Example 78

A mixture of 6.0 g of 3-ethylpyridine N-oxide and 23 g of iodoethane was stirred while heating at 60° C. for one hour. The reaction mixture was cooled to room temperature, and diethyl ether was added. Precipitated crystal was collected by filtration. To a mixture of the resultant solid and 55 ml of water, a mixture of 4.46 g of sodium cyanide and 16 ml of water 16 ml was added dropwise at 50° C., and stirred while heating at the same temperature for one hour. The reaction mixture was cooled to room temperature, followed by extraction with diethyl ether three times. The combined organic layers were washed with a saturated sodium chloride solution, dried over anhydrous magnesium sulfate, and concentrated under reduced pressure. The residue was subjected to silica gel column chromatography to give 2.7 g of 3-ethyl isonicotinonitrile.

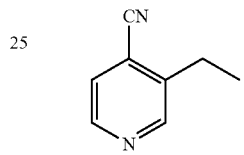

¹H-NMR (CDCl₃) δ: 8.69 (s, 1H), 8.61 (d, J=4.9 Hz, 1H), 7.48-7.46 (m, 1H), 2.90 (q, J=7.6 Hz, 2H), 1.35 (t, J=7.6 Hz, 3H)

Reference Production Example 79

A mixture of 2.7 g of 3-ethyl isonicotinonitrile, 1.63 g of sodium hydroxide, 20 ml of ethanol and 20 ml of water was heated to reflux for five hours. The reaction mixture was cooled to room temperature, and concentrated under reduced pressure. 3 M hydrochloric acid was added so that pH of the resultant residue became about 3, which was concentrated under reduced pressure again. To the resultant solid, 50 ml of ethanol was added and heated to reflux for five minutes, followed by hot filtration. To the solid collected by filtration, the same operation was carried out by using 50 ml each of ethanol. Combined filtrates were concentrated to give 2.49 g of 3-ethyl isonicotinic acid.

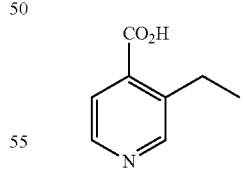

¹H-NMR (DMSO-d₆) δ: 13.58 (br s, 1H), 8.59 (s, 1H), 8.54 (d, J=5.0 Hz, 1H), 7.60 (d, J=5.0 Hz, 1H), 2.89 (q, J=7.5 Hz, 2H), 1.17 (t, J=7.4 Hz, 3H)

Next, Formulation Examples of Active compounds are shown. Note here that part represents part by weight.

Formulation Example 1

Ten parts of any one of the above-mentioned active compounds 1 to 162 are dissolved in a mixture of 35 parts of xylene and 35 parts of N,N-dimethylformamide. To the mixture, 14 parts of polyoxyethylene styrylphenyl ether and 6 parts of calcium dodecylbenzenesulfonate are added. The mixture is well stirred and mixed to give 10% emulsion for each of the active compounds.

Formulation Example 2

Twenty parts of any one of the above-mentioned active compounds 1 to 162 are added to a mixture of 4 parts of sodium lauryl sulfate, 2 parts of calcium lignin sulfonate, 20 parts of fine powder of water-containing synthetic silicon oxide and 54 parts of diatomite. The mixture is well stirred and mixed to give 20% wettable powder for each of the active compounds.

Formulation Example 3

To 2 parts of any one of the above-mentioned active compounds 1 to 162, 1 part of fine powder of water-containing synthetic silicon oxide, 2 parts of calcium lignin sulfonate, 30 parts of bentonite and 65 parts of kaolin clay are added, followed by sufficient stirring and mixing. Then, a suitable amount of water is added to the mixture. The mixture is further stirred, granulated by a granulator, and air-dried to give 2% granules for each of the active compounds.

Formulation Example 4

One part of any one of the above-mentioned active compounds 1 to 162 is dissolved in a suitable amount of acetone. To the solution, 5 parts of fine powder of synthesized hydrated silicon oxide, 0.3 parts of PAP (isopropyl phosphate) and 93.7 parts of Fubasami clay are added. The mixture solution is sufficiently stirred and mixed, and acetone is removed by evaporation to give 1% dusting powder formulation for each of the active compounds.

Formulation Example 5

Thirty-five parts of mixture of polyoxyethylene alkyl ether sulfate ammonium salt and white carbon (weight ratio of 1:1), 10 parts of any one of the above-mentioned active compounds 1 to 162, and 55 parts of water are mixed. The mixture is pulverized by wet method to give 10% flowables for each of the active compounds.

Formulation Example 6

0.1 parts of any one of the above-mentioned active compounds 1 to 162 is dissolved in 5 parts of xylene and 5 parts of trichloroethane, which is mixed with 89.9 parts of deodorized kerosene to give 0.1% oil solution for each of the active compounds.

Formulation Example 7

10 mg of any one of the above-mentioned active compounds 1 to 162 is dissolved in 0.5 ml of acetone. The solution is treated into 5 g of solid feed powder for animals (Breeding Solid Feed Powder CE-2, available from Japan Clea Co., Ltd.) and mixed homogeneously. Then, acetone is removed by evaporation to give a poisonous bait for each of the active compounds.

Formulation Example 8

0.1 parts of any one of the above-mentioned active compounds 1 to 162 and 49.9 parts of Neo-chiozol (Chuo Kasei Co., Ltd.) are put into an aerosol can, to which an aerosol valve is attached. Then, 25 parts of dimethyl ether and 25 parts of LPG are filled in the aerosol can, followed by shaking and attachment of an actuator. Thus, an oil-based aerosol is obtained.

Formulation Example 9

0.6 parts of any one of the above-mentioned active compounds 1 to 162, 0.01 parts of BHT (2,6-di-tert-butyl-4-methylphenol), 5 parts of xylene, 3.39 parts of deodorized kerosene and 1 part of emulsifier {Atmos 300 (registered trade name for ATMOS CHEMICAL LTD)} are mixed and dissolved. The mixture solution and 50 parts of distilled water are filled in an aerosol container, and a valve is fixed to the container. 40 parts of propellant (LPG) are charged under pressure through the valve to give an aqueous aerosol.

Formulation Example 10

Ten parts of any one of the above-mentioned active compounds 1 to 162, and 10 parts of substances that can be mixed and formulated with the active compound, for example, insecticide, acaricide, nematicide or antimicrobial agent, plant hormone, plant growth substance, herbicide, and the like, harmful organism controlling agent (containing isomers and salt thereof) such as herbicide, synergist, or agents for reducing drug-induced sufferings are added to a mixture of 4 parts of sodium lauryl sulfate, 2 parts of calcium lignin sulfonate, 20 parts of fine powder of synthesized hydrated silicon oxide and 54 parts of diatomite. The mixture is well stirred and mixed to give mixed wettable powder.

Next, arthropod pest control effects of active compounds are shown by Test Examples.

Test Example 1

Formulations were prepared by the method described in Formulation Example 5 with respect to each of the active compounds 1 to 3, the active compound 5, the active compound 6, the active compounds 8 to 16, the active compounds 18 to 20, the active compounds 23 to 25, the active compounds 27 to 32, the active compound 34, the active compound 35, the active compound 37, the active compounds 39 to 44, the active compound 46, the active compounds 52 to 58, the active compound 61, the active compounds 63 to 74, the active compounds 76 to 79, the active compounds 81 to 86, the active compound 88, the active compound 89, the active compounds 91 to 94, the active compound 97, the active compound 98, the active compound 100, the active compound 101, the active compound 104, the active compound 105, the active compound 110, the active compound 111, the active compound 115, the active compound 116, the active compounds 118 to 120, the active compound 122, the active compound 125, the active compound 126, the active compounds 128 to 136 and the active compounds 138 to 145. The formulations were diluted with water so that the concentration of the active ingredient became 500 ppm and thus test diluents were prepared.

On the other hand, a cucumber seedling (second true leaf development stage) planted in a plastic cup was inoculated with about 30 cotton aphids (Aphis gossypii Glover) and allowed to stand for one day. To the seedling, any one of the diluents (10 ml) was scattered.

Five days after the scattering, the number of survived cotton aphids parasitic on the cucumber leaves was counted, and the control value was calculated by the following equation.

Control value (%)={1−(Cb×Tai)/(Cai×Tb)}×100 wherein each character represents the following meaning:
Cb: the number of insects in non-treated section before treatment
Cai: the number of insects in non-treated section during observation
Tb: the number of insects in treated section before treatment
Tai: the number of insects in treated section during observation As a result, the treated sections treated with any one of the test diluents of the active compounds 1 to 3, the active compound 5, the active compound 6, the active compounds 8 to 16, the active compounds 18 to 20, the active compounds 23 to 25, the active compounds 27 to 32, the active compound 34, the active compound 35, the active compound 37, the active compounds 39 to 44, the active compound 46, the active compounds 52 to 58, the active compound 61, the active compounds 63 to 74, the active compounds 76 to 79, the active compounds 81 to 86, the active compound 88, the active compound 89, the active compounds 91 to 94, the active compound 97, the active compound 98, the active compound 100, the active compound 101, the active compound 104, the active compound 105, the active compound 110, the active compound 111, the active compound 115, the active compound 116, the active compounds 118 to 120, the active compound 122, the active compound 125, the active compound 126, the active compounds 128 to 136 and the active compounds 138 to 145 showed not less than 90% of control value.

Test Example 2

Formulations were prepared by the method described in Formulation Example 5 with respect to each of the active compound 14, the active compound 18, the active compound 19, the active compounds 23 to 27, the active compound 29, the active compound 30, the active compound 35, the active compound 37, the active compound 55, the active compound 56, the active compound 58, the active compound 63, the active compounds 69 to 71, the active compound 76, the active compound 88, the active compound 93, the active compound 94, the active compound 107, the active compound 110, the active compound 119, the active compound 120, the active compound 125, the active compound 126, the active compound 128, the active compound 131, the active compounds 133 to 136, the active compounds 138 to 150 and the active compounds 153 to 155. The formulations were diluted with water so that the concentration of the active ingredient became 500 ppm and thus test diluents were prepared.

On the other hand, a plant foot of cucumber seedling (second true leaf development stage) planted in a urethane mat was irrigated with any one of diluents (5 ml). One day after the treatment, the cucumber leaves were inoculated with 30 cotton aphids (all stages). Further seven days after, the number of survived cotton aphids parasitic on the cucumber leaves was counted, and the control value was calculated by the following equation.

Control value (%)={1−(Cb×Tai)/(Cai×Tb)}×100 wherein each character represents the following meaning:
Cb: number of insects in non-treated section before treatment
Cai: number of insects in non-treated section during observation
Tb: number of insects in treated section before treatment
Tai: number of insects in treated section during observation As a result, the treated sections treated with any one of the test diluents of the active compound 14, the active compound 18, the active compound 19, the active compounds 23 to 27, the active compound 29, the active compound 30, the active compound 35, the active compound 37, the active compound 55, the active compound 56, the active compound 58, the active compound 63, the active compounds 69 to 71, the active compound 76, the active compound 88, the active compound 93, the active compound 94, the active compound 107, the active compound 110, the active compound 119, the active compound 120, the active compound 125, the active compound 126, the active compound 128, the active compound 131, the active compounds 133 to 136, the active compounds 138 to 150 and the active compounds 153 to 155 showed not less than 90% of control value.

Test Example 3

Formulations were prepared by the method described in Formulation Example 5 with respect to each of the active compound 13, the active compound 14, the active compound 19, the active compound 24, the active compound 25, the active compound 30, the active compound 37, the active compound 58, the active compound 63, the active compound 125, the active compound 135, the active compounds 139 to 142, the active compound 144 and the active compound 145. The formulations were diluted with water so that the concentration of the active ingredient became 500 ppm and thus test diluents were prepared.

On the other hand, a plant foot of cucumber seedling (second true leaf development stage) planted in a plastic cup was irrigated with any one of diluents (5 ml). The seedling was kept in a green house of 25° C. for seven days. The cucumber leaves were inoculated with 30 cotton aphids (all stages) and kept in the green house for further six days. Thereafter, the number of survived cotton aphids parasitic on the cucumber leaves was counted, and the control value was calculated by the following equation.

Control value (%)={1−(Cb×Tai)/(Cai×Tb)}×100 wherein each character represents the following meaning:
Cb: number of insects in non-treated section before treatment
Cai: number of insects in non-treated section during observation
Tb: number of insects in treated section before treatment
Tai: number of insects in treated section during observation As a result, the treated sections treated with any one of the test diluents of the active compound 13, the active compound 14, the active compound 19, the active compound 24, the active compound 25, the active compound 30, the active compound 37, the active compound 58, the active compound 63, the active compound 125, the active compound 135, the active compounds 139 to 142, and the active compound 144 and 145 showed not less than 90% of control value.

Test Example 4

Formulations were prepared by the method described in Formulation Example 5 with respect to each of the active compound 1, the active compound 3, the active compound 5, the active compound 6, the active compound 8, the active compounds 11 to 20, the active compounds 23 to 32, the active compound 34, the active compound 35, the active compound 37, the active compounds 39 to 44, the active compound 46, the active compound 52, the active compound 53, the active compounds 55 to 58, the active compound 63, the active compounds 65 to 70, the active compounds 72 to 74, the active compounds 77 to 81, the active compounds 83 to 86, the active compound 88, the active compound 89, the active compounds 91 to 94, the active compound 97, the active compound 98, the active compound 100, the active compound 101, the active compound 104, the active compound 105, the active compound 107, the active compound 110, the active compound 111, the active compounds 115 to 120, the active compound 122, the active compound 123, the active compound 125, the active compound 126, the active compounds 128 to 136, the active compounds 138 to 145, the active compounds 153 and the active compound 154. The formulations were diluted with water so that the concentration of the active ingredient became 500 ppm and thus test diluents were prepared.

On the other hand, by releasing tobacco whitefly images to a tomato seedling planted in a plastic cup to allow them to lay eggs for about 24 hours. The tomato seedling was kept in a green house for eight days. At the stage in which larvae hatched from the laid eggs, any of the test diluents was scattered at the rate of 10 ml/cup. The tomato seedling was kept in the greenhouse at 25° C. for seven days. The number of survived larvae on tomato leaves was counted, and the control value was calculated by the following equation.

Control value (%)={1−(Cb×Tai)/(Cai×Tb)}×100 wherein each character represents the following meaning:
Cb: number of insects in non-treated section before treatment
Cai: number of insects in non-treated section during observation
Tb: number of insects in treated section before treatment
Tai: number of insects in treated section during observation As a result, the treated sections treated with any one of the test diluents of the active compound 1, the active compound 3, the active compound 5, the active compound 6, the active compound 8, the active compounds 11 to 20, the active compounds 23 to 32, the active compound 34, the active compound 35, the active compound 37, the active compounds 39 to 44, the active compound 46, the active compound 52, the active compound 53, the active compounds 55 to 58, the active compound 63, the active compounds 65 to 70, the active compounds 72 to 74, the active compounds 77 to 81, the active compounds 83 to 86, the active compound 88, the active compound 89, the active compounds 91 to 94, the active compound 97, the active compound 98, the active compound 100, the active compound 101, the active compound 104, the active compound 105, the active compound 107, the active compound 110, the active compound 111, the active compounds 115 to 120, the active compound 122, the active compound 123, the active compound 125, the active compound 126, the active compounds 128 to 136, the active compounds 138 to 145, the active compound 153 and the active compound 154 showed not less than 90% of control value.

Test Example 5

Formulations were prepared by the method described in Formulation Example 5 with respect to each of the active compound 1, the active compounds 4 to 6, the active compound 8, the active compounds 12 to 15, the active compounds 18 to 20, the active compounds 24 to 30, the active compound 32, the active compound 34, the active compound 35, the active compounds 37 to 44, the active compound 46, the active compounds 52 to 54, the active compound 58, the active compound 59, the active compound 61, the active compound 67, the active compound 68, the active compounds 71 to 86, the active compound 88, the active compound 89, the active compounds 91 to 94, the active compound 97, the active compound 98, the active compounds 100 to 105, the active compound 107, the active compounds 110 to 113, the active compounds 115 to 120, the active compound 122, the active compound 123, the active compounds 125 to 136, the active compound 138, the active compound 139 and the active compounds 142 to 145. The formulations were diluted with water so that the concentration of the active ingredient became 500 ppm and thus test diluents were prepared.

On the other hand, to a rice plant seedling (two weeks after seeding, second leaf development stage) planted in a plastic cup, any one of the diluents (10 ml) was scattered. After the drug solution scattered on the rice plant was dried, 30 first-instars of rice brown planthopper were released on the rice plant, which was kept in the green house at 25° C. for six days. Thereafter, the number of rice brown planthopper parasitic on rice plant was counted and the control value was calculated by the following equation.

Control value (%)={1−(Cb×Tai)/(Cai×Tb)}×100 wherein each character represents the following meaning:
Cb: number of insects in non-treated section before treatment
Cai: number of insects in non-treated section during observation
Tb: number of insects in treated section before treatment
Tai: number of insects in treated section during observation As a result, the treated sections treated with any one of the test diluents of the active compound 1, the active compounds 4 to 6, the active compound 8, the active compounds 12 to 15, the active compounds 18 to 20, the active compounds 24 to 30, the active compound 32, the active compound 34, the active compound 35, the active compounds 37 to 44, the active compound 46, the active compounds 52 to 54, the active compound 58, the active compound 59, the active compound 61, the active compound 67, the active compound 68, the active compounds 71 to 86, the active compound 88, the active compound 89, the active compounds 91 to 94, the active compound 97, the active compound 98, the active compounds 100 to 105, the active compound 107, the active compounds 110 to 113, the active compounds 115 to 120, the active compound 122, the active compound 123, the active compounds 125 to 136, the active compound 138, the active compound 139 and the active compounds 142 to 145 showed not less than 90% of control value.

Test Example 6

Formulations were prepared by the method described in Formulation Example 5 with respect to each of the active compound 14, the active compound 18, the active compound 24, the active compound 25, the active compound 30, the active compound 35, the active compound 37, the active compound 39, the active compound 41, the active compound 44, the active compound 46, the active compound 58, the active compounds 69 to 72, the active compound 75, the active compound 92, the active compound 93, the active compound 97, the active compound 98, the active compound 100, the active compound 101, the active compound 107, the active compound 110, the active compound 111, the active compounds 116 to 120, the active compound 125, the active compound 126, the active compound 139 and the active compounds 142 to 144. The formulations were diluted with water so that the concentration of the active ingredient became 500 ppm and thus test diluents were prepared.

On the other hand, a plant foot of rice plant seedling (two weeks after seeding, second leaf development stage) planted in a plastic cup was irrigated with any one of diluents (5 ml). The seedling was kept in a green house of 25° C. for seven days. Thirty first-instars of rice brown planthopper were released to the seedling, which was kept in the green house at 25° C. for six days. Thereafter, the number of survived rice brown planthopper parasitic on rice plant leaves was counted, and the control value was calculated by the following equation.

Control value (%)={1−($Cb×Tai$)/($Cai×Tb$)}×100 wherein each character represents the following meaning:
Cb: number of insects in non-treated section before treatment
Cai: number of insects in non-treated section during observation
Tb: number of insects in treated section before treatment
Tai: number of insects in treated section during observation As a result, the treated sections treated with any one of the test diluents of the active compound 14, the active compound 18, the active compound 24, the active compound 25, the active compound 30, the active compound 35, the active compound 37, the active compound 39, the active compound 41, the active compound 44, the active compound 46, the active compound 58, the active compounds 69 to 72, the active compound 75, the active compound 92, the active compound 93, the active compound 97, the active compound 98, the active compound 100, the active compound 101, the active compound 107, the active compound 110, the active compound 111, the active compounds 116 to 120, the active compound 125, the active compound 126, the active compound 139 and the active compounds 142 to 144 showed not less than 90% of control value.

Test Example 7

Formulations were prepared by the method described in Formulation Example 1 with respect to each of the active compound 13, the active compound 15, the active compound 18, the active compound 35, the active compound 37, the active compound 44, the active compound 65, the active compound 68 and the active compound 82. The formulations were diluted with water so that the concentration of the active ingredient became 100 ppm and thus test diluents were prepared.

On the other hand, a tissue paper placed in an aluminum cup was irrigated with any one of the above-mentioned diluents (5 ml). The tissue paper was placed in a polyethylene cup together with three budding soybeans. In the polyethylene cup, ten halymorpha halys were released, and the polyethylene cup was lidded by a polyethylene lid. Seven days after the releasing of the insects, the number of survived insects was counted, and the mortality was calculated by the following equation.

Mortality (%)=(number of dead insects/number of insects to be tested)×100

As a result, the treated sections treated with any one of the test diluents of the active compound 13, the active compound 15, the active compound 18, the active compound 35, the active compound 37, the active compound 44, the active compound 65, the active compound 68 and the active compound 82 showed not less than 80% of mortality.

Test Example 8

Formulations were prepared by the method described in Formulation Example 5 with respect to each of the active compound 2 and the active compound 13. The formulations were diluted with water so that the concentration of the active ingredient became 200 ppm and thus test diluents were prepared.

On the other hand, a cucumber seedling (second true leaf development stage) planted in a plastic cup was inoculated with about 30 cotton aphids and allowed to stand for one day. To the seedling, any one of the diluents (10 ml) was scattered.

Five days after scattering, the number of survived cotton aphids parasitic on the cucumber leaves was counted, and the control value was calculated by the following equation.

Control value (%)={1−($Cb×Tai$)/($Cai×Tb$)}×100 wherein each character represents the following meaning:
Cb: number of insects in non-treated section before treatment
Cai: number of insects in non-treated section during observation
Tb: number of insects in treated section before treatment
Tai: number of insects in treated section during observation As a result, the treated sections treated with any one of the test diluents of the active compound 2 and the active compound 13 showed not less than 90% of control value.

Comparative Test Example

A compound shown in the following formula (B) disclosed in Chem. Pharm. Bull., 30(8), 2996 (1982) (hereinafter, referred to as comparative compound (B)) was subjected to the same test as in Test Example 8. The treated section treated with the test scattering solution of comparative compound (B) showed control value of less than 30%.

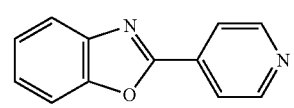

(B)

Industrial Applicability

A composition of the present invention has an excellent control effect on arthropod pests and is useful.

The invention claimed is:
1. An arthropod pest control composition comprising a carrier and, as an active ingredient, a compound represented by formula (1):

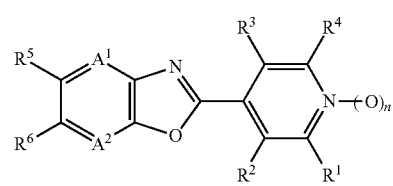

(1)

wherein
$A^1$ represents =C($R^7$)—;
$A^2$ represents a nitrogen atom;
each of $R^1$ and $R^4$ independently represents a halogen atom or a hydrogen atom;

each of $R^2$ and $R^3$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; —$OR^8$; —$NR^8R^9$; —$NR^8C(O)R^9$; —$NR^{10}C(O)NR^9R^{14}$; —$NR^{10}CO_2R^{15}$; —$S(O)_mR^8$; —$CO_2R^{10}$; —$CONR^8R^9$; —$C(O)R^{10}$; —$C(NOR^8)R^{10}$; —$CONR^{10}NR^{11}R^{12}$; a cyano group; a nitro group; a halogen atom; or a hydrogen atom;

each of $R^5$ and $R^6$ independently represents a C1-C6 acyclic hydrocarbon group optionally substituted with one or more members selected from Group X; a C3-C6 alicyclic hydrocarbon group optionally substituted with one or more members selected from Group X; —$OR^{13}$; —$S(O)_mR^{13}$; a halogen atom; or a hydrogen atom, provided that both $R^5$ and $R^6$ do not represent a hydrogen atom simultaneously;

$R^7$ represents a C1-C3 alkyl group optionally substituted with one or more halogen atoms; a C1-C3 alkoxy group optionally substituted with one or more halogen atoms; a cyano group; a halogen atom; or a hydrogen atom;

each of $R^8$ and $R^9$ independently represents a C1-C6 acyclic hydrocarbon group optionally substituted with one or more members selected from Group X; a C4-C7 cycloalkylmethyl group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; or a hydrogen atom; provided that $R^8$ does not represent a hydrogen atom when m in —$S(O)_mR^8$ is 1 or 2;

each of $R^{10}$ and $R^{14}$ independently represents a C1-C4 alkyl group optionally substituted with one or more halogen atoms; or a hydrogen atom;

each of $R^{11}$ and $R^{12}$ independently represents a C1-C4 alkyl group optionally substituted with one or more halogen atoms; a C2-C4 alkoxycarbonyl group; or a hydrogen atom;

$R^{13}$ represents a C1-C6 acyclic hydrocarbon group optionally substituted with one or more members selected from Group X; or a C3-C6 alicyclic hydrocarbon group optionally substituted with one or more members selected from Group X;

$R^{15}$ represents a C1-C4 alkyl group optionally substituted with one or more halogen atoms;

m represents 0, 1, or 2;

n represents 0 or 1;

Group X represents one selected from the group consisting of a C1-C4 alkoxy group optionally substituted with one or more halogen atoms; a cyano group; and a halogen atom; and Group Y represents one selected from the group consisting of a C1-C4 alkyl group optionally substituted with one or more halogen atoms; a C1-C4 alkoxy group optionally substituted with one or more halogen atoms; a cyano group; a nitro group; and a halogen atom.

2. The arthropod pest control composition according to claim 1, wherein in the compound each of $R^2$ and $R^3$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; —$OR^8$; —$NR^8R^9$; —$NR^8C(O)R^9$; —$S(O)_mR^8$; —$CO_2R^{10}$; —$CONR^8R^9$; —$CONR^{10}NR^{11}R^{12}$; a cyano group; a nitro group; a halogen atom; or a hydrogen atom; and each of $R^8$ and $R^9$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a 5- or 6-membered heterocyclic group optionally substituted with one or more members selected from Group Y; or a hydrogen atom.

3. The arthropod pest control composition according to claim 2, wherein in the compound each of $R^1$ and $R^4$ represents a hydrogen atom.

4. The arthropod pest control composition according to claim 2, wherein in the compound $R^2$ represents a hydrogen atom or a halogen atom.

5. The arthropod pest control composition according to claim 2, wherein in the compound $R^3$ represents a C3-C6 alicyclic hydrocarbon group optionally substituted with one or more members selected from Group X; a phenyl group optionally substituted with one or more members selected from Group Y; a benzyl group optionally substituted with one or more members selected from Group Y; or a 5- or 6-membered heterocyclic group optionally substituted with one or more members selected from Group Y.

6. The arthropod pest control composition according to claim 2, wherein in the compound $R^3$ represents a C1-C6 acyclic hydrocarbon group optionally substituted with one or more members selected from Group X; —$OR^8$; —$NR^8R^9$; —$S(O)_mR^8$; a halogen atom; or a hydrogen atom; and each of $R^8$ and $R^9$ independently represents a C1-C6 acyclic hydrocarbon group optionally substituted with one or more members selected from Group X; or a hydrogen atom; provided that $R^8$ represents a C1-C6 acyclic hydrocarbon group optionally substituted with one or more members selected from Group X when m in —$S(O)_mR^8$ is 1 or 2.

7. The arthropod pest control composition according to claim 2, wherein in the compound each of $R^5$ and $R^6$ independently represents a C1-C6 acyclic hydrocarbon group optionally substituted with one or more members selected from Group X; —$OR^{13}$; —$S(O)_mR^{13}$; a halogen atom; or a hydrogen atom; wherein at least one of $R^5$ and $R^6$ represents a C1-C6 acyclic hydrocarbon group optionally substituted with one or more members selected from Group X; —$OR^{13}$; —$S(O)_mR^{13}$; or a halogen atom; and $R^{13}$ represents a C1-C6 acyclic hydrocarbon group optionally substituted with one or more members selected from Group X.

8. The arthropod pest control composition according to claim 1, wherein in the compound each of $R^1$ and $R^4$ represents a hydrogen atom.

9. The arthropod pest control composition according to claim 1, wherein in the compound $R^2$ represents a hydrogen atom or a halogen atom.

10. The arthropod pest control composition according to claim 1, wherein in the compound $R^3$ represents a C3-C6 alicyclic hydrocarbon group optionally substituted with one or more members selected from Group X; a phenyl group optionally substituted with one or more members selected from Group Y; a benzyl group optionally substituted with one or more members selected from Group Y; or a 5- or 6-membered heterocyclic group optionally substituted with one or more members selected from Group Y.

11. The arthropod pest control composition according to claim 1, wherein in the compound $R^3$ represents a C1-C6 acyclic hydrocarbon group optionally substituted with one or more members selected from Group X; —$OR^8$; —$NR^8R^9$; —$NR^8C(O)R^9$; —$NR^{10}C(O)NR^9R^{14}$; —$NR^{10}CO_2R^{15}$; —$S(O)_mR^8$; —$CO_2R^{10}$; —$CONR^8R^9$; —$C(O)R^{10}$; —$C(NOR^8)R^{10}$; —$CONR^{10}NR^{11}R^{12}$; a cyano group; a nitro group; a halogen atom; or a hydrogen atom; and each of $R^8$ and $R^9$ independently represents a C1-C6 acyclic hydrocarbon group optionally substituted with one or more members selected from Group X; or a hydrogen atom; provided that $R^8$ represents a C1-C6 acyclic hydrocarbon group optionally substituted with one or more members selected from Group X when m in —$S(O)_mR^8$ is 1 or 2.

12. The arthropod pest control composition according to claim 1, wherein in the compound $R^3$ represents a C1-C6 acyclic hydrocarbon group optionally substituted with one or more members selected from Group X; —$OR^8$; —$NR^8R^9$; —$S(O)_mR^8$; a halogen atom; or a hydrogen atom; and each of $R^8$ and $R^9$ independently represents a C1-C6 acyclic hydrocarbon group optionally substituted with one or more members selected from Group X; or a hydrogen atom; provided that $R^8$ represents a C1-C6 acyclic hydrocarbon group optionally substituted with one or more members selected from Group X when m in —$S(O)_mR^8$ is 1 or 2.

13. The arthropod pest control composition according to claim 1, wherein in the compound each of $R^5$ and $R^6$ independently represents a C1-C6 acyclic hydrocarbon group optionally substituted with one or more members selected from Group X; —$OR^{13}$; —$S(O)_mR^{13}$; a halogen atom; or a hydrogen atom; wherein at least one of $R^5$ and $R^6$ represents a C1-C6 acyclic hydrocarbon group optionally substituted with one or more members selected from Group X; —$OR^{13}$; —$S(O)_mR^{13}$; or a halogen atom; and $R^{13}$ represents a C1-C6 acyclic hydrocarbon group optionally substituted with one or more members selected from Group X.

14. An arthropod pest control method, which comprises applying, to arthropod pests or areas where arthropod pests live, an arthropod pest control composition comprising a carrier and, as an active ingredient, an effective amount of a compound represented by formula (1):

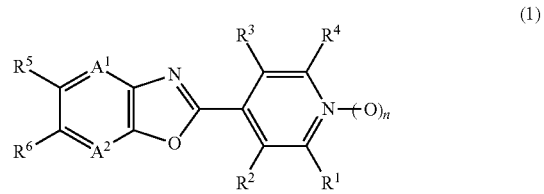

wherein $A^1$ represents =$C(R^7)$—;

$A^2$ represents a nitrogen atom;

each of $R^1$ and $R^4$ independently represents a halogen atom or a hydrogen atom;

each of $R^2$ and $R^3$ independently represents a C1-C6 acyclic hydrocarbon group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; —$OR^8$; —$NR^8R^9$; —$NR^8C(O)R^9$; —$NR^{10}C(O)NR^9R^{14}$; —$NR^{10}CO_2R^{15}$; —$S(O)_mR^8$; —$CO_2R^{10}$; —$CONR^8R^9$; —$C(O)R^{10}$; —$C(NOR^8)R^{10}$; —$CONR^{10}NR^{11}R^{12}$; a cyano group; a nitro group; a halogen atom; or a hydrogen atom;

each of $R^5$ and $R^6$ independently represents a C1-C6 acyclic hydrocarbon group optionally substituted with one or more members selected from Group X; a C3-C6 alicyclic hydrocarbon group optionally substituted with one or more members selected from Group X; —$OR^{13}$; —$S(O)_mR^{13}$; a halogen atom; or a hydrogen atom provided that both $R^5$ and $R^6$ do not represent a hydrogen atom simultaneously;

$R^7$ represents a C1-C3 alkyl group optionally substituted with one or more halogen atoms; a C1-C3 alkoxy group optionally substituted with one or more halogen atoms; a cyano group; a halogen atom; or a hydrogen atom;

each of $R^8$ and $R^9$ independently represents a C1-C6 acyclic hydrocarbon group optionally substituted with one or more members selected from Group X; a C4-C7 cycloalkylmethyl group optionally substituted with one or more members selected from Group X; a C3-C6 alicyclic hydrocarbon group optionally substituted with one or more members selected from Group X; a phenyl group optionally substituted with one or more members selected from Group Y; a benzyl group optionally substituted with one or more members selected from Group Y; a 5- or 6-membered heterocyclic group optionally substituted with one or more members selected from Group Y; or a hydrogen atom; provided that $R^8$ does not represent a hydrogen atom when m in —$S(O)_mR^8$ is 1 or 2;

each of $R^{10}$ and $R^{14}$ independently represents a C1-C4 alkyl group optionally substituted with one or more halogen atoms; or a hydrogen atom;

each of $R^{11}$ and $R^{12}$ independently represents a C1-C4 alkyl group optionally substituted with one or more halogen atoms; a C2-C4 alkoxycarbonyl group; or a hydrogen atom;

$R^{13}$ represents a C1-C6 acyclic hydrocarbon group optionally substituted with one or more members selected from Group X; or a C3-C6 alicyclic hydrocarbon group optionally substituted with one or more members selected from Group X;

$R^{15}$ represents a C1-C4 alkyl group optionally substituted with one or more halogen atoms;

m represents 0, 1, or 2;

n represents 0 or 1;

Group X represents one selected from the group consisting of a C1-C4 alkoxy group optionally substituted with one or more halogen atoms; a cyano group; and a halogen atom; and Group Y represents one selected from the group consisting of a C1-C4 alkyl group optionally substituted with one or more halogen atoms; a C1-C4 alkoxy group optionally substituted with one or more halogen atoms; a cyano group; a nitro group; and a halogen atom.

15. The arthropod pest control method according to claim 14, wherein the arthropod pests are Hemiptera insect pests.

* * * * *